US012533124B2

(12) United States Patent
Shelton, IV et al.

(10) Patent No.: US 12,533,124 B2
(45) Date of Patent: Jan. 27, 2026

(54) SURGICAL STAPLER SLED ASSEMBLY

(71) Applicant: Cilag GmbH International, Zug (CH)

(72) Inventors: Frederick E. Shelton, IV, Hillsboro, OH (US); Adam D. Hensel, Blue Ash, OH (US); Jason L. Harris, Lebanon, OH (US); Chad P. Boudreaux, Cincinnati, OH (US)

(73) Assignee: CILAG GMBH INTERNATIONAL, Zug (CH)

(*) Notice: Subject to any disclaimer, the term of this patent is extended or adjusted under 35 U.S.C. 154(b) by 0 days.

(21) Appl. No.: 18/909,378

(22) Filed: Oct. 8, 2024

(65) Prior Publication Data

US 2025/0025156 A1 Jan. 23, 2025

Related U.S. Application Data

(63) Continuation of application No. 17/211,197, filed on Mar. 24, 2021, now abandoned.

(51) Int. Cl.
*A61B 17/072* (2006.01)
*A61B 17/068* (2006.01)

(52) U.S. Cl.
CPC ........ *A61B 17/0686* (2013.01); *A61B 17/072* (2013.01); *A61B 2017/07228* (2013.01); *A61B 2017/07235* (2013.01); *A61B 2017/07242* (2013.01); *A61B 2017/07271* (2013.01); *A61B 2017/07285* (2013.01)

(58) Field of Classification Search
CPC ................ A61B 17/068; A61B 17/072; A61B 17/07278
See application file for complete search history.

(56) References Cited

U.S. PATENT DOCUMENTS

| | | | |
|---|---|---|---|
| 4,272,002 | A | 6/1981 | Moshofsky |
| 4,991,764 | A | 2/1991 | Mericle |
| 5,141,144 | A | 8/1992 | Foslien |
| 5,395,034 | A | 3/1995 | Allen et al. |
| 5,452,836 | A | 9/1995 | Huitema et al. |

(Continued)

FOREIGN PATENT DOCUMENTS

| | | | |
|---|---|---|---|
| CN | 103169516 | A | 6/2013 |
| CN | 103750873 | A | 4/2014 |

(Continued)

OTHER PUBLICATIONS

European Search Report, Partial, and Provisional Written Opinion dated Jan. 7, 2020, for Application No. 19202542.7, 13 pages.

(Continued)

*Primary Examiner* — Gloria R Weeks
(74) *Attorney, Agent, or Firm* — FROST BROWN TODD LLP

(57) ABSTRACT

A surgical device having at least one rotary input screw in the end effector is provided. A rotary input screw can extend through a central longitudinal portion of the end effector. The end effector can include an improved closure system, firing systems, leveraging and alignment features between the staple cartridge and the surgical device, staple cartridges having multi-staple drivers, single-firing knifes and lockout/safety features for the same, and/or modified staple patterns, for example. Certain components can be 3D-printed components.

20 Claims, 120 Drawing Sheets

(56) References Cited

U.S. PATENT DOCUMENTS

| | | | | |
|---|---|---|---|---|
| 5,632,432 | A * | 5/1997 | Schulze | A61B 17/07207 227/176.1 |
| 5,636,779 | A | 6/1997 | Palmer | |
| 5,651,491 | A | 7/1997 | Heaton et al. | |
| 5,792,135 | A | 8/1998 | Madhani et al. | |
| 5,817,084 | A | 10/1998 | Jensen | |
| 5,878,193 | A | 3/1999 | Wang et al. | |
| 5,911,352 | A | 6/1999 | Racenet et al. | |
| 6,155,473 | A | 12/2000 | Tompkins et al. | |
| 6,231,565 | B1 | 5/2001 | Tovey et al. | |
| 6,364,888 | B1 | 4/2002 | Niemeyer et al. | |
| 6,783,524 | B2 | 8/2004 | Anderson et al. | |
| 7,524,320 | B2 | 4/2009 | Tierney et al. | |
| 7,635,074 | B2 * | 12/2009 | Olson | A61B 17/0682 227/176.1 |
| 7,691,098 | B2 | 4/2010 | Wallace et al. | |
| 7,806,891 | B2 | 10/2010 | Nowlin et al. | |
| 7,905,381 | B2 | 3/2011 | Baxter, III et al. | |
| 7,954,686 | B2 | 6/2011 | Baxter, III et al. | |
| 8,348,129 | B2 | 1/2013 | Bedi et al. | |
| 8,479,969 | B2 | 7/2013 | Shelton, IV | |
| 8,523,041 | B2 | 9/2013 | Ishitsuki et al. | |
| 8,573,461 | B2 | 11/2013 | Shelton, IV et al. | |
| 8,573,465 | B2 | 11/2013 | Shelton, IV | |
| 8,602,288 | B2 | 12/2013 | Shelton, IV et al. | |
| 8,616,431 | B2 | 12/2013 | Timm et al. | |
| 8,783,541 | B2 * | 7/2014 | Shelton, IV | A61B 17/072 227/180.1 |
| 8,789,740 | B2 | 7/2014 | Baxter, III et al. | |
| 8,800,838 | B2 | 8/2014 | Shelton, IV | |
| 8,820,605 | B2 | 9/2014 | Shelton, IV | |
| 8,844,789 | B2 | 9/2014 | Shelton, IV et al. | |
| 9,155,537 | B2 | 10/2015 | Katre et al. | |
| 9,301,759 | B2 | 4/2016 | Spivey et al. | |
| 9,402,629 | B2 | 8/2016 | Ehrenfels et al. | |
| 9,539,007 | B2 | 1/2017 | Dhakad et al. | |
| 9,724,095 | B2 | 8/2017 | Gupta et al. | |
| 10,070,863 | B2 * | 9/2018 | Swayze | A61B 17/07207 |
| 10,631,866 | B2 | 4/2020 | Laurent et al. | |
| 10,667,818 | B2 | 6/2020 | McLain et al. | |
| 10,687,819 | B2 | 6/2020 | Stokes et al. | |
| 10,874,398 | B2 | 12/2020 | Baxter, III et al. | |
| 10,898,187 | B2 | 1/2021 | Deck et al. | |
| 10,898,197 | B2 | 1/2021 | Baxter, III et al. | |
| 10,905,419 | B2 | 2/2021 | Schings et al. | |
| 10,932,781 | B2 | 3/2021 | Jones et al. | |
| 11,033,266 | B2 | 6/2021 | Jones et al. | |
| 11,045,193 | B2 | 6/2021 | Schings et al. | |
| 11,278,285 | B2 | 3/2022 | Deck et al. | |
| 11,464,601 | B2 * | 10/2022 | Shelton, IV | A61B 90/98 |
| 12,082,809 | B2 | 9/2024 | Schings et al. | |
| 2005/0159778 | A1 | 7/2005 | Heinrich et al. | |
| 2007/0056932 | A1 | 3/2007 | Whitman et al. | |
| 2007/0167960 | A1 | 7/2007 | Roth et al. | |
| 2009/0308907 | A1 | 12/2009 | Nalagatla et al. | |
| 2009/0308909 | A1 | 12/2009 | Nalagatla et al. | |
| 2015/0018875 | A1 | 1/2015 | Knodel | |
| 2015/0034695 | A1 | 2/2015 | Kapadia | |
| 2015/0327855 | A1 | 11/2015 | Katre | |
| 2016/0135811 | A1 | 5/2016 | Gupta et al. | |
| 2016/0249920 | A1 | 9/2016 | Gupta et al. | |
| 2016/0262756 | A1 | 9/2016 | Patankar et al. | |
| 2016/0310136 | A1 | 10/2016 | Gupta et al. | |
| 2016/0338701 | A1 | 11/2016 | Patankar et al. | |
| 2016/0338702 | A1 | 11/2016 | Ehrenfels et al. | |
| 2017/0079652 | A1 | 3/2017 | Dhakad et al. | |
| 2017/0143335 | A1 | 5/2017 | Gupta et al. | |
| 2017/0143336 | A1 | 5/2017 | Shah et al. | |
| 2017/0325811 | A1 | 11/2017 | Gupta et al. | |
| 2017/0367699 | A1 * | 12/2017 | Shelton, IV | A61B 17/064 |
| 2018/0168625 | A1 * | 6/2018 | Posada | A61B 17/07207 |
| 2018/0353180 | A1 * | 12/2018 | Huitema | A61B 17/0644 |
| 2020/0054322 | A1 | 2/2020 | Harris et al. | |
| 2020/0054326 | A1 | 2/2020 | Harris et al. | |
| 2022/0304682 | A1 * | 9/2022 | Shelton, IV | A61B 17/07207 |
| 2023/0121658 | A1 * | 4/2023 | Stokes | A61B 17/072 227/178.1 |
| 2023/0121835 | A1 * | 4/2023 | Estera | A61B 17/07207 227/178.1 |

FOREIGN PATENT DOCUMENTS

| | | | |
|---|---|---|---|
| EP | 0061466 | A1 | 10/1982 |
| EP | 0178941 | A2 | 4/1986 |
| EP | 0677273 | A2 | 10/1995 |
| EP | 1702567 | A2 | 9/2006 |
| EP | 2532312 | A2 | 12/2012 |
| EP | 3065649 | A1 | 9/2016 |
| EP | 2741685 | B1 | 1/2017 |
| EP | 3155988 | A1 | 4/2017 |
| EP | 3162296 | A2 | 5/2017 |
| EP | 2804541 | B1 | 10/2017 |
| WO | 2017/056028 | A1 | 4/2017 |
| WO | 2018/044669 | A1 | 3/2018 |

OTHER PUBLICATIONS

European Search Report, Extended, and Written Opinion dated Jun. 25, 2020, for Application No. 19202542.7, 12 pages.

International Search Report and Written Opinion dated Mar. 19, 2020, for International Application PCT/IB2019/058687, 17 pages.

* cited by examiner

SURGICAL STAPLER SLED ASSEMBLY

PRIORITY

The present application is a continuation of U.S. patent application Ser. No. 17/211,197, entitled "Fastener Cartridge with Non-Repeating Fastener Rows," filed Mar. 24, 2021, published as U.S. Pub. No. 2022/0304682 on Sep. 29, 2022, now abandoned, the disclosure of which is incorporated by reference herein in its entirety.

BACKGROUND

The present invention relates to surgical instruments and, in various arrangements, to surgical stapling and cutting instruments, end effectors, and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 114 is a perspective view of the portion of the end effector and the cartridge body of FIG. 113 with the lockout key in the distal position, according to various aspects of the present disclosure.

FIG. 115 is a perspective partial cutaway view of a portion of the end effector of FIG. 108 with the cartridge body of FIG. 110 installed in the end effector and partially cutaway for illustrative purposes to expose the lock nut in the locked position, according to various aspects of the present disclosure.

FIG. 116 is a perspective view of a portion of an end effector with certain portions removed and other portions transparent and shown with phantom lines for illustrative purposes, depicting a lockout arrangement in a locked configuration, according to various aspects of the present disclosure.

FIG. 117 is a perspective view of a portion of the end effector of FIG. 116 with certain portions removed and other portions transparent for illustrative purposes, depicting the lockout arrangement in the locked configuration, according to various aspects of the present disclosure.

FIG. 118 is a plan view of a staple cartridge depicting patterns of staple cavities, according to various aspects of the present disclosure.

FIG. 119 is a schematic depicting staple cavity patterns for a staple cartridge, according to various aspects of the present disclosure.

FIG. 120 is a schematic depicting staple cavity patterns for a staple cartridge, according to various aspects of the present disclosure.

FIG. 121 is a plan view of a staple cartridge depicting patterns of staple cavities, according to various aspects of the present disclosure.

FIG. 122 is a plan view of staple cartridges schematically depicting a tissue stops, according to various aspects of the present disclosure.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
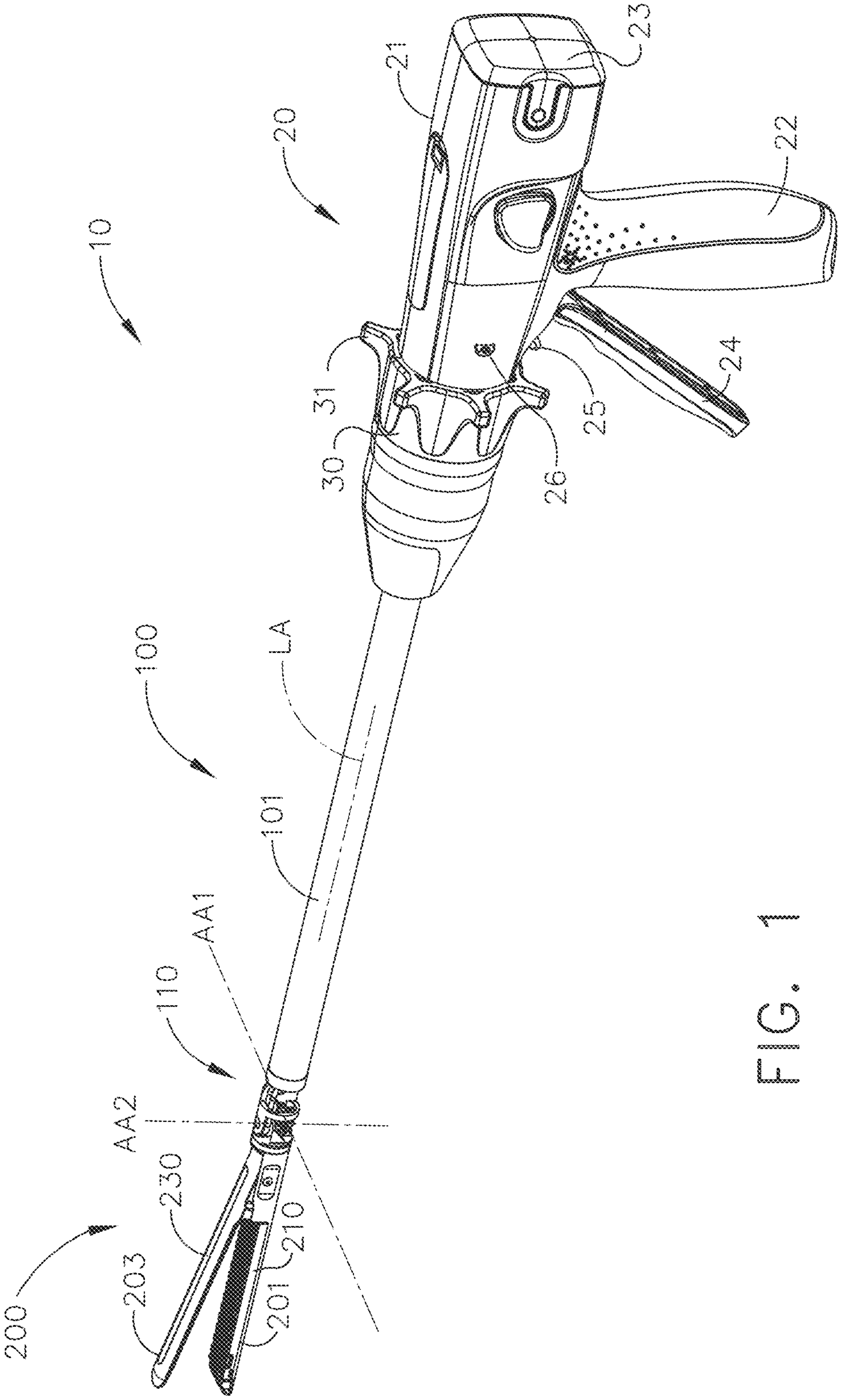
FIG. 1 is a perspective view of a surgical stapling instrument comprising a handle, a shaft assembly, and an end effector, in accordance with at least one aspect of the present disclosure.
Figure 2:
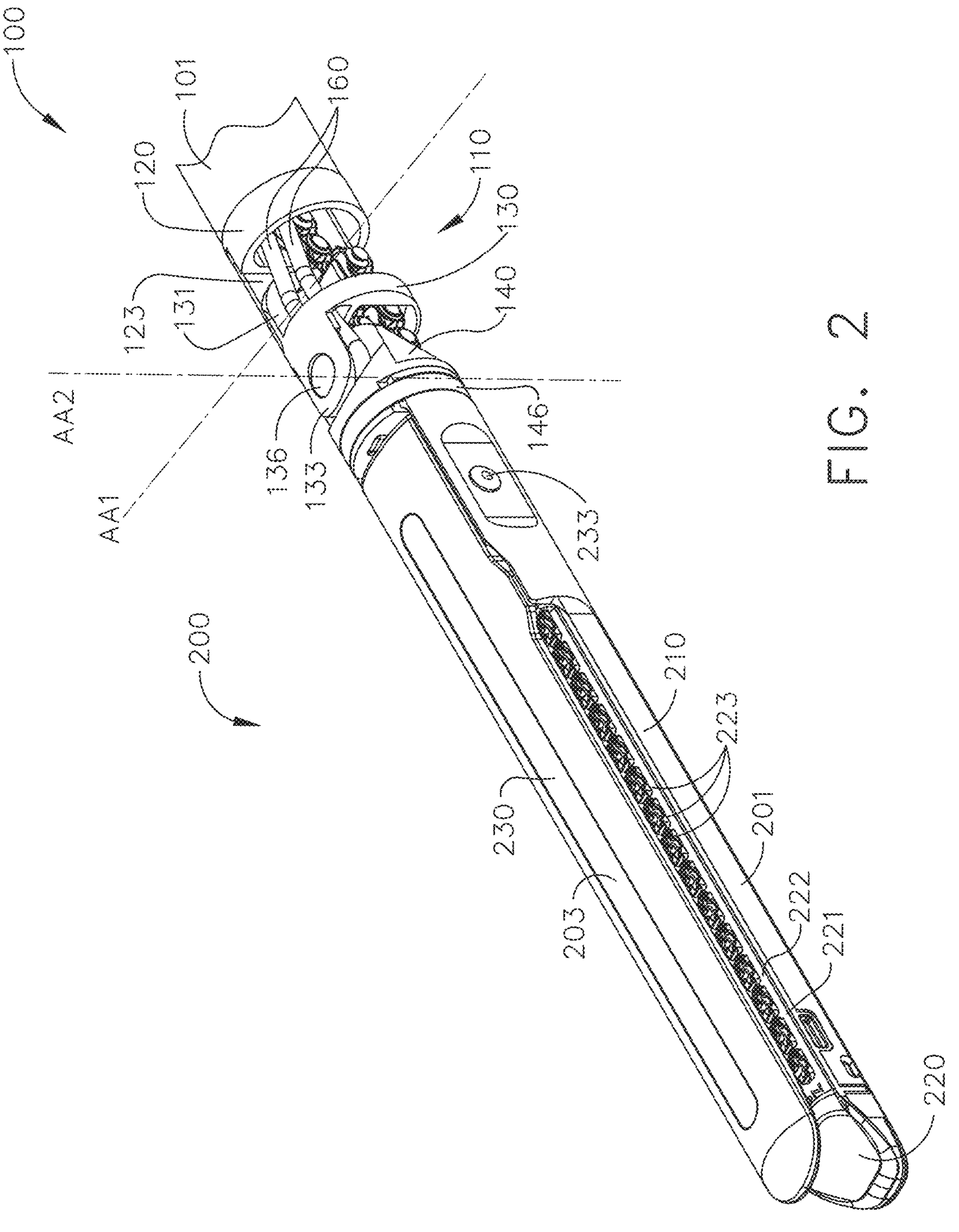
FIG. 2 is a perspective view of the end effector and a portion of the shaft assembly of the surgical stapling instrument of FIG. 1, wherein the end effector is illustrated in a straight, or non-articulated, configuration, in accordance with at least one aspect of the present disclosure.
Figure 3:
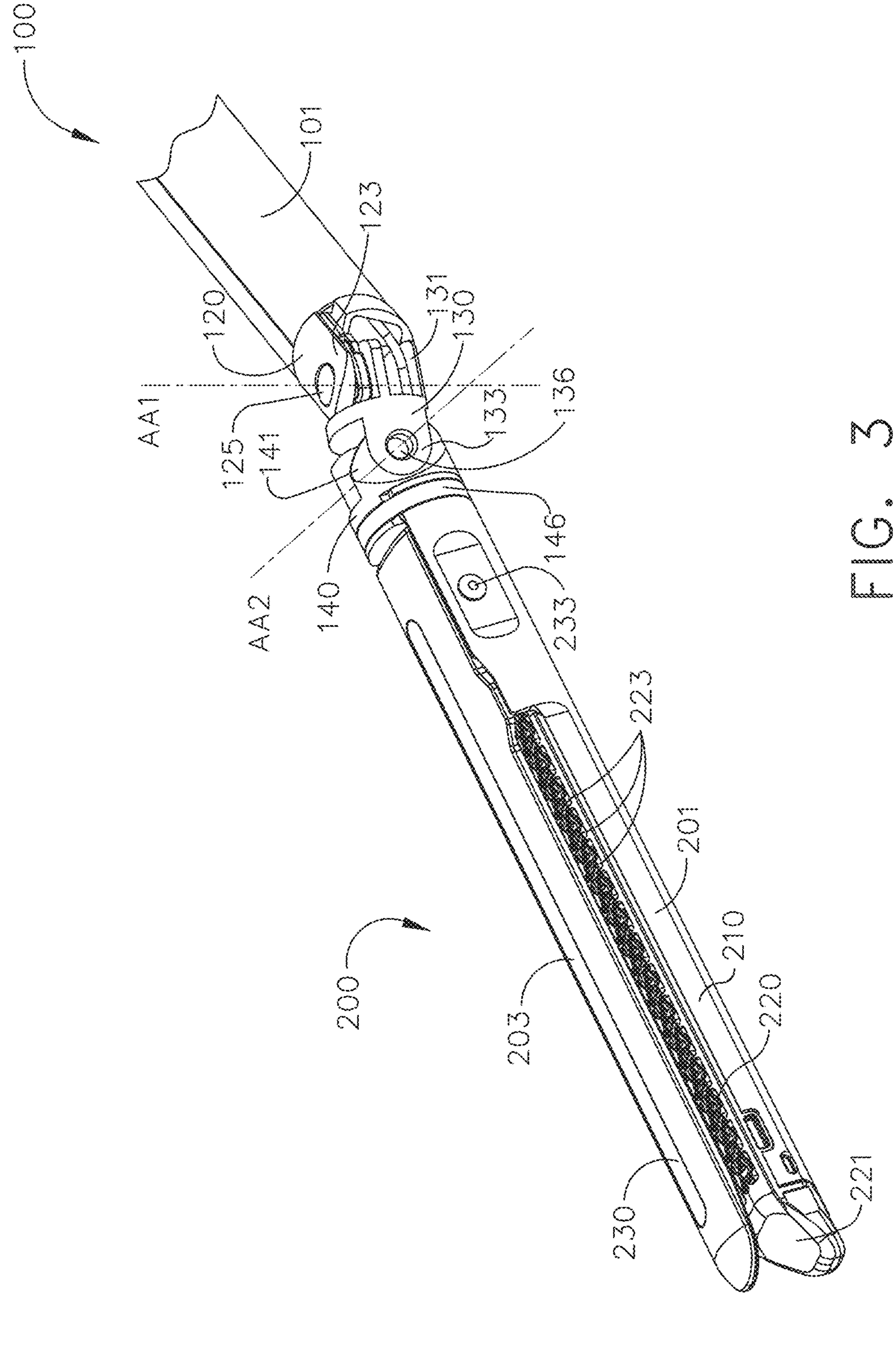
FIG. 3 is a perspective view of the end effector and a portion of the shaft assembly of the surgical stapling instrument of FIG. 1, wherein the end effector is illustrated in an articulated configuration, in accordance with at least one aspect of the present disclosure.

Applicant of the present application owns the following U.S. Patent Applications that were filed on even date herewith and which are each herein incorporated by reference in their respective entireties:

- U.S. patent application Ser. No. 17/211,145 entitled METHOD OF USING A POWERED STAPLING DEVICE, filed Mar. 24, 2021, issued as U.S. Pat. No. 11,896,218 on Feb. 13, 2024;
- U.S. patent application Ser. No. 17/211,161 entitled SURGICAL STAPLING ASSEMBLY COMPRISING NONPLANAR STAPLES AND PLANAR STAPLES, filed Mar. 24, 2021, issued as U.S. Pat. No. 11,832,816 on Dec. 5, 2023;
- U.S. patent application Ser. No. 17/211,168 entitled SURGICAL STAPLE CARTRIDGE COMPRISING LONGITUDINAL SUPPORT BEAM, filed Mar. 24, 2021, issued as U.S. Pat. No. 11,793,516 on Oct. 24, 2023;
- U.S. patent application Ser. No. 17/211,172 entitled ROTARY-DRIVEN SURGICAL STAPLING ASSEMBLY COMPRISING ECCENTRICALLY DRIVEN FIRING MEMBER, filed Mar. 24, 2021, issued as U.S. Pat. No. 11,849,945 on Dec. 26, 2023;
- U.S. patent application Ser. No. 17/211,175 entitled ROTARY-DRIVEN SURGICAL STAPLING ASSEMBLY COMPRISING A FLOATABLE COMPONENT, filed Mar. 24, 2021, issued as U.S. Pat. No. 12,102,323 on Oct. 1, 2024;
- U.S. patent application Ser. No. 17/211,182 entitled DRIVERS FOR FASTENER CARTRIDGE ASSEMBLIES HAVING ROTARY DRIVE SCREWS, filed Mar. 24, 2021, issued as U.S. Pat. No. 11,849,944 on Dec. 26, 2023;
- U.S. patent application Ser. No. 17/211,189 entitled MATING FEATURES BETWEEN DRIVERS AND UNDERSIDE OF A CARTRIDGE DECK, filed Mar. 24, 2021, issued as U.S. Pat. No. 11,896,219 on Feb. 13, 2024;
- U.S. patent application Ser. No. 17/211,192 entitled LEVERAGING SURFACES FOR CARTRIDGE INSTALLATION, filed Mar. 24, 2021, issued as U.S. Pat. No. 11,903,582 on Feb. 20, 2024;
- U.S. patent application Ser. No. 17/211,207 entitled FIRING MEMBERS HAVING FLEXIBLE PORTIONS FOR ADAPTING TO A LOAD DURING A SURGICAL FIRING STROKE, filed Mar. 24, 2021, issued as U.S. Pat. No. 11,786,243 on Oct. 17, 2023;
- U.S. patent application Ser. No. 17/211,210 entitled STAPLING ASSEMBLY COMPONENTS HAVING METAL SUBSTRATES AND PLASTIC BODIES, filed Mar. 24, 2021, issued as U.S. Pat. No. 11,857,183 on Jan. 2, 2024;
- U.S. patent application Ser. No. 17/211,222 entitled MULTI-AXIS PIVOT JOINTS FOR SURGICAL INSTRUMENTS AND METHODS OF MANUFACTURING SAME, filed Mar. 24, 2021, issued as U.S. Pat. No. 11,744,603 on Sep. 5, 2023;
- U.S. patent application Ser. No. 17/211,230 entitled JOINT ARRANGEMENTS FOR MULTI-PLANAR ALIGNMENT AND SUPPORT OF OPERATIONAL DRIVE SHAFTS IN ARTICULATABLE SURGICAL INSTRUMENTS, filed on Mar. 24, 2021, issued as U.S. Pat. No. 11,944,336 on Apr. 2, 2024; and
- U.S. patent application Ser. No. 17/211,242 entitled SURGICAL INSTRUMENT ARTICULATION JOINT ARRANGEMENTS COMPRISING MULTIPLE MOVING LINKAGE FEATURES, filed Mar. 24, 2021, issued as U.S. Pat. No. 11,786,239 on Oct. 17, 2023.

Applicant of the present application owns the following U.S. Patent Applications and U.S. Patents that were filed on Dec. 19, 2017 and which are each herein incorporated by reference in their respective entireties:

- U.S. Pat. No. 10,835,330, entitled METHOD FOR DETERMINING THE POSITION OF A ROTATABLE JAW OF A SURGICAL INSTRUMENT ATTACHMENT ASSEMBLY;
- U.S. Pat. No. 10,716,565, entitled SURGICAL INSTRUMENTS WITH DUAL ARTICULATION DRIVERS;
- U.S. patent application Ser. No. 15/847,325, entitled SURGICAL TOOLS CONFIGURED FOR INTERCHANGEABLE USE WITH DIFFERENT CONTROLLER INTERFACES, issued as U.S. Pat. No. 11,020,112 on Jun. 1, 2021;
- U.S. Pat. No. 10,729,509, entitled SURGICAL INSTRUMENT COMPRISING CLOSURE AND FIRING LOCKING MECHANISM;
- U.S. patent application Ser. No. 15/847,315, entitled ROBOTIC ATTACHMENT COMPRISING EXTERIOR DRIVE ACTUATOR, issued as U.S. Pat. No. 11,045,270 on Jun. 29, 2021; and
- U.S. Design Pat. No. D910,847, entitled SURGICAL INSTRUMENT ASSEMBLY.

Applicant of the present application owns the following U.S. Patent Applications and U.S. Patents that were filed on Jun. 28, 2017 and which are each herein incorporated by reference in their respective entireties:

- U.S. patent application Ser. No. 15/635,693, entitled SURGICAL INSTRUMENT COMPRISING AN OFFSET ARTICULATION JOINT, issued as U.S. Pat. No. 11,058,424 on Jul. 13, 2021;
- U.S. patent application Ser. No. 15/635,729, entitled SURGICAL INSTRUMENT COMPRISING AN ARTICULATION SYSTEM RATIO, issued as U.S. Pat. No. 11,000,279 on May 11, 2021;
- U.S. patent application Ser. No. 15/635,785, entitled SURGICAL INSTRUMENT COMPRISING AN ARTICULATION SYSTEM RATIO, issued as U.S. Pat. No. 11,083,455 on Aug. 10, 2021;
- U.S. patent application Ser. No. 15/635,808, entitled SURGICAL INSTRUMENT COMPRISING FIRING MEMBER SUPPORTS, issued as U.S. Pat. No. 11,259,805 on Mar. 1, 2022;
- U.S. patent application Ser. No. 15/635,837, entitled SURGICAL INSTRUMENT COMPRISING AN ARTICULATION SYSTEM LOCKABLE TO A FRAME, issued as U.S. Pat. No. 11,246,592 on Feb. 15, 2022;

U.S. Pat. No. 10,779,824, entitled SURGICAL INSTRUMENT COMPRISING AN ARTICULATION SYSTEM LOCKABLE BY A CLOSURE SYSTEM;

U.S. patent application Ser. No. 15/636,029, entitled SURGICAL INSTRUMENT COMPRISING A SHAFT INCLUDING A HOUSING ARRANGEMENT, issued as U.S. Pat. No. 11,678,880 on Jun. 20, 2023;

U.S. patent application Ser. No. 15/635,958, entitled SURGICAL INSTRUMENT COMPRISING SELECTIVELY ACTUATABLE ROTATABLE COUPLERS, issued as U.S. Pat. No. 11,389,161 on Jul. 19, 2022;

U.S. patent application Ser. No. 15/635,981, entitled SURGICAL STAPLING INSTRUMENTS COMPRISING SHORTENED STAPLE CARTRIDGE NOSES, issued as U.S. Pat. No. 11,696,759 on Jul. 11, 2023;

U.S. patent application Ser. No. 15/636,009, entitled SURGICAL INSTRUMENT COMPRISING A SHAFT INCLUDING A CLOSURE TUBE PROFILE, issued as U.S. Pat. No. 11,484,310 on Nov. 1, 2022;

U.S. Pat. No. 10,765,427, entitled METHOD FOR ARTICULATING A SURGICAL INSTRUMENT;

U.S. patent application Ser. No. 15/635,530, entitled SURGICAL INSTRUMENTS WITH ARTICULATABLE END EFFECTOR WITH AXIALLY SHORTENED ARTICULATION JOINT CONFIGURATIONS, issued as U.S. Pat. No. 11,020,114 on Jun. 1, 2021;

U.S. Pat. No. 10,588,633, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING;

U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS, published as U.S. Patent Application Publication No. 2019/0000459, now abandoned;

U.S. Pat. No. 10,786,253, entitled SURGICAL END EFFECTORS WITH IMPROVED JAW APERTURE ARRANGEMENTS;

U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT AXIS, published as U.S. Patent Application Publication No. 2019/0000461, now abandoned;

U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW, issued as U.S. Pat. No. 11,478,242 on Oct. 25, 2022;

U.S. Pat. No. 10,758,232, entitled SURGICAL INSTRUMENT WITH POSITIVE JAW OPENING FEATURES;

U.S. Pat. No. 10,639,037, entitled SURGICAL INSTRUMENT WITH AXIALLY MOVABLE CLOSURE MEMBER;

U.S. Pat. No. 10,695,057, entitled SURGICAL INSTRUMENT LOCKOUT ARRANGEMENT;

U.S. Design Pat. No. D851,762, entitled ANVIL;

U.S. Design Pat. No. D854,151, entitled SURGICAL INSTRUMENT SHAFT; and

U.S. Design Pat. No. D869,655, entitled SURGICAL FASTENER CARTRIDGE.

Applicant of the present application owns the following U.S. Patent Applications and U.S. Patents that were filed on Jun. 27, 2017 and which are each herein incorporated by reference in their respective entireties:

U.S. patent application Ser. No. 15/634,024, entitled SURGICAL ANVIL MANUFACTURING METHODS, issued as U.S. Pat. No. 11,266,405 on Mar. 8, 2022;

U.S. Pat. No. 10,772,629, entitled SURGICAL ANVIL ARRANGEMENTS;

U.S. patent application Ser. No. 15/634,046, entitled SURGICAL ANVIL ARRANGEMENTS, issued as U.S. Pat. No. 10,993,716 on May 4, 2021;

U.S. Pat. No. 10,856,869, entitled SURGICAL ANVIL ARRANGEMENTS;

U.S. patent application Ser. No. 15/634,068, entitled SURGICAL FIRING MEMBER ARRANGEMENTS, issued as U.S. Pat. No. 11,324,503 on May 10, 2022;

U.S. patent application Ser. No. 15/634,076, entitled STAPLE FORMING POCKET ARRANGEMENTS, published as U.S. Patent Application Publication No. 2018/0368844, now abandoned;

U.S. patent application Ser. No. 15/634,090, entitled STAPLE FORMING POCKET ARRANGEMENTS, issued as U.S. Pat. No. 11,090,049 on Aug. 17, 2021;

U.S. patent application Ser. No. 15/634,099, entitled SURGICAL END EFFECTORS AND ANVILS, issued as U.S. Pat. No. 11,141,154 on Oct. 21, 2021; and U.S. Pat. No. 10,631,859, entitled ARTICULATION SYSTEMS FOR SURGICAL INSTRUMENTS.

Applicant of the present application owns the following U.S. Patent Applications that were filed on Jun. 2, 2020 and which are each herein incorporated by reference in their respective entireties:

U.S. Design patent application Ser. No. 29/736,648, entitled STAPLE CARTRIDGE, issued as U.S. Design Pat. No. D967,421 on Oct. 18, 2022;

U.S. Design patent application Ser. No. 29/736,649, entitled STAPLE CARTRIDGE, issued as U.S. Design Pat. No. D966,512 on Oct. 11, 2022;

U.S. Design patent application Ser. No. 29/736,651, entitled STAPLE CARTRIDGE, issued as U.S. Design Pat. No. D975,278 on Jan. 10, 2023;

U.S. Design patent application Ser. No. 29/736,652, entitled STAPLE CARTRIDGE, issued as U.S. Design Pat. No. D975,850 on Jan. 17, 2023;

U.S. Design patent application Ser. No. 29/736,653, entitled STAPLE CARTRIDGE, issued as U.S. Design Pat. No. D974,560 on Jan. 3, 2023;

U.S. Design patent application Ser. No. 29/736,654, entitled STAPLE CARTRIDGE, issued as U.S. Design Pat. No. D975,851 on Jan. 17, 2023; and U.S. Design patent application Ser. No. 29/736,655, entitled STAPLE CARTRIDGE, issued as U.S. Design Pat. No. D976,401 on Jan. 24, 2023.

Applicant of the present application owns the following U.S. Design Patent Applications and U.S. Patents that were filed on Nov. 14, 2016, and which are each herein incorporated by reference in their respective entireties:

U.S. patent application Ser. No. 15/350,621, published as U.S. Patent Application Publication No. 2018/0132849, entitled STAPLE FORMING POCKET CONFIGURATIONS FOR CIRCULAR STAPLER ANVIL, now abandoned;

U.S. patent application Ser. No. 15/350,624, entitled CIRCULAR SURGICAL STAPLER WITH ANGULARLY ASYMMETRIC DECK FEATURES, issued as U.S. Pat. No. 10,603,041 on Mar. 31, 2020;

U.S. Design Pat. No. D833,608, titled STAPLING HEAD FEATURE FOR SURGICAL STAPLER; and U.S. Design Pat. No. D830,550, titled SURGICAL STAPLER.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical device. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical device are used in many orientations and positions, and these terms are not intended to be limiting and/or absolute. In the following description, terms such as "first," "second," "top," "bottom," "up," "down," and the like are words of convenience and are not to be construed as limiting terms.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various surgical devices disclosed herein can be inserted into a body in any way, such as through a natural orifice, through an incision or puncture hole formed in tissue, etc. The working portions or end effector portions of the surgical devices can be inserted directly into a patient's body or can be inserted through an access device that has a working channel through which the end effector and elongate shaft of a surgical device can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue to be stapled. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples are contemplated.

The staples are supported by staple drivers in the cartridge body. The drivers are movable between a first, or unfired, position and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent a proximal end of the cartridge body and a distal position adjacent a distal end of the cartridge body. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected into the tissue ahead of the knife transecting the tissue.

FIGS. 1-8 depict a surgical stapling instrument 10 configured to clamp, staple, and cut tissue of a patient. The surgical stapling instrument 10 comprises a handle 20, a shaft assembly 100 attached to the handle 20, and an end effector 200. To cut and staple tissue of a patient, the end effector 200 comprises a cartridge jaw 201 and an anvil jaw 203. The anvil jaw 203 is pivotable relative to the cartridge jaw 203 to clamp tissue between the anvil jaw 203 and the cartridge jaw 203. Once tissue is clamped between the jaws 201, 203, the surgical stapling instrument 10 may be actuated to advance a firing member through the jaws 201, 203 to staple and cut tissue with the end effector 200 as discussed in greater detail below.

Discussed in greater detail below, the end effector 200 is articulatable by way of an articulation region 110 of the shaft assembly 100. Such articulation provides a user of the surgical stapling instrument 10 with the ability to position and/or maneuver the end effector 200 near the target tissue more accurately.

The handle 20 comprises a housing 21 configured to house various mechanical and electrical components and a handle portion 22 extending from the housing 21. The handle portion 22 is configured to fit in the palm of a user and/or be gripped and/or held by a user using the surgical stapling instrument 10. The handle 20 further comprises various actuators and/or triggers configured to be actuated by a user to operate one or more functions of the surgical stapling instrument 10. The handle 20 comprises a closure trigger 24, a firing trigger 25, and at least one articulation actuator 26. When actuated by a user, the closure trigger 24 is configured to clamp tissue with the end effector 200 by moving the anvil jaw 203 toward the cartridge jaw 201. When actuated by a user, the firing trigger 25 is configured to cut and staple tissue with the end effector 200 by advancing a firing member to eject staples and cut tissue with a knife. When actuated by a user, the articulation actuator 26 is configured to articulate the end effector 200 relative to the shaft assembly 100 by way of the articulation region 110. The triggers and actuators of the surgical stapling instrument 10 can either trigger one or more motors within the handle 20 to actuate various function of the surgical stapling instrument 10 and/or manually drive various drive shafts and components to actuate various function of the surgical stapling instrument 10.

The handle 20 further comprises a nozzle assembly 30 configured to support the shaft assembly 100 therein. The nozzle assembly 30 comprises an actuation wheel 31 configured to be rotated by a user to rotate the shaft assembly 100 and end effector 200 about a longitudinal axis LA relative to the handle 20. Such a mechanism permits the user of the surgical stapling instrument 10 to rotate only the shaft assembly 100 and/or end effector 200 without having to rotate the entire handle 20.

The handle 20 further comprises a battery 23 configured to provide power to various electronic components, sensors, and/or motors of the surgical stapling instrument 10. Embodiments are envisioned where the surgical stapling instrument 10 is directly connected to a power source. Embodiments are also envisioned where the surgical stapling instrument 10 is entirely manual or, non-powered, for example. Embodiments are further envisioned where articulation of the end effector, clamping and unclamping of the jaws, firing of the end effector staple and cut tissue, and shaft and/or end effector rotation are all powered systems.

In at least one instance, the shaft assembly 100 and the end effector 200 may be modular and removable from the handle 20. In at least one instance, the end effector 200 may be modular in that the end effector 200 can be removed from the shaft assembly 100 and replaced with a different end effector. In at least one instance, the shaft assembly 100 and/or the end effector 200 is employable in a surgical robotic environment. Such an embodiment would provide powered inputs from a surgical robotic interface to actuate each function of the end effector 200. Examples of such surgical robots and surgical tools are further described in U.S. Patent Application Publication No. 2020/0138534, titled ROBOTIC SURGICAL SYSTEM, which published on May 7, 2020, issued as U.S. Pat. No. 11,812,924 on Nov. 14, 2023, which is incorporated by reference herein in its entirety.

In at least one instance, the shaft assembly 100 and the end effector 200 are configured to be used with a surgical robot. In such an instance, the shaft assembly 100 and the end effector 200 are configured to be coupled to a surgical robot comprising a plurality of output drives. The plurality of output drives of the surgical robot are configured to mate with the drive systems of the shaft assembly 100 and end effector 200. In such an instance, the surgical robot can actuate the various different functions of the end effector 200 such as, for example, articulating the end effector about multiple different articulation joints, rotating the shaft assembly 100 and/or end effector 200 about its longitudinal axis, clamping the end effector 200 to clamp tissue between the jaws of the end effector 200, and/or firing the end effector 200 to cut and/or staple tissue.

The shaft assembly 100 is configured to house various drive system components and/or electronic components of the surgical stapling instrument 10 so that the end effector 200 and shaft assembly 100 may be inserted through a trocar for laparoscopic surgery. The various drive system components are configured to be actuated by the various triggers and actuators of the handle 20. Such components can include drive shafts for articulation, drive shafts for clamping and unclamping the end effector 200, and/or drive shafts for firing the end effector 200. Such drive shafts may be rotated by a drive system in the handle 20 or a surgical robotic interface in the instance where the shaft assembly 100 is connected to the same. In various aspects, a stapling end effector can include two independently rotatable drive members—one for grasping tissue and one for firing staples, for example. The stapling end effector can further include an articulation joint, and the rotary motions can be transmitted through the articulation joint. In various aspects, the stapling end effector can include one or more 3D printed assemblies, which can be incorporated into an articulation, grasping, or firing systems.

Such drive shafts may be actuated by a drive system in the handle 20 or a surgical robotic interface in the instance where the shaft assembly 100 is connected to the same. Such drive shafts may comprise linear actuation, rotary actuation, or a combination thereof. A combination of rotary actuation and linear actuation may employ a series of rack gears and/or drive screws, for example.

In at least one instance, the shaft assembly 100 is also configured to house electrical leads for various sensors and/or motors, for example, positioned within the shaft assembly 100 and/or end effector 200, for example.

The shaft assembly 100 comprises an outer shaft 101 extending from the nozzle assembly 30 to the articulation region 110 comprising dual articulation joints, discussed in greater detail below. The articulation region 110 allows the end effector 200 to be articulated relative to the outer shaft 101 in two distinct planes about two separate axes AA1, AA2.

Figure 4:
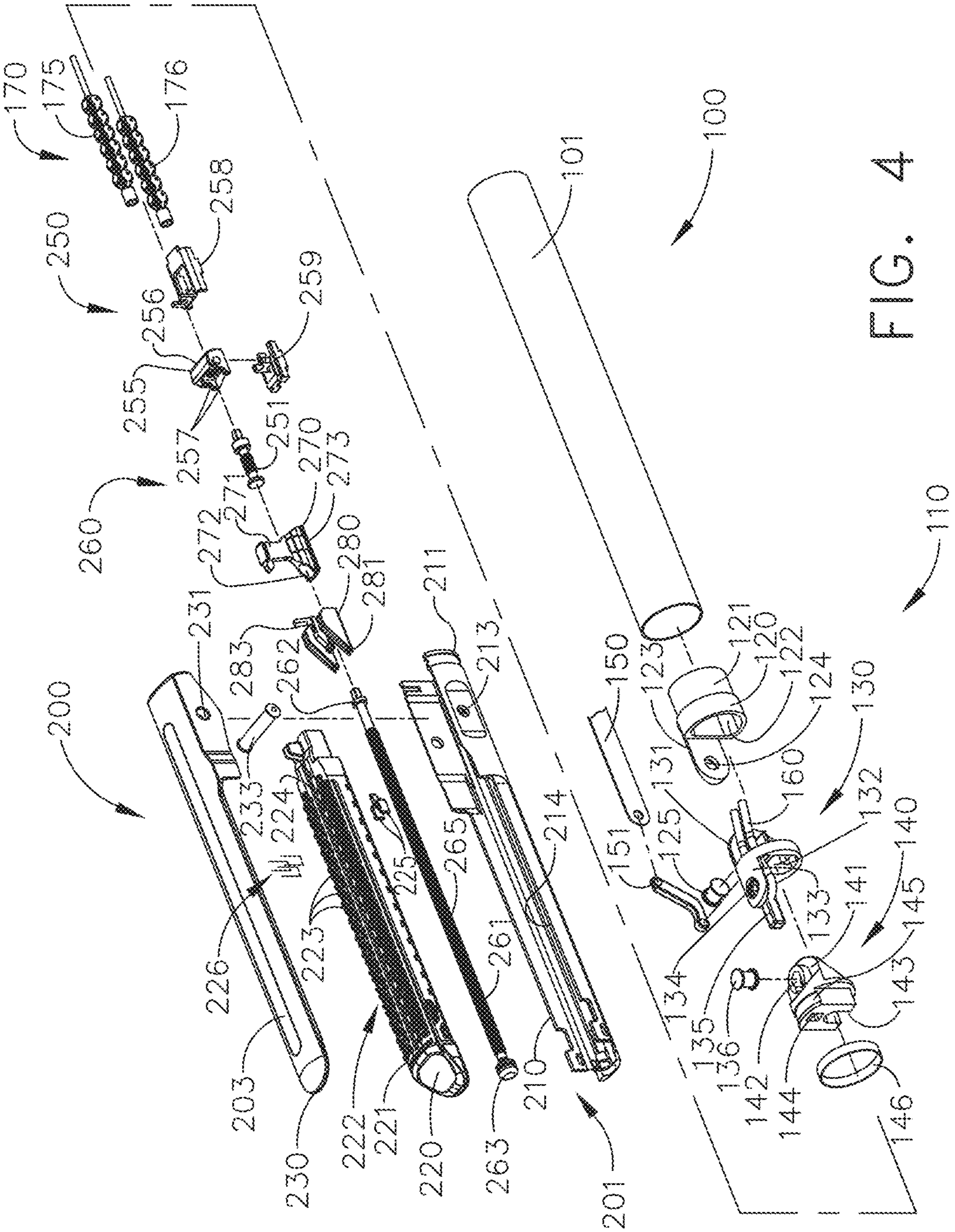
FIG. 4 is an exploded perspective view of the end effector and a portion of the shaft assembly of the surgical stapling instrument of FIG. 1, in accordance with at least one aspect of the present disclosure.
Figure 5:
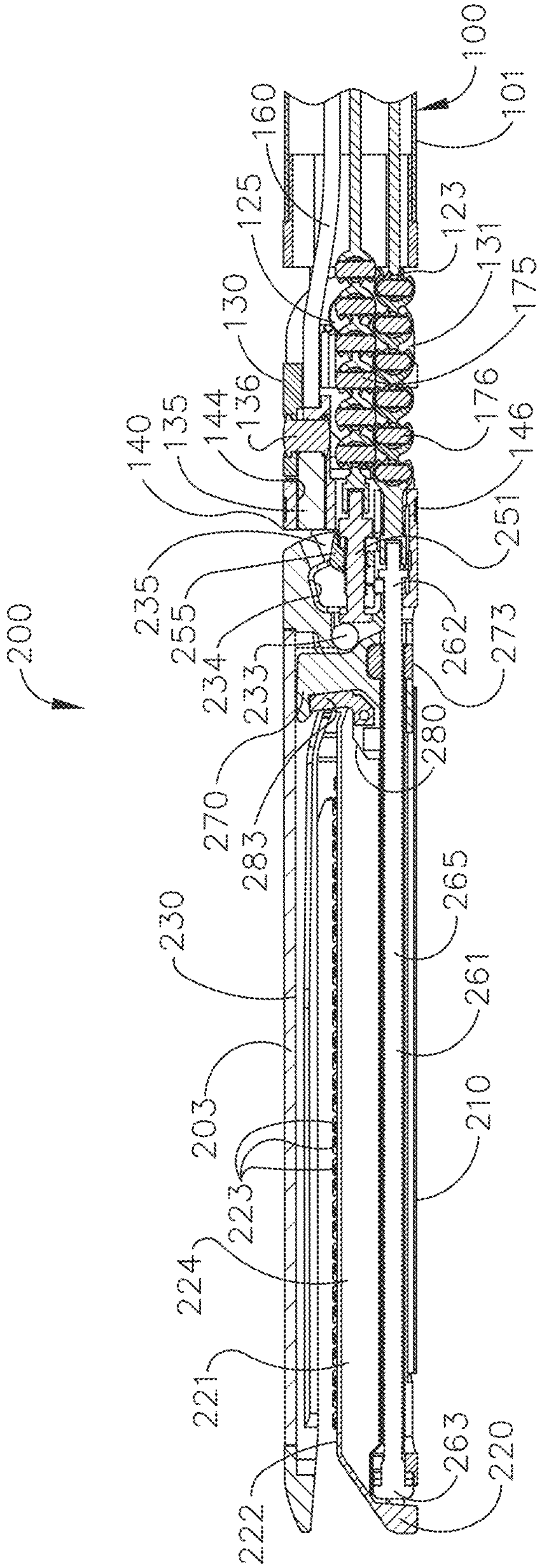
FIG. 5 is a cross-sectional elevation view of the end effector and a portion of the shaft assembly of the surgical stapling instrument of FIG. 1, wherein the end effector is illustrated in an unfired, clamped configuration, in accordance with at least one aspect of the present disclosure.
Figure 6:
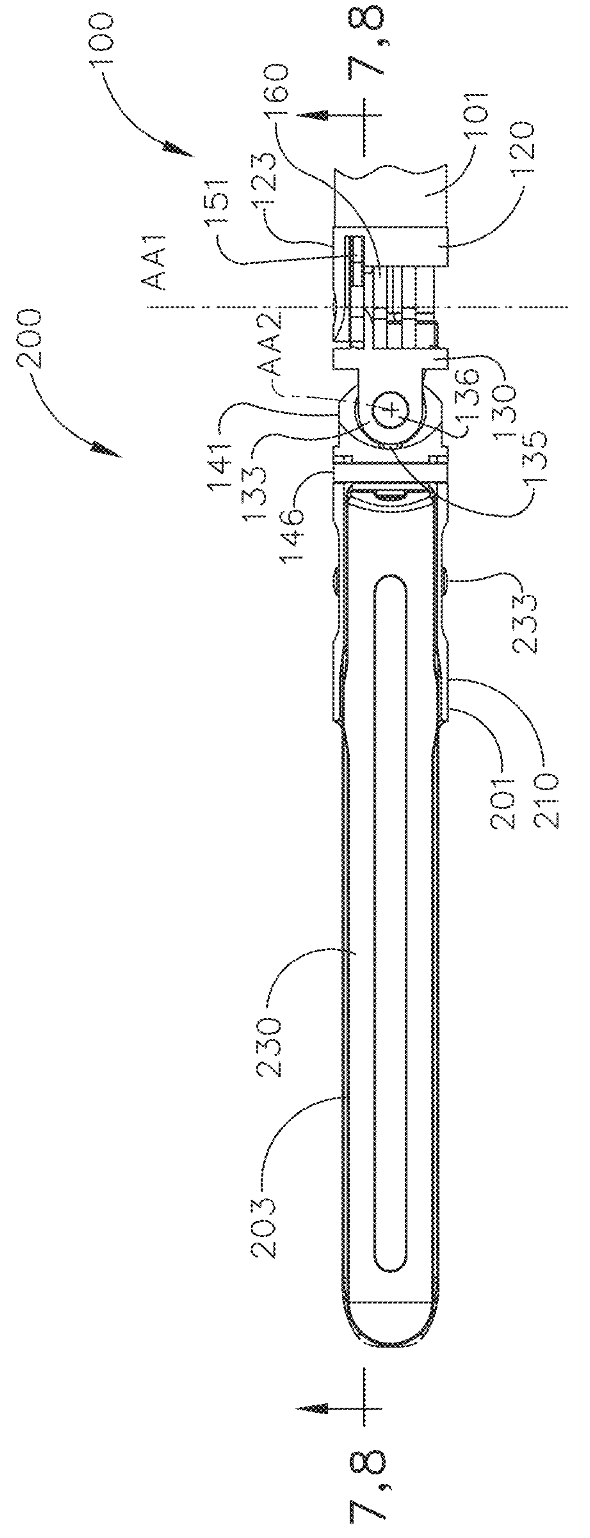
FIG. 6 is a plan view of the end effector and a portion of the shaft assembly of the surgical stapling instrument of FIG. 1, in accordance with at least one aspect of the present disclosure.
Figure 7:
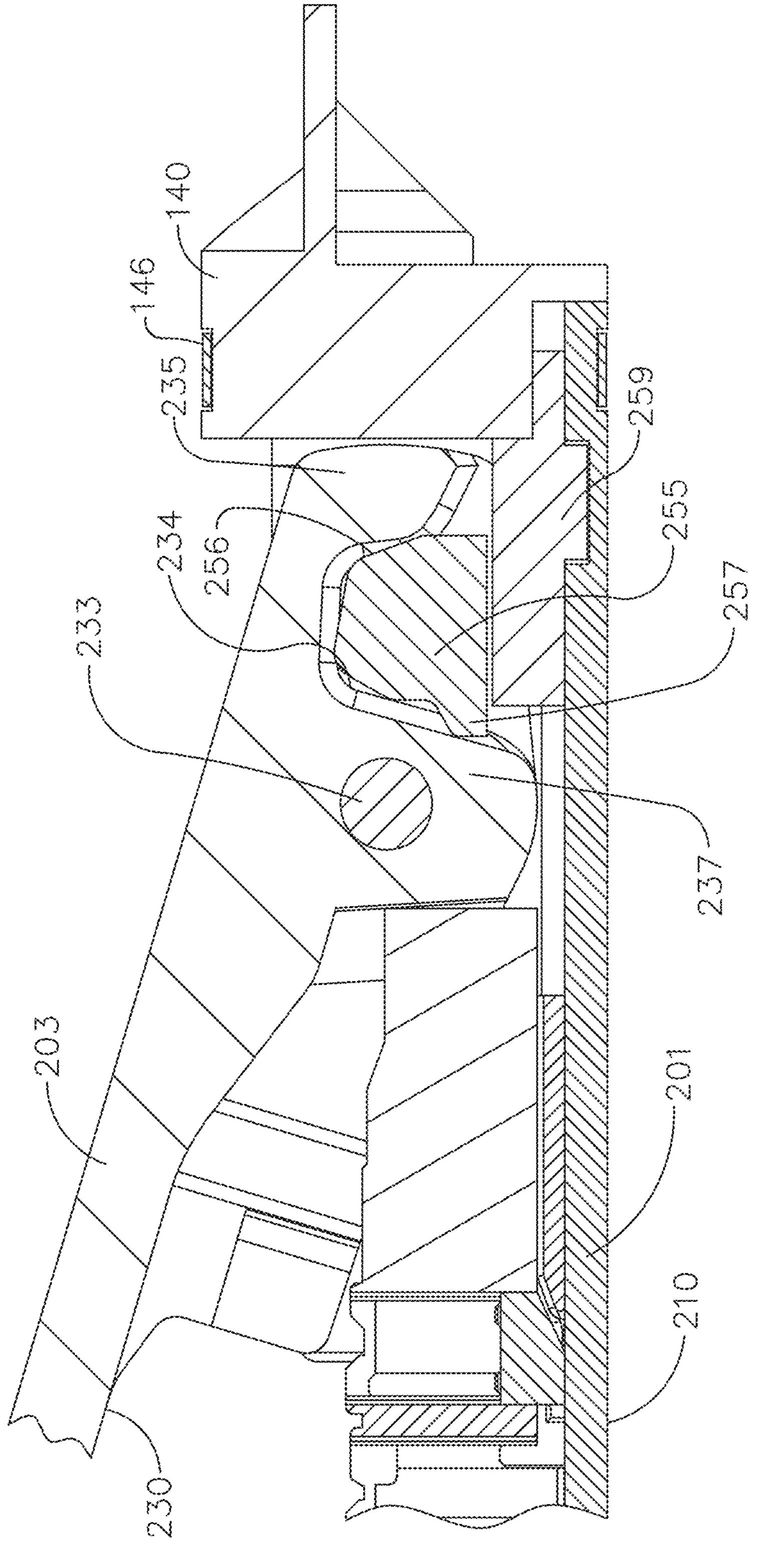
FIG. 7 is a cross-sectional elevation view of the end effector and a portion of the shaft assembly of FIG. 1 taken along section line 6-6 in FIG. 6, wherein the end effector is illustrated in an open configuration, in accordance with at least one aspect of the present disclosure.

Referring now primarily to FIG. 4, articulation of the end effector 200 will now be described. The articulation region 110 comprises two distinct articulation joints and two articulation actuators 150, 160. This allows the end effector 200 to be articulated in two different planes about two different axes AA1, AA2 independently of each other. The articulation region 110 comprises a proximal joint shaft component 120, an intermediate joint shaft component 130, and a distal joint shaft component 140. The proximal joint shaft component 120 is attached to a distal end of the shaft assembly 100, the intermediate joint shaft component 130 is pivotally connected to the proximal joint shaft component 120 and the distal joint shaft component 140, and the distal joint shaft component 140 is fixedly attached to the end effector 200 by way of a retention ring 146. Discussed in greater detail below, this arrangement provides articulation of the end effector 200 relative to the shaft assembly 100 about axis AA1 and axis AA2 independently of each other.

The proximal joint shaft component 120 comprises a proximal annular portion 121 fixedly fitted within the outer shaft 101. The proximal joint shaft component 120 also includes a hollow passage 122 to allow various drive system components to pass therethrough, and further includes an articulation tab 123 comprising a pin hole 124 configured to receive articulation pin 125. The articulation pin 125 pivotally connects the proximal joint shaft component 120 to a proximal articulation tab 131 of the intermediate joint shaft component 130. To articulate the end effector 200 about axis AA1, the articulation actuator 150 is actuated linearly either in a distal direction or a proximal direction. Such an actuator may comprise a bar or rod made of any suitable material such as metal and/or plastic, for example. The articulation actuator 150 is pivotally mounted to an articulation crosslink 151. The articulation crosslink 151 is pivotally mounted to the intermediate joint shaft component 130 off-axis relative to the articulation pin 125 so that when the articulation actuator 150 is actuated, a torque is applied to the intermediate joint shaft component 130 off-axis relative to the articulation pin 125 by the articulation crosslink 151 to cause the intermediate joint shaft component 130 and, thus, the end effector 200, to pivot about axis AA1 relative to the proximal joint shaft component 120.

The intermediate joint shaft component 130 is pivotally connected to the proximal joint shaft component 120 by way of the articulation pin 125 which defines axis AA1. Specifically, the intermediate joint shaft component 130 comprises a proximal articulation tab 131 that is pivotally connected to the proximal joint shaft component 120 by way of the articulation pin 125. The intermediate joint shaft component 130 further comprises a hollow passage 132 configured to allow various drive system components to pass therethrough and a distal articulation tab 133. The distal articulation tab 133 comprises a pin hole 134 configured to receive another articulation pin 136, which defines axis AA2, and a distally-protruding key 135.

To articulate the end effector 200 about axis AA2, the articulation cable 160 is actuated to apply an articulation torque to a proximal tab 141 of the distal joint shaft component 140 by way of the key 135. The articulation cable 160 is fixed to the key 135 such that, as the cable 160 is rotated, the key 135 is pivoted relative to the intermediate joint shaft component 130. The key 135 is fitted within a key hole 144 of the distal joint shaft component 140. Notably, the key 135 is not fixed to the intermediate joint shaft component 130 and the key 135 can be rotated relative to the intermediate joint shaft component 130. The articulation cable 160 also contacts the proximal tab 141 around the pin hole 142. This provides an additional torque moment from the articulation cable 160 to the distal joint shaft component 140. The articulation pin 136 is received within the pin hole 142 to pivotally couple the intermediate joint shaft component 130 and the distal joint shaft component 140.

In at least one instance, the articulation cable 160 is only able to be pulled in a proximal direction. In such an instance, only one side of the articulation cable 160 would be pulled proximally to articulate the end effector 200 in the desired direction. In at least one instance, the articulation cable 160 is pushed and pulled antagonistically. In other words, the cable 160 can comprise a rigid construction such that one side of the articulation cable 160 is pushed distally while the other side of the articulation cable 160 is pulled proximally. Such an arrangement can allow the articulation forces to be divided between the pushed half of the cable 160 and the pulled half of the cable 160. In at least one instance, the push-pull arrangement allows greater articulation forces to be transmitted to the corresponding articulation joint. Such forces may be necessary in an arrangement with two articulation joints. For example, if the proximal articulation joint is fully articulated, more force may be required of the articulation actuator meant to articulate the distal articulation joint owing to the stretching and/or lengthened distance that the articulation actuator for the distal articulation joint must travel.

The distal joint shaft component 140 further comprises a cutout 143 to allow various drive components to pass therethrough. The retention ring 146 secures a channel 210 of the cartridge jaw 201 to the distal joint shaft component 140 thereby fixing the end effector assembly 200 to a distal end of the articulation region 110.

As discussed above, the anvil jaw 201 is movable relative to the cartridge jaw 203 to clamp and unclamp tissue with the end effector 200. Operation of this function of the end effector 200 will now be described. The cartridge jaw 201 comprises the channel 210 and a staple cartridge 220 configured to be received within a cavity 214 of the channel 210. The channel 210 further comprises an annular groove 211 configured to receive the retention ring 146 and a pair of pivot holes 213 configured to receive a jaw-coupling pin 233. The jaw coupling pin 233 permits the anvil jaw 203 to be pivoted relative to the cartridge jaw 201.

The anvil jaw 203 comprises an anvil body 230 and a pair of pivot holes 231. The pivot holes 231 in the proximal portion of the anvil jaw 203 are configured to receive the jaw-coupling pin 233 thereby pivotally coupling the anvil jaw 203 to the cartridge jaw 201. To open and close the anvil jaw 203 relative to the cartridge jaw 201, a closure drive 250 is provided.

The closure drive 250 is actuated by a flexible drive segment 175 comprised of universally-movable joints arranged or formed end-to-end. In various instances, the flexible drive segment 175 can includes serial 3D-printed universal joints, which are printed all together as a single continuous system. Discussed in greater detail below, the flexible drive segment 175 is driven by an input shaft traversing through the shaft assembly 100. The flexible drive segment 175 transmits rotary actuation motions through the dual articulation joints. The closure drive 250 comprises a closure screw 251 and a closure wedge 255 threadably coupled to the closure screw 251. The closure wedge 255 is configured to positively cam the anvil jaw 203 open and closed. The closure screw 251 is supported by a first support body 258 and a second support body 259 secured within the channel 210.

To move the anvil jaw 203 between a clamped position (FIG. 8) and an unclamped position (FIG. 7), a closure drive shaft is actuated to actuate the flexible drive segment 175. The flexible drive segment 175 is configured to rotate the closure screw 251, which displaces the closure wedge 255. For example, the closure wedge 255 is threadably coupled to the closure screw 251 and rotational travel of the closure wedge 255 with the staple cartridge 220 is restrained. The closure screw 251 drives the closure wedge 255 proximally or distally depending on which direction the closure screw 251 is rotated.

To clamp the end effector 200 from an unclamped position (FIG. 7), the closure wedge 255 is moved proximally. As the closure wedge 255 is moved proximally, a proximal cam surface 256 of the closure wedge 255 contacts a corresponding cam surface 234 defined in a proximal end 235 of the anvil body 230. As the cam surface 256 contacts the cam surface 234, a force is applied to the proximal end 235 of the anvil body 230 causing the anvil body 230 to rotate into the clamped position (FIG. 8) about the pin 233.

To open or unclamp the end effector 200 from a clamped position (FIG. 8), the closure wedge 255 is moved distally by rotating the closure screw 251 in a direction opposite to the direction that causes the closure wedge 255 to move proximally. As the closure wedge 255 is moved distally, a pair of nubs 257 extending from a distal end of the closure wedge 255 contact the cam surface 234 near a downwardly extending tab 237 of the anvil body 230. As the nubs 257 contact the cam surface 234 near the tab 237, a force is applied to the anvil body 230 to rotate the anvil body 230 into the open position (FIG. 7) about the pin 233.

Figure 8:
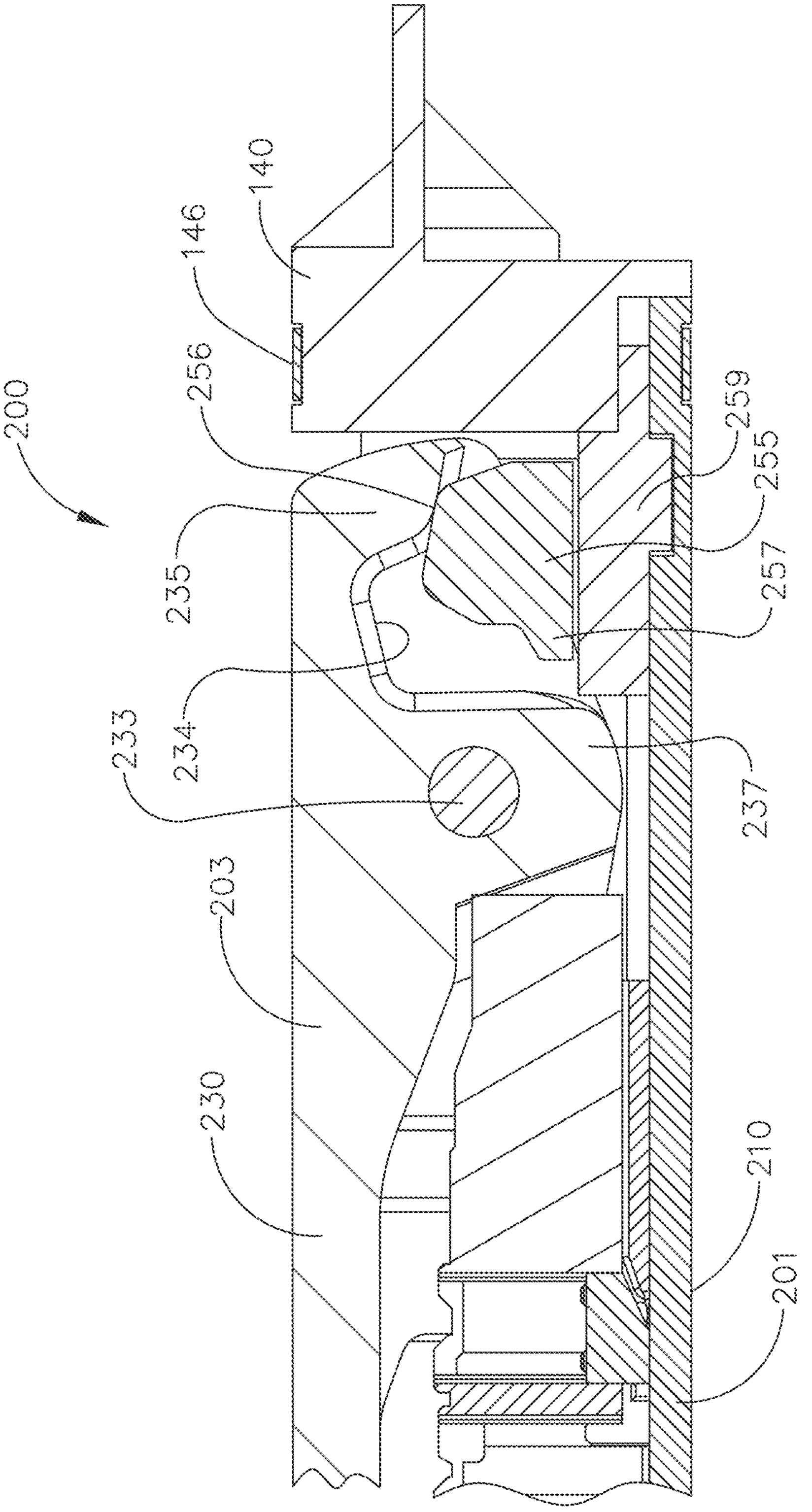
FIG. 8 is a cross-sectional elevation view of the end effector and a portion of the shaft assembly of FIG. 1 taken along section line 7-7 in FIG. 6, wherein the end effector is illustrated in a clamped configuration, in accordance with at least one aspect of the present disclosure.

In at least one instance, the profile of the cam surface 234 corresponds to the profile of the cam surface 256. For example, the cam surface 234 and the cam surface 256 may match such that a maximum cam force is applied to the anvil body 230 to cause the desired rotation of the anvil body 230. As can be seen in FIG. 8, for example, the cam surface 234 defined by the proximal end 235 of the anvil body 230 comprises a ramped section similar to that of the upper ramped section of the cam surface 256.

As discussed above, the surgical stapling instrument 10 may be actuated to advance a firing member through the jaws 201, 203 to staple and cut tissue with the end effector 200. The function of deploying staples 226 from the staple cartridge 220 and cutting tissue with knife 283 will now be described. The staple cartridge 220 comprises a cartridge body 221, a plurality of staple drivers 225, and a plurality of staples 226 removably stored within the cartridge body 221. The cartridge body 221 comprises a deck surface 222, a plurality of staple cavities 223 arranged in longitudinal rows defined in the cartridge body 221, and a longitudinal slot 224 bifurcating the cartridge body 221. The knife 283 is configured to be driven through the longitudinal slot 224 to cut tissue clamped between the anvil body 230 and the deck surface 221.

The deck surface 221 comprises a laterally-contoured tissue-supporting surface. In various aspects, the contour of the deck surface 221 can form a peak along a central portion of the cartridge body 221. Such a peak can overlay a longitudinally-extending firing screw 261 that extends through the central portion of the cartridge body 221, which is further described herein. The increased height along the peak can be associated with a smaller tissue gap along a firing path of the knife 283 in various instances. In certain aspects of the present disclosure, driver heights, formed staple heights, staple pocket extension heights, and/or staple overdrive distances can also vary laterally along the deck surface 221. Laterally-variable staple formation (e.g. a combination of 2D staples and 3D staples) is also contemplated and further described herein.

The staple drivers 225 are configured to be lifted by a sled 280 as the sled 280 is pushed distally through the staple cartridge 220 to eject the staples 226 supported by the staple drivers 225 in the staple cavities 223. The sled 280 comprises ramps 281 to contact the staple drivers 225. The sled 280 also includes the knife 283. The sled 280 is configured to be pushed by a firing member 270.

To deploy the staples 226 and cut tissue with the knife 283, the end effector 200 comprises a firing drive 260. The firing drive 260 is actuated by a flexible drive shaft 176. Discussed in greater detail below, the flexible drive shaft 176 is driven by an input shaft traversing through the shaft assembly 100. The flexible drive shaft 176 transmits rotary actuation motions through the dual articulation joints. The firing drive 260 comprises a firing screw 261 configured to be rotated by the flexible drive shaft 176. The firing screw 261 comprises journals supported within bearings in the support member 259 and the channel 210. In various instances, the firing screw 261 can float relative to the channel 210, as further described herein. The firing screw 261 comprises a proximal end 262 supported within the support member 259 and the channel 210, a distal end 263 supported within the channel 210, and threads 265 extending along a portion of the length of the firing screw 261.

The firing member 270 is threadably coupled to the firing screw 261 such that as the firing screw 261 is rotated, the firing member 270 is advanced distally or retracted proximally along the firing screw 261. Specifically, the firing member 270 comprises a body portion 271 comprising a hollow passage 272 defined therein. The firing screw 261 is configured to be received within the hollow passage 272 and is configured to be threadably coupled with a threaded component 273 of the firing member 270. Thus, as the firing screw 261 is rotated, the threaded component 273 applies a linear force to the body portion 271 to advance the firing member 270 distally or retract the firing member 270 proximally. As the firing member 270 is advanced distally, the firing member 270 pushes the sled 280. Distal movement of the sled 280 causes the ejection of the staples 223 by engaging the plurality of staple drivers 225, as further described herein. The driver 225 is a triple driver, which is configured to simultaneously fire multiple staples 223. The driver 225 can comprise lateral asymmetries, as further described herein, to maximum the width of the sled rails and accommodate the firing screw 261 down the center of the cartridge 220 in various instances.

At a point during firing of the end effector 200, a user may retract the firing member 270 to allow unclamping of the jaws 201, 203. In at least one instance, the full retraction of the firing member 270 is required to open the jaws 201, 203 where upper and lower camming members are provided on the body portion 271 which can only be disengaged from the jaws 201, 203 once the firing member 270 is fully retracted.

In various instances, the firing member 270 can be a hybrid construction of plastic and metal portions as further described herein. In various instances, the threaded component 273 can be a metal component, for example, which is incorporated into the firing member body 271 with insert molding or over molding.

The firing member 270 can also be referred to an I-beam in certain instances. The firing member 270 can include a complex 3D-printed geometry comprising a lattice pattern of spaces therein. In various instances, 3D printing can allow the firing member or a portion thereof to act as a spring and allows a portion to more readily flex, which can improve the force distribution and/or tolerances during a firing stroke, for example.

Figure 9:
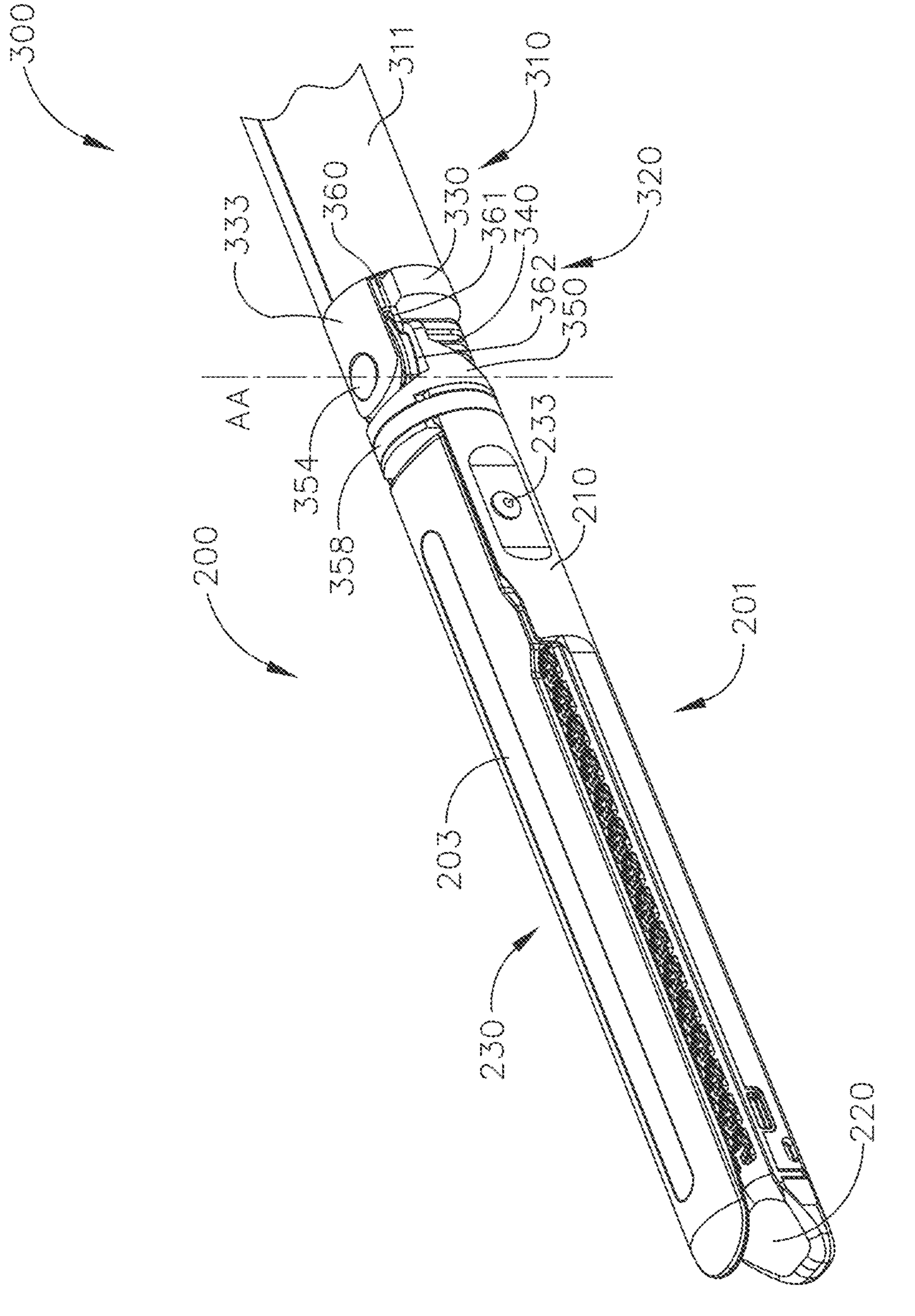
FIG. 9 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 10:
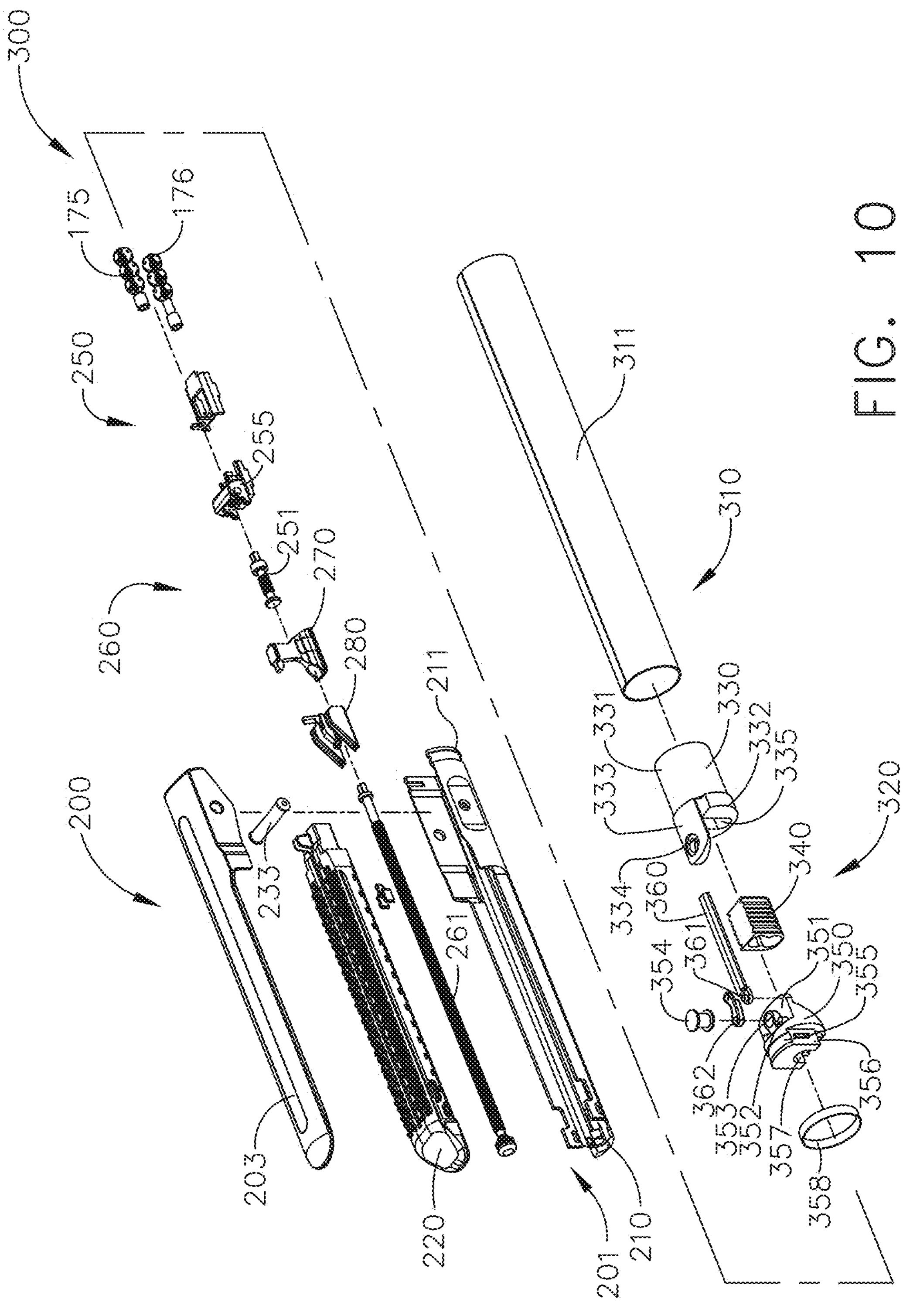
FIG. 10 is an exploded perspective view of the surgical stapling assembly of FIG. 9, in accordance with at least one aspect of the present disclosure.
Figure 11:
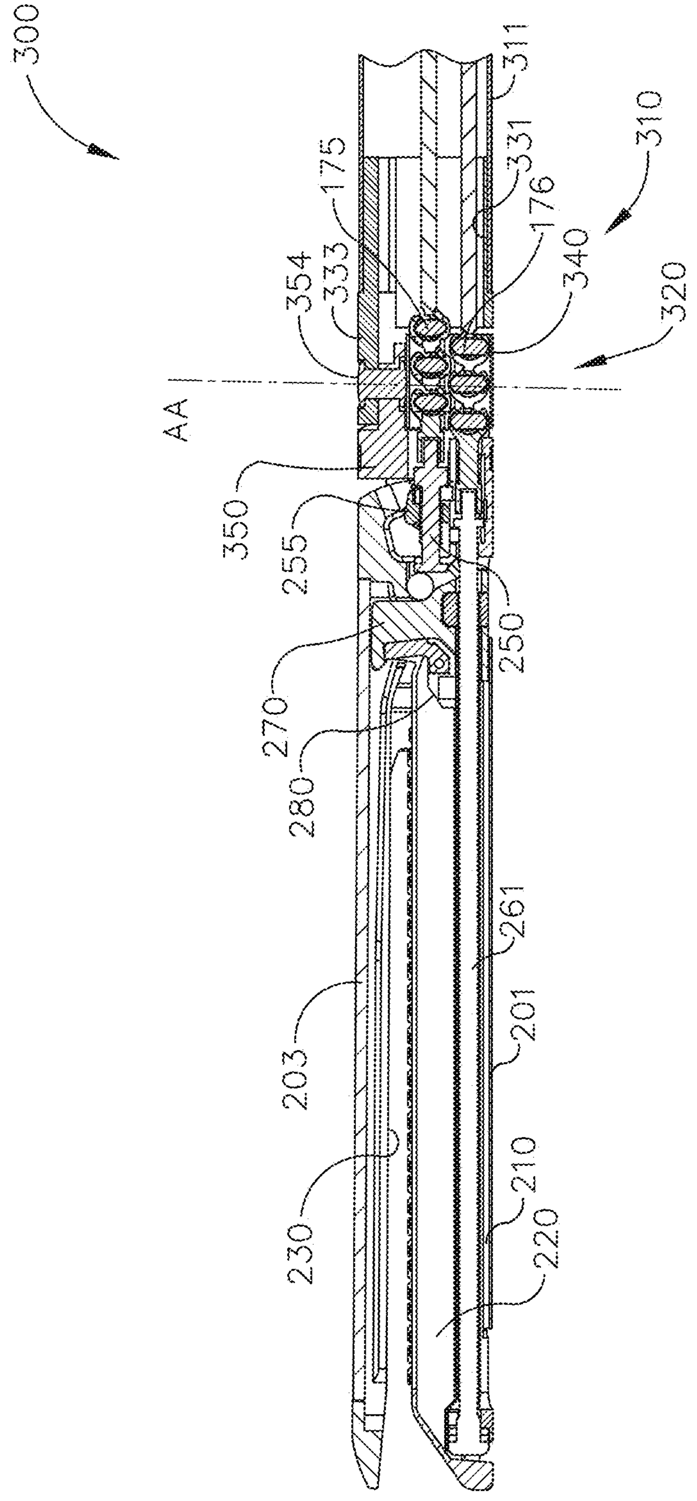
FIG. 11 is a cross-sectional elevation view of the surgical stapling assembly of FIG. 9, wherein the end effector is illustrated in an unfired, clamped configuration, in accordance with at least one aspect of the present disclosure.

FIGS. 9-11 depict a surgical stapling assembly 300 comprising a shaft assembly 310 and the end effector 200 of FIGS. 1-8 attached to the shaft assembly 310. The shaft assembly 310 may be similar in many respects to various other shaft assemblies discussed herein; however, the shaft assembly 310 comprises a single articulation joint and an articulation bar configured to articulate the end effector 200 about the single articulation joint. The surgical stapling assembly 300 is configured to cut and staple tissue. The surgical stapling assembly 300 may be attached to a surgical instrument handle and/or surgical robotic interface. The surgical instrument handle and/or surgical robotic interface can be configured to actuate various functions of the surgical stapling assembly 300. The shaft assembly 310 comprises an articulation joint 320. Discussed in greater detail below, the end effector 200 is configured to be articulated relative to an outer shaft 311 of the shaft assembly 310 about axis AA.

The shaft assembly 310 comprises the outer shaft 311, a first shaft joint component 330, and a second shaft joint component 350 pivotally coupled to the first shaft joint component 330 by way of an articulation pin 354. The first shaft joint component 330 comprises a proximal tube portion 331 configured to fit within the inner diameter of the outer shaft 311. Such a fit may comprise a press fit, for example. However, any suitable attachment means can be used. The first shaft joint component 330 also includes a distal portion 332. The distal portion 332 comprises an articulation tab 333 comprising a pin hole 334 defined therein and a hollow passage 335 through which various drive components of the surgical stapling assembly 300 can pass. Such drive components can include articulation actuators, closure actuators, and/or firing actuators for example.

The first shaft joint component 330 is pivotally connected to the second shaft joint component 350 by way of the articulation pin 354. The articulation pin 354 is also received within a pin hole 353 of a proximally-extending articulation tab 351 of the second shaft joint component 350. The pin hole 353 is axially aligned with the pin hole 334. The articulation pin 354 allows the second shaft joint component 350 to be articulated relative to the first shaft joint component 330 about the articulation axis AA. The second shaft joint component 350 further comprises a pin protrusion 352 extending from the proximal-extending articulation tab 351. Discussed in greater detail below, the pin protrusion 352 is configured to be pivotally coupled to an articulation drive system. The second shaft joint component 350 further comprises a distal portion 355 comprising an annular groove 356 configured to receive a retention ring 358. The distal portion 355 also includes a hollow passage 357 through which various drive components of the surgical stapling assembly 300 can pass. The retention ring 358 is configured to hold the first jaw 201 to the second shaft joint component 350 by fitting within the annular groove 211 of the cartridge channel 210 and the annular groove 356 of the second shaft joint component 350.

To articulate the end effector 200 about the articulation axis AA, an articulation bar 360 is provided. The articulation bar 360 may be actuated by any suitable means such as, for example, by a robotic or motorized input and/or a manual handle trigger. The articulation bar 360 may be actuated in a proximal direction and a distal direction, for example. Embodiments are envisioned where the articulation system comprises rotary driven actuation in addition to or, in lieu of, linear actuation. The articulation bar 360 extends through the outer shaft 311. The articulation bar 360 comprises a distal end 361 pivotally coupled to an articulation link 362. The articulation link 362 is pivotally coupled to the pin protrusion 352 extending from the proximally-extending articulation tab 351 off center with respect to the articulation axis AA. Such off-center coupling of the articulation link 362 allows the articulation bar 360 to apply a force to the second joint shaft component 350 to rotate the second shaft joint component 350 and, thus, the end effector 200, relative to the first joint shaft component 330. The articulation bar 360 can be advanced distally to rotate the end effector 200 in a first direction about the articulation axis AA and retracted proximally to rotate the end effector 200 in a second direction opposite the first direction about the articulation axis AA.

The shaft assembly 310 further comprises an articulation component support structure 340 positioned within the articulation joint 320. Such a support structure can provide support to various drive components configured to pass through the articulation joint 320 to the end effector 200 as the end effector 200 is articulated. The support structure 340 may also serve to isolate the drive components from tissue remnants during use.

Figure 12:
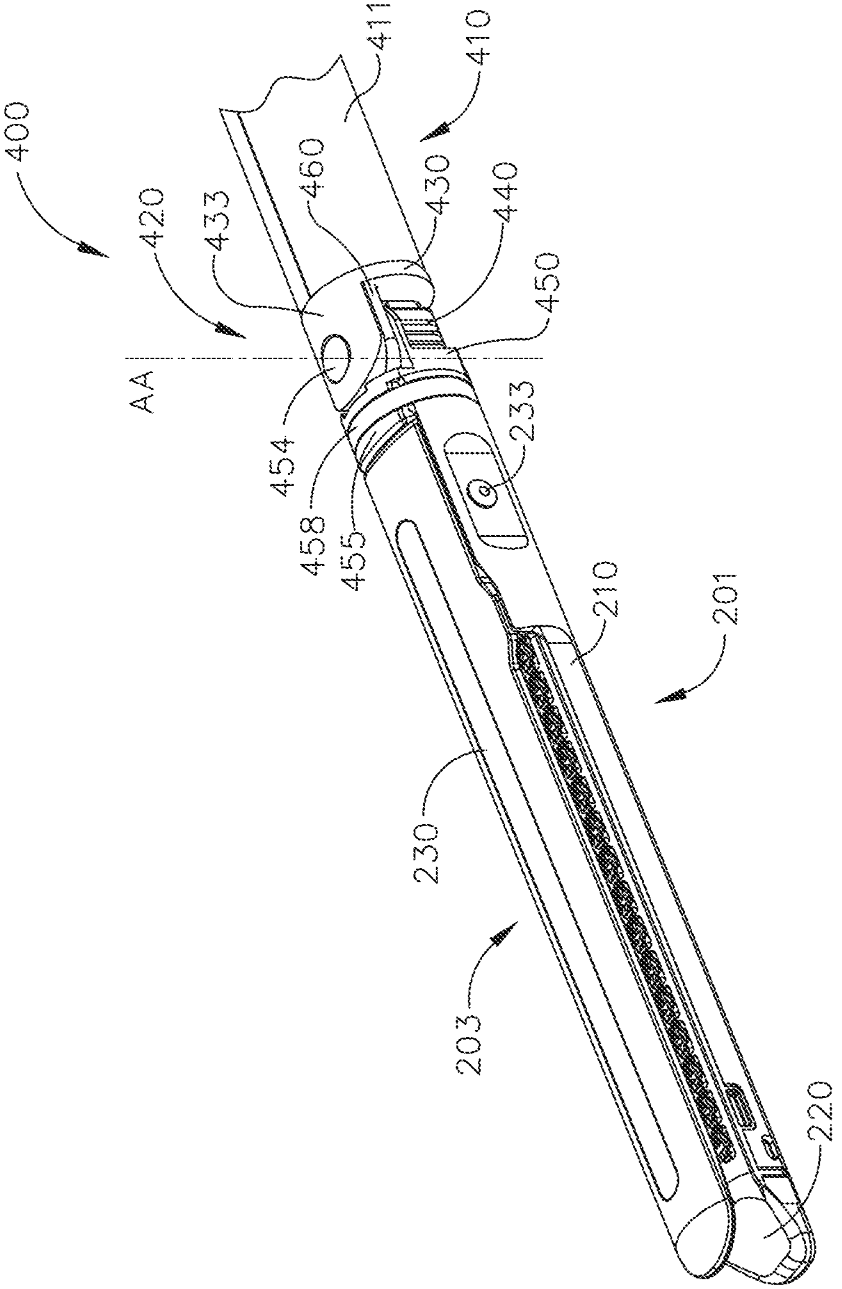
FIG. 12 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 13:
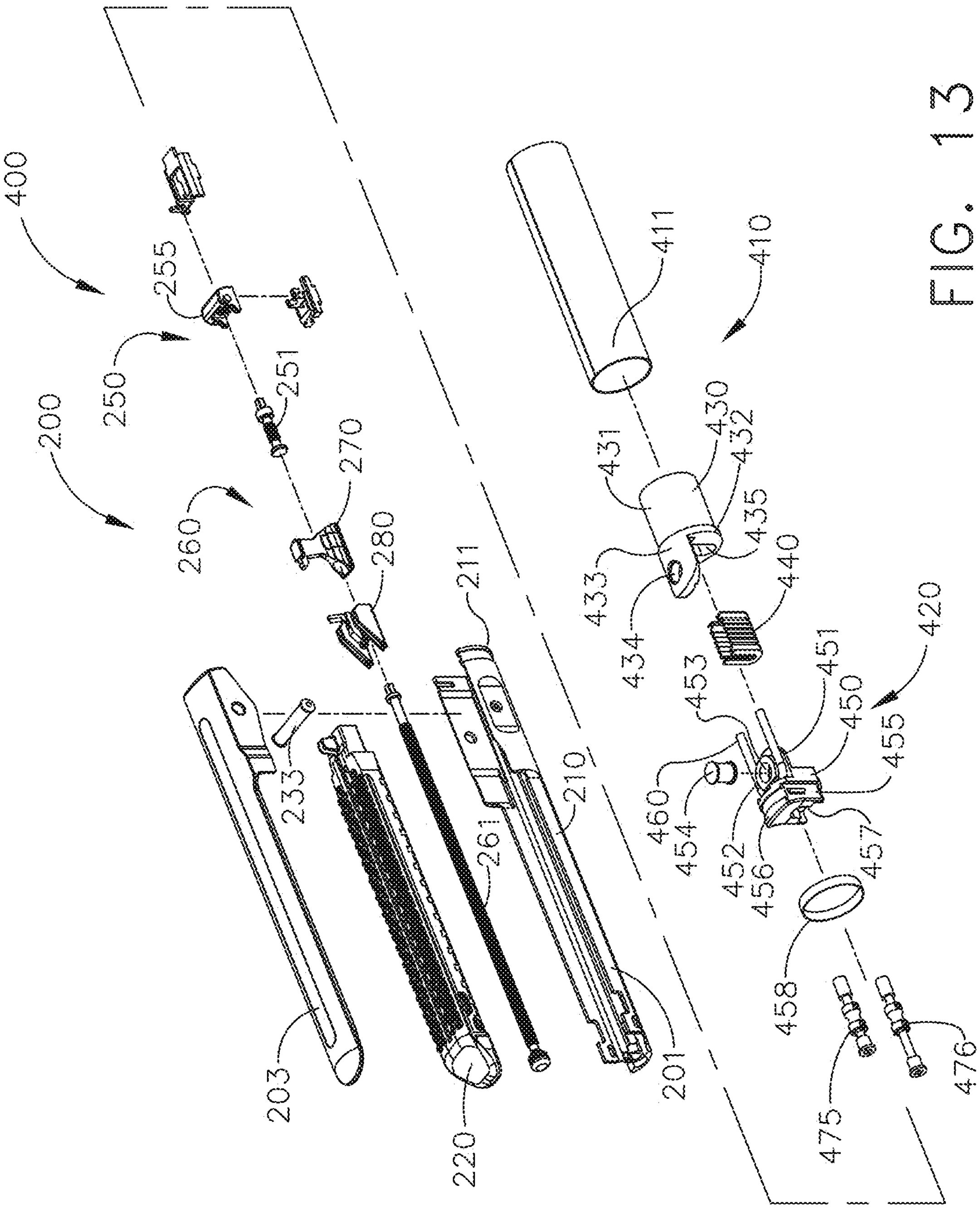
FIG. 13 is an exploded perspective view of the surgical stapling assembly of FIG. 12, in accordance with at least one aspect of the present disclosure.
Figure 14:
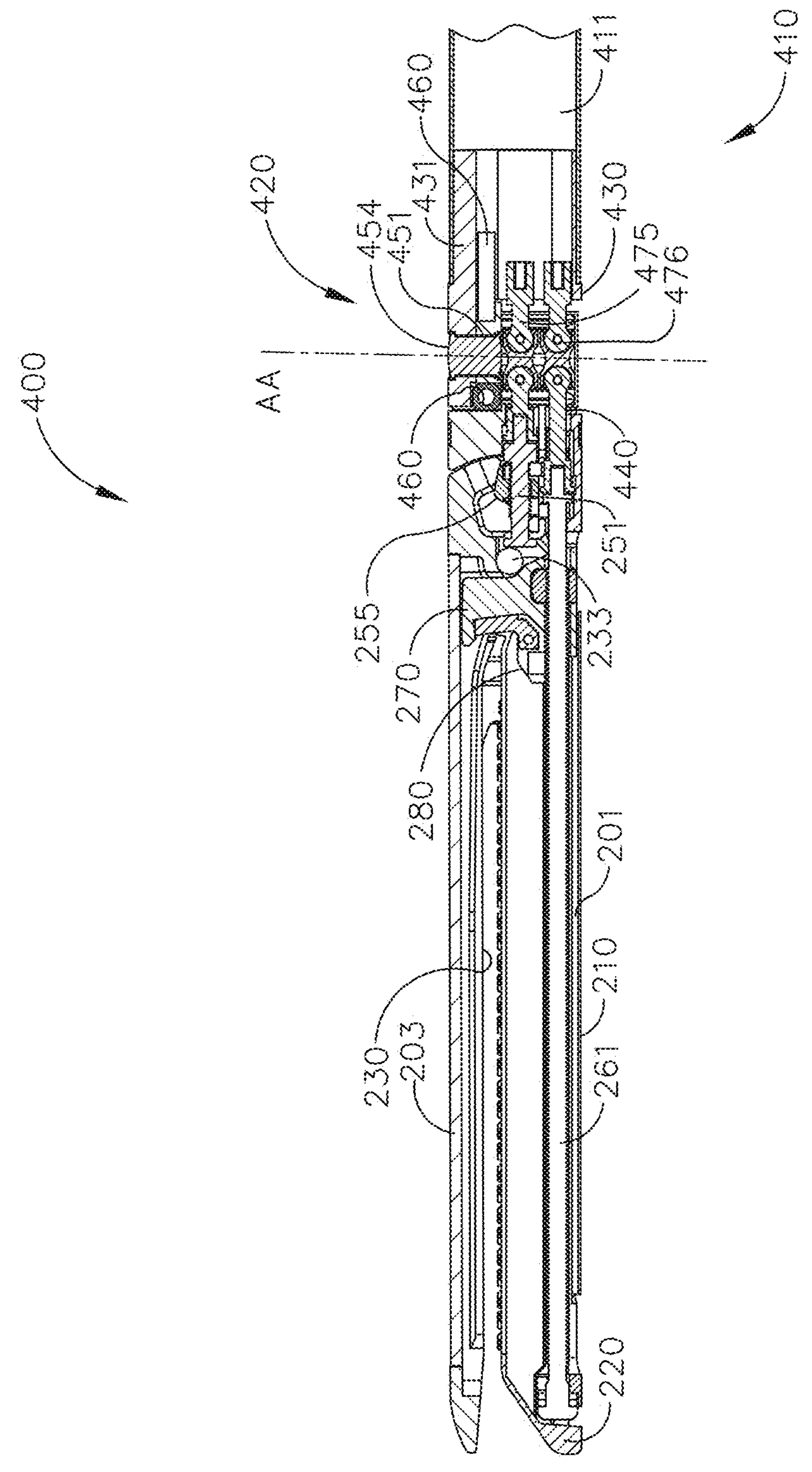
FIG. 14 is a cross-sectional elevation view of the surgical stapling assembly of FIG. 12, wherein the end effector is illustrated in an unfired, clamped configuration, in accordance with at least one aspect of the present disclosure.

FIGS. 12-14 depict a surgical stapling assembly 400 comprising a shaft assembly 410 and the end effector 200 of FIGS. 1-8 attached to the shaft assembly 410. The shaft assembly 410 may be similar in many respects to various other shaft assemblies discussed herein; however, the shaft assembly 410 comprises a single articulation joint and an articulation cable configured to articulate the end effector 200 about the single articulation joint. The surgical stapling assembly 400 is configured to cut and staple tissue. The surgical stapling assembly 400 may be attached to a surgical instrument handle and/or surgical robotic interface. The surgical instrument handle and/or surgical robotic interface can be configured to actuate various functions of the surgical stapling assembly 400. The shaft assembly 410 comprises an articulation joint 420. Discussed in greater detail below, the end effector 200 is configured to be articulated relative to an outer shaft 411 of the shaft assembly 310 about an axis AA.

The shaft assembly 410 comprises the outer shaft 411, a first shaft joint component 430, and a second shaft joint component 450 pivotally coupled to the first shaft joint component 430 by way of an articulation pin 454. The first shaft joint component 430 comprises a proximal tube portion 431 configured to fit within the inner diameter of the outer shaft 411. Such a fit may comprise a press fit, for example. However, any suitable attachment means can be used. The first shaft joint component 430 also includes a distal portion 432, which comprises an articulation tab 433 comprising a pin hole 434 defined therein. The distal portion 432 further defines a hollow passage 435 through which various drive components of the surgical stapling assembly 400 can pass. Such drive components can include articulation actuators, closure actuators, and/or firing actuators, for example.

The first shaft joint component 430 is pivotally connected to the second shaft joint component 450 by way of the articulation pin 454. The articulation pin 454 is also received within a pin hole 453 of a proximally-extending articulation tab 451 of the second shaft joint component 450. The articulation pin 454 allows the second shaft joint component 450 to be articulated relative to the first shaft joint component 430 about the articulation axis AA. The second shaft joint component 450 further comprises a drive ring structure 452. The drive ring structure 452 extends from the proximally-extending articulation tab 451 and further defines a portion of the pin hole 453. Discussed in greater detail below, the drive ring structure 452 is configured to be engaged by an articulation drive system. The second shaft joint component 450 further comprises a distal portion 455 comprising an annular groove 456 configured to receive a retention ring 458. A hollow passage 457 through the distal portion 455 is configured to receive various drive components of the surgical stapling assembly 400 therethrough. The retention ring 458 is configured to hold the first jaw 201 to the second shaft joint component 450 by fitting within the annular groove 211 of the cartridge channel 210 and the annular groove 456 of the second shaft joint component 450.

To articulate the end effector 200 about the articulation axis AA, an articulation cable 460 is provided. The articulation cable 460 may be actuated by any suitable means such as, for example, by a robotic input and/or a manual trigger on a handle of a handheld surgical instrument. The articulation cable 460 may comprise an antagonistic actuation profile. In other words, as a first side of the articulation cable 460 is pulled proximally a second side of the articulation cable 460 is allowed to advance distally like a pulley system. Similarly, as the second side is pulled proximally, the first side is allowed to advance distally. The articulation cable 460 extends through the outer shaft 411. The articulation cable 460 is positioned around the drive ring structure 452 and frictionally retained thereon to permit rotation of the second shaft joint component 450 as the articulation cable 460 is actuated. As the articulation cable 460 is actuated, the articulation cable 460 is configured to apply a rotational torque to the drive ring structure 452 of the second joint shaft component 450 and, thus, the end effector 200. Such torque is configured to cause the second joint shaft component 450 to rotate, or pivot, relative to the first joint shaft component 430 thereby articulating the end effector 200 relative to the outer shaft 411. A first side of the articulation cable 460 can pulled to rotate the end effector 200 in a first direction about the articulation axis AA and a second side of the articulation cable 460 can be pulled to rotate the end effector 200 in a second direction opposite the first direction about the articulation axis AA.

The shaft assembly 410 further comprises an articulation component support structure 440 positioned within the articulation joint 420. Such a support structure 440 can provide support to various drive components configured to pass through the articulation joint 420 to the end effector 200 as the end effector 200 is articulated. The support structure 440 may also serve to isolate the drive components from tissue remnants during use.

The surgical stapling assembly 400 further comprises a closure drive shaft segment 475 and a firing drive shaft segment 476 each configured to transmit rotary motion through the articulation joint 420 to the end effector 200. The drive shaft segments 475, 476 are configured to passively expand and contract longitudinally as the end effector 200 is articulated. For example, articulation can cause expansion and contraction of the drive shaft segments 475, 476 to account for the respective longitudinal stretching of or contracting of the length of the drive shafts owing to articulation of the end effector 200 relative to the shaft assembly 410. During expansion and contraction of the drive shaft segments 475, 476, the drive shaft segments 475, 476 maintain rotary driving engagement with corresponding input shafts extending through the outer shaft 411 and output shafts in the end effector 200. In at least one instance, the output shafts comprise the closure screw 251, which is configured to effect grasping, closing, or tissue manipulation with the jaws 201, 203, and the firing screw 261, which is configured to effect clamping of the jaws 201, 203 and firing of the firing member 270.

Figure 15:
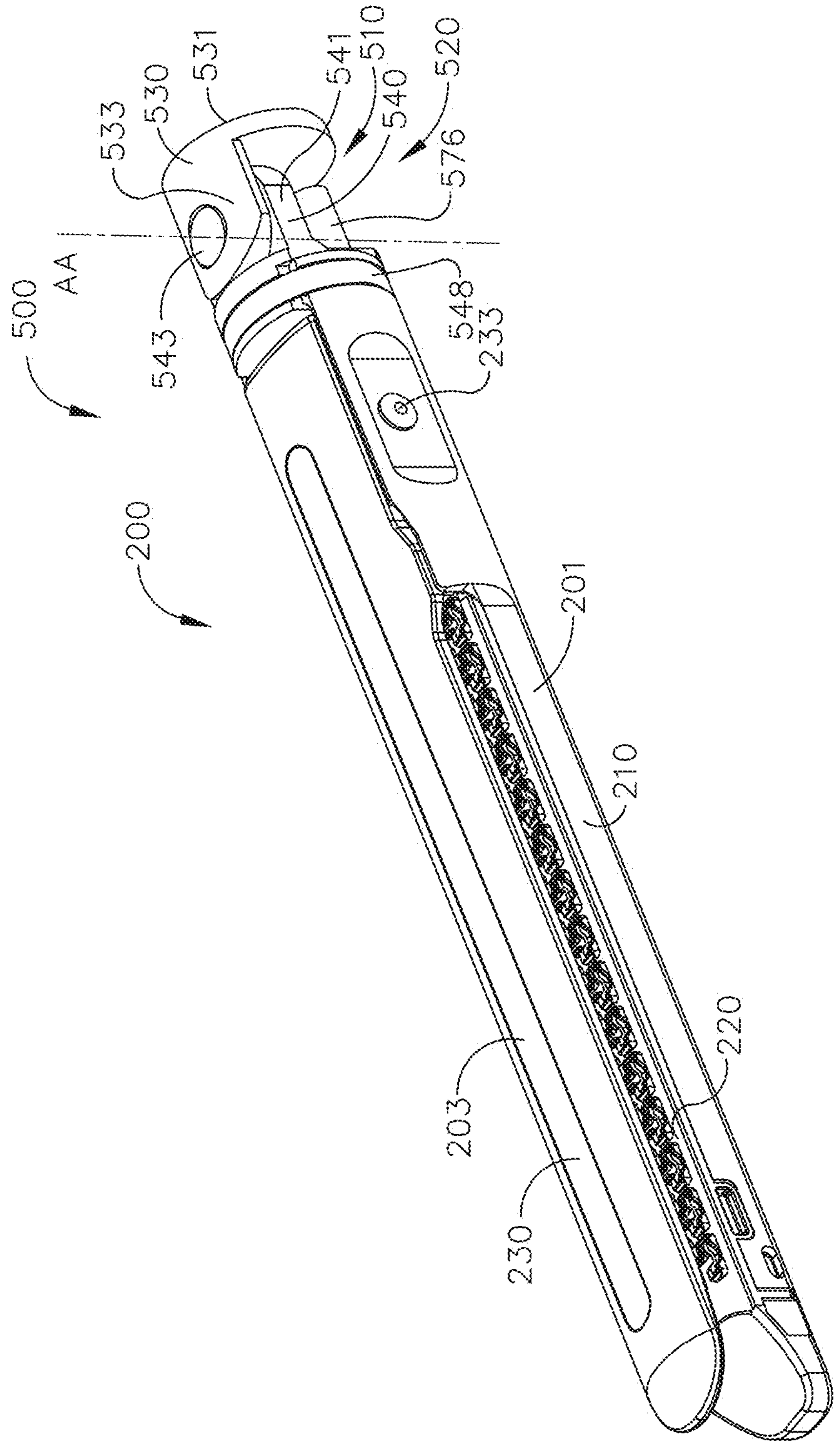
FIG. 15 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 16:
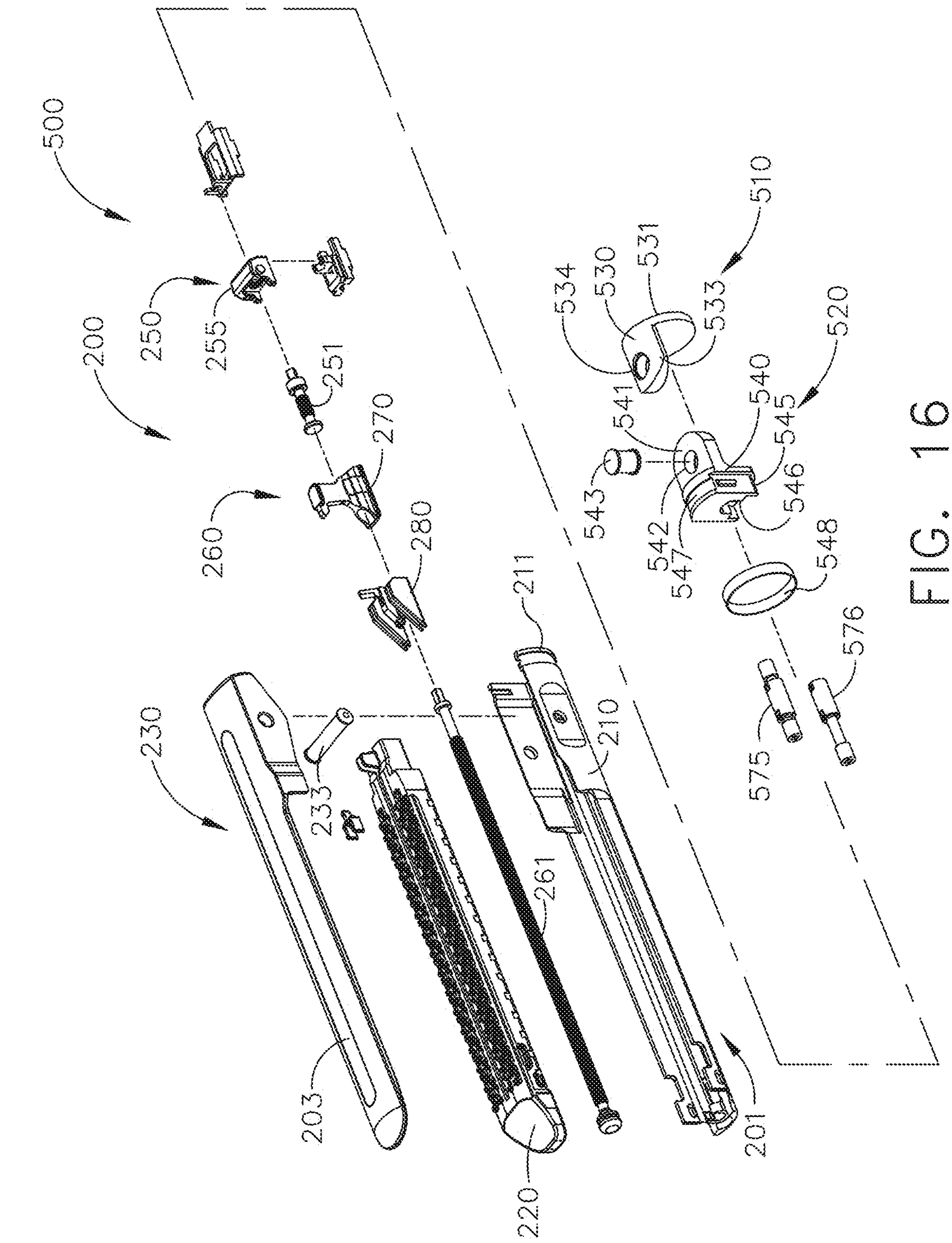
FIG. 16 is an exploded perspective view of the surgical stapling assembly of FIG. 15, in accordance with at least one aspect of the present disclosure.
Figure 17:
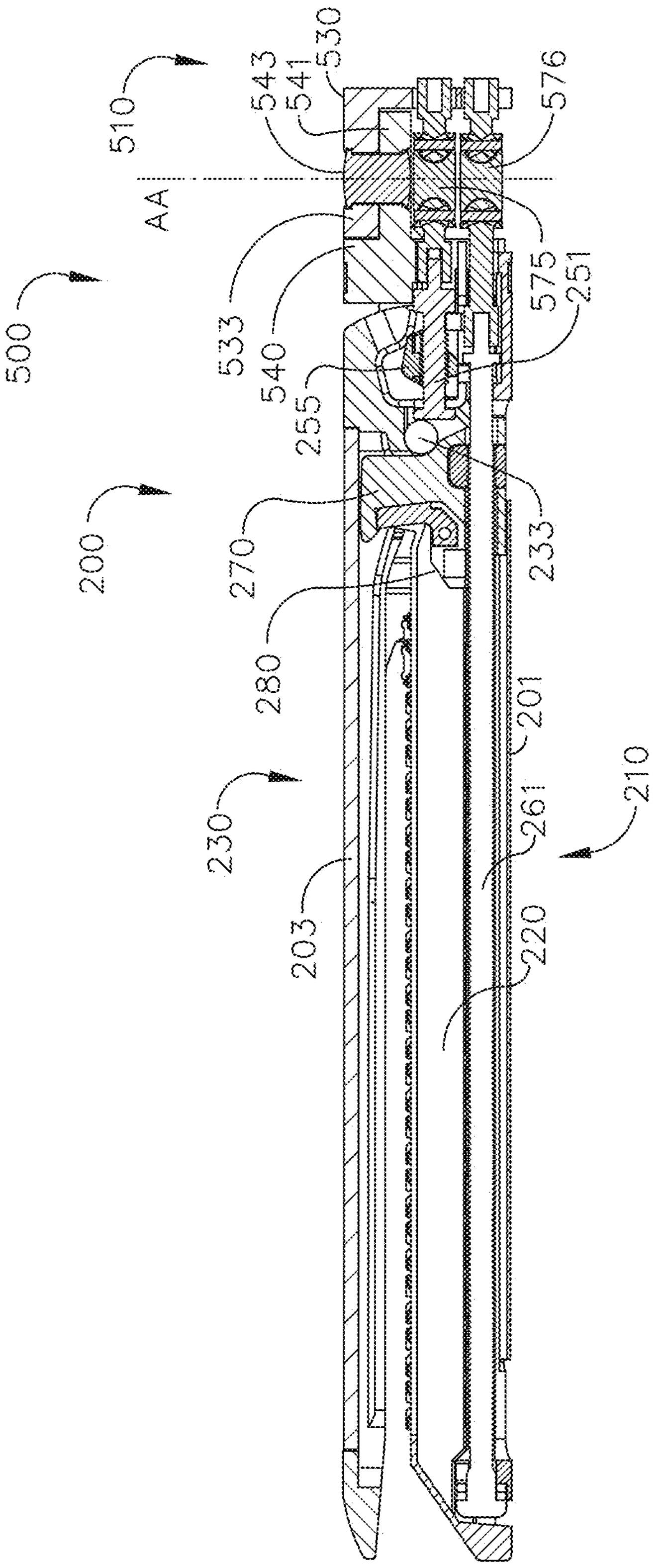
FIG. 17 is a cross-sectional elevation view of the surgical stapling assembly of FIG. 15, wherein the end effector is illustrated in an unfired, clamped configuration, in accordance with at least one aspect of the present disclosure.

FIGS. 15-17 depict a surgical stapling assembly 500 comprising a shaft assembly 510 and the end effector 200 of FIGS. 1-8 attached to the shaft assembly 510. The shaft assembly 510 may be similar in many respects to various other shaft assemblies discussed herein; however, the shaft assembly 510 comprises a single articulation joint and drive shaft segments configured to passively expand and contract. The surgical stapling assembly 500 is configured to cut and staple tissue. The surgical stapling assembly 500 may be attached to a surgical instrument handle and/or surgical robotic interface. The surgical instrument handle and/or surgical robotic interface can be configured to actuate various functions of the surgical stapling assembly 500. The shaft assembly 510 comprises an articulation joint 520. Discussed in greater detail below, the end effector 200 is configured to be articulated about an axis AA.

The shaft assembly 510 comprises a first shaft joint component 530 and a second shaft joint component 540 pivotally coupled to the first shaft joint component 530 by way of an articulation pin 543. The first shaft joint component 530 is configured to be attached to a shaft of a surgical instrument assembly and/or a surgical robotic interface. The first shaft joint component 530 comprises a proximal portion 531 and an articulation tab 533 comprising a pin hole 534 defined therein. In at least one instance, the first shaft joint component 530 comprises a hollow passage through which various drive components of the surgical stapling assembly 400 can pass. Such drive components can include articulation actuators, closure actuators, and/or firing actuators for example.

The first shaft joint component 530 is pivotally connected to the second shaft joint component 540 by way of the articulation pin 543. The articulation pin 543 is also received within a pin hole 542 of a proximally-extending articulation tab 541 of the second shaft joint component 540. The articulation pin 543 allows the second shaft joint component 540 to be articulated relative to the first shaft joint component 530 about the articulation axis AA. The second shaft joint component 540 further comprises a distal portion 545 comprising an annular groove 547 configured to receive a retention ring 548 and a hollow passage 546 through which various drive components of the surgical stapling assembly 500 can pass. The retention ring 548 is configured to hold the first jaw 201 to the second shaft joint component 540 by fitting within the annular groove 211 of the cartridge channel 210 and the annular groove 547 of the second shaft joint component 540.

Any suitable articulation drive system can be used to articulate the end effector 200 about axis AA. In at least one instance, the end effector 200 is passively articulated. In such an instance, the end effector 200 may be pressed against tissue, for example, to apply a force to the end effector 200 and cause the end effector 200 to articulate about an articulation axis. In at least one instance, the end effector 200 further comprises a spring configured to apply a neutral biasing force to the second shaft joint segment 540, for example, to cause the end effector 200 to be biased toward an unarticulated configuration.

The surgical stapling assembly 500 further comprises a closure drive shaft segment 575 and a firing drive shaft segment 576 each configured to transmit rotary motion through the articulation joint 520 to the end effector 200. The drive shaft segments 575, 576 are configured to passively expand and contract longitudinally as the end effector 200 is articulated. Articulation causes the drive shaft segments 575, 576 to expand and contract to account for the longitudinal stretching of or contracting of the length of the drive shafts owing to articulation of the end effector 200. During expansion and contraction of the drive shaft segments 575, 576, the drive shaft segments 575, 576 maintain rotary driving engagement with corresponding input shafts and output shafts in the end effector 200. In at least one instance, the output shafts comprise the closure screw 251 and the firing screw 261, which are further described herein.

Figure 18:
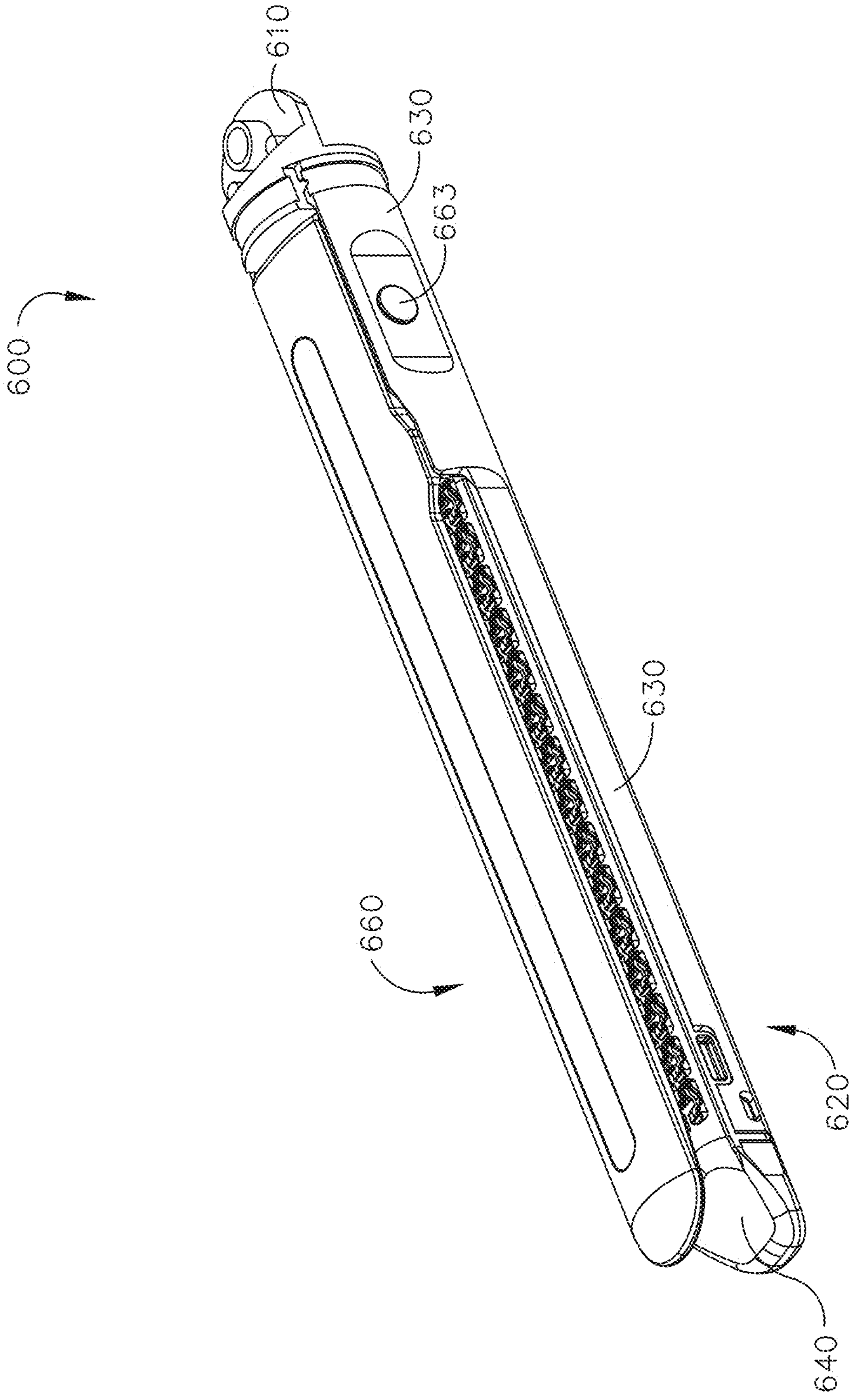
FIG. 18 is a perspective view of a surgical end effector assembly comprising the end effector of FIG. 1 and a flexible firing drive system, in accordance with at least one aspect of the present disclosure.
Figure 19:
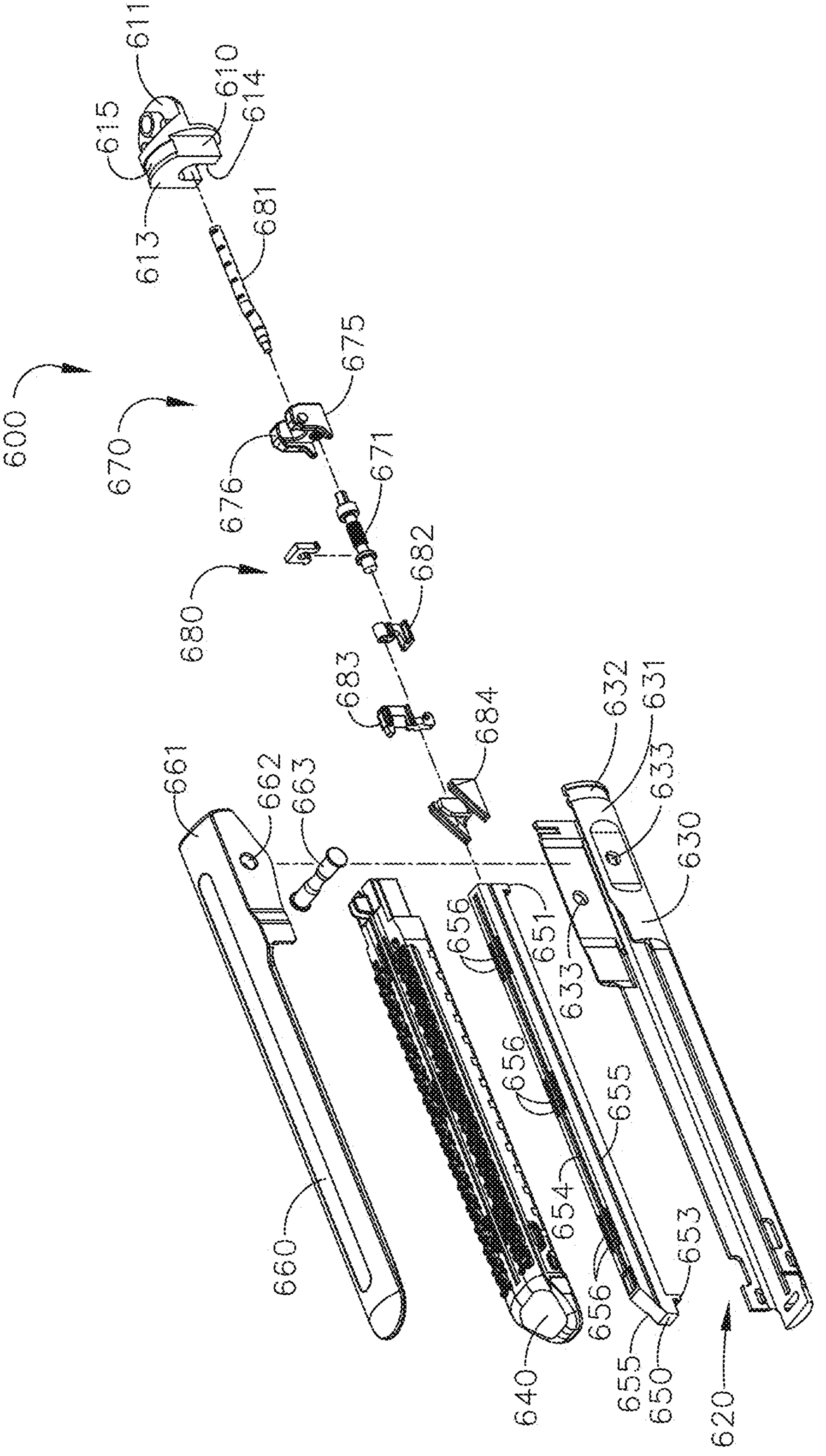
FIG. 19 is an exploded perspective view of the surgical stapling assembly of FIG. 18, in accordance with at least one aspect of the present disclosure.
Figure 20:
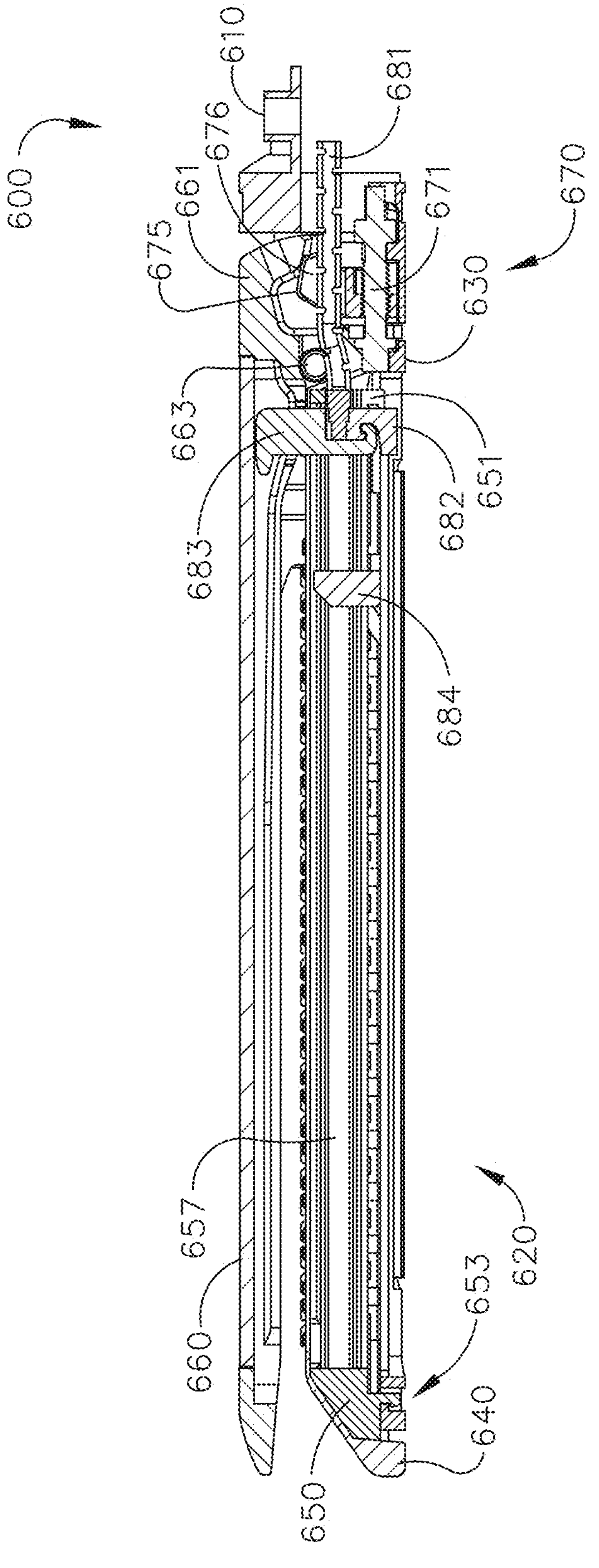
FIG. 20 is a cross-sectional elevation view of the surgical end effector assembly of FIG. 18, wherein the surgical end effector assembly is illustrated in an unfired, clamped configuration, in accordance with at least one aspect of the present disclosure.

FIGS. 18-20 depict a surgical stapling end effector assembly 600 comprising a shaft portion 610 and an end effector 600. The end effector assembly 600 is similar in many respects to various other end effector assemblies disclosed herein; however, the end effector assembly 600 comprises a multi-component firing member driven by a flexible firing shaft. The end effector assembly 600 is configured to cut and staple tissue. The end effector assembly 600 may be attached to a surgical instrument handle and/or surgical robotic interface by way of a proximal tab 611 of the shaft portion 610. The surgical instrument handle and/or surgical robotic interface can be configured to actuate various functions of the end effector assembly 600. The end effector assembly 600 comprises a cartridge channel jaw 620 and an anvil jaw 660 pivotally mounted to the cartridge channel jaw 620 to clamp tissue between the cartridge channel jaw 620 and the anvil jaw 660.

The cartridge channel jaw 620 comprises a channel 630 comprising a proximal end 631, a staple cartridge 640 configured to store a plurality of staples therein and configured to be received within the channel 630, and a support brace 650 fitted within the staple cartridge 640. The staple cartridge 640 and the support brace 650 are configured to be assembled together prior to installing the staple cartridge 640 into the channel 630. Discussed in greater detail below, the support brace 650 is configured to further support a firing member assembly as the firing member assembly is advanced through the end effector assembly 600.

The anvil jaw 660 is configured to form staples ejected from the staple cartridge 640. The anvil jaw 660 comprises a proximal end 661 comprising a pair of pin holes 662 defined therein configured to receive a coupling pin 663. The anvil jaw 660 is pivotable about the coupling pin 663 between an unclamped position and a fully clamped position. The coupling pin 663 is also received within a pair of pin holes 633 defined in the proximal end 631 of the channel 630. The coupling pin 663 serves to pivotally mount the anvil jaw 660 to the channel 630. In at least one instance, the channel 630 is mounted to the shaft portion 610 by way of a retention ring, or band, that fits around an annular groove 632 of the channel 630 and annular groove 615 of the shaft portion 610. The retention ring, or band, is configured to hold the channel 630 to the shaft portion 610.

The end effector assembly 600 comprises a closure drive 670 configured to grasp tissue between the anvil jaw 660 and the cartridge channel jaw 620 by pivoting the anvil jaw 660 relative to the channel 630. The end effector assembly 600 also includes a firing drive 680 configured to clamp, staple, and cut tissue by deploying a plurality of staples from the staple cartridge 640. The closure drive 670 comprises a closure screw 671 positioned within the channel 630 and a closure wedge 675 threadably coupled to the closure screw 671. As the closure screw 671 is rotated, the closure wedge 675 is advanced distally or retracted proximally to open or close the anvil jaw 660, respectively. The closure drive 670 may be actuated by any suitable means. For example, a rotary drive shaft may extend through the shaft portion 610 from an actuation interface, for example, to rotate the closure screw 671. Other examples of suitable rotary drive shafts are further described herein.

The firing drive 680 comprises a flexible drive shaft 681 that is configured to be moved linearly through the end effector assembly 600. The flexible drive shaft 681 may be actuated by a robotic input and/or a manually-actuated drive shaft of a handle assembly, for example. The flexible drive shaft 681 is configured to extend through a hollow passage 614 of a distal end 613 of the shaft portion 610 and is flexible so that the end effector assembly 600 may be articulated relative to a shaft from which the end effector 600 extends. The flexible drive shaft 681 extends through a clearance slot 676 defined in the closure wedge 675 and is fixedly attached to a lower firing member 682. The lower firing member 682 is configured to be reused with different staple cartridges.

The staple cartridge 640 comprises a disposable upper firing member 683 configured to hookingly engage or, latch, onto the lower firing member 682 such that the lower firing member 582 can push or, drive, the upper firing member 683 through the staple cartridge 640 and support brace 650. In other words, the firing actuation involves a two-part firing member-a disposable upper firing member 683 incorporated into the cartridge 640 and a reusable lower firing member 682 incorporated into the firing drive 680, which can be coupled together when the cartridge 640 is seated in the elongate channel 630. The two-part firing member is further described herein.

The upper firing member 683 comprises an upper flange configured to engage and position the anvil jaw 660, a knife edge configured to cut tissue, and a latch portion configured to hookingly engage the lower firing member 682. The staple cartridge 640 further comprises a sled 684 configured to engage staple drivers positioned within the staple cartridge 640 to eject staples from the staple cartridge 640. Because a knife and cutting edge are incorporated into the disposable upper firing member 683 of the staple cartridge 640, a new and/or fresh cutting edge can be supplied with each staple cartridge loaded into the end effector assembly 600.

The lower firing member 682 and the upper firing member 683 are configured to move through the support brace 650 such that the vertical loads associated with the firing sequence are configured to be distributed through the support brace 650, the staple cartridge 640, the channel 630, and the anvil jaw 660. The support brace 650 may be comprised of a metal material, for example, to be inserted within the staple cartridge 640. The support brace 650 comprises key rails 655 configured to fit within corresponding key slots defined in a longitudinal slot of the staple cartridge 640. The support brace 650 further comprises a longitudinal slot 653 configured to receive the knife of the upper firing member 683, a cylindrical passage 657 configured to receive a portion of the upper firing member 683, a portion of the lower firing member 682, and the flexible drive shaft 681. The support brace 650 further comprises vertical key extensions 656 configured to be received within corresponding key holes in the cartridge deck. Such extensions may be visible through the cartridge deck when the support brace 650 is installed within the staple cartridge 640. In at least one instance, the support brace 650 is configured to be inserted into the staple cartridge 640 from the bottom of the staple cartridge 640 facing the channel 630.

The support brace 650 further comprises a proximal tab 651 and a distal tab 653, which are both configured to be engaged with the channel 630. The tabs 651, 653 are configured to distribute at least some of the forces transmitted through the assembly 600 by the firing drive 680 and corresponding components. The distal tab 651 may serve to block the upper and lower firing members 683, 682 from being pushed through a distal end of the support brace 650 by sharing and/or redistributing the load applied to the support brace 650 by the firing drive 680 with the channel 630.

When the staple cartridge 640 is replaced so that the end effector assembly 600 can be reused, the staple cartridge 640 is removed from the channel jaw 630. Removing the staple cartridge 640 from the channel jaw 630 removes the upper firing member 683, the sled 684, the support brace 650, and the staple cartridge 640. A fresh knife can be provided with a replacement staple cartridge.

Figure 21:
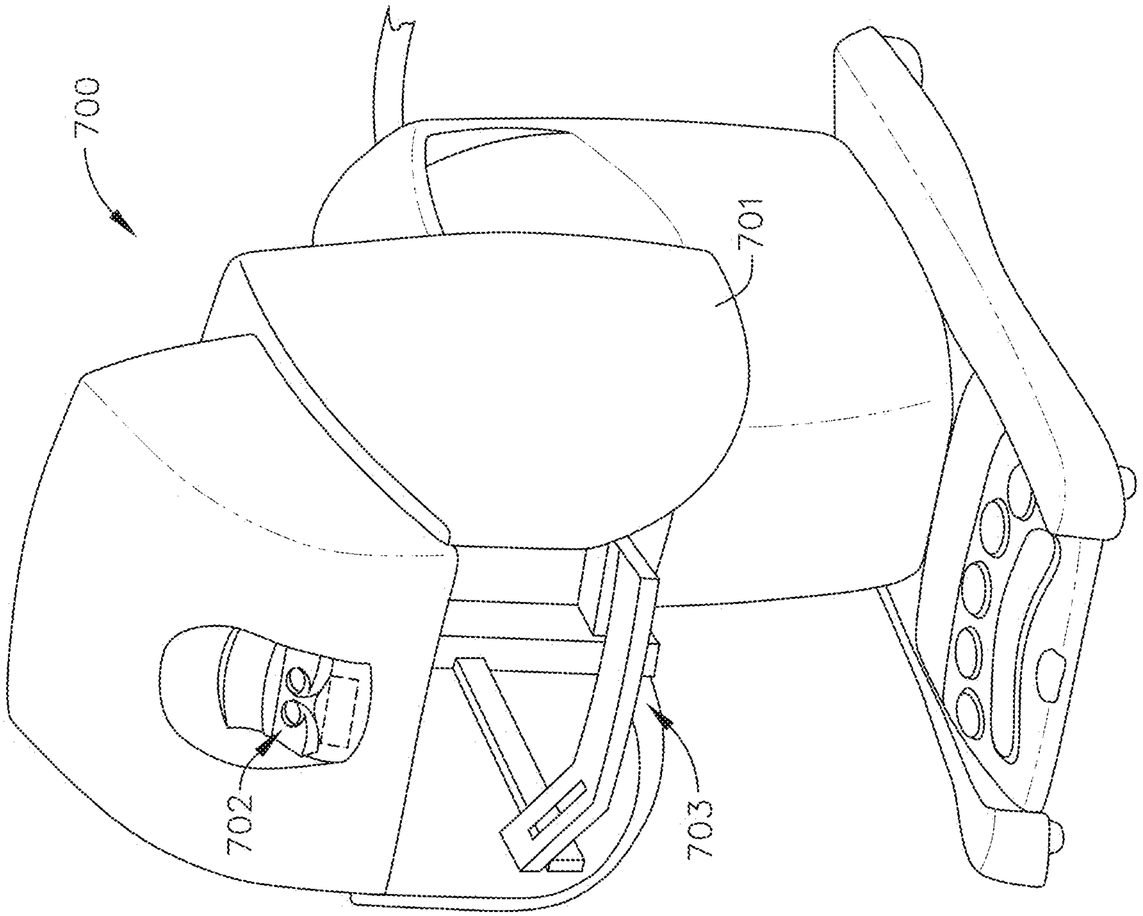
FIG. 21 is a perspective view of robotic controller, in accordance with at least one aspect of the present disclosure.
Figure 22:
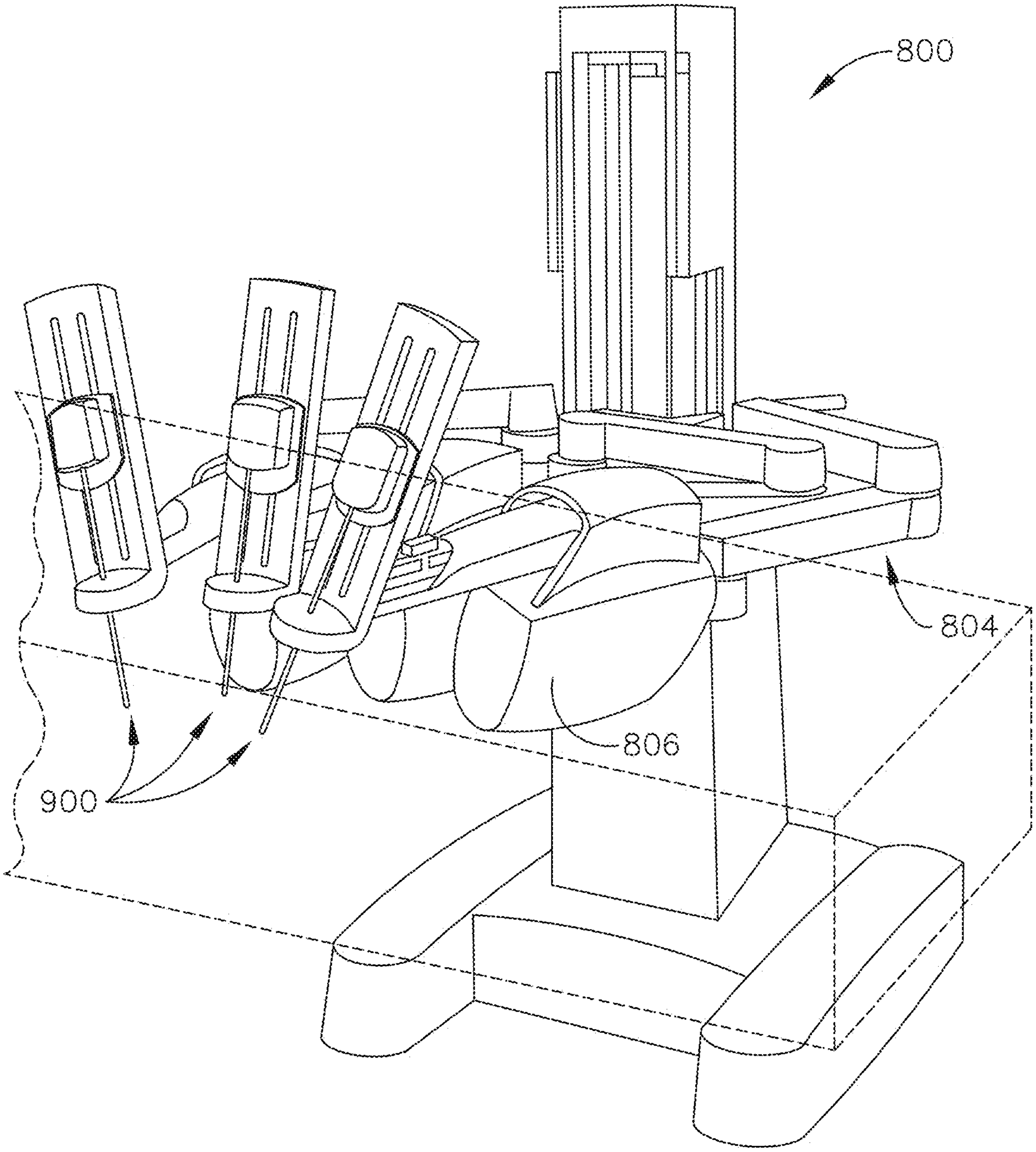
FIG. 22 is a perspective view of a robotic arm cart for a robotic surgical system, depicting manipulators on the robotic arm cart operably supporting surgical tools, in accordance with at least one aspect of the present disclosure.
Figure 23:
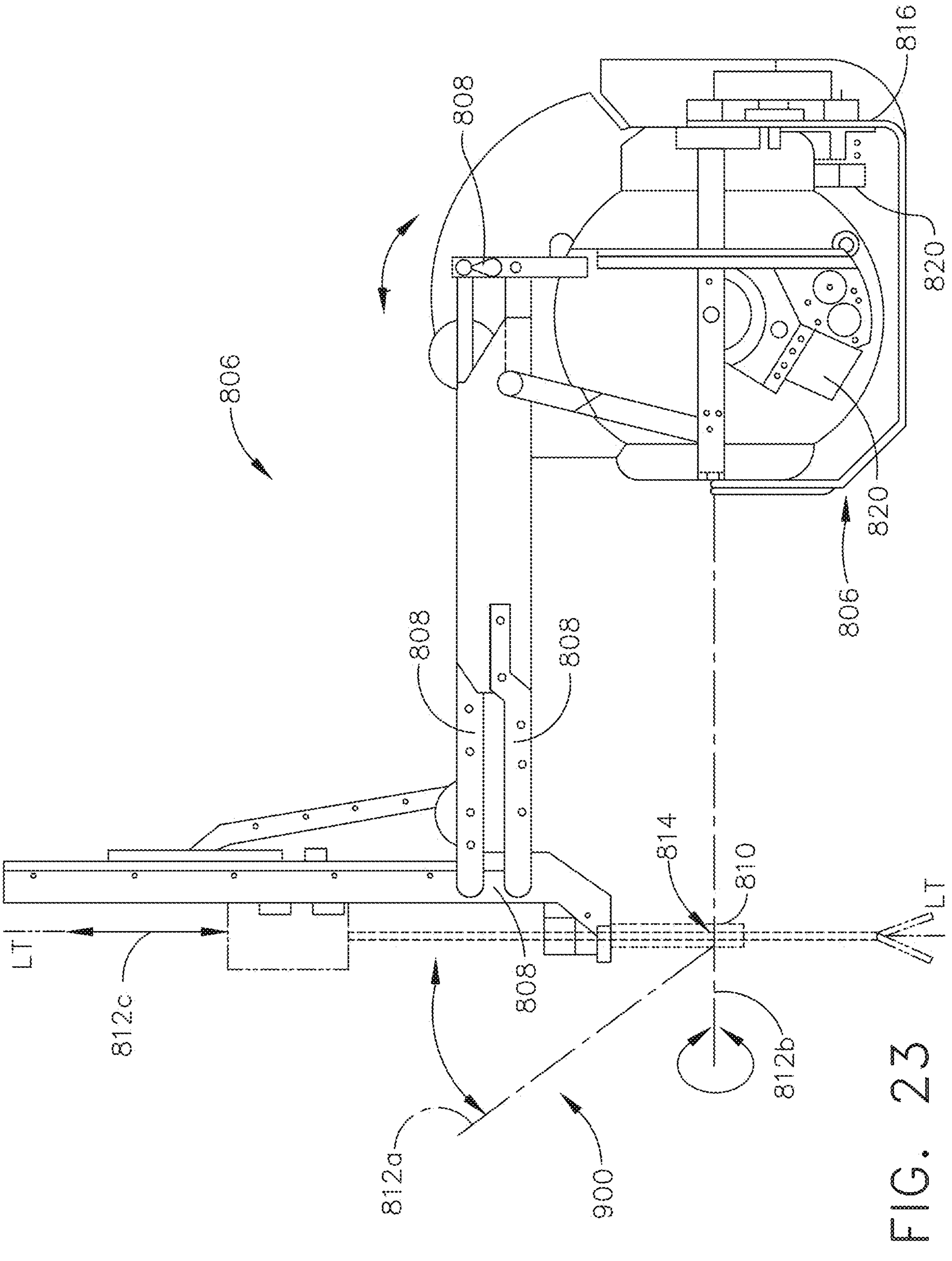
FIG. 23 is a side view of a manipulator of the surgical arm cart of FIG. 22 and a surgical grasping tool, in accordance with at least one aspect of the present disclosure.

Various embodiments disclosed herein may be employed in connection with a robotic system 700. An exemplary robotic system is depicted in FIGS. 21-23, for example. FIG. 21 depicts a master controller 701 that may be used in connection with a surgical robot, such as the robotic arm slave cart 800 depicted in FIG. 22, for example. Master controller 701 and robotic arm slave cart 800, as well as their respective components and control systems are collectively referred to herein as a robotic system 700. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. As is known, the master controller 701 generally includes controllers (generally represented as 703 in FIG. 21) which are grasped by the surgeon and manipulated in space while the surgeon views the procedure via a stereo display 702. The controllers 701 generally comprise manual input devices which preferably move with multiple degrees of freedom, and which often further have an actuatable handle, trigger, or actuator for actuating tools (for example, for closing grasping jaws, applying an electrical potential to an electrode, or the like).

As can be seen in FIG. 22, in one form, the robotic arm cart 800 may be configured to actuate one or more surgical tools, generally designated as 900. Various robotic surgery systems and methods employing master controller and robotic arm cart arrangements are disclosed in U.S. Pat. No. 6,132,368, entitled MULTI-COMPONENT TELEPRESENCE SYSTEM AND METHOD, the entire disclosure of which is hereby incorporated by reference herein.

In various forms, the robotic arm cart 800 includes a base 702 from which, in the illustrated embodiment, surgical tools 900 may be supported. In various forms, the surgical tool(s) 900 may be supported by a series of manually articulatable linkages, generally referred to as set-up joints 804, and a robotic manipulator 806. In various embodiments, the linkage and joint arrangement may facilitate rotation of a surgical tool around a point in space, as more fully described in U.S. Pat. No. 5,817,084, entitled REMOTE CENTER POSITIONING DEVICE WITH FLEXIBLE DRIVE, the entire disclosure of which is hereby incorporated by reference herein. The parallelogram arrangement constrains rotation to pivoting about an axis 812*a*, sometimes called the pitch axis. The links supporting the parallelogram linkage are pivotally mounted to set-up joints 804 (FIG. 22) so that the surgical tool further rotates about an axis 812*b*, sometimes called the yaw axis. The pitch and yaw axes 812*a*, 812*b* intersect at the remote center 814, which is aligned along an elongate shaft of the surgical tool 900. The surgical tool 900 may have further degrees of driven freedom as supported by the manipulator 806, including sliding motion of the surgical tool 900 along the longitudinal axis "LT-LT". As the surgical tool 900 slides along the tool axis LT-LT relative to manipulator 806 (arrow 812*c*), the remote center 814 remains fixed relative to the base 816 of the manipulator 806. Hence, the entire manipulator is generally moved to re-position the remote center 814. Linkage 808 of manipulator 806 may be driven by a series of motors 820. These motors actively move linkage 808 in response to commands from a processor of a control system. The motors 820 may also be employed to manipulate the surgical tool 900. Alternative joint structures and set up arrangements are also contemplated. Examples of other joint and set up arrangements, for example, are disclosed in U.S. Pat. No. 5,878,193, entitled AUTOMATED ENDOSCOPE SYSTEM FOR OPTIMAL POSITIONING, the entire disclosure of which is hereby incorporated by reference herein.

While the data communication between a robotic component and the processor of the robotic surgical system is primarily described herein with reference to communication between the surgical tool and the master controller 701, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 21-23 and described in the aforementioned references.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

Various surgical instruments employ a variety of different drive shaft arrangements that serve to transmit drive motions from a corresponding source of drive motions that is supported in a handle of the surgical instrument or other portion of an automated or robotically controlled system. These drive shaft arrangements must be able to accommodate significant articulated orientations of the end effector while effectively transmitting such drive motions across the articulation joint of the surgical instrument. In addition, due to the above-mentioned size constraints dictated by the sizes of trocars through which the instrument shafts must be inserted, these drive shaft components must occupy as little space as possible within the shaft. To accommodate such requirements, many drive shaft arrangements comprise several movable elements that are coupled together in series. The small sizes (e.g., 4 mm diameter) and numbers of components lead to difficult and lengthy assembly procedures that add to the cost and complexity of the device.

As further described herein, a powered stapling device can include two independently rotatable drive members: a first rotary drive member configured to effect closing of the jaws of the end effector and a second rotary drive member configured to effect firing of a staple cartridge installed in the end effector. The first and second rotary drive members are flexible and configured to extend through at least one articulation joint. In such instances, the first and second rotary drive members can transmit rotary actuation motions through the articulation joint(s) when in a non-flexed configuration and when in a flexed configuration. Exemplary rotary drive members are further described herein.

The powered stapling assembly further comprises a first jaw, a second jaw, a closure drive comprising the first rotary drive member extending through the articulation joint, and a firing drive comprising the second rotary drive member extending through the articulation joint. The second rotary drive member can be rotatable independent of the first rotary drive member. The closure drive can be activated by a closure trigger, for example, whereupon an actuation of the closure drive effects a rotation of the first rotary drive member, which transmits a rotary motion through the articulation joint to a closure screw. The closure drive further comprises a closure wedge threadably coupled to the closure screw, wherein the closure wedge is configured to engage the first jaw to move the first jaw from an open position to a closed position upon rotation of the first rotary drive member.

The firing drive can be activated by a firing trigger, for example, which is separate from the closure trigger. The rotation of the second rotary drive member is separate from the rotation of the first rotary drive member, and a closure motion is separate and distinct from a firing motion. Activation of the firing drive effects a rotation of the second rotary drive member, which transmits a rotary motion through the articulation joint to a firing screw. The firing drive further comprises a firing member threadably coupled to the firing screw, wherein the firing member is configured to camming engage the first jaw and the second jaw and to move a cutting member and/or a staple-firing sled upon rotation of the second rotary drive member.

In various instances, at least one component in the powered stapling device can be a 3D-printed component. 3D-printed components can be incorporated into an articulation system, a closure/grasping system, and/or a firing system, as further described herein. 3D printing technology can be utilized to improve component capabilities in certain instances. For example, 3D printing can allow the printed component to exhibit metamaterial properties, such that the 3D-printed components exhibits greater structural strength and stiffness while allowing precision in the forming of small detailed features and optimizing other properties of the component such as selective flexibility and/or lubrication, for example. Exemplary 3D-printed components for the powered stapling device are further described herein and include the flexible rotatable drive member(s), e.g. serial 3D-printed universal joints, the firing member or I-beam, and/or the staple cartridge and/or sub-components thereof.

In one instance, the staple cartridge can be a composite plastic-metal 3D-printed component. 3D printing of various components and considerations therefor are further described herein.

A method of stapling with such surgical stapling assemblies is also contemplated. The method can include obtaining the surgical stapling assembly and activating, by the closure trigger, the closure drive, wherein the closure wedge is configured to engage the first jaw to move the first jaw from an open position to a closed position upon a rotation of the first rotary drive member. The method can further includes activating, by the firing trigger, the firing drive, wherein the firing member is configured to camming engage the first jaw and the second jaw and to advance a cutting member and a staple-firing sled during a firing motion upon a rotation of the second rotary drive member. Various applications of 3D-printed components in such assemblies are further described herein.

In various instances, a surgical end effector and or stapling assembly for a surgical device can include a rotary drive screw or rotary drive member, as further described herein. A rotary drive screw can extend through a channel and/or portion of a staple cartridge to a distal location in the end effector. The rotary drive screw can facilitate clamping and/or firing of the staple cartridge, as further described herein. The rotary drive screw can extend along a longitudinal axis and can be aligned with a centerline of the staple cartridge extending from a proximal end to a distal end thereof.

A rotary drive screw through an end effector can take up a substantial portion of the limited real estate along the longitudinal center portion of the end effector and staple cartridge thereof. In various instances, the rotary drive screw may interfere with certain existing firing components, such as the drivers and/or the sled, for example. The small footprint of the staple cartridge and the significant firing forces applied to various components in an end effector and staple cartridge can pose various challenges to structural variations and/or the relocation of certain components.

For example, the firing component(s) in a staple cartridge having a rotary drive screw therethrough need to be modified to avoid interference and provide a sufficient clearance around the rotary drive screw while withstanding the firing forces and balancing torques during the firing stroke in order to minimize damage to the components and/or misfiring of the staples. In various instances, the rows of staples can be condensed (i.e. a denser staple arrangement) and/or shifted laterally outboard away from the rotary drive screw to increase lateral space around the centerline of the staple cartridge. Relocation and/or increased density of the staple rows may require various adaptions to the firing components such as the drivers and/or the sled, for example.

In various instances, the drivers and/or the sled can be modified to correspond to the relocated and/or condensed staple rows while minimizing jams and/or incidences of misfiring. Modifications to the staple drivers may include structural and geometric variations to the staple support columns and/or bridges therebetween, for example. In certain instances, an upper portion of the driver (e.g. the widths of the staple supporting columns) can be asymmetric relative to a centerline of the driver. Additionally or alternatively, a lower portion of the driver (e.g. the bridges and/or base of the staple supporting columns) can be asymmetric relative to a centerline of the driver.

For example, in one aspect of the present disclosure, a staple cartridge can include a body extending along a longitudinal axis, rows of staples, and a triple driver configured to fire three staples simultaneously. The rows of staples can include an inner row on a first side of the longitudinal axis, wherein the inner row comprises an inner staple. The rows of staples can also include an intermediate row on the first side of the longitudinal axis, wherein the intermediate row comprises an intermediate staple. Furthermore, the rows of staples can include an outer row on the first side of the longitudinal axis, wherein the outer row comprises an outer staple. The intermediate row can be equilaterally spaced from the inner row and the outer row. The triple driver can include an inner support column defining a first width, wherein the inner support column is configured to support the inner staple. The triple driver can also include an intermediate support column defining a second width, wherein the intermediate support column is configured to support the intermediate staple. Further, the triple driver can include an outer support column defining a third width, wherein the outer support column is configured to support the outer staple. The first width can be less than the second width and less than the third width. In certain instances, the first width, the second width, and the third width can all be different.

In various aspects of the present disclosure, varied widths of the staple support columns of a multi-staple driver can be configured to provide a wider space for the sled rails while optimizing real estate for a rotary drive screw along a central longitudinal portion of the staple cartridge. Various improvements to the staple cartridge, including to the drivers and the cartridge body, for example, and advantages thereof are further described herein.

Figure 24:
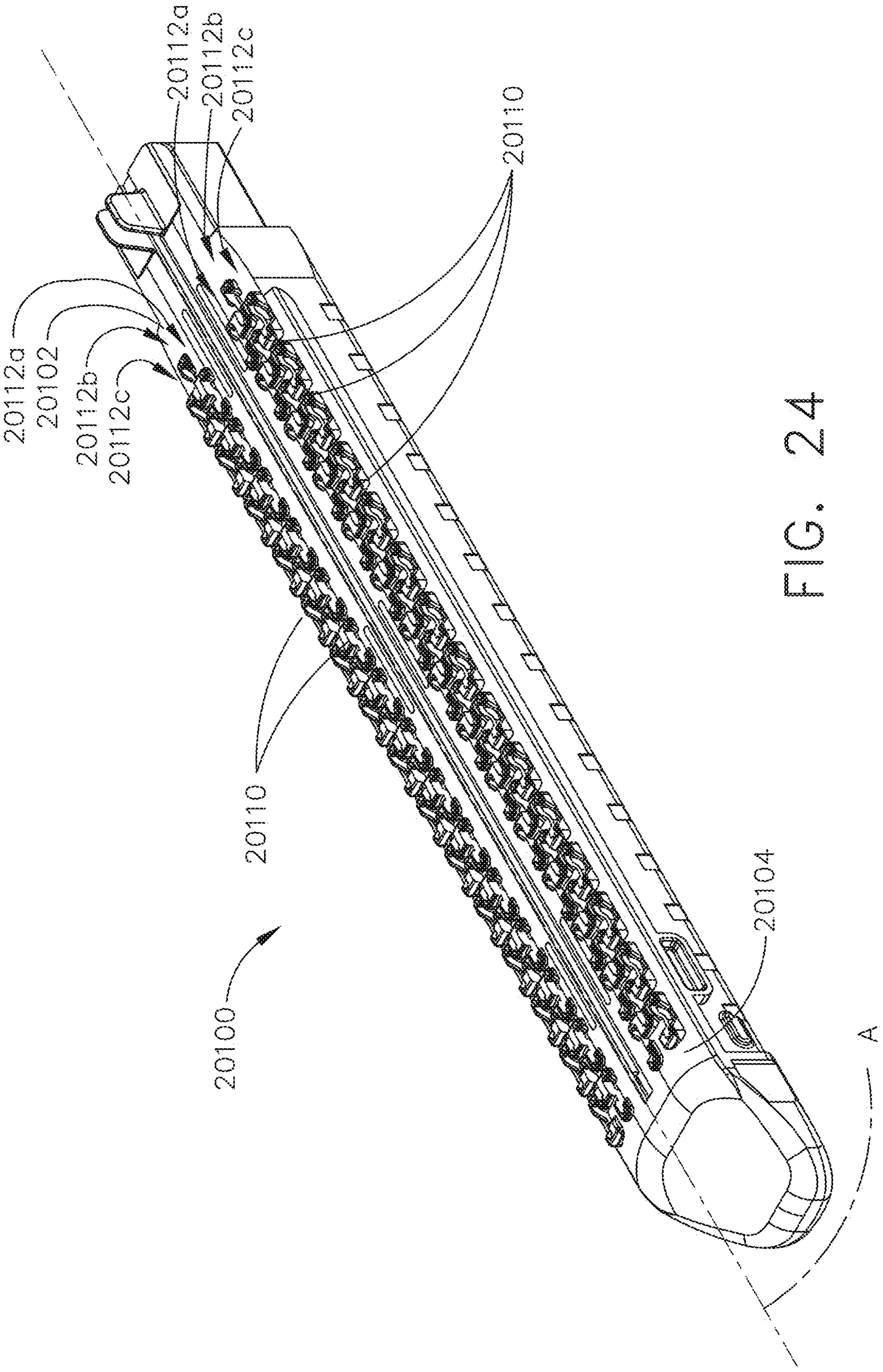
FIG. 24 is a perspective view of a staple cartridge, according to various aspects of the present disclosure.
Figure 25:
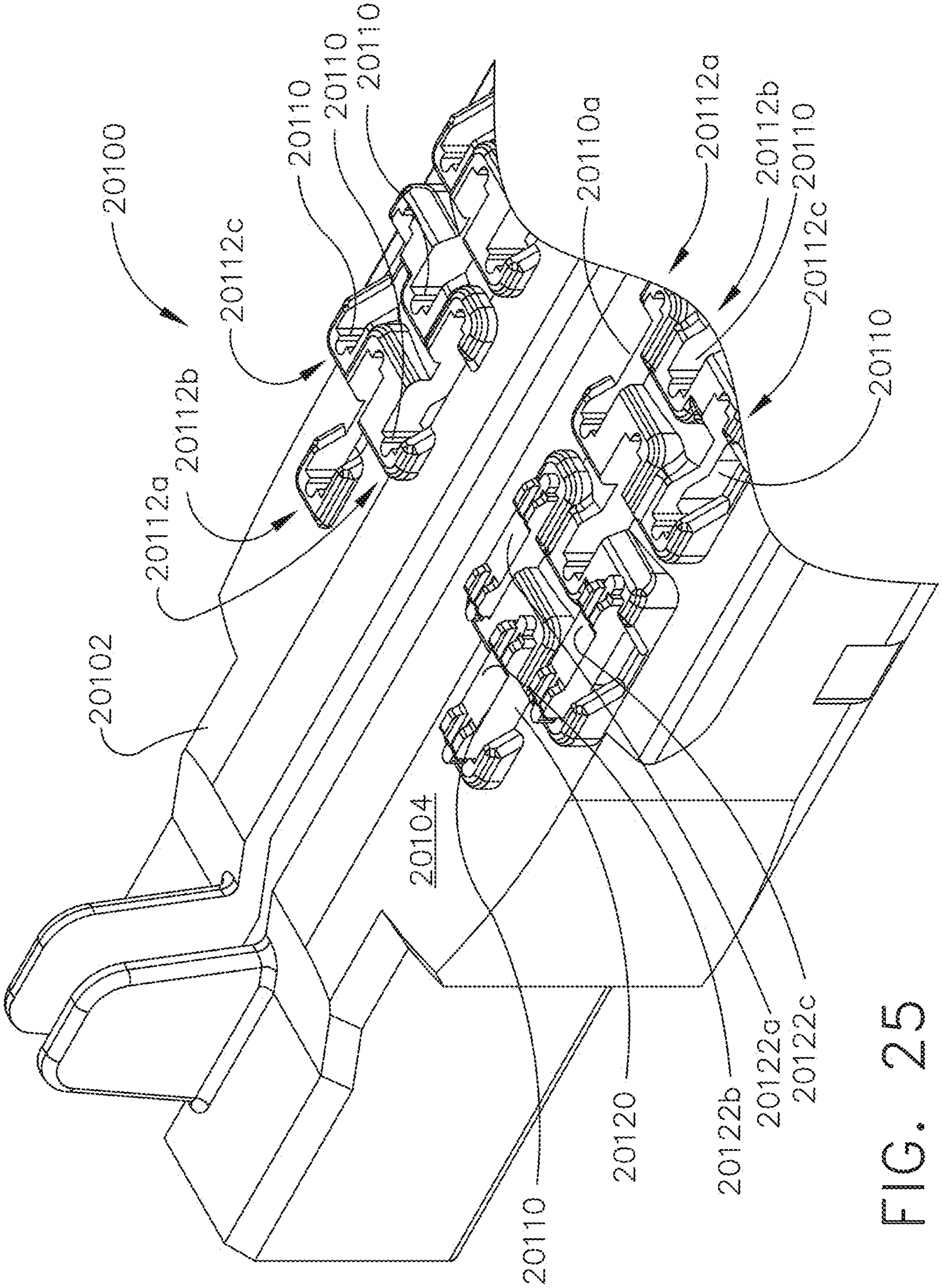
FIG. 25 is a perspective view of a portion of the staple cartridge of FIG. 24, depicting a triple driver in a fired configuration in the staple cartridge, according to various aspects of the present disclosure.

Referring now to FIGS. 24 and 25, a staple cartridge 20100 includes a body 20102 extending along a longitudinal axis A. Staples are removably positioned in the body 20102. The staples can be ejected from the body 20102 and fired into tissue, for example, during a firing stroke. The staples are arranged in longitudinal rows on either side of the longitudinal axis A. The cartridge body 20102 also includes a deck 20104, which can be referred to as a tissue-supporting surface, for example. The deck 20104 is a laterally-curved tissue-supporting surface and defines a curved surface or contour from a first lateral side of the body 20102 to a second lateral side of the body 20102. A peak in the laterally-curved tissue-supporting deck 20104 is defined at an intermediate portion of the body 20102. The peak can be positioned between the longitudinal rows of staples and overlie the longitudinal axis A, for example. In various instances, a rotary drive screw, like the firing screw 261 (FIGS. 4 and 5), for example, extends through a portion of the staple cartridge 20100, as further described herein.

The staples are positioned in cavities 20110 defined in the cartridge body 20102. The staples are arranged in longitudinal rows on either side of the longitudinal axis A. For example, the cavities 20110 are arranged in cavity rows 20112. The cavity rows include an inner row **20112*a*, an intermediate row 20112*b*, and an outer row 20112*c* on each side of the longitudinal axis A. The intermediate row 20112*b* is equilaterally spaced between the inner row 20112*a* and the outer row 20112*c*. For example, the inner cavity row 20112*a* can be laterally spaced inward from the intermediate cavity row 20112*b* by a distance, and the outer cavity row 20112*c* can be laterally spaced outward from the intermediate cavity row 20112*b* by the same distance. The rotary drive screw can be aligned with the longitudinal axis A, and can extend through the cartridge body 20102 adjacent to the inner cavity rows 20112*a*. The rotary drive screw can be between and parallel to the inner cavity rows 20112*a***, for example.

The inner rows **20112*a* hold inner staples, the intermediate rows 20112*b* hold intermediate staples, and the outer rows 20112*c*** hold outer staples. In various instances, the inner staples, the intermediate staples, and the outer staples can be identical. In other instances, the inner staples, the intermediate staples, and/or the outer staples can be each be different with respect to staple type (e.g. wire or stamped), material, and/or size (e.g. different heights), for example. The reader will appreciate that various staples, staple cavities, staple drivers, and staple cartridges are described herein. However, in certain instances, alternative fasteners can be utilized and such fasteners can be incorporated into fastener cavities, driven by fastener drivers, and/or fired from fastener cartridges which can be similar to the staple cavities, staple drivers and/or staple cartridges described herein in many aspects.

The staple cartridge 20100 may have a different arrangement of staples. For example, the staple cartridge 20100 may have less than three rows of staples on each side of the longitudinal axis A and, in one aspect, may only have two rows of staples on each side of the longitudinal axis A. In still other instances, the staple cartridge 20100 can include four or more rows of staples on one or more sides of the longitudinal axis A. In various instances, the rows of staples may be asymmetrical relative to the longitudinal axis A. For example, the first side of the staple cartridge 20100 can have a different number of rows of staples than the second side of the staple cartridge 20100.

Each staple cavity 20110 includes a proximal end, a distal end, and lateral guide surfaces intermediate the proximal end and the distal end. The staple cavities 20110 are structured and dimensioned to guide drivers 20120 through the staple cavities 20110 toward the deck 20104. More specifically, the geometry of the staple cavities 20110 can complement the geometry of the drivers 20120. For example, the lateral guide surfaces in each staple cavity 20110 are configured to guide sidewalls 20134 of the driver 20120 (e.g. sidewalls of the staple-supporting columns) as the driver 20120 moves through the staple cavity 20110. Additionally or alternatively, the proximal end and/or the distal end of each staple cavity 20110 can include an upright groove configured to slidably receive an end and/or tongue thereof of the driver 20120. Alternative tongue and groove arrangements are also contemplated, which can be configured to guide the drivers 20120 through the staple cavities 20110 during firing of the staples from the staple cartridge 20100.

The drivers 20120 are configured to support and drive multiple staples from the cartridge body 20102 during a firing stroke. The drivers 20120 can movably support staples spanning two or more longitudinal rows of staple cavities 20112. For example, the drivers 20120 can movably support an inner staple, an intermediate staple, and an outer staple on the same side of the staple cartridge 20100.

Figure 26:
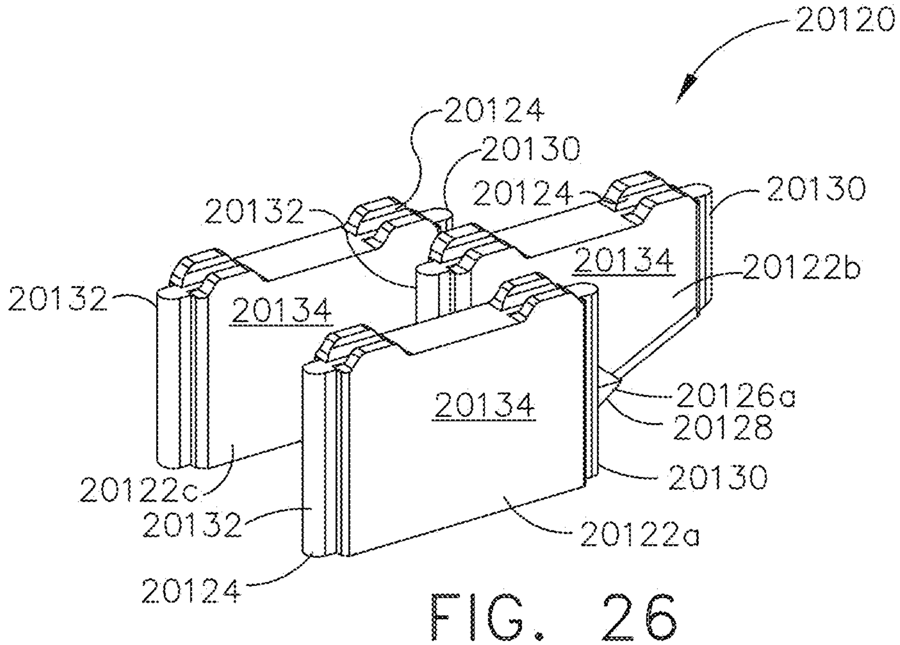
FIG. 26 is a perspective view of the triple driver of FIG. 25, according to various aspects of the present disclosure.
Figure 27:
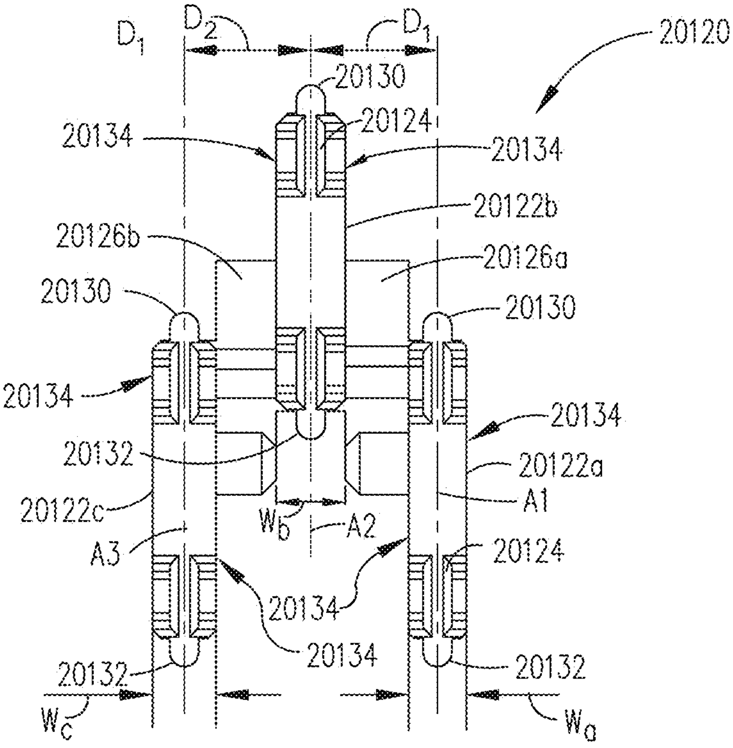
FIG. 27 is a plan view of the triple driver of FIG. 26, according to various aspects of the present disclosure.
Figure 28:
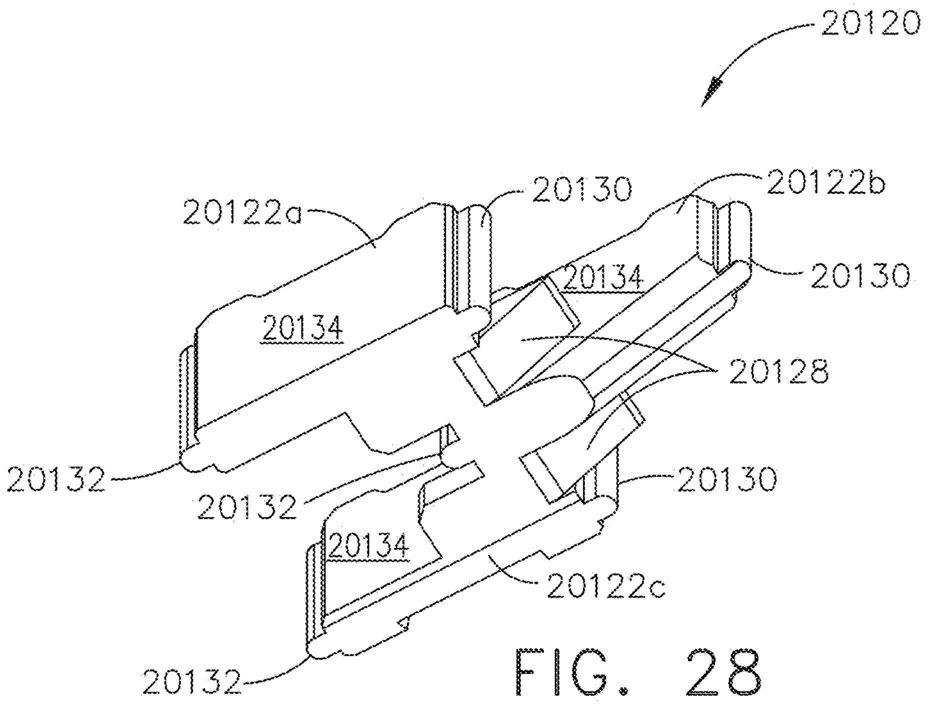
FIG. 28 is a bottom perspective view of the triple driver of FIG. 26, according to various aspects of the present disclosure.

Referring primarily now to FIGS. 26-28, the driver 20120 is shown. Multiple drivers like the driver 20120 are incorporated into the staple cartridge 20100, for example. The driver 20120 is a triple driver, which is configured to drive three staples simultaneously. The driver 20120 includes three support columns—an inner support column **20122*a* configured to support an inner staple in an inner row of staples, an intermediate support column 20122*b* laterally outboard of the inner support column 20122*a* configured to support an intermediate staple in an intermediate row of staples, and an outer support column 20122*c* laterally outboard of the intermediate support column 20122*b* and configured to support an outer staple in an outer row of staples. The support columns 20122*a*, 20122*b*, 20122*c* of each drive 20120** can be longitudinally staggered in various instances.

The driver 20120 also includes bridges 20126 extending between adjacent support columns 20122. For example, a first bridge **20126*a* extends between the inner support column 20122*a* and the intermediate support column 20122*b*, and a second bridge 20126*b* extends between the intermediate support column 20122*b* and the outer support column 20122*c*. The bridges 20126*a*, 20126*b* each include a ramped underside 20128 configured to be drivingly engaged by a sled during a firing stroke. Stated differently, each driver 20120 is configured to be engaged and lifted by two parallel sled rails along the ramped undersides 20128 of the driver 20120. For example, a sled can be configured to move along a firing path during a firing stroke. The sled can comprise a central portion aligned with the longitudinal axis A, a first rail on a first side of the longitudinal axis A that is configured to driving engage the ramped underside 20128 of the first bridge 20126*a*, and a second rail on a second side of the longitudinal axis A that is configured to drivingly engage the ramped underside 20128 of the second bridge 20126*b***. Sleds and firing motions thereof are further described herein.

Each support column 20122 includes a proximal end 20130, a distal end 20132, and a pair of opposing sidewalls 20134 extending longitudinally between the proximal end 20130 and the distal end 20132. The sidewalls 20134 are configured to slidably engage the lateral guide surfaces in the respective staple cavity 20110 during a firing motion. Each support column 20122 includes a staple-supporting cradle 20124. A base of the staple can be held in the staple-supporting cradle 20124.

The staple-supporting cradles 20124 are each aligned with one of an inner axis A1, an intermediate axis A2, or an outer axis A3, which correspond to the axes defining the longitudinal rows of staples and staple cavities 20110 on one side of the staple cartridge 20100. A first lateral distance D1 is defined between the inner axis A1 and the intermediate axis A2, and a second lateral distance D2 is defined between the outer axis A3 and the intermediate axis A2. The axes are equilaterally spaced; the first lateral distance D1 and the second lateral distance D2 are the same. Though the lateral distances D1, D2 between the axes and adjacent rows of staple cavities 20110 are the same, the driver 20120 is asymmetrical relative to a centerline of the driver 20120. For example, the centerline of the driver 20120 corresponds to the intermediate axis A2 and the inner and outer staples are positioned equidistant from intermediate axis A2; however, the driver 20120 is not symmetrical about the intermediate axis A2.

Referring primarily to FIG. 27, the inner support column **20122*a* defines a first width Wa between its sidewalls 20134, the intermediate support column 20122*b* defines a second width Wb between its sidewalls 20134, and the outer support column 20122*c* defines a third width Wc between its sidewalls 20134. The first width Wa is different than the second width Wb and the third width Wc. For example, the first width Wa can be reduced or narrowed to less than the second width Wb and less than the third width Wc to accommodate the rotary drive screw through a center portion of the staple cartridge 20100. In certain instances, one or more narrower support columns 20122 can effectively narrow and reduce the footprint of the driver 20120 while maximizing the width the bridge 20126 and, thus, maximizing the width of the sled rails, which engage the ramped undersides 20128 of the bridges 20126 and deliver the firing force to the driver 20120, for example. In various instances, increasing the width of the bridge 20126** and the sled rails may improve the stiffness of the sled rails and minimize deformations and/or damage to the sled during a firing stroke.

The widths Wa, Wb, and We are all different. For example, the width Wb of the intermediate support column 20122*b* is greater than the width Wa of the inner support column 20122*a* and the width Wc of the outer support column 20122*c*. The width Wc is less than the width Wb of the intermediate support column 20122*b* and greater than the width Wa of the inner support column 20122*a*. The differing widths Wa, Wb, and Wc are configured to optimize the width of the driver 20120 to accommodate a rotary drive screw along the longitudinal axis A, while effectively transferring the firing force and minimizing torque and mis-firings, for example.

As provided herein, in certain instances, the width of the staple support columns on the drivers can be varied to accommodate a rotary drive screw positioned in the staple cartridge. Additionally or alternatively, in certain aspects of the present disclosure, the lower portions of a driver can also vary laterally and the lower portion (e.g. the lower portion of the support columns and/or the bridges) may be asymmetric relative to a centerline through the intermediate support column. For example, a lower portion of the drivers can be improved to increase the available real estate in a longitudinal center portion of the staple cartridge. An asymmetric geometry for the lower portion of the drivers can be selected to improve the strength and stiffness of the triple driver while minimizing the height of the driver. In various instances, though the support column thickness and/or bridge geometry can vary laterally, the support columns can be equally spaced from a centroid of the substantially triangular triple driver. For example, the intermediate support column can be longitudinally aligned with the centroid, and the inner and outer support columns can be longitudinally offset from the centroid. In various instances, the ramped surfaces can be equilaterally spaced from the centroid of the triple driver.

Figure 29:
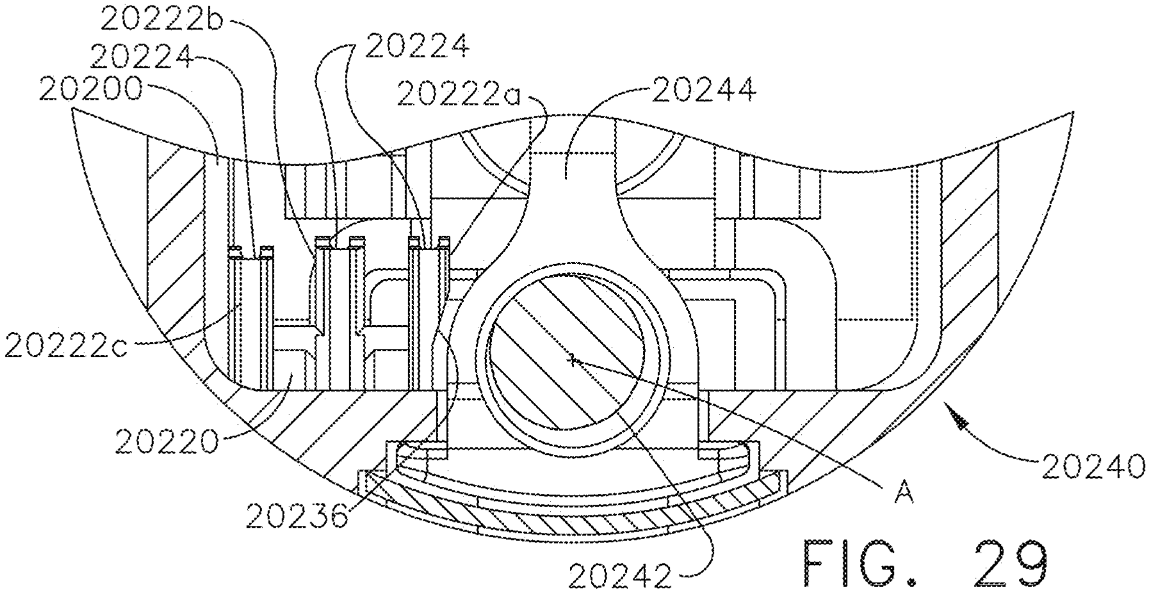
FIG. 29 is an elevation cross-section view of a portion of an end effector, depicting a staple cartridge therein with portions of the staple cartridge hidden for illustrative purposes, according to various aspects of the present disclosure.
Figure 30:
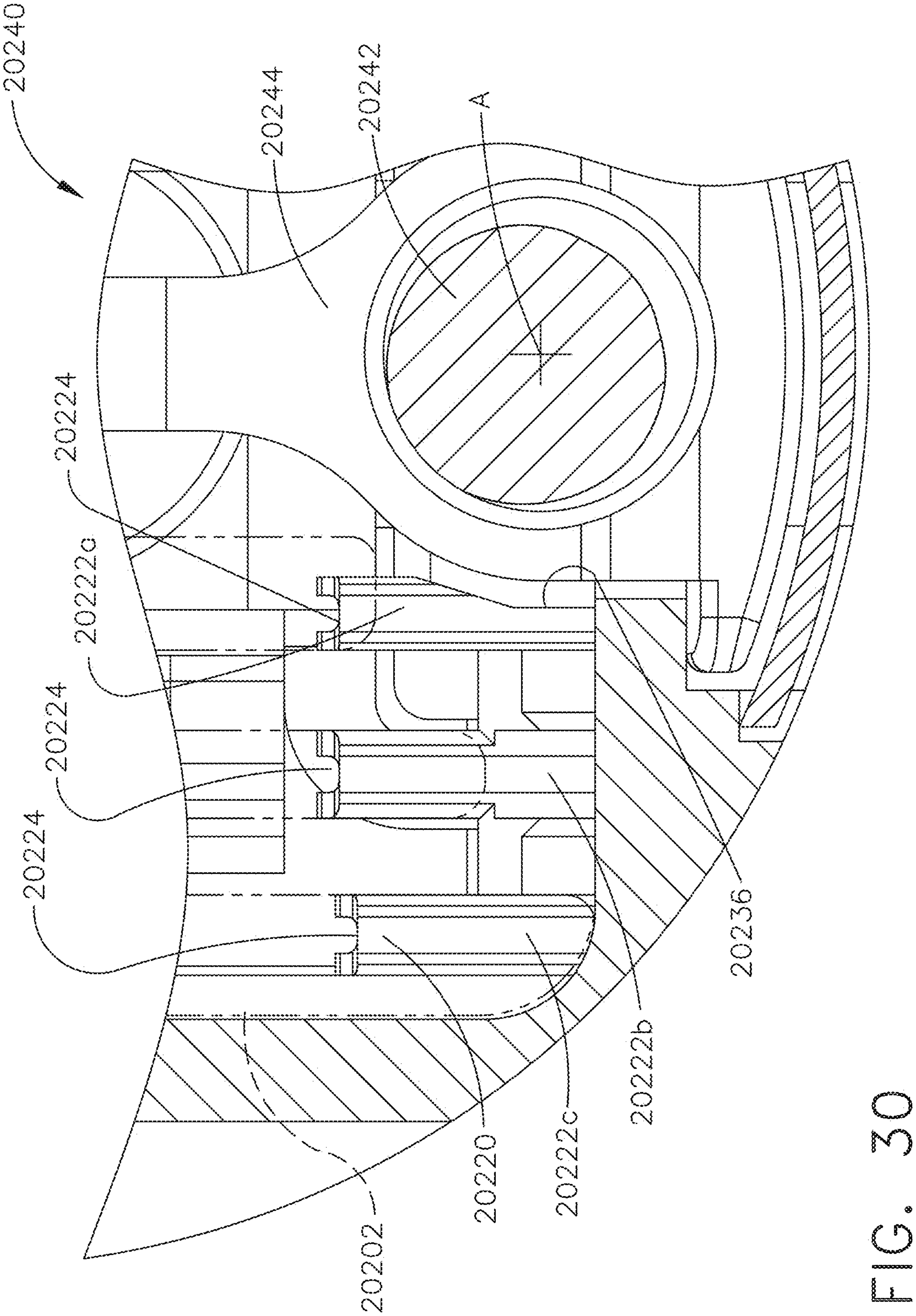
FIG. 30 is a detail view of the end effector of FIG. 29, according to various aspects of the present disclosure.

Referring to FIGS. 29 and 30, an end effector 20240 including a staple cartridge 20200 and a triple driver 20220 is shown. The staple cartridge 20200 is similar in many aspects to the staple cartridge 20100 (FIG. 24), and the triple driver 20220 is similar in many aspects to the triple driver 20120 (FIG. 26). For example, the staple cartridge 20200 includes a cartridge body 20202 including three rows of staple cavities on each side of the rotary drive screw 20242, and the triple driver 20220 include three parallel staple-supporting cradles 20224 configured to support staples, wherein the triple driver 20220 is configured to fire staples from an inner row, an intermediate row, and an outer row.

The end effector 20240 includes a rotary drive screw 20242 and a firing member 20244, which are similar to the firing screw 261 (FIGS. 4 and 5) and the firing member 270 (FIGS. 4 and 5), respectively. The firing member 20244 is configured to move through the staple cartridge 20200 during a firing stroke to advance the sled and lift the driver 20220.

The driver 20220 includes an inner support column 20222*a*, an intermediate support column 20222*b*, and an outer support column 20222*c*. The columns 20222 comprise different widths, as further described herein. In various aspects of the present disclosure, one or more of the columns 20222 can also include a different height than the other columns. In various instances, the different heights are configured to form staples to varying heights, which can correspond to the contour of a laterally-curved tissue-support surface or deck of the cartridge body, for example.

The lower portion of the driver 20220 includes a chamfered inner edge 20236. The chamfered inner edge 20236 is a cutaway or scalloped edge dimensioned to accommodate the drive screw 20242 and a lower portion of the firing member 20244. For example, the drive screw 20242 extends along the longitudinal axis A and is positioned between the drivers 20220 on opposite sides of the longitudinal axis A. In such instances, the drive screw 20242 can extend through the staple cartridge 20200 while minimizing the dimensions of staple cartridge 20200 and end effector 20240. The chamfered inner edge 20236 comprises a cutaway into a base portion of the inner support column 20222*a*, which provides a clearance for the firing components positioned along the longitudinal center portion of the end effector 20240. Moreover, the chamfered inner edge 20236 is configured to provide a space closer to a vertical centerline of the of the end effector, i.e. equidistance between the upper cam and the lower cam, which can improve and/or help to balance the forces during the firing stroke.

Figure 31:
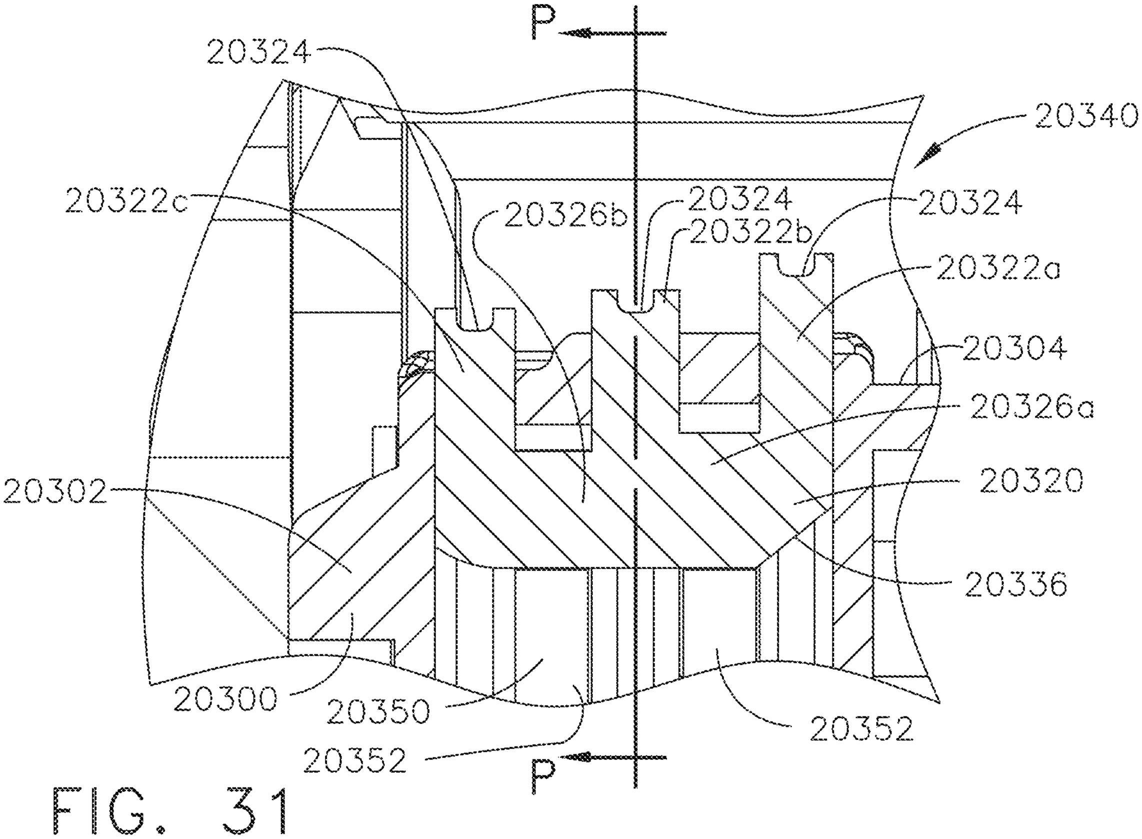
FIG. 31 is an elevation cross-section view of a portion of an end effector including a staple cartridge therein, according to various aspects of the present disclosure.

Additionally or alternatively, the bridges of a driver can vary laterally and/or be asymmetric relative to a centerline through the intermediate support column of the driver. Referring now to FIG. 31, an end effector 20340 including a staple cartridge 20300 and a triple driver 20320 is shown. The staple cartridge 20300 is similar in many aspects to the staple cartridge 20100 (see FIG. 24), and the triple driver 20320 is similar in many aspects to the triple driver 20120 (see FIG. 26). For example, the staple cartridge 20300 includes a cartridge body 20302 and deck 20304; three rows of staple cavities are positioned on each side of the rotary drive screw, and the triple driver 20320 includes three parallel staple-supporting cradles 20324 configured to support staples, wherein the triple driver 20320 is configured to fire staples from an inner row, an intermediate row, and an outer row. The driver 20320 is depicted in a fired configuration in FIG. 31, in which an upper portion of staple support columns extend through the deck 20304 (i.e. staple overdrive).

The end effector 20340 can include a rotary drive screw and a firing member, as further described herein, the firing member moves through the staple cartridge 20300 during a firing stroke to advance a sled 20350 having rails 20352 to lift the driver 20320. The driver 20320 includes an inner support column 20322*a*, an intermediate support column 20322*b*, and an outer support column 20322*c*. The columns 20322 comprise different widths, as further described herein. In various aspects of the present disclosure, one or more of the columns 20322 can also include a different height than the other columns, as further described herein.

The lower portion of the driver 20320 includes a chamfered inner edge 20336, which is similar in many aspects to the chamfered edge 20236 (FIG. 29). The lower portion of the driver 20320 also includes the bridges 20326 between adjacent staple support columns 20322. A first bridge 20326*a* connects the inner support column 20322*a* to the intermediate support column 20322*b*, and a second bridge 20326*b* connects the intermediate support column 20322*b* to the outer support column 20322*c*. The geometry of the first bridge 20326*a* is different than the geometry of the second bridge 20326*b*. Stated differently, the bridges 20326*a* are asymmetric relative to a vertical plane P (FIG. 31) through the driver 20320 and aligned with an axis of an intermediate staple base/crown supported thereon.

The first bridge 20326*a* is taller than the second bridge 20326*b*. In various instances, as further described herein, a central longitudinal portion of the staple cartridge 20300 can be taller and define a greater height at a peak of the laterally-curved tissue support surface than along the sides of the staple cartridge 20300. As a result, the staple cartridge 20300 can accommodate additional material and/or increased height/volume of the driver 20320 between the inner support column 20322*a* and the intermediate support column 20322*b* than between the outer support column 20322*c* and the intermediate support column 20322*b*. The increased height of the first bridge 20326*a* from the base surface compared to the second bridge 20326*b* can compensate for rigidity losses resulting from the chamfered inner edge 20336, for example. Additionally or alternatively, the greater height of the first bridge 20326*a* compared to the second bridge 20326*b* can improve the stiffness and strength of the triple driver 20320, while minimizing the dimensions and maintaining a compact form factor for the staple cartridge 20300 and the end effector 20340.

In certain instances, an upper portion of the first bridge 20326*a* can be configured to guide the driver 20320 through the staple cavities during an initial portion of the firing motion through the staple cavities. For example, when the inner support column 20322*a* is in an unfired position, the inner support column 20322*a* may be at least partially unsupported or unguided by lateral guide surfaces because of cutouts in a central portion of the cartridge body assembly 20300 to accommodate the rotary drive screw. In the absence of certain lateral support surfaces around the inner support column 20322*a*, the driver 20320 may be prone to torque and/or misfiring. However, the increased height of the first bridge 20326*a* can be configured to engage an upright support surface in the cartridge body during an initial portion of the firing motion to improve the guidance and support of the driver 20320.

Figure 32:
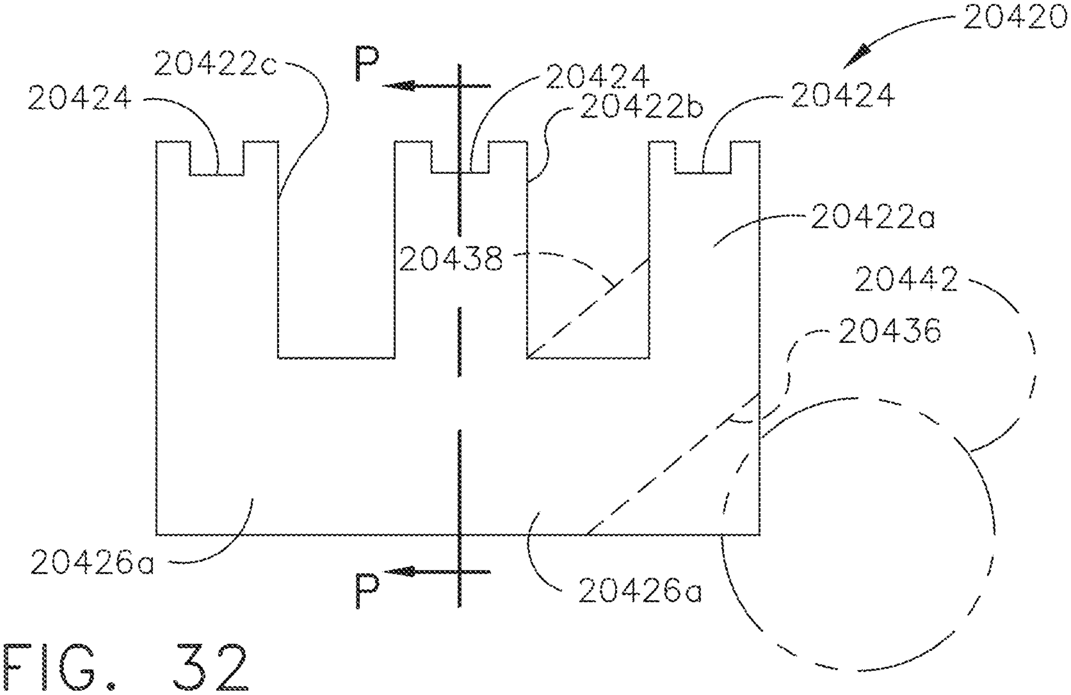
FIG. 32 is a schematic of a triple driver, depicting a modified geometry with dashed lines and showing relative positioning of a rotary drive screw with phantom lines, according to various aspects of the present disclosure.

Referring now to FIG. 32, an alternative driver geometry for a driver 20420 is shown. The driver 20420 is a triple driver and is similar in many aspects to the triple driver 20120 (FIG. 26). For example, the triple driver 20420 includes three parallel staple-supporting cradles 20424 configured to support staples, and the triple driver 20420 is configured to fire staples from an inner row, an intermediate row, and an outer row. The driver 20420 can be incorporated in various staple cartridges disclosed herein. For example, the driver 20420 can be utilized with a staple cartridge adapted to receive a rotary drive screw extending along a longitudinal axis and with a variable height deck.

The driver 20420 includes an inner support column 20422*a*, an intermediate support column 20422*b*, and an outer support column 20422*c*. The columns 20422 comprise different widths, as further described herein. In various aspects of the present disclosure, one or more of the support columns 20422 can also include a different height than the other support columns, as further described herein.

The lower portion of the driver 20420 includes a chamfered inner edge 20436, which is similar in many aspects to the chamfered edge 20236 (FIG. 29). The lower portion of the driver 20420 also includes bridges between adjacent staple support columns 20422. A first bridge 20426*a* connects the inner support column 20422*a* to the intermediate support column 20422*b*, and a second bridge 20426*b* connects the intermediate support column 20422*b* to the outer support column 20422*c*. Variations to the geometry of a lower portion of the driver 20420 are indicated with dashed lines in the schematic illustration of FIG. 32. For example, to provide adequate space and clearance along a central longitudinal portion of the staple cartridge for a rotary drive screw 20442, which is similar to the firing screw 261 (FIGS. 4 and 5) in many aspects, the driver 20420 includes the chamfered inner edge 20436 and the upper gusset 20438 between the first bridge 20426*a* and the inner support column 20422*a*. In such instances, the driver 20420 can provide a space and clearance for the rotary drive screw 20442 while maintaining sufficient structural integrity and stiffness to appropriately transfer the firing loads.

In various instances, a tallest height of the variable height deck and the staple cartridge can be adjacent to the rotary drive screw 20442. In such instances, a tighter tissue gap can be defined along the firing bar and cutting edge. The portion of the variable height deck overlaying the inner support column 20422*a* and/or first bridge 20426*a* can define the greatest height and, thus, in certain aspects, can fit the heightened first bridge 20426*a* and/or the gusset 20438 intermediate the first bridge 20426*a* and the inner support column 20422*a*.

In certain instances, one or more gusset plates can extend between an upper edge of the first bridge 20426*a* and the inner support column 20424. In certain instances, the gusset 20438 can comprise a longitudinal gusset rib along at least a portion of the length of the inner support column 20422*a* and the first bridge 20426*a*. The driver 20420 is asymmetric relative to a vertical plane P (FIG. 32) through the intermediate support column 20422*b* and aligned with the longitudinal axis of a staple base supported therein. For example, the first bridge 20426*a* can define a different geometry and different cross-sectional profile than the second bridge 20426*b* owing to the gusset 20438 and/or to the chamfered inner edge 20436.

In certain instances, to accommodate a rotary drive screw along a central portion of the staple cartridge, a portion of the cartridge body can be cutaway. The cartridge body can include additional guides and support features configured to guide the driver through the staple cavity and toward the deck of the cartridge body. The guides can be configured to engage and support the driver even when a portion the driver is not fully seated within the staple cavity.

Figure 33:
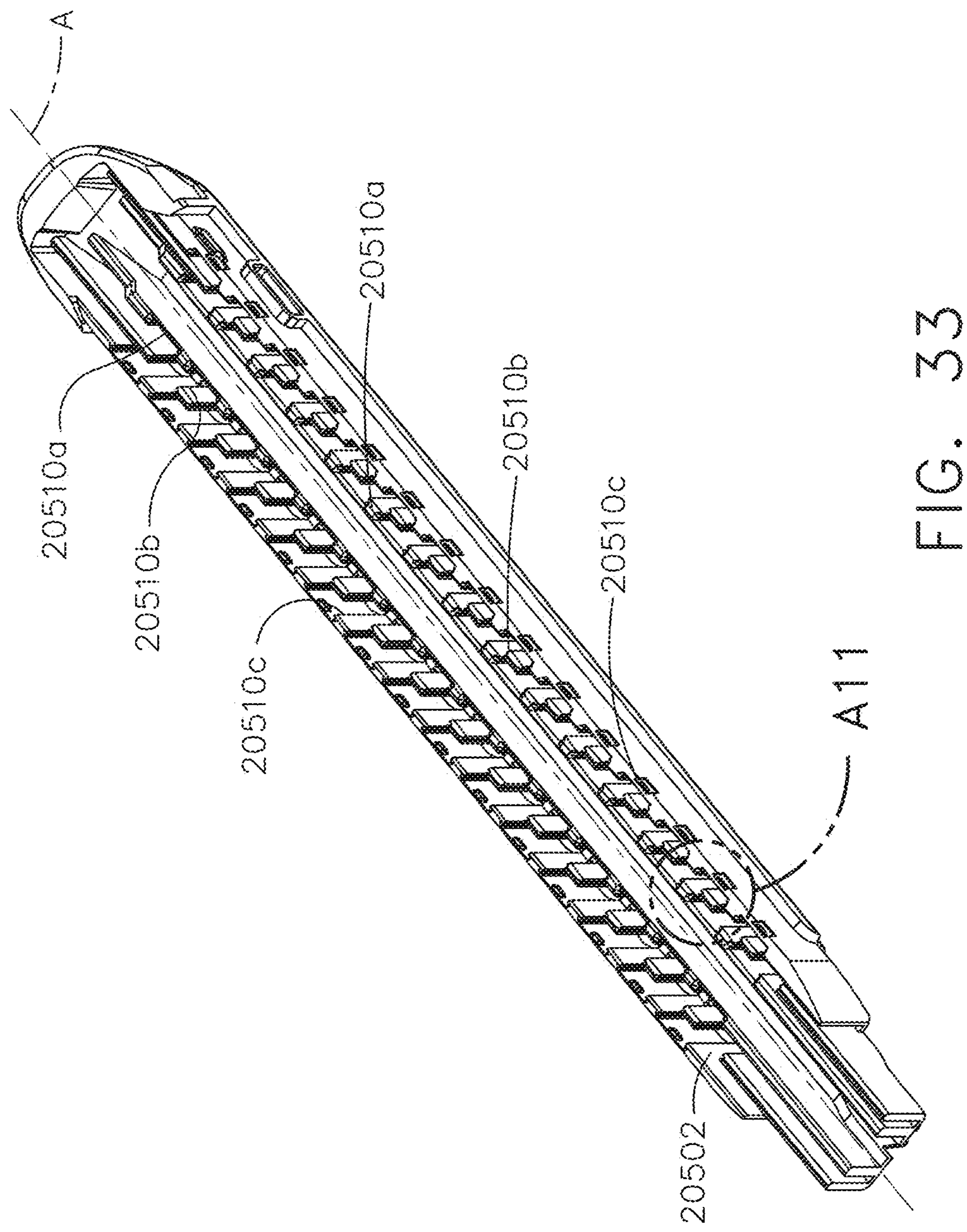
FIG. 33 is a bottom perspective view of a cartridge body with portions hidden for illustrative purposes, according to various aspects of the present disclosure.
Figure 34:
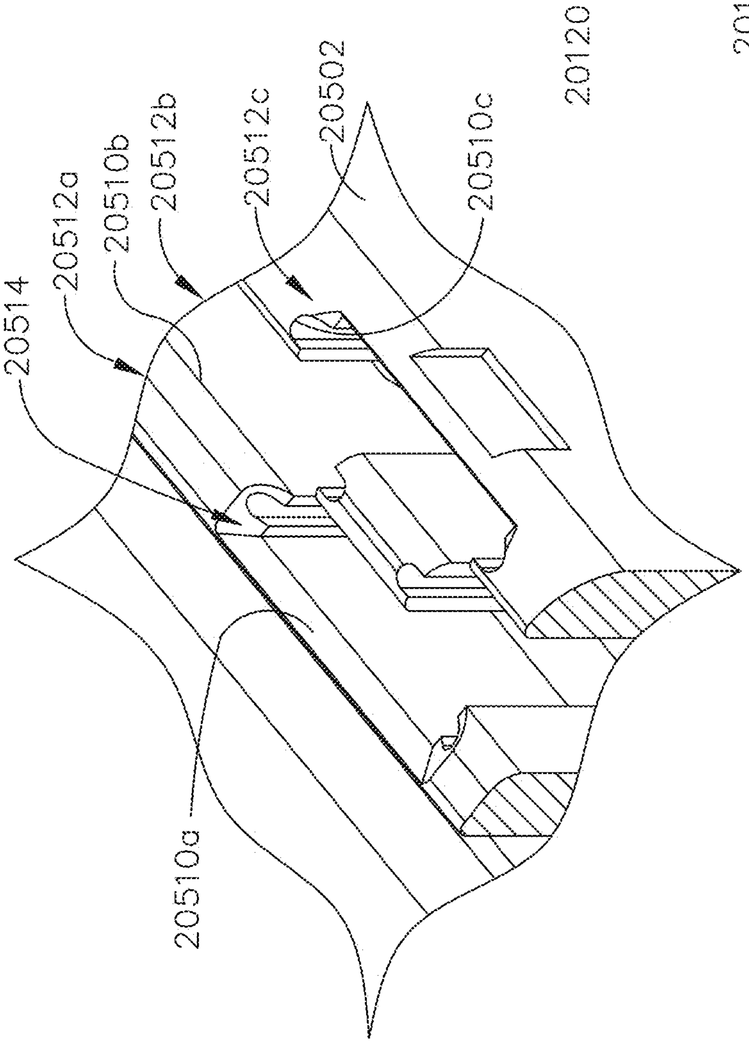
FIG. 34 is a detail view of a portion of the cartridge body of FIG. 33, depicting a chamfer defined into the cartridge body around an inner staple cavity, according to various aspects of the present disclosure.

Referring to FIGS. 33 and 34, a cartridge body 20502 is shown. In various instances, the cartridge body 20502 can be similar in many aspects to the cartridge body 20102 (FIG. 24) and can be incorporated into the staple cartridge 20100 and use the drivers 20120 (FIG. 26). Staples can be positioned in cavities 20510*a*, 20510*b*, 20510*c* defined in the cartridge body 20502. The staples are arranged in longitudinal rows on either side of a longitudinal axis A along a centerline of the cartridge body 20502. For example, the cavities 20510*a*, 20510*b*, 20510*c* are arranged in cavity rows. The cavity rows include an inner row 20512*a*, an intermediate row 20512*b*, and an outer row 20512*c* on each side of the longitudinal axis. A rotary drive screw (e.g. firing screw 261 in FIGS. 4 and 5) can be aligned with the longitudinal axis A, and can extend through the cartridge body 20502 adjacent to the inner cavity rows 20512*a*. The rotary drive screw can be between and parallel to the inner cavity rows 20512*a*, for example.

Referring primarily to FIG. 34, the cartridge body 20502 includes guide surfaces 20514 extending around the inner cavities 20510*a* in the inner row 20512*a*. In various instances, the guide surfaces 20514 are configured to guide the driver (e.g. the inner support column 20122*a* of the triple driver 20120) into and through the inner cavity 20510*a* even when the inner support column 20122*a* is not fully seated in the inner cavity 20510*a* before firing. In various instances, the guide surfaces 20514 are circumferential chamfers on the underside cartridge surface extending around the inner cavities 20510*a*. Such circumferential chamfers are configured to prevent inadvertent snags and hang-ups as the inner support column of the driver is advanced into the inner cavity 20510*a*. In other instances, the guide surfaces 20514 can comprise a fillet, for example. The guide surfaces 20514 can extend around the entire perimeter of the inner cavities 20510*a*. In other instances, the guide surfaces 20514 can be positioned around a portion of the perimeter, e.g. a first lateral side, a proximal end, and/or a distal end.

Figure 35:
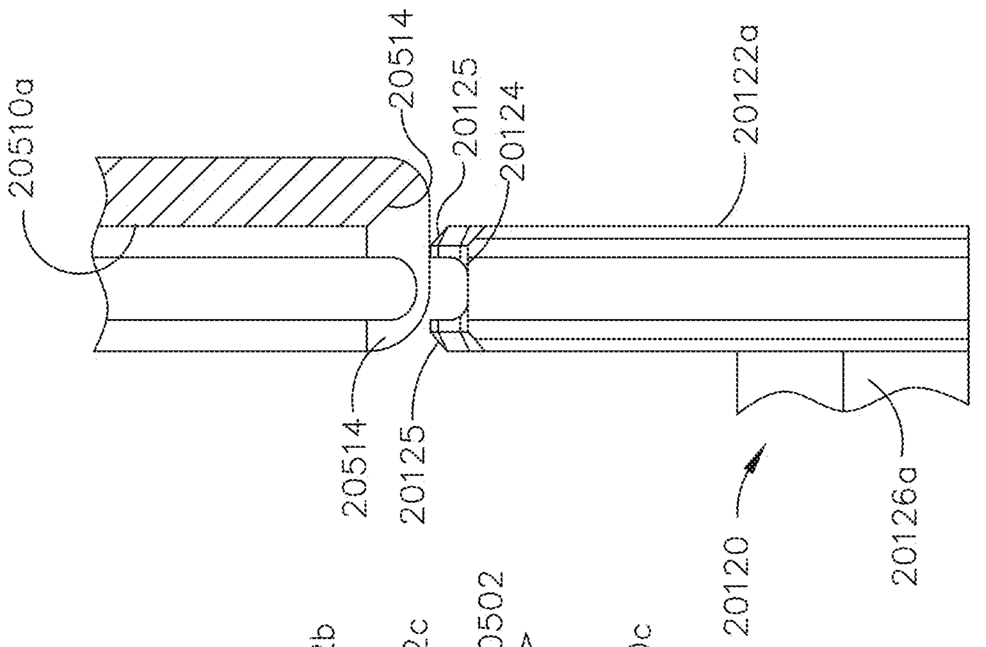
FIG. 35 is an elevation cross-section view of an inner support column of a driver and a portion of the cartridge body of FIG. 33, depicting the inner support column in an unfired configuration relative to an inner staple cavity, according to various aspects of the present disclosure.

Referring also to FIG. 35, a portion of the inner cavity 20510*a* and the driver 20120 is shown. The lower edge of the inner cavity 20510*a* includes the guide surfaces 20514 extending around the inner cavity 20510*a*. The top edge of the inner support column 20122*a* also includes a guide surface 20125, which is configured to guide the inner support column 20122*a* into alignment with the inner cavity 20510*a* even when the inner support column 20122*a* is not fully seated in the inner cavity 20510*a* prior to the firing stroke and initial lift of the driver 20120 by a sled. In such instances, the guide surfaces 20514, 20125 on the lower edge of the inner cavity 20510*a* and the top edge of the inner support column 20122*a*, respectively, are configured to interact to ensure the inner support column 20122*a* moves smoothly into the inner cavity 20510*a* during a firing stroke. As further described herein, the inner support column 20122*a* may not be fully seated in the inner cavity 20510*a* prior to the firing stroke owing to the space required by the rotary drive screw along a central longitudinal portion of the cartridge body 20502.

Figure 36:
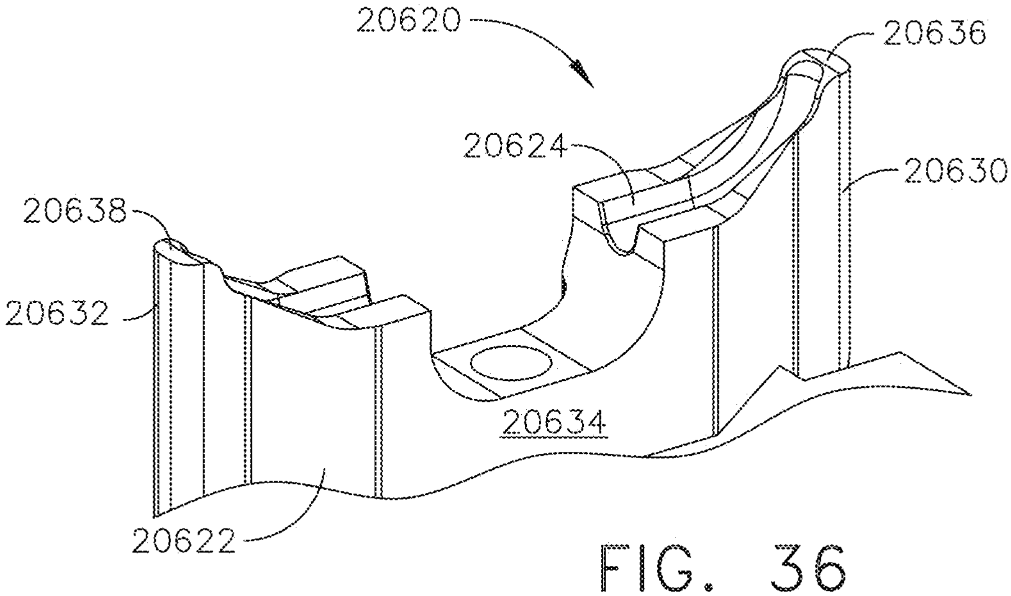
FIG. 36 is a perspective view of a portion of a support column of a driver, according to various aspects of the present disclosure.
Figure 37:
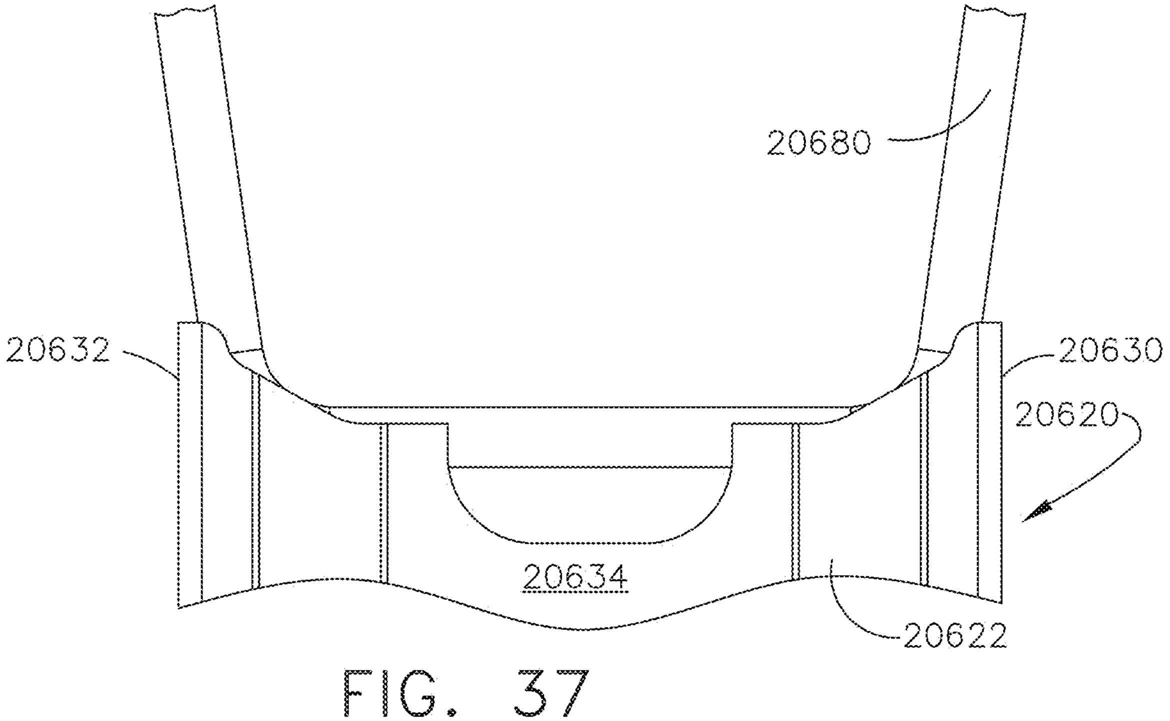
FIG. 37 is an elevational view of the portion of the support column of FIG. 36, depicting a portion of a staple supported on the support column, according to various aspects of the present disclosure.

Referring now to FIGS. 36 and 37, a portion of a driver 20620 is shown. In various aspects of the present disclosure, the driver 20620 can be a triple driver and similar in many aspects to the driver 20120 (FIG. 26). The driver 20620 can be incorporated into the staple cartridge 20100 (FIG. 24) in various aspects of the present disclosure. The driver 20620 includes a support column 20622 configured to support a staple 20680 (FIG. 37). The support column 20622 includes a proximal end 20630, a distal end 20632, and a pair of opposing sidewalls 20634 extending longitudinally between the proximal end 20630 and the distal end 20632. The sidewalls 20634 are configured to slidably engage the lateral guide surfaces in the respective staple cavity. The support column 20622 also includes a staple-supporting cradle 20624, and a base of the staple 20860 can be held in the staple-supporting cradle 20624.

The driver 20630 further includes proximal and distal upright features 20636, 20638 or extensions, which extend away from the base of the driver 20630 and away from the staple-supporting cradle 20624. The proximal upright feature 20636 is a proximal-most feature of the support column 20622 and extends from the proximal end 20630 of the support column 20622. The distal upright feature 20638 is a distal-most feature of the support column 20622 and extends from the distal end 20636 of the support column 20622. In the driver's unfired position, the proximal and distal upright features 20636, 20638 can be below the deck of the staple cartridge and extend toward the deck. The proximal and distal upright features 20636, 20638 can be configured to support the staple 20680 and guide the staple legs during formation, for example.

The proximal and distal upright features 20636, 20638 are the tallest portions of the support column 20622. In certain instances, when the driver is moved to the fired position, the proximal and distal upright features 20636, 20638 can extend above the deck and facilitate gripping and/or holding of tissue adjacent to the staples 20860. For example, the proximal and distal upright features 20636, 20638 can grip tissue at the proximal end and the distal end of the staple cavity. Moreover, the proximal and distal upright features 20636, 20638 can act as guide surfaces for the driver 20630 and can guide the support column 20632 into the fastener cavity in certain instances. For example, when the support column 20622 is not fully seated in the staple cavity prior to firing, as further described herein, the proximal and distal upright features 20636, 20638 are configured to guide the support column 20622 into alignment with the staple cavity during the firing motion.

In certain instances, the proximal and distal upright features 20636, 20638 may be incorporated into an inner support column (i.e. the support column adjacent to a firing path and/or rotary drive screw). In such instances, the proximal and distal upright features 20636, 20638 can engage the staple cavity during the firing stroke and are configured to guide the inner support column even if the inner support column is not fully seated in the staple cavity prior to firing, as further described herein. In other instances, the intermediate support column and/or the outer support column can also include at least one of a proximal upright feature 20636 and/or a distal upright feature 20638.

In certain aspects of the present disclosure, the proximal and distal upright features 20636, 20638 are configured to be received into recesses along an underside of the tissue-supporting deck when the driver 20620 is in the fully advanced position. As further described herein, the underside of the tissue-supporting deck can include an array of recesses that fit within the pocket extenders on the anvil-facing side of the deck. Pocket extenders can surround or at least partially surround the openings in the tissue-supporting deck to grip tissue and/or guide the staple legs during the firing stroke. The nesting of features on the driver with underside recesses in the tissue-supporting deck is further described herein. Nesting of the proximal and distal upright features in the pocket extenders or ridges of the cartridge deck can maintain the desired tissue gap and deck thickness in various instances.

In certain instances, a replaceable staple cartridge can be used with each firing stroke and then replaced with another replaceable staple cartridge for a subsequent firing stroke. The replaceable staple cartridge can include a cartridge body, drivers, staples, and a sled, as further described herein. Reusable, multi-fire cutting edges can be incorporated into the end effector and advanced relative to the replaceable staple cartridge in certain instances. For example, an end effector can include a firing member, such as an I-beam or an E-beam, for example, having a distal-facing upright cutting edge along a leading edge thereof. Exemplary firing members having a reusable cutting edge for use during multiple firing strokes are further described herein. In certain instances, reusable knives and the cutting edge(s) thereof can be a hardened part, which may be expensive to manufacture. In certain instances, the placement of a reusable knife in a surgical device may limit the number of times the surgical device can be reused. Moreover, to resist dulling of the knife with multiple firings, a reusable knife may not be as sharp as a single-use knife in certain instances.

In other instances, a firing member, end effector, and/or surgical device may not include a multi-fire tissue-transecting knife. Instead of being incorporated into the surgical device itself, for example, a knife can be incorporated into a replaceable staple cartridge, for example. In such instances, a fresh cutting edge can be used with each firing stroke.

Various replaceable staple cartridge assemblies having a tissue-transecting knife are described herein. In one instance, the firing member can include an integral sled component and the knife can be releasably attached or mounted to the firing member upon insertion of the staple cartridge into the surgical device or end effector thereof having the firing member.

Figure 99:
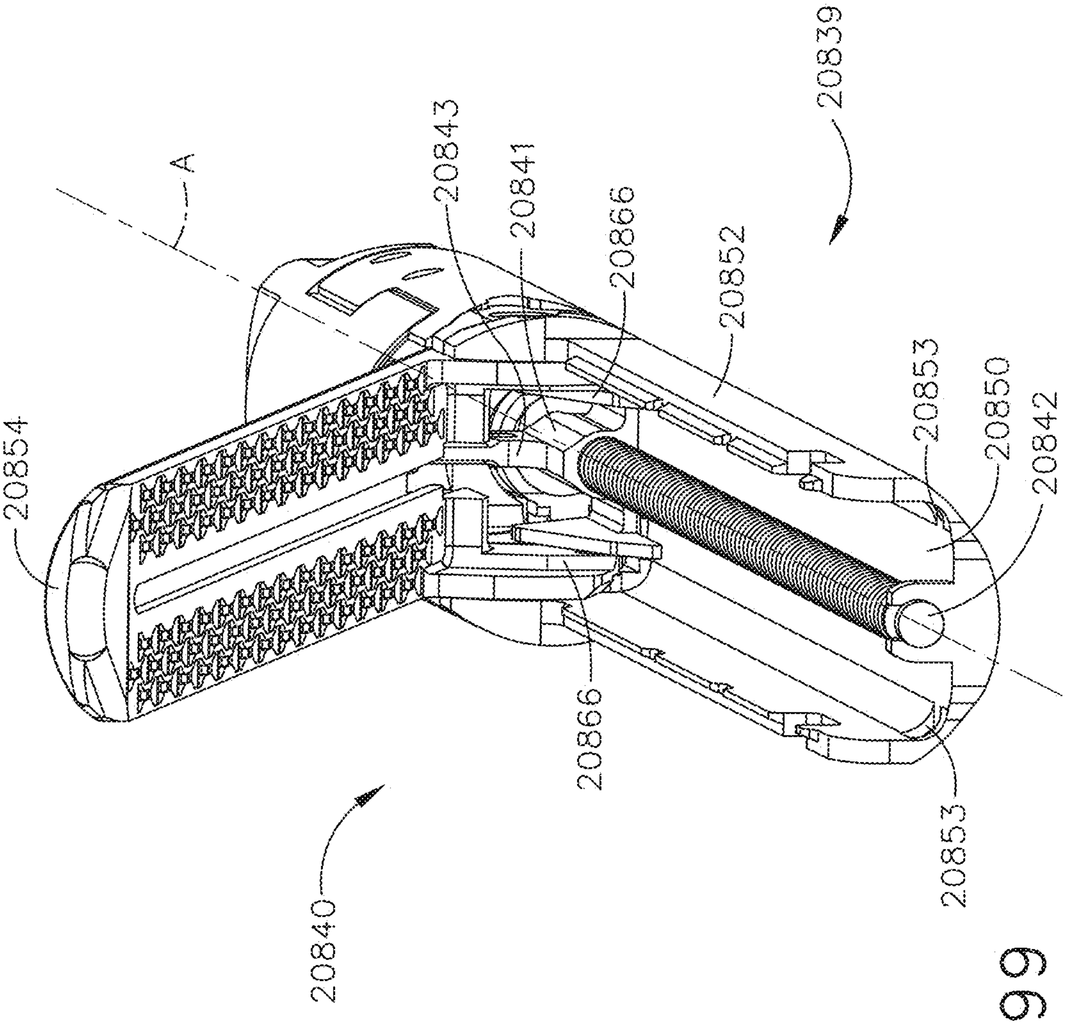
FIG. 99 is a perspective view of a surgical end effector having a firing assembly including a rotary drive screw and a reusable firing member with an integral two-rail sled, according to various aspects of the present disclosure.
Figure 105:
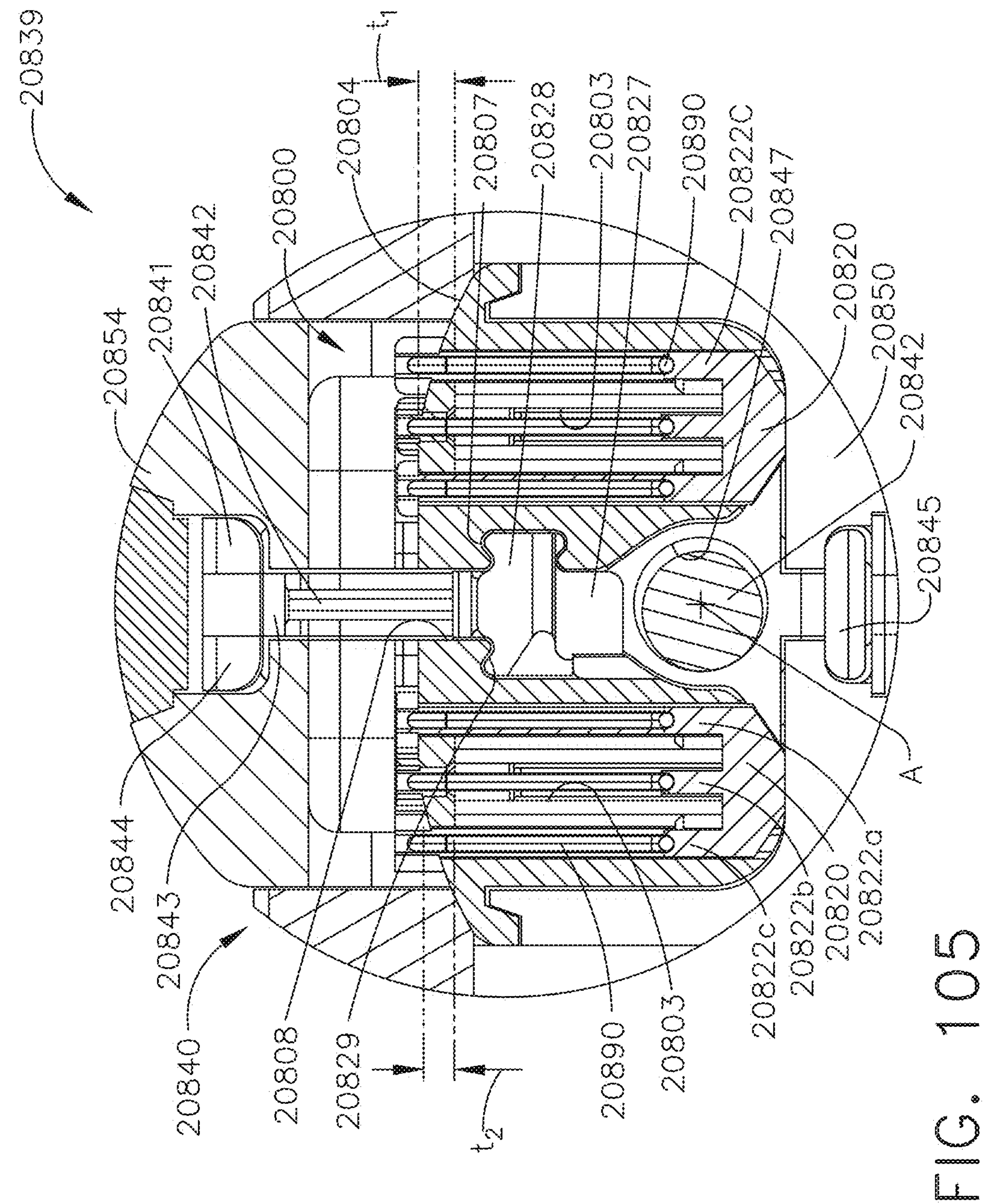
FIG. 105 is an elevation cross-section view of an end effector including the cartridge body, the firing member, and the triple drivers of FIG. 103, according to various aspects of the present disclosure.

Referring now to FIG. 99, an end effector 20840 having a firing member 20841 with an integral sled 20860 and attachment features (e.g. a recess 20846) for connecting to a single-use knife 20830 is shown. The end effector 20840 is similar in many aspects to the end effector 200 (see FIGS. 4 and 5) and is configured to cut and staple the tissue of a patient. For example, the end effector 20840 includes a cartridge jaw 20850 having opposing sidewalls 20852, and the end effector 20840 also includes an anvil jaw 20854. The cartridge jaw 20850 is configured to receive a staple cartridge, such as a replaceable staple cartridge 20800 shown in FIG. 103, for example. The end effector 20840 also includes a firing drive system 20839 that includes a rotary drive screw 20842 (FIG. 105) and the firing member 20841, which are similar to the firing screw 261 (FIGS. 4 and 5) and the firing member 270 (FIGS. 4 and 5), respectively. The firing member 20841 is driven through the end effector 20840 upon a rotation of the rotary drive screw 20842 during a firing stroke to fire staples from the staple cartridge 20800. The rotary drive screw 20842 extends along a longitudinal axis A through the fastener cartridge 20800.

Figure 100A:
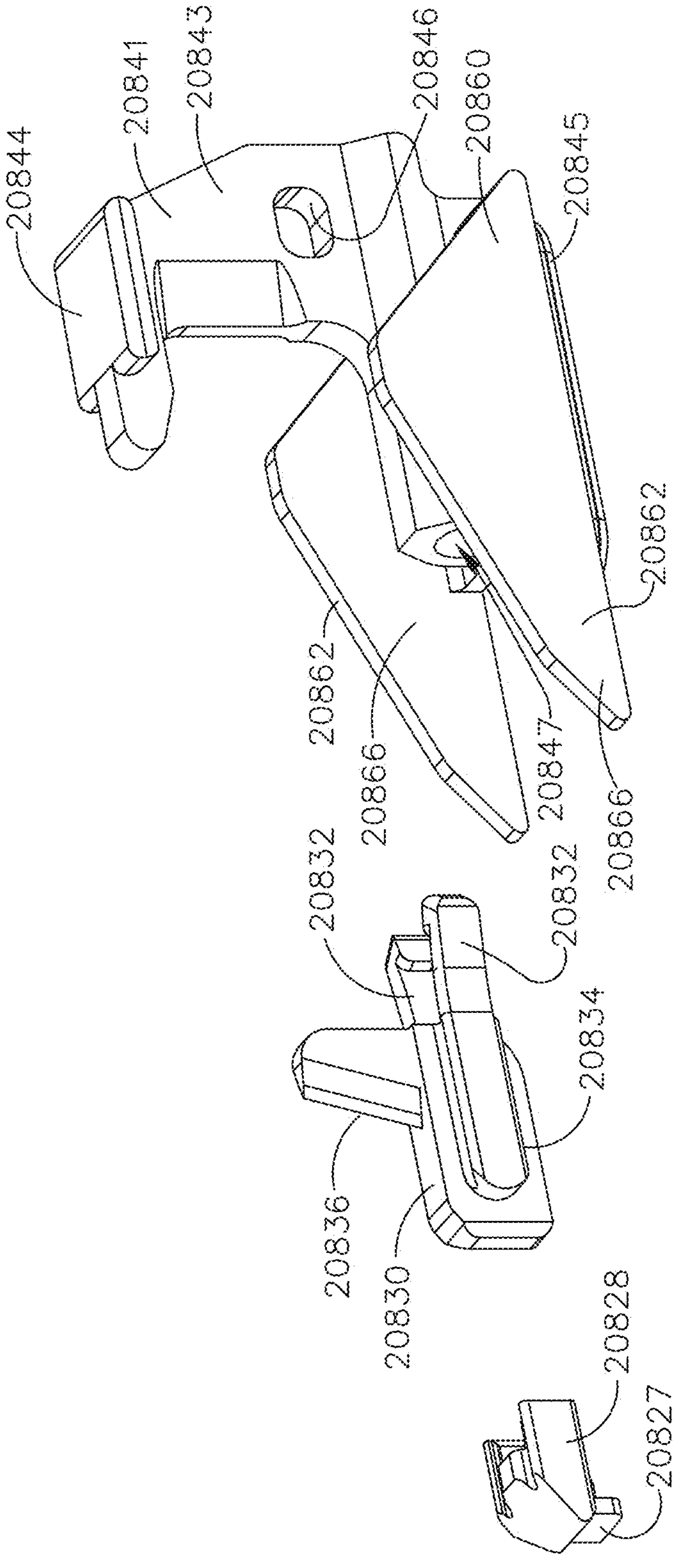
FIG. 100A is an exploded perspective view of the reusable firing member of FIG. 99 and a single-use knife and a firing indicator for use with the reusable firing member, according to various aspects of the present disclosure.

Referring primarily to FIG. 100A, the firing member 20841 includes an upright body portion 20843, upper cam members 20844 extending laterally from both sides of the upright body portion 20843, and lower cam members 20845 extending laterally from both sides of the upright body portion 20843. When the end effector 20840 is in a clamped configuration (FIG. 105), the upper cam members 20844 are configured to cammingly engage an anvil jaw 20854 of the end effector 20840 during a firing stroke, and the lower cam members 20845 are configured to cammingly engage the cartridge jaw 20850 of the end effector 20840 during the firing stroke. The upper and lower cam members 20844, 20845 are configured to clamp the jaws of the end effector 20840 and define a tissue gap during a firing stroke, as further described herein with respect to various firing members (e.g. I-beams and E-beams). A threaded opening 20847 through the upright body portion 20843 is configured to receive the rotary drive screw 20842 therethrough. In other instances, a threaded nut can be threadably coupled to the rotary drive screw 20842 and mounted to the firing member 20841. Various threaded nuts and alternative firing members are further described herein.

Figure 103:
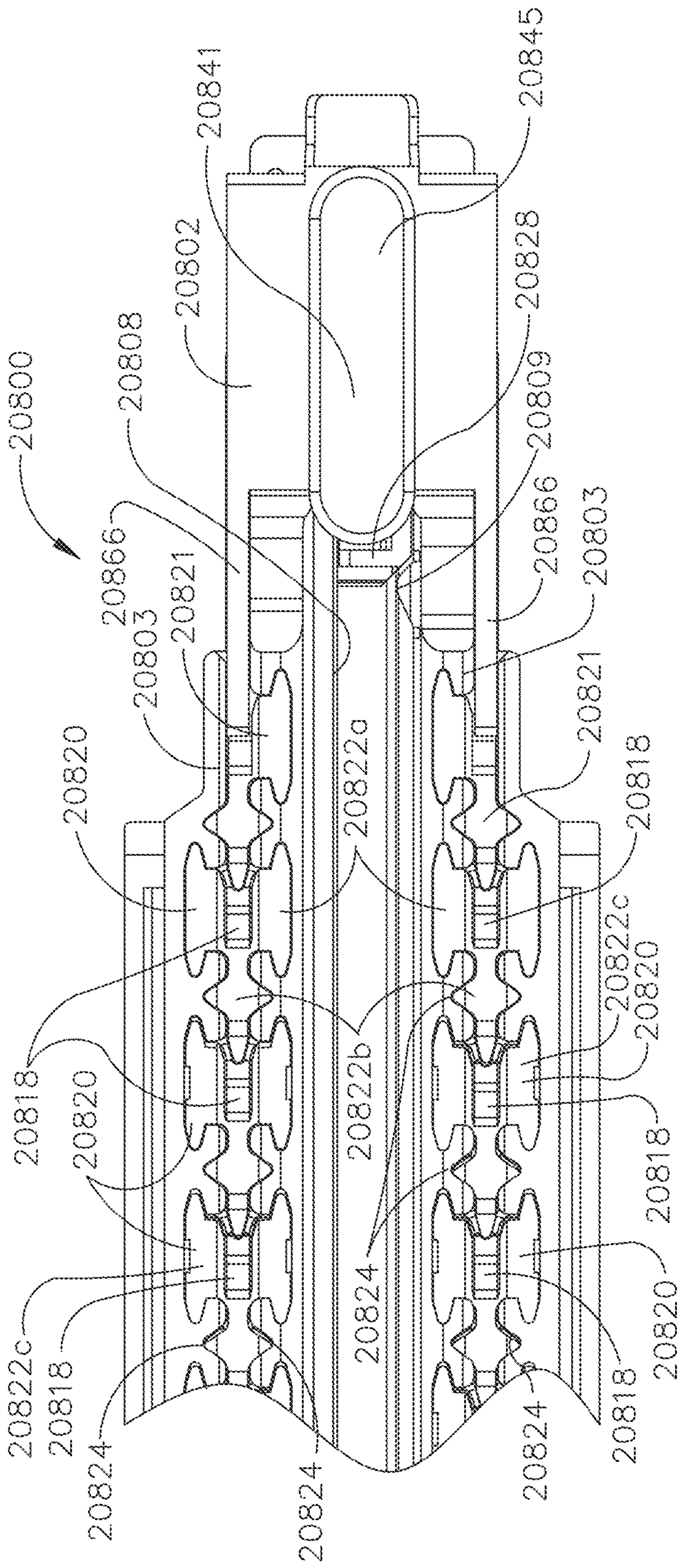
FIG. 103 is a plan view of a portion of a cartridge body housing the triple drivers of FIG. 100B, and further depicting the firing member of FIG. 100A, according to various aspects of the present disclosure.

Referring still to FIG. 100A, the firing member 20841 further includes an integrated sled 20860. The sled 20860 has two rails 20866. One of the rails 20866 is configured to engage a row of staple drivers on each side of the surgical end effector 20800. Stated differently, the sled 20860 includes a single rail 20866 for each side of the surgical end effector 20800, i.e. for each side of the staple cartridge 20800 (FIG. 103). A single rail on each side can save lateral space in the surgical end effector 20840, which can provide additional space to accommodate the rotary drive screw 20842 along the central portion of the surgical end effector 20840. In such instances, the sled 20860 can be a reusable component that is provided with the firing member 20841 and the surgical device, for example.

Referring primarily to FIG. 103, the firing member 20841 is driven through the staple cartridge 20800, which includes a cartridge body 20802 and drivers 20820, 20821 movably positioned therein. The drivers 20820 are triple drivers, and the drivers 20821 are double drivers. In various instances, the proximal-most drivers in the staple cartridge 20800 are the double drivers 20821 and, in other instances, one or more of the proximal-most drivers can be single drivers. The double drivers 20821 include a lateral flange that includes a ramped surface for driving engagement by the sled rail 20866 that is also aligned with ramped recesses 20818 (FIG. 102) on the triple drivers 20820. Stated differently, the double drives 20821 and the triple drivers 20820 are both driven by a single sled rail 20866 on each side of the fastener cartridge 20800.

Parallel longitudinal slots 20803 (FIG. 103) through the cartridge body 20802 are dimensioned to receive the rails 20866 during the firing stroke. Stated differently, as the upright body portion 20843 of the firing member 20841 moves through a central longitudinal slot 20808 in the cartridge body 20802, the rails 20866 move along parallel slots 20803 along an underside of the cartridge body 20802. The parallel longitudinal slots 20803 are also parallel to the longitudinal slot 20808 through which the upright body portion 20843 of the firing member 20841 protrudes.

In other instances, the integral sled of a firing member 20841 can more than one rail on each side. For example, integrated sleds having four rails and six rails are also contemplated.

The firing member 20841 is adapted to releasably connect to the knife 20830. The knife 20830 includes opposing spring arms 20832, which extend proximally toward the upright body portion 20843 of the firing member 20841 and resiliently engage the upright body portion 20843. The spring arms 20832 snap around the upright body portion 20843 and extend into a cavity 20846 defined into the upright body portion 20843. The knife 20830 also includes a longitudinal body 20834, which is configured to rest and/or nest on a complementary surface on the firing member 20841 over the threaded opening 20847 for the rotary drive screw 20842, for example. The knife 20830 further includes an upright cutting edge 20836, which is configured to extend above a tissue-supporting deck 20804 (FIG. 105) to transect tissue during a firing stroke.

In various instances, the fastener cartridge 20800 and the cartridge jaw 20850 can include alignment and/or leveraging features for facilitating installation of the fastener cartridge 20800 into the cartridge jaw 20850. Various alignment and leveraging features are further described herein. These features can also align the knife 20830 with the firing member 20841 and, more specifically, align the spring arms 20832 with the cavity 20846, to ensure the knife 20830 is connected to the firing member 20841 upon insertion of the staple cartridge 20800 into the cartridge jaw 20850.

In the unfired staple cartridge 20800, the knife 20830 is aligned with the indicator sled 20828, which is configured to be pushed distally by the knife 20830 during the firing stroke. As further described herein, the indicator sled 20828 provides a visible indication to a clinician and/or user when a firing stroke has been completed by moving into a window 20806 (FIG. 114) in the nose of the cartridge body 20802, as further described herein. Moreover, the indicator sled 20808 is configured to selectively overcome a missing and/or spent cartridge lockout in certain instances, as further described herein.

The indicator sled 20828 and the knife 20830 are components of the staple cartridge 20800. When the staple cartridge 20800 is installed in the surgical end effector 20840, the knife 20830 is brought into alignment with the firing member 20841 such that the spring arms 20832 resiliently engage the opening 20846. The insertion angle of the staple cartridge 20800 is configured to ensure the proper alignment of the spring arms 20832 and the opening 20846.

In such instances, a fresh knife can be provided with each staple cartridge 20800 and for each firing stroke.

Figure 100B:
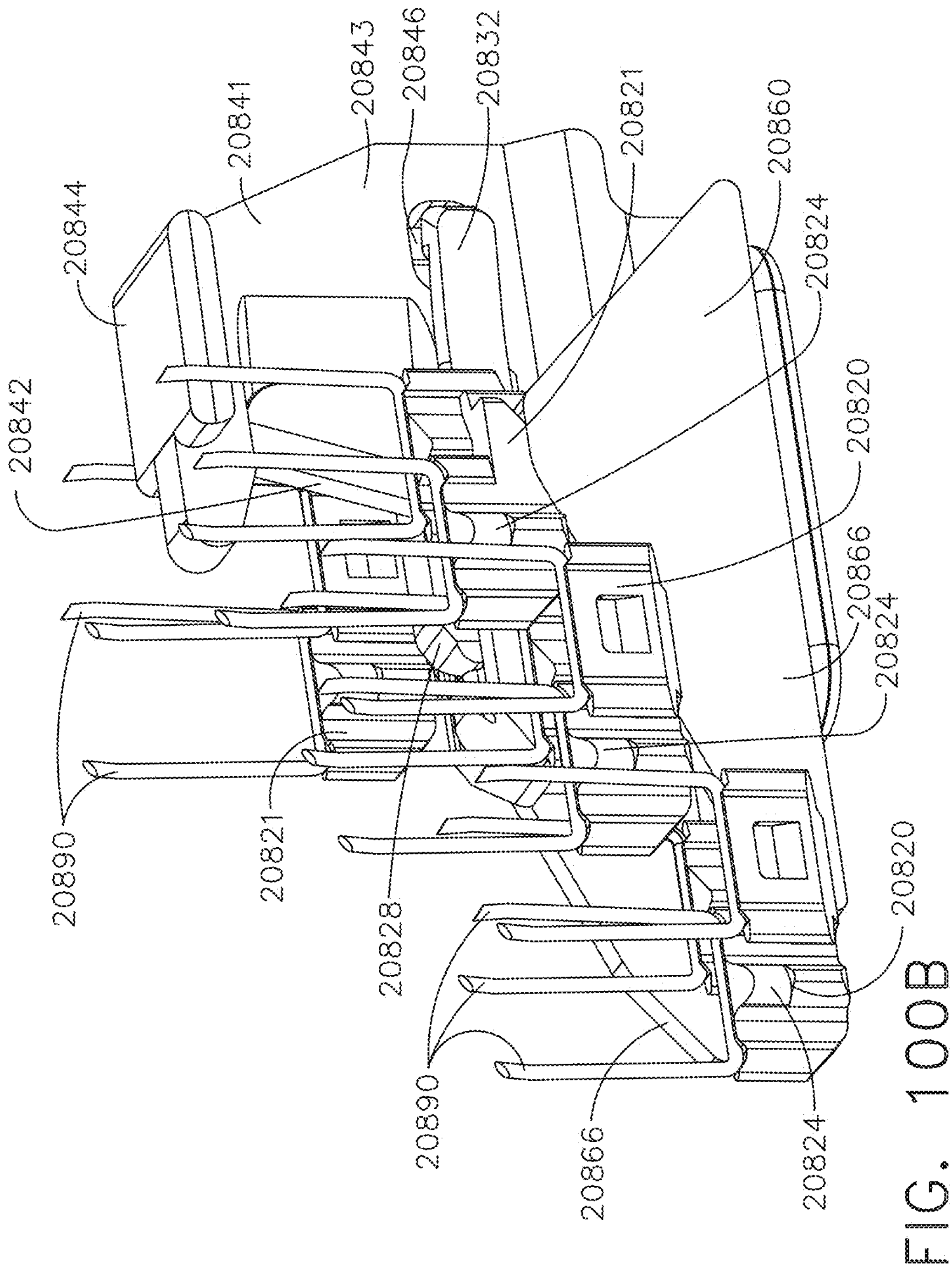
FIG. 100B is a perspective view of the single-use knife and firing indicator of FIG. 100A assembled to the reusable firing member of FIG. 99, and further depicting triple drivers and staples thereon being deployed by the integral two-rail sled of the reusable firing member, according to various aspects of the present disclosure.
Figure 101:
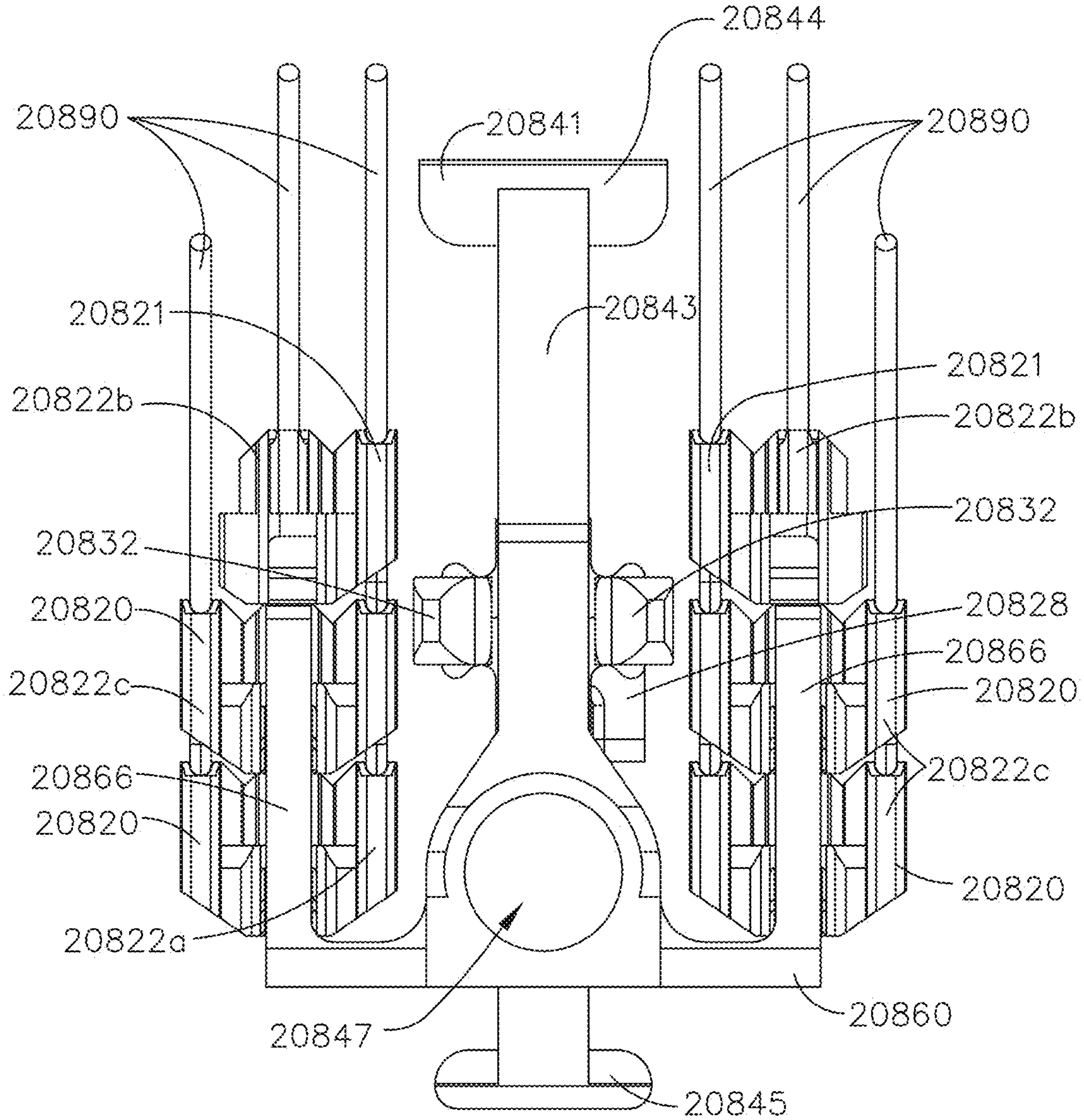
FIG. 101 is an elevation view of the triple drivers, staples, and the reusable firing member of FIG. 100B, according to various aspects of the present disclosure.

Referring primarily to FIGS. 100B and 101, the integral sled 20862 is configured to drivingly engage the triple drivers 20820 during a firing stroke. The firing member 20841 and the sled 20862 move along a longitudinal path in the staple cartridge 20800 during a firing stroke to lift the drivers 20820 along transverse axes.

Figure 102:
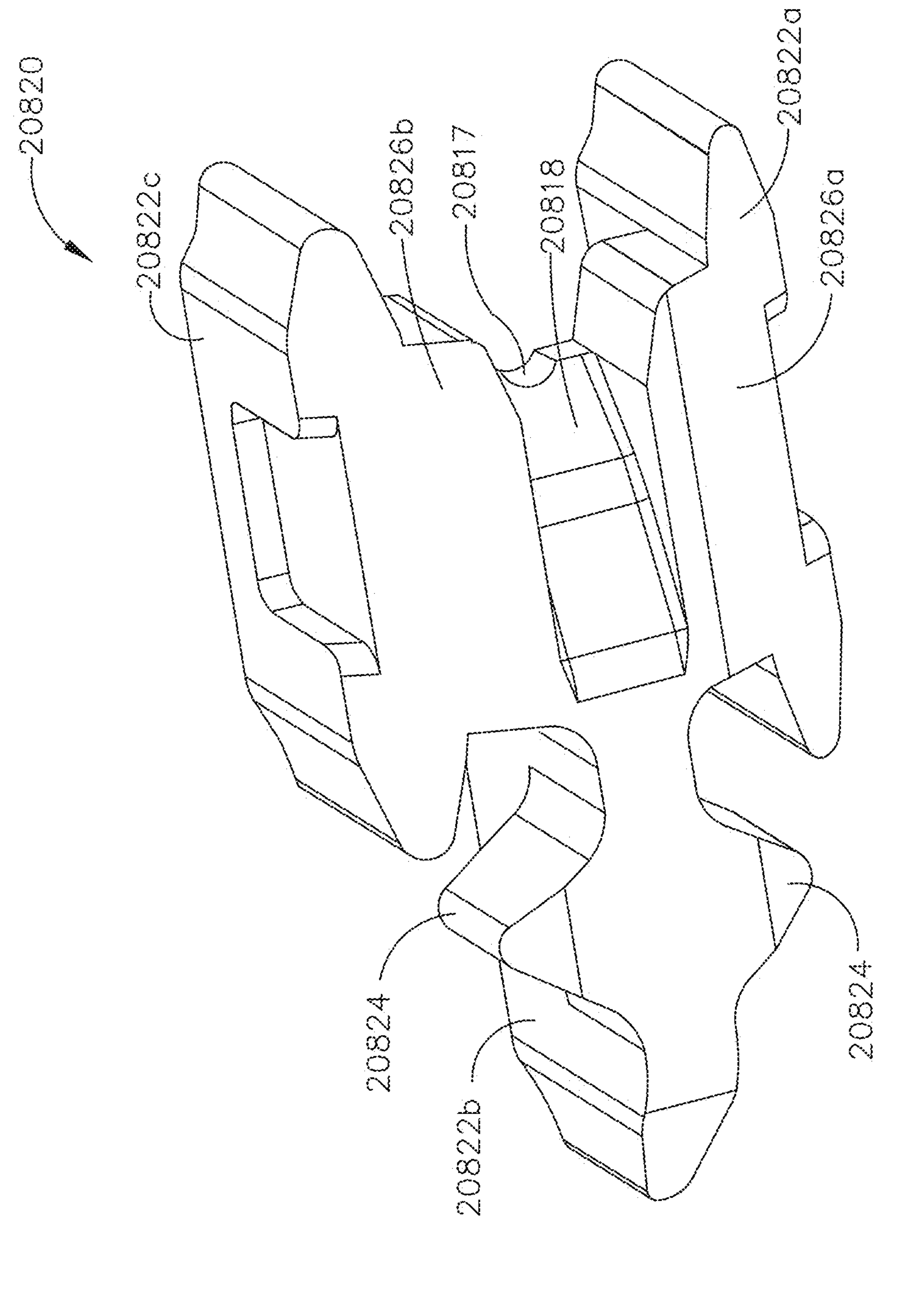
FIG. 102 is a perspective view of one of the triple drivers of FIG. 100B, according to various aspects of the present disclosure.

The triple drivers 20820 are lifted by a single sled rail 20862 on each side of the staple cartridge 20800. Each triple driver 20820 includes a recessed ramp 20818 (FIG. 102), which is positioned and dimensioned to receive the sled rail 20862. Stated differently, the sled 20860 has a single rail 20862 on each side of the central portion, and the single rail 20872 is configured to lift and drive the triple drivers 20820. In effect, a single rail 20862 is configured to fire all the staples on one side of the staple cartridge 20800 and is configured to fire staples across three rows (e.g. inner row, intermediate row, outer row) via the triple drivers 20820. Referring primarily to FIG. 102, the triple driver 20820 includes the recessed ramp 20818 (FIG. 102), which is dimensioned to receive the sled rail 20862. The recessed ramp 20818 extends along a central portion of the triple driver 20820 (e.g. underlying an intermediate/middle support column), as further described herein.

The triple driver 20820 can be similar to the triple driver 20120 (FIG. 26) in many aspects. For example, the triple driver 20820 is configured to support three staples 20890 (FIGS. 100B and 101), and to lift the three staples 20890 simultaneously. The triple driver 20820 also includes three support columns—an inner support column 20822*a* configured to support an inner staple 20890 in an inner row of staples, an intermediate support column 20822*b* laterally outboard of the inner support column 20822*a* configured to support an intermediate staple 20890 in an intermediate row of staples, and an outer support column 20822*b* laterally outboard of the intermediate support column 20822*b* and configured to support an outer staple 20890 in an outer row of staples.

The triple driver 20820 also includes bridges 20826 extending between adjacent support columns 20822. For example, a first bridge 20826*a* extends between the inner support column 20822*a* and the intermediate support column 20822*b*, and a second bridge 20826*b* extends between the intermediate support column 20822*b* and the outer support column 20822*c*. The recessed ramp 20818, which is aligned with the drive rail 20866, is positioned between the first bridge 20826*a* and the second bridge 20826*b* and proximal to the intermediate support column 20822*b*.

More specifically, the recessed ramp 20818 is longitudinally aligned with the intermediate support column 20822*b*. Consequently, the intermediate support columns 20822*b* of the drivers 28020 are positioned in the parallel longitudinal slots 20803 through the cartridge body 20802 and are unsupported, or at least unsupported along a lower portion thereof, by the cartridge body 20802 when in the unfired positions in the cartridge body 20802. In such instances, the staple 20890 in the intermediate row of staples on each side of the cartridge body is supported by the intermediate support column 20822*b* and guided largely by a tissue-supporting deck 20804 of the cartridge body 20802. In certain instances, pocket extenders and/or ridges along the tissue-supporting deck 20804 can further guide the staples 20890 during the firing stroke.

The triple driver 20820 can be symmetrical about a longitudinal axis along the recessed ramp 20818. In various instances, the triple driver 20820 can include wings 20824, which extend laterally outward on both sides of the intermediate support column 20822*b*. The wings 20824 are configured to prevent driver roll and to strengthen the intermediate support column 20822*b*, in certain instances. For example, the wings 20824 can help balance the intermediate support column 20822*b* during the firing stroke when the intermediate support column 20822*b* is unsupported, or largely unsupported, by the cartridge body 20802.

Figure 104:
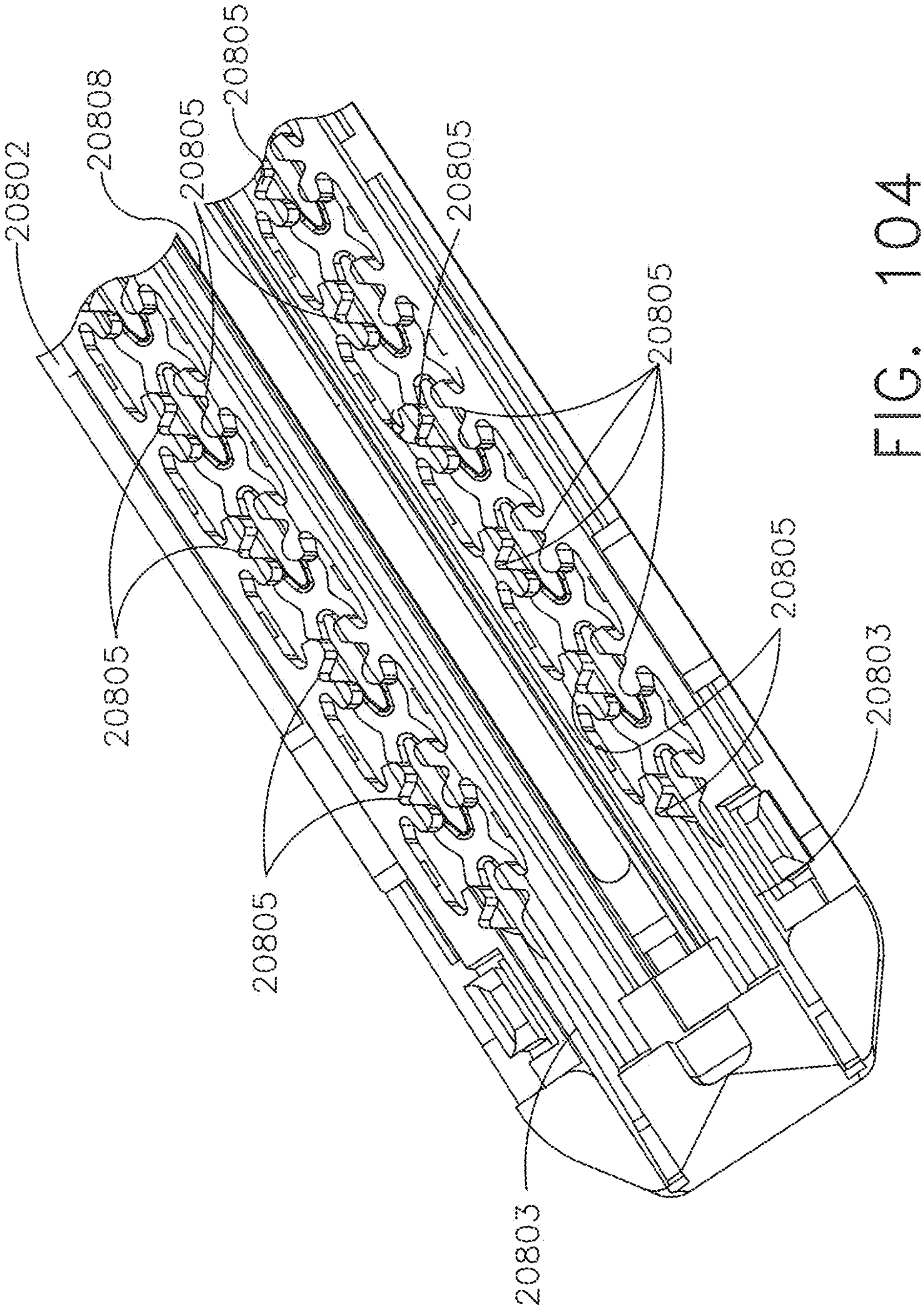
FIG. 104 is perspective view of the underside of a portion of the cartridge body of FIG. 103, according to various aspects of the present disclosure.

Referring primarily to FIG. 103, the wings 20824 extend into complementary grooves 20805 in the cartridge body 20802. During a firing stroke, the wings 20824 move in the grooves 20805 upward toward the tissue-supporting deck 20804. Referring primarily to FIG. 104, the grooves 20805 are positioned on either side of the intermediate staple cavities and extend from the underside of the cartridge body 20802 to the tissue-supporting deck 20804. In certain instances, the tissue-supporting deck 20804 can catch, block, and/or stop further upward motion of the wings 20824 to retain the drivers 20820 in the cartridge body 20800 upon completion of the firing stroke.

Referring still to FIG. 103, a distal portion of the intermediate support column 20822*b* is further configured to nest in a portion of the adjacent triple driver 20820. More specifically, the triple driver 20820 include a proximal groove 20817 (FIG. 102), which is dimensioned to receive a distal tip of the adjacent (e.g. directly behind/proximal) triple driver 20820. The nesting arrangement of triple drivers 20820 arranged end-to-end with nesting features therebetween is configured to further facilitate alignment and cooperative support of the triple drivers 20820 in the cartridge body 20802.

In short, the staple cartridge 20800 can include triple drivers 20820 which are configured to be lifted by a single sled rail 20866 that pushes on a center portion and ramped recess 20818 of the triple driver 20820 during a firing stroke. The triple drivers 20820 can further includes wings 20824 on both sides, which prevent roll of the triple driver 20820 during the firing stroke. The wings 20824 can move in corresponding slots in the cartridge body 20802. In certain instances, the sled 20860 can be integrally-formed with the firing member 20841 (e.g. an I-beam or E-beam). In such instances, the sled 20860 can be a reusable component along with the firing member 20842; however, a fresh knife 20830 can be provided with each staple cartridge 20800. In other instances, the sled can be a discrete component in the staple cartridge and, in certain instances, the firing member 20841 can include an integral cutting edge.

In various instances, triple drivers and a firing member with an integral two-rail sled, as described herein, can allow the triple driver to be narrower and, thus, allow more space in the cartridge body for a rotary drive screw. For example, the rotary drive screw can be positioned farther upward in the end effector closer to the upper cam of the firing member, rather than along the lowest portion of the end effector. Narrower drivers can provide a tighter staple line, for example, which may also improve homeostasis in certain instances. Additionally, the inner rows of staples can be moved laterally outward to accommodate the rotary drive screw, which may reduce the likelihood and/or incidences of staple tear out. Moreover, the cartridge body can provide a robust design without narrower support columns, towers, and/or thin sidewalls between the staple cavities and/or the longitudinal slot for the firing member. The sled rails can also be wider in certain instances and, thus, may be less prone to bending under substantial firing loads. In certain instances, the staple overdrive can be minimized when bending and flexing of the sled rails is limited.

Figure 106:
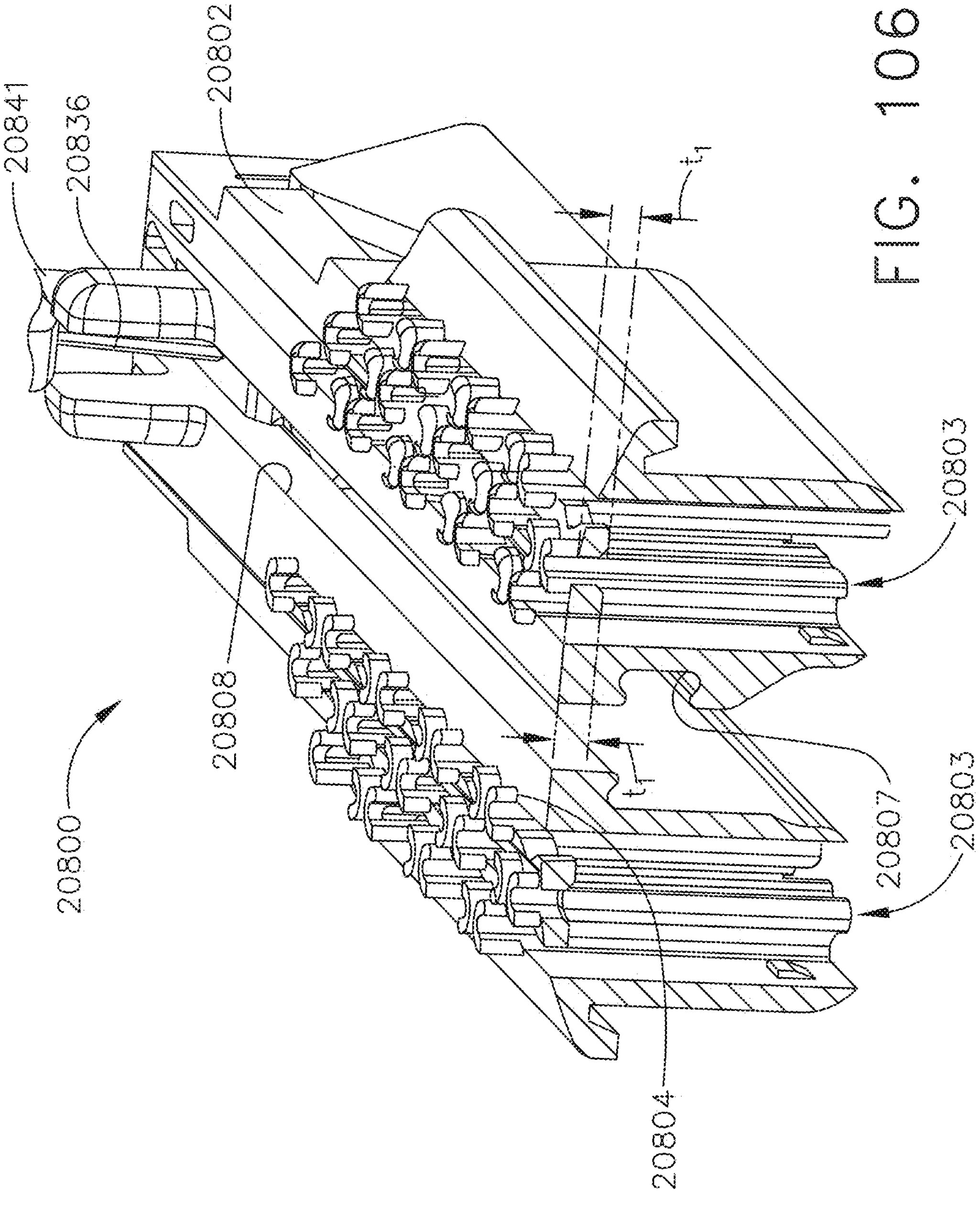
FIG. 106 is a perspective cross-section view of the cartridge body of FIG. 103, according to various aspects of the present disclosure.
Figure 107:
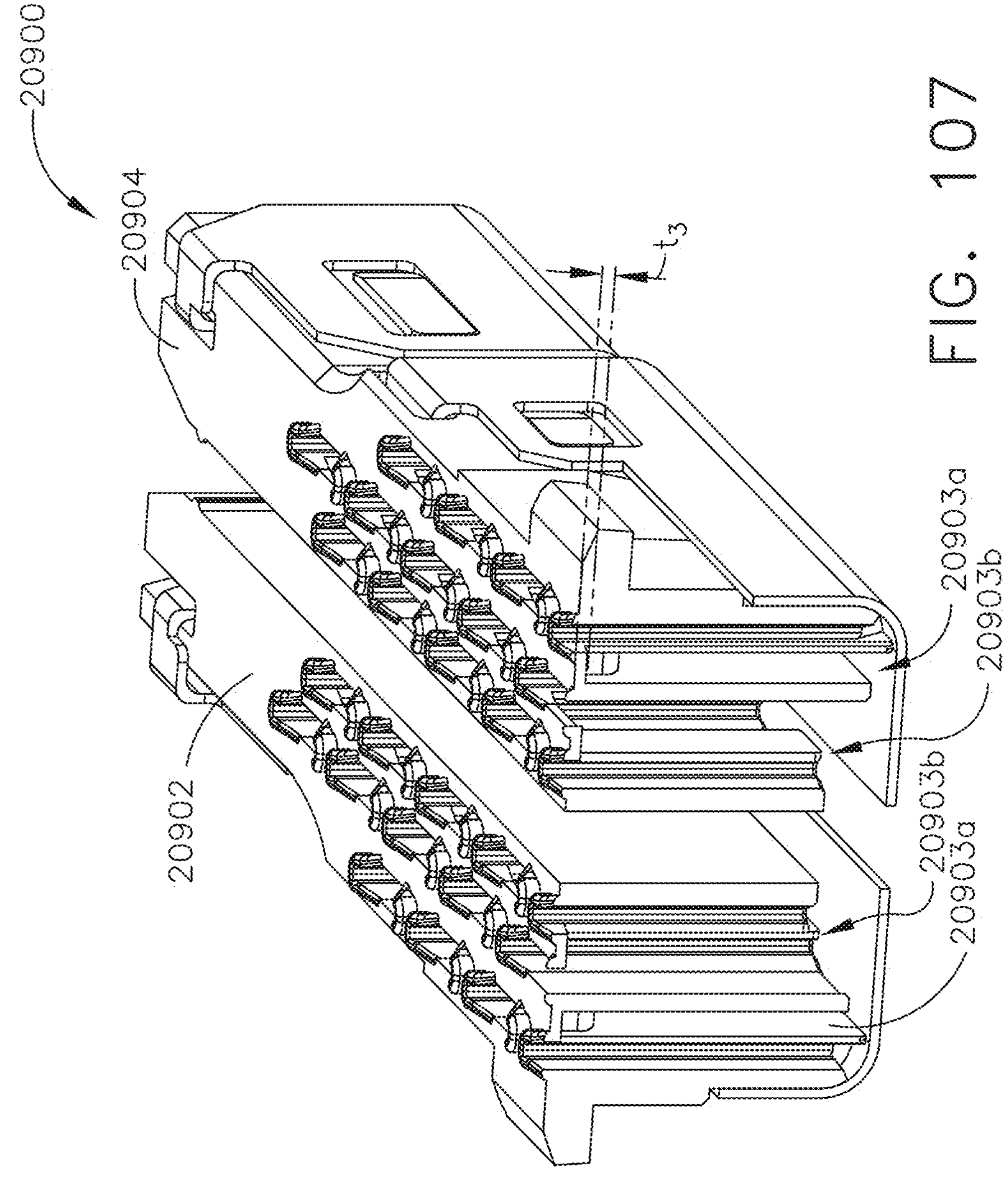
FIG. 107 is a perspective view of a cartridge body, according to various aspects of the present disclosure.
Figure 108:
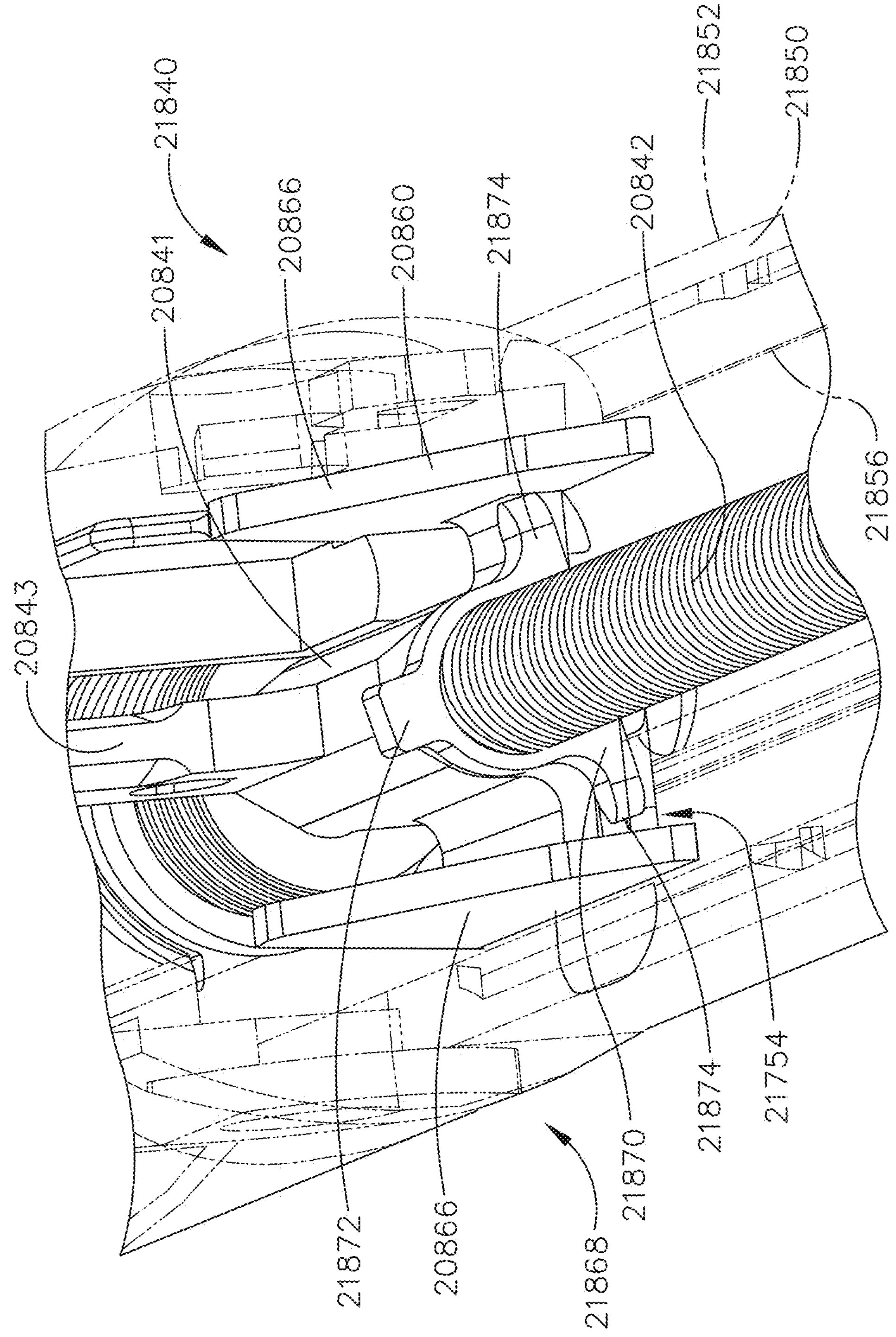
FIG. 108 is a perspective view of a portion of an end effector including the drive assembly of FIG. 99, depicting a lockout arrangement including a lock nut mounted to the rotary drive screw, wherein the lockout nut is in a locked position, according to various aspects of the present disclosure.

Referring primarily to FIG. 106, the staple cartridge 20800 includes robust support walls for withstanding a clamping load, and the tissue-supporting deck 20804 defines a thickness t1 along an inner edge of the intermediate staple cavity and a thickness t2 along an outer edge of the intermediate staple cavity. Conversely, referring now to a staple cartridge 20900 having a cartridge body 20902 and a tissue-supporting deck 20904, the support walls of the cartridge body 20902 can be narrower than the walls in the cartridge body 20802. Moreover, the tissue-supporting deck 20904 has a thickness t3, which is less than the thickness t1 and thickness t2 of the tissue-supporting deck 20804. The cartridge body 20902 is adapted to receive a four-rail sled, for example.

Effecting a firing stroke when a staple cartridge is missing from the surgical end effector can result in a knife transecting the clamped tissue without any means for sealing the transection. For example, without staples, such as staples, for example, a stapling device cannot staple and seal the cut tissue. Similarly, if an empty or spent staple cartridge is loaded in the end effector, i.e. a staple cartridge without staples or without a full set of staples, the tissue also would not be fully sealed along the transection. A missing cartridge lockout can prevent a firing stroke when a staple cartridge is missing from the end effector and a spent cartridge lockout can prevent a firing stroke when a spent staple cartridge is loaded in the end effector. In certain instances, a lockout can prevent a firing stroke when the staple cartridge is missing and spent. In instances in which a rotary firing screw extends through the end effector, the lockout can be configured to limit and/or prevent rotation of the rotary firing screw and, thus, to prevent the firing stroke.

In one aspect, a lock nut can be positioned on the rotary drive screw and a lockout key can be incorporated into a movable feature in the staple cartridge. In the locked configuration, the lock nut rotates out of firing alignment and into a lockout notch in the end effector. Upon installing an unfired staple cartridge in the end effector, the lockout key engages the lock nut to rotate it into firing alignment and out of the lockout notch. The lock nut moves distally along the rotary drive screw during the firing stroke and the lockout key is also pushed distally during the firing stroke. The lockout key can remain in a distal position upon completion of the firing stroke and/or retraction of the firing member; however, the lock nut can return to a proximal position in the end effector. Because the staple cartridge has been fired (e.g. spent), the lock nut again rotates out of firing alignment and into the lockout notch to prevent a subsequent firing stroke until a replacement unfired staple cartridge is installed in the end effector. In other instances, a lock on the rotary drive screw may not be threadably engaged with the rotary drive screw and a spring can bias the lock into a lockout notch to selectively prevent a firing stroke.

Such a lockout arrangement can be configured to prevent a firing stroke when a staple cartridge is missing and/or when the staple cartridge in the end effector has been spent/fired. Moreover, these arrangements can take up a minimal amount of space in the end effector. Moreover, the components can be simple and robust. In the instances of a lock nut threadably coupled to the rotary drive screw, only a single additional component in the end effector is needed for the lockout configuration. In various instances, the lockout key can provide a visual indication to a clinician that the staple cartridge has already been fired.

Referring now to FIGS. 108-115, a lockout arrangement 21868 and various components thereof are shown. The lockout arrangement 21868 is incorporated into a surgical end effector 21840, which is similar to the surgical end effector 20840 (see FIG. 99) in many aspects. Moreover, the end effector 21840 is adapted to receive the staple cartridge 20800 (see FIG. 103). The end effector 21840 includes a cartridge jaw 21850, which is similar to the cartridge jaw 20850 (see FIG. 99); however, the cartridge jaw 21850 further includes a lockout notch 21854 defined in a bottom side 21856.

More specifically, the cartridge jaw 21850 includes a bottom side 21856 and sidewalls 21852 forming a channel that is dimensioned and structured to receive the staple cartridge 20800 therein. The lockout notch 21854 comprises a lateral recess or opening in a proximal portion of the bottom side 21856. The lockout notch 21854 is aligned with a lockout nut 21874 threadably coupled to the rotary drive screw 20842 when the rotary drive screw 20842 and lockout nut 21874 thereon are in an unfired or proximal position.

The lock nut 21870 includes a central threaded aperture through a body portion, opposing flanges 21874, and a lug 21872. The flanges 21874 and the lug 21872 extend radially outward from the body portion. In an unlocked position (FIGS. 109B and 111), the flanges 21874 extend laterally outward to an inside surface of the bottom side 21856 of the cartridge channel 21850 and are positioned to ride along and/or adjacent to the inside surface. Moreover, in an unlocked positioned, the lug 21872 is aligned with the upright body portion 20843 of the firing member 20841. In the locked position (see FIGS. 108, 109A, 115), the flanges 21874 are rotated out of alignment with the inside surface of the bottom side 21856 such that one of the flanges 21874 rotates into the lockout notch 21854. Moreover, in the locked position, the lug 21872 is rotated out of firing alignment with the upright body portion 20843 of the firing member 20841.

Figure 109A:
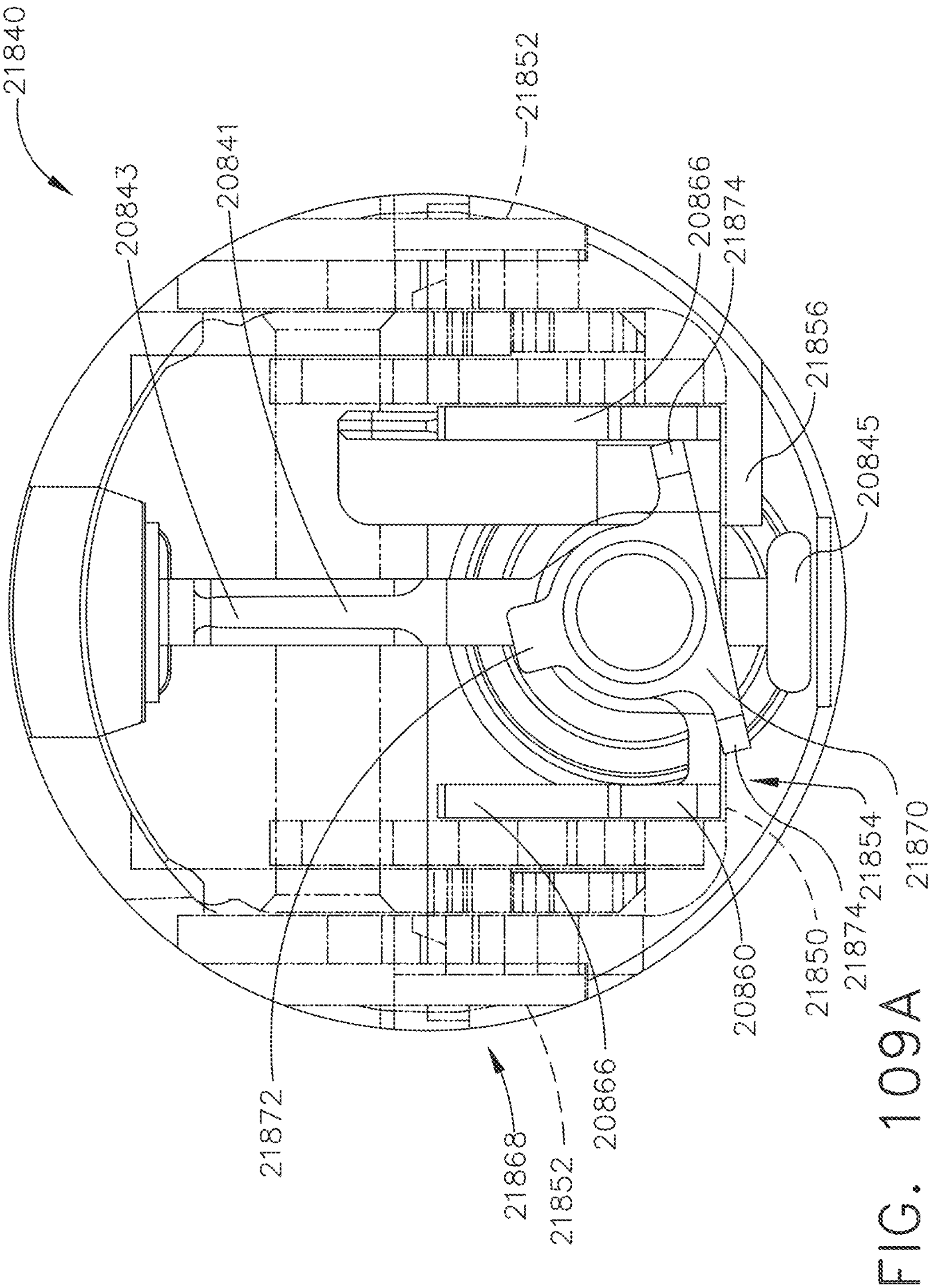
FIG. 109A is an elevation view of the end effector of FIG. 108 with certain parts removed and other parts hidden and shown with phantom lines, depicting the lock nut in the locked position, according to various aspects of the present disclosure.
Figure 109B:
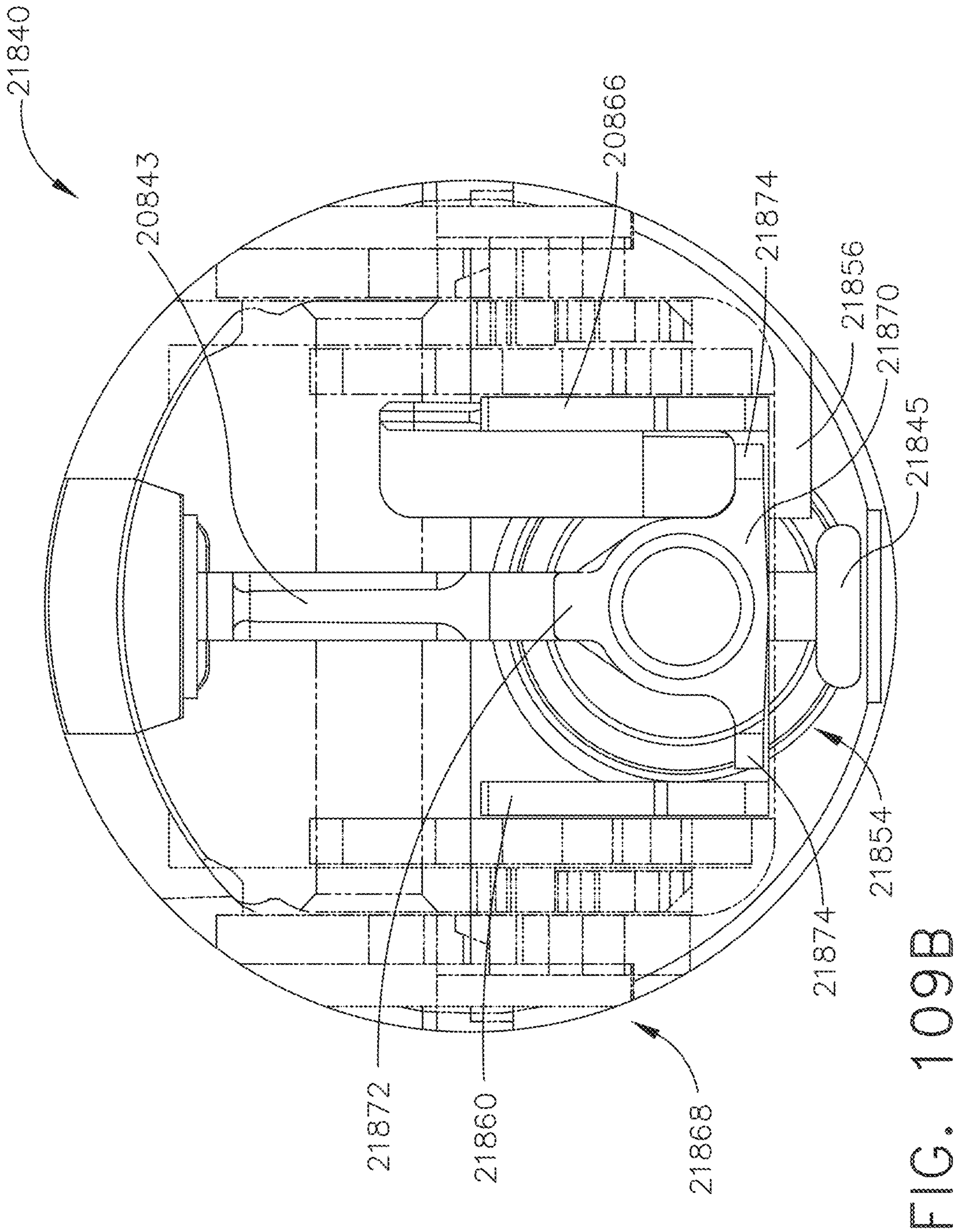
FIG. 109B is an elevation cross-section view of the end effector of FIG. 108 with certain parts removed and other parts hidden and shown with phantom lines, depicting the lock nut in an unlocked position, according to various aspects of the present disclosure.
Figure 110:
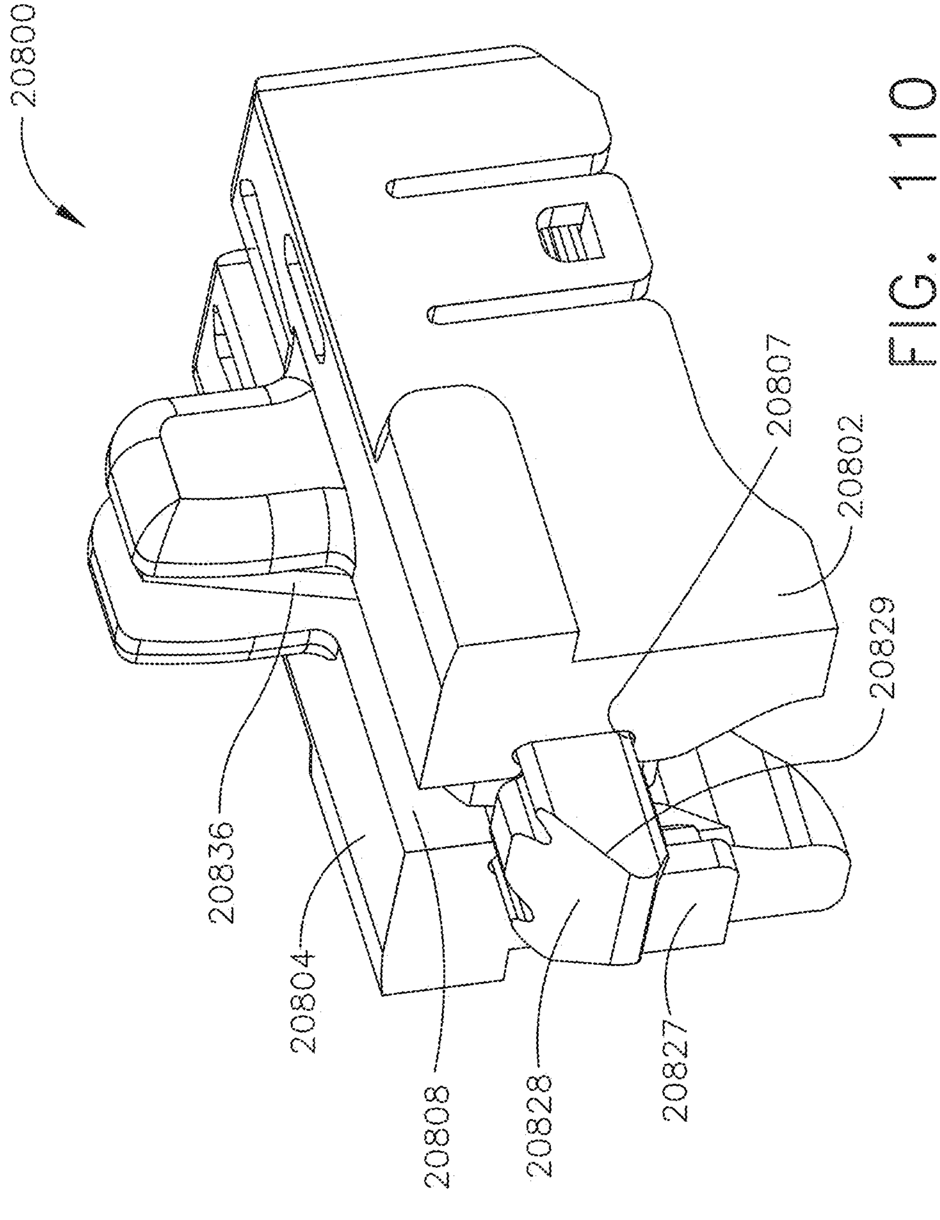
FIG. 110 is a perspective view of a portion of the cartridge body of FIG. 103 and further depicting a lockout key in a proximal position in the cartridge body, according to various aspects of the present disclosure.

The lock nut 21870 is threadably coupled to the rotary drive screw 20842. A rotation of the rotary drive screw 20842 can rotate the lock nut 21870 therewith unless the rotation of the lock nut 21870 is prevented or blocked. Initially, when the end effector 21840 is without a staple cartridge therein (FIGS. 108 and 109A), the rotation of the rotary drive screw 20842 is configured to rotate the lock nut 21870 such that one of the flanges 21874 is rotated into the lockout notch 21854 aligned therewith. When an unspent staple cartridge 20800 is installed in the surgical end effector 21840, the lockout nut 21854 is rotated to the unlocked position. The unlocked position of the lockout nut 21854 is shown in FIG. 109B; however, the staple cartridge is hidden for illustrative purposes.

Figure 111:
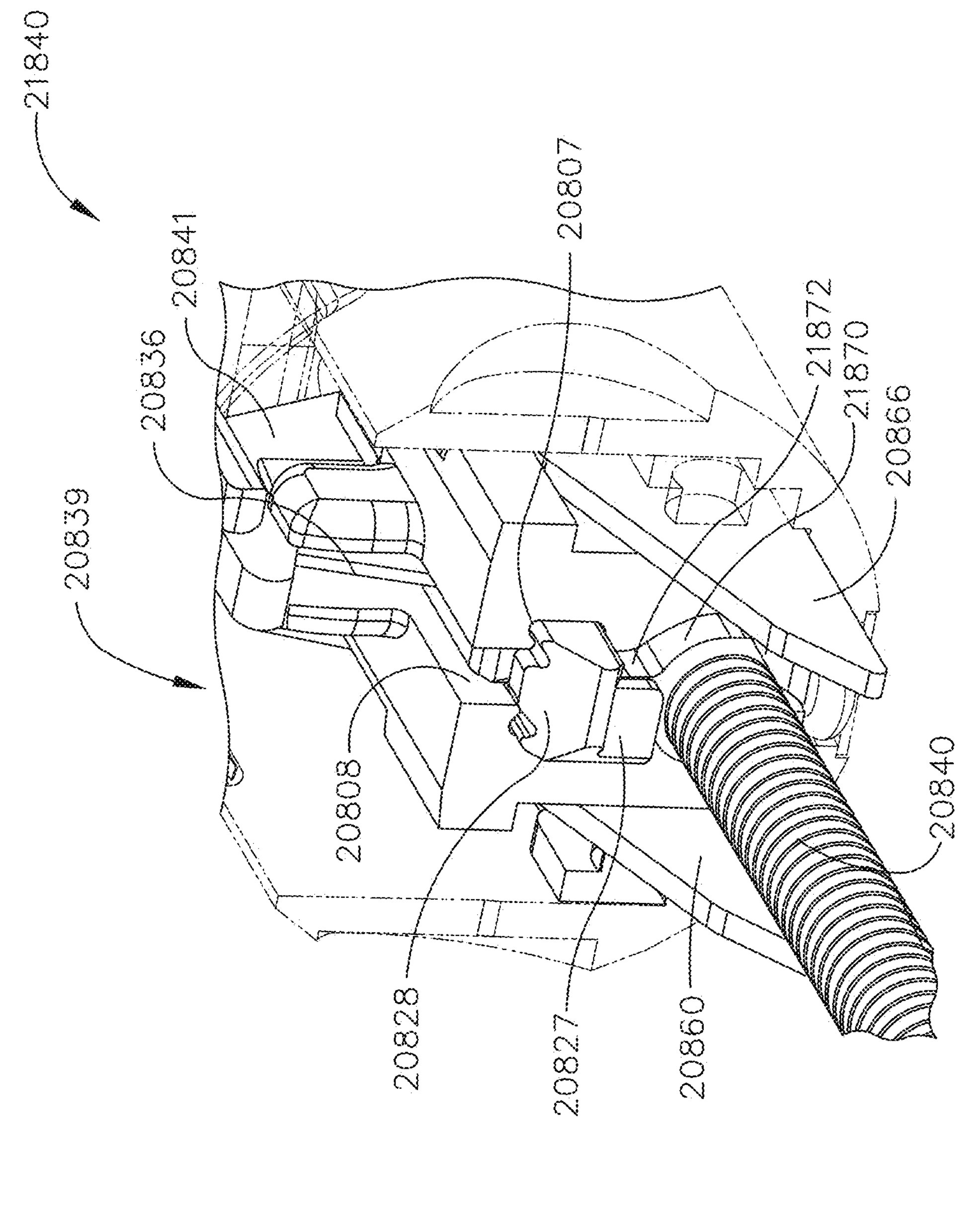
FIG. 111 is a perspective view of a portion of the end effector of FIG. 108 with the cartridge body of FIG. 110 installed in the end effector and the lockout key in a proximal position in which the lockout key is positioned to overcome the lockout arrangement by moving the lock nut to the unlocked position of FIG. 109B, according to various aspects of the present disclosure.
Figure 112:
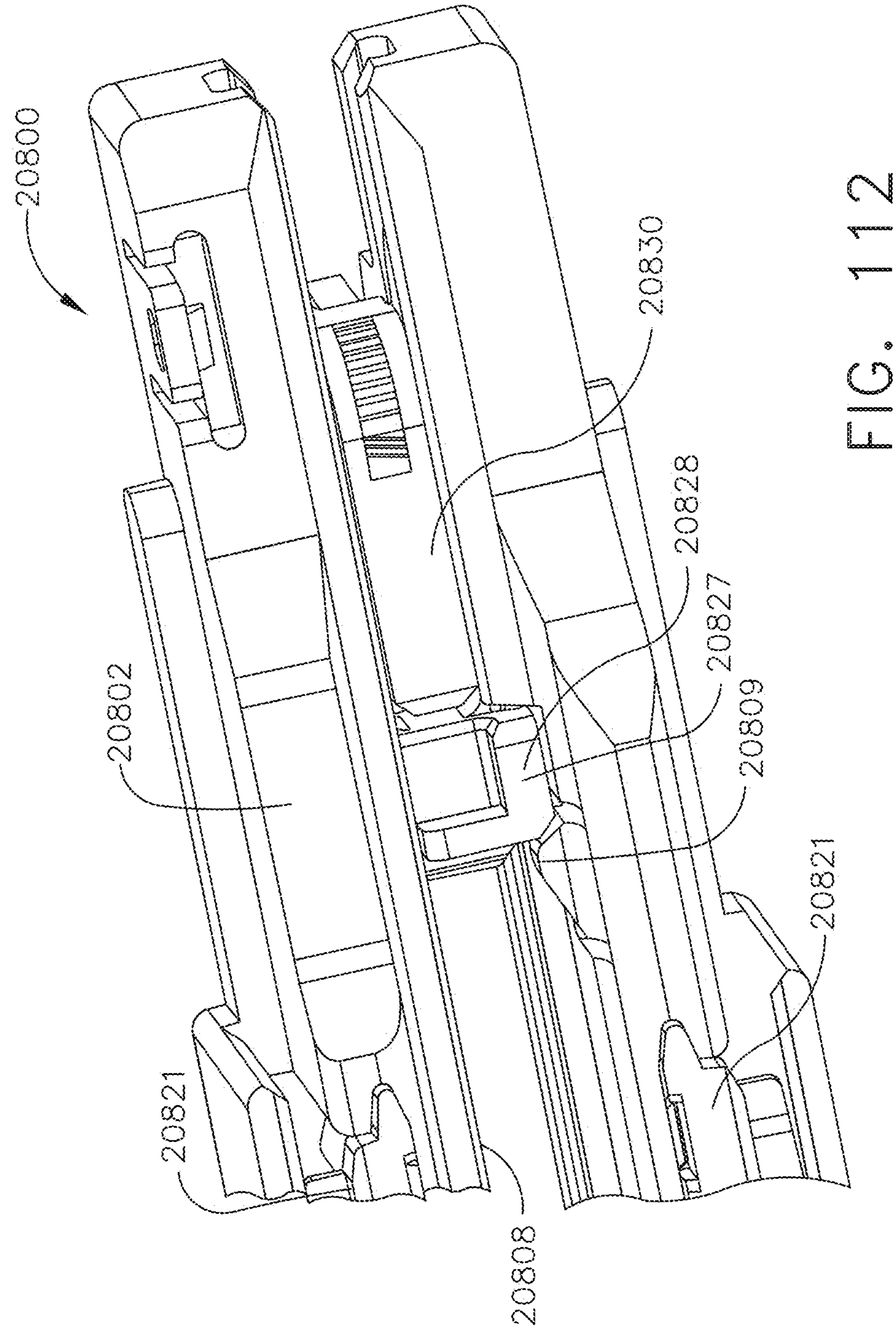
FIG. 112 is a perspective view of a portion of the underside of the cartridge body of FIG. 110, depicting the lockout key in the unfired position, according to various aspects of the present disclosure.

Referring primarily to FIGS. 111 and 112, the lockout key 20828 includes a foot 20827, which extends into a space in the cartridge body 20802 above the rotary drive screw 20842. When an unfired staple cartridge 20800 is installed in the end effector 21840, the foot 20827 of the lockout key 20828 rotates the lockout nut 21870 into the unlocked position. More specifically, the foot 20827 includes beveled surfaces configured to engage and abut the lug 21872 to bias and rotate the lug 21872 into alignment with the upright body portion 20843. Referring primarily to FIG. 112, the cartridge body 20802 includes a detent 20809, which extends toward the longitudinal slot 20808 in the cartridge body 20802. The detent 20809 is configured to hold the lockout key 20828 in place upon insertion of the staple cartridge 20800 into the end effector 21840.

The lockout key 20828 also defines a contoured profile 20829 that corresponds to a contoured profile track 20807 in the cartridge body 20802. The contoured profile track 20807 is configured to resist rotation of the lockout key 20828 as the lockout key 20828 is pushed distally. In various instances, the foot 20827 forms a nook into which the lug 21872 is received. The foot 20827 rotates the lug 20872 into the unlocked position. Subsequently, during a firing stroke, the lug 21872 can remain engaged with the nook in the lockout key 20828 and can push the lockout key 20828 distally through the contoured profile track 20807. The firing force can be sufficient to overcome the detent 20809 holding the foot 20827 in a proximal position the cartridge body 20802.

Additionally or alternatively, the knife 20830 can push the lockout key 20828 distally through the cartridge body 20802. The knife 20830 also comprises a contoured profile, which is configured to travel through the contoured profile track 20807 without rotating out of firing alignment during the firing stroke.

Figure 113:
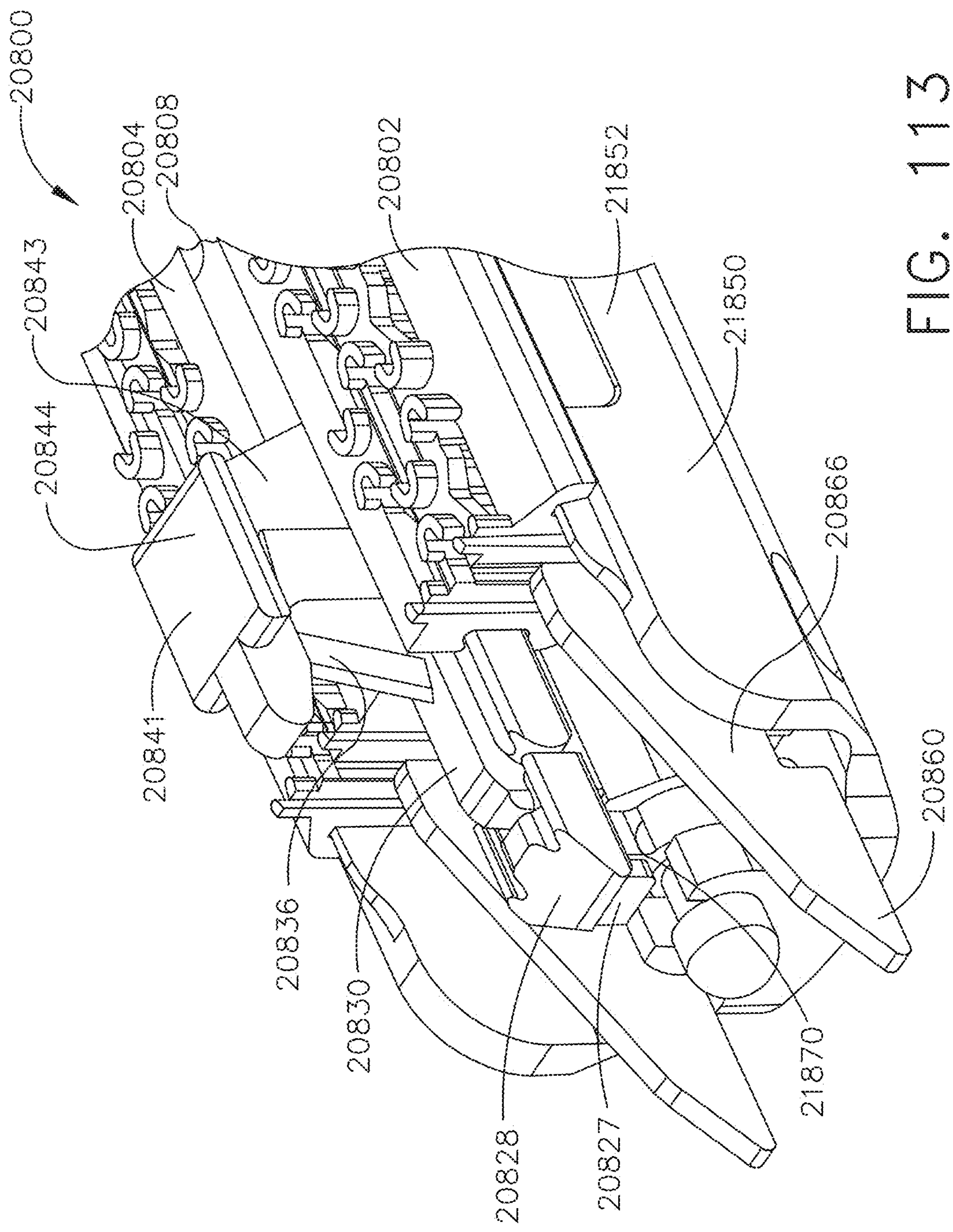
FIG. 113 is a perspective partial cutaway view of a portion of the end effector of FIG. 108 with the cartridge body of FIG. 110 installed in the end effector and partially cutaway for illustrative purposes to expose the lockout key advanced to a distal position, according to various aspects of the present disclosure.
Figure 114:
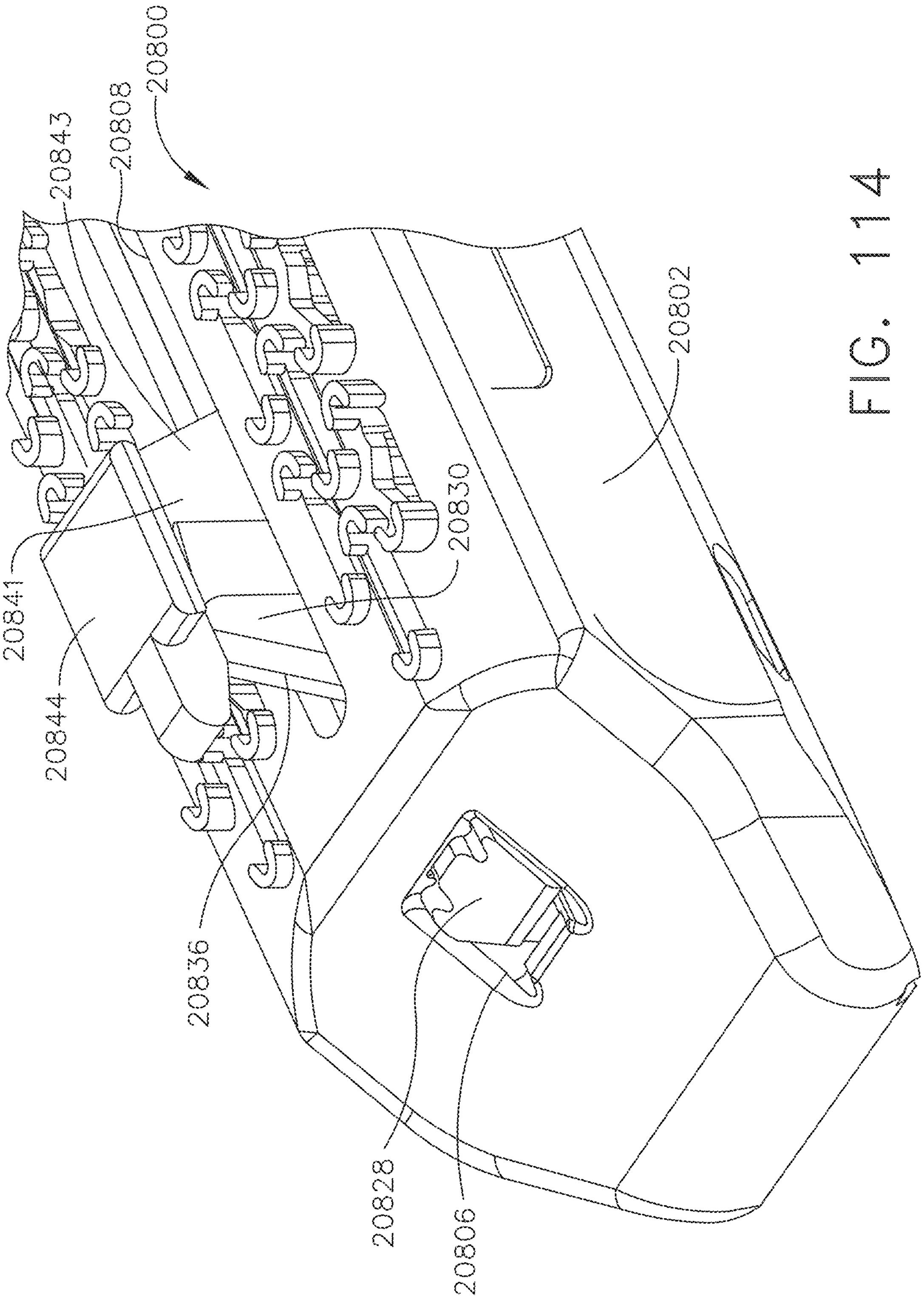

Referring now to FIGS. 113 and 114, upon completion of the firing stroke, the lockout key 20828 can be pushed to a distal position in the cartridge body 20802. In the distal position, the lockout key 20828 is visible through the window 20806 in the cartridge body 20802. For example, the distal nose of the cartridge body 20802 can include the window 20806 and the lockout key 20828 can be parked near the window 20806 such that the lockout key 20828 is visible. The foot 20827 of the lockout key 20828 prevents the lockout key 20828 from falling out of the cartridge body 20802 through the window 20808.

Figure 115:
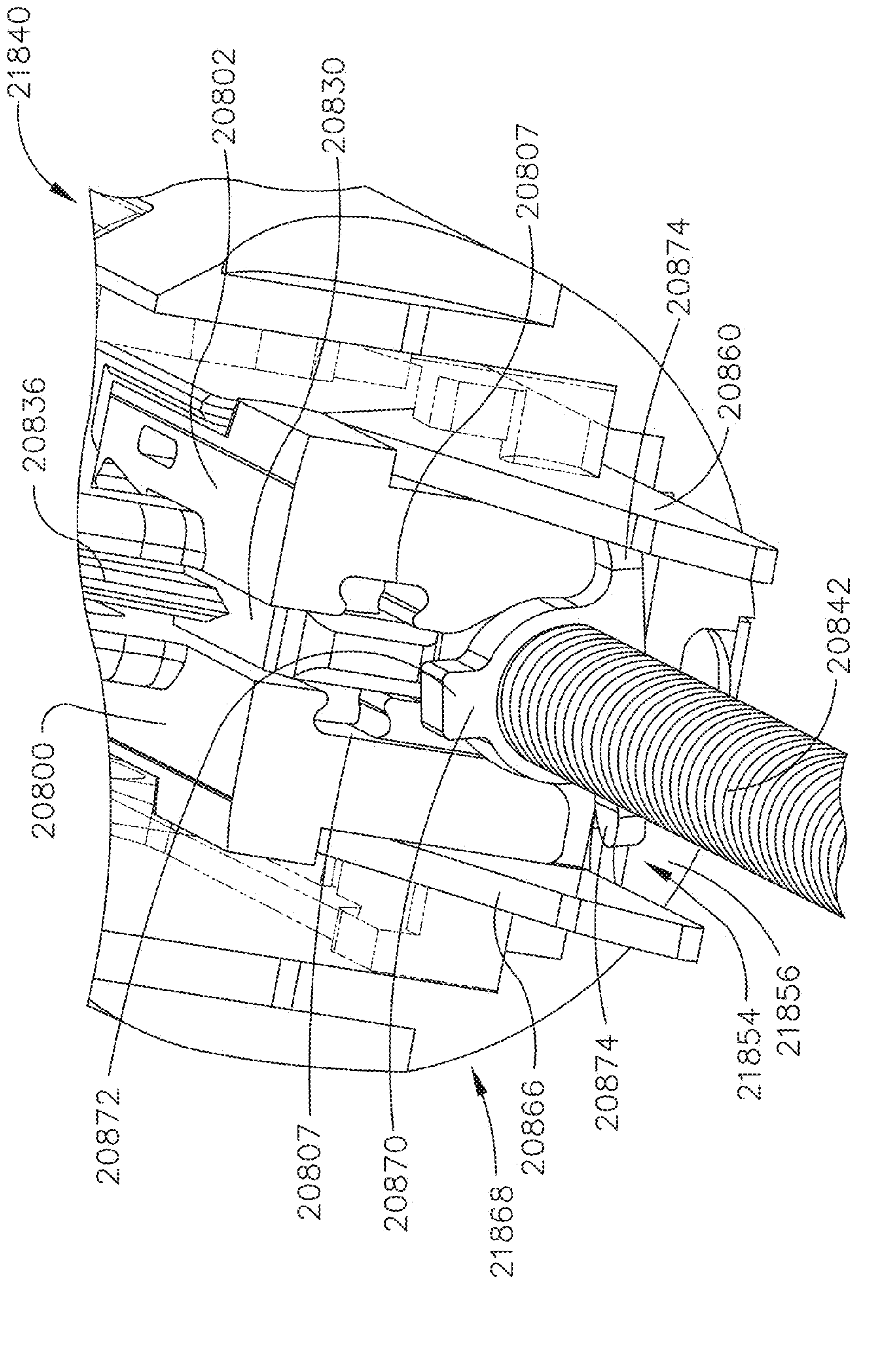

Reversing rotary motion of the rotary drive screw 20842 is configured to retract the firing member 20841. As further described herein, the knife 20830 can be retracted along with the firing member 20841 in various instances. However, the lockout key 21828 can be released from the knife 20830 and can remain at the distal position in the cartridge body 20802. Referring primarily to FIG. 115, when the firing member 20841 is retracted back to a proximal position in the cartridge body 20802, the lockout nut 21870 is also retracted proximally along the rotary drive screw 20842. Owing to the rotary direction of the rotary drive screw 20840 during a retraction motion, the lockout nut 21870 is not rotated into the lockout notch 21854. Stated differently, the lockout nut 21870 can remain in the unlocked position and move proximally past the lockout notch 21854 during the retraction motion. However, if another firing motion is initiated and the rotary direction of the rotary drive screw 20842 is reversed, upon moving distally in the end effector 21840, the lockout nut 21870 will again rotate out of alignment with the firing member 20841 and a flange 21874 of the lockout nut 21870 can be rotated into the lockout notch 21854.

In the locked position, the lockout nut 21870 cannot rotate relative to the rotary drive screw 20842 and cannot translate longitudinally through the end effector 21840. As a result, rotary motion of the rotary drive screw 20842 is resisted and the firing stroke is prevented until the lockout nut 21870 assumes the unlocked position.

Figure 116:
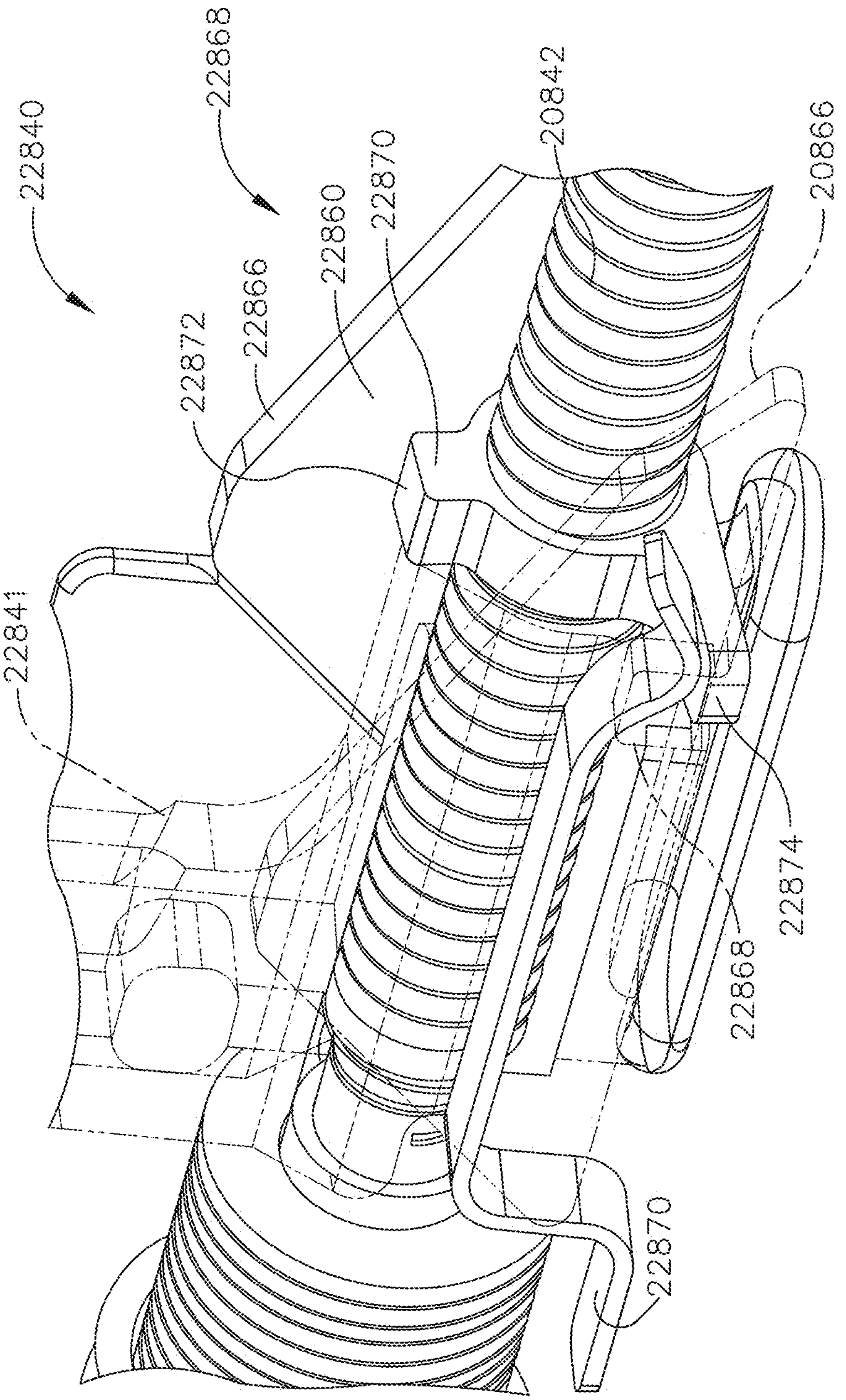
Figure 117:
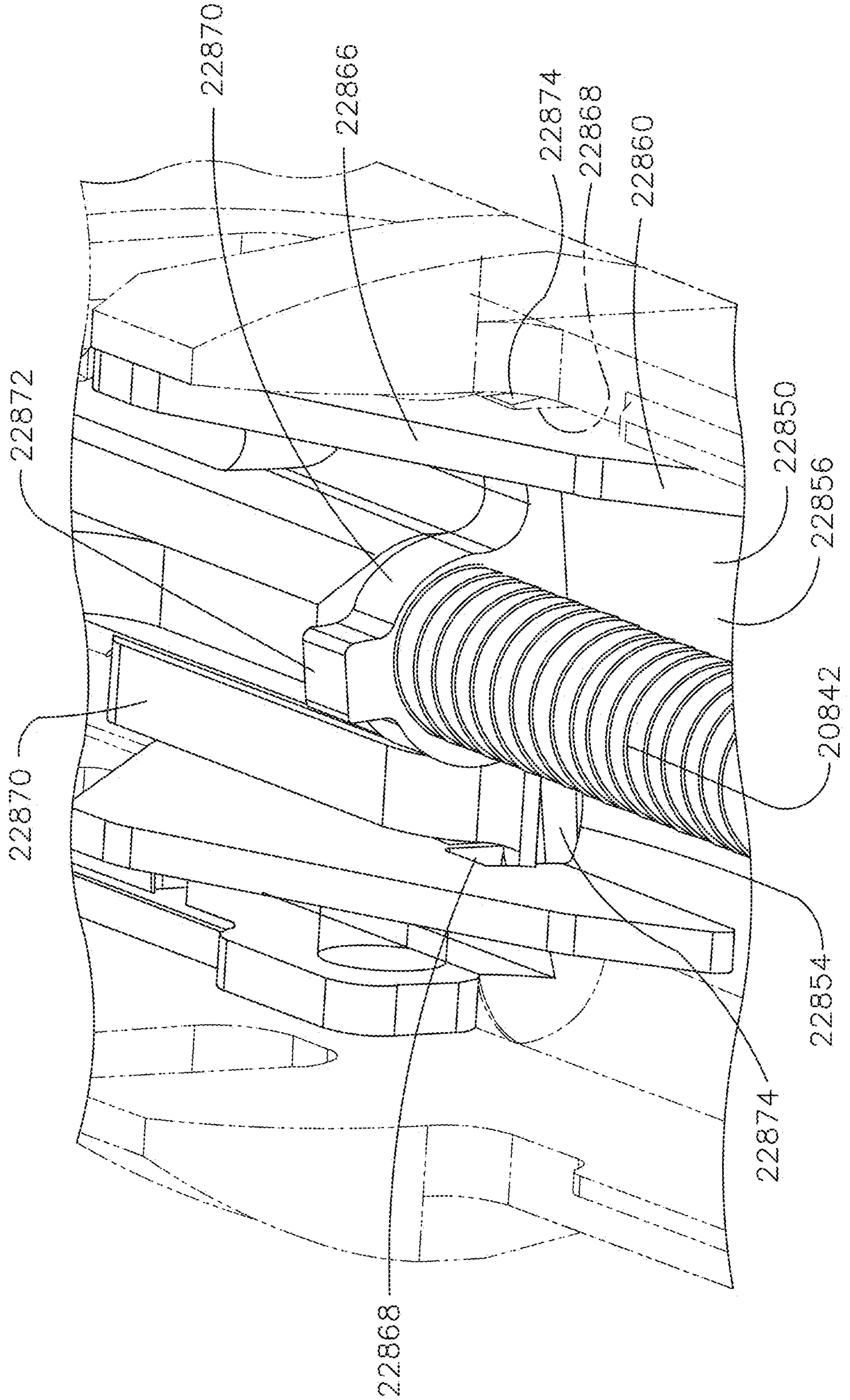

The lockout arrangement 21868 described herein with respect to FIGS. 108-115 includes a threaded lockout nut 21870, which is coupled to the rotary drive screw 20842. Displacement of the threaded lockout nut 21870 is a function of the rotation of the rotary drive screw 20840. In other instances, a lockout arrangement can includes a non-threaded lock positioned around the rotary drive screw 20842. Referring now to FIGS. 116 and 117, a lockout arrangement 22868 and various components thereof are shown. The lockout arrangement 22868 is incorporated into a surgical end effector 22840, which is similar to the surgical end effector 20840 (see FIG. 99) in many aspects. The end effector 22840 is adapted to receive the staple cartridge 20800 (see FIG. 103). The end effector 22840 includes a cartridge jaw 22850, which is similar to the cartridge jaw 20850 (see FIG. 99); however, the cartridge jaw 22850 further includes a lockout notch 22854 defined in a bottom side 21856. Moreover, the end effector 22840 includes a firing member 22841, which is similar to the firing member 20841 in many aspects; however, the integral sled 20860 of the firing member 22841 includes sled rails 22868 having holes 22868 therein, as further described here.

The lockout arrangement 22868 includes a lock 22870, which is similar in many aspects to the lockout nut 21870; however, the lock 22870 is not threadably coupled to the rotary drive screw 20842. The lock 22870 includes central non-threaded aperture through a body portion, opposing flanges 22874, and a lug 22872. The flanges 22874 and the lug 22872 extend radially outward from the body portion.

In an unlocked position, the flanges 22874 extend laterally outward to an inside surface of the bottom side 22856 of the cartridge channel 22850 and are positioned to ride along and/or adjacent to the inside surface. The flanges 22874 are received in the holes 22868 in the sled 22860. For example, the holes 22868 are through-holes in the sled rails 20866 that are dimensioned and positioned to receive the opposing flanges 22874 when the lock 22870 is in the unlocked position. As a result, the firing member 22841 and sled rails 22868 thereof are configured to pull the lock 22870 along the rotary drive screw 20842 during the firing stroke. Moreover, in the unlocked positioned, the lug 22872 is aligned with the upright body portion of the firing member 22841.

In the locked position (FIGS. 116 and 117), the flanges 22874 are rotated out of alignment with the inside surface of the bottom side 22856 such that one of the flanges 22874 rotates into the lockout notch 22854. Moreover, in the locked position, the lug 22872 is rotated out of firing alignment with the upright body portion of the firing member 22841.

The lockout arrangement 22868 also includes a spring 22870, which is configured to bias the lock 22870 into the lockout notch 22854. The lockout arrangement 22868 can function like the lockout arrangement 21868; however, the spring 22870 can bias the lock 22870 into the lockout notch 22854 such that the lockout arrangement 22868 is always locked unless an unfired staple cartridge 20800 is loaded into the end effector 22840 and the lockout key 21828 thereof temporarily overcomes the lockout arrangement 22868 until the completion of the firing stroke. As described above with respect to the lockout arrangement 21868, the lockout key 21828 is configured to move through the window 20806 in the cartridge body 20802 at the completion of the firing stroke to communicate the completion of a firing stroke and that the staple cartridge has been fired/spent.

The formed staple height is a function of the space between the staple-supporting surface and the staple-forming surface. More specifically, a vertical space between (A) a staple-supporting cradle on a driver in a fired position and (B) a staple-forming pocket surface in an anvil in the clamped position controls the formed height of the staples. Different formed staple heights are selected for different surgical procedures and/or different tissue types, for example. When a staple cartridge includes a rotary firing screw therethrough, the arrangement of staples and corresponding staple cavities and drivers can be altered to accommodate the rotary firing screw. For example, the drivers can include at least one asymmetry, as further described herein. Additionally or alternatively, the drivers can be narrower and, thus, need additional support and/or strength. Moreover, in various instances, it is desirable to optimize a tissue gap while maintaining a desired formed staple height. For example, the tissue gap between the tissue-supporting deck surface and the anvil can be maximized when the end effector is in a closed configuration while the desired formed staple height is maintained.

In various instances, an underside of the tissue-supporting deck can include a contoured and/or rutted surface, which is configured to receive one or more portions of the drivers when the drivers are in their fully fired and/or overdriven positions. The interlocking and/or nesting between the underside of the tissue-supporting deck and the tissue-facing side of the drivers can maximize the tissue gap while still maintaining a desired formed staple height. Moreover, the interlocking features can improve the strength of the drivers in various instances.

In one example, a staple cartridge can include a body comprising a tissue-supporting deck, wherein staple cavities are defined through the tissue-supporting deck in the body, and wherein the tissue-supporting deck includes a tissue-facing side comprising a bumpy or ridged surface. The tissue-support deck further includes an underside opposite the tissue-facing side, wherein the underside comprises a rutted surface. Staples can be removably positioned in the staple cavities. Drivers can movably support the staples and be configured to move through a portion of the staple cavities to fired positions to eject the staples from the staple cavities. Each driver can include a base housed in the staple cartridge and comprising surface contours configured to mate with the rutted surface on the underside of the tissue-supporting deck when moved to the fired position.

Figure 38:
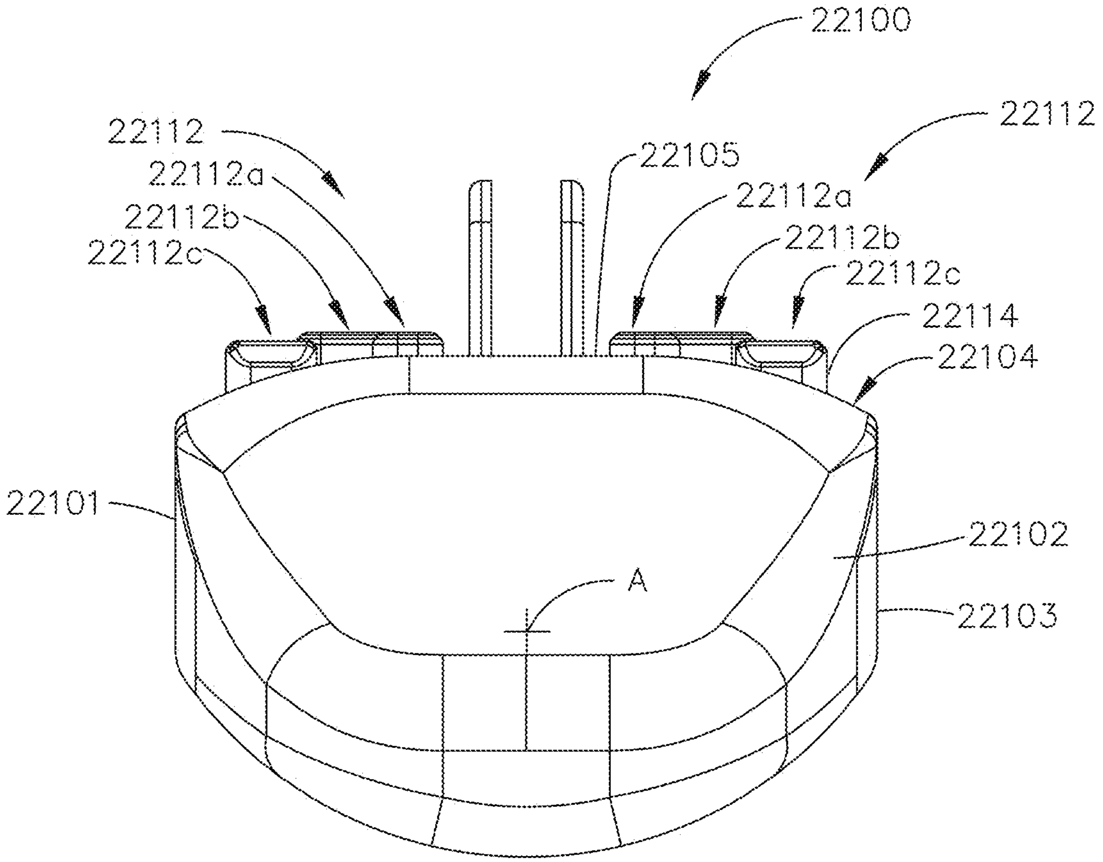
FIG. 38 is an elevation view of a staple cartridge, according to various aspects of the present disclosure.
Figure 39:
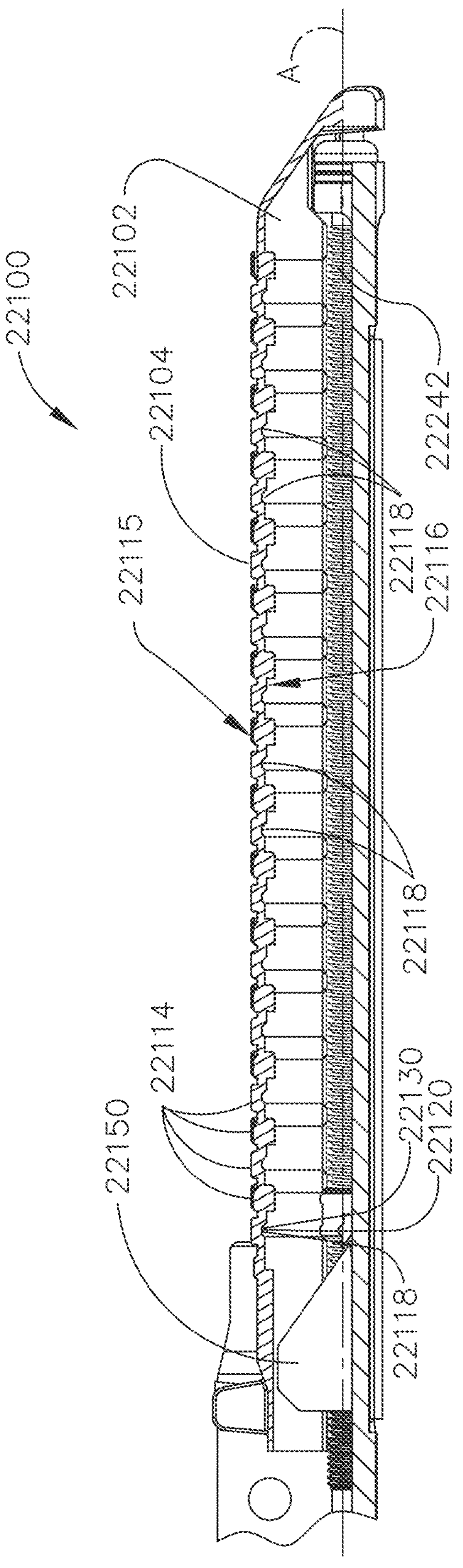
FIG. 39 is an elevation cross-section view of the staple cartridge of FIG. 38 taken along a plane shown in FIG. 38, according to various aspects of the present disclosure.
Figure 40:
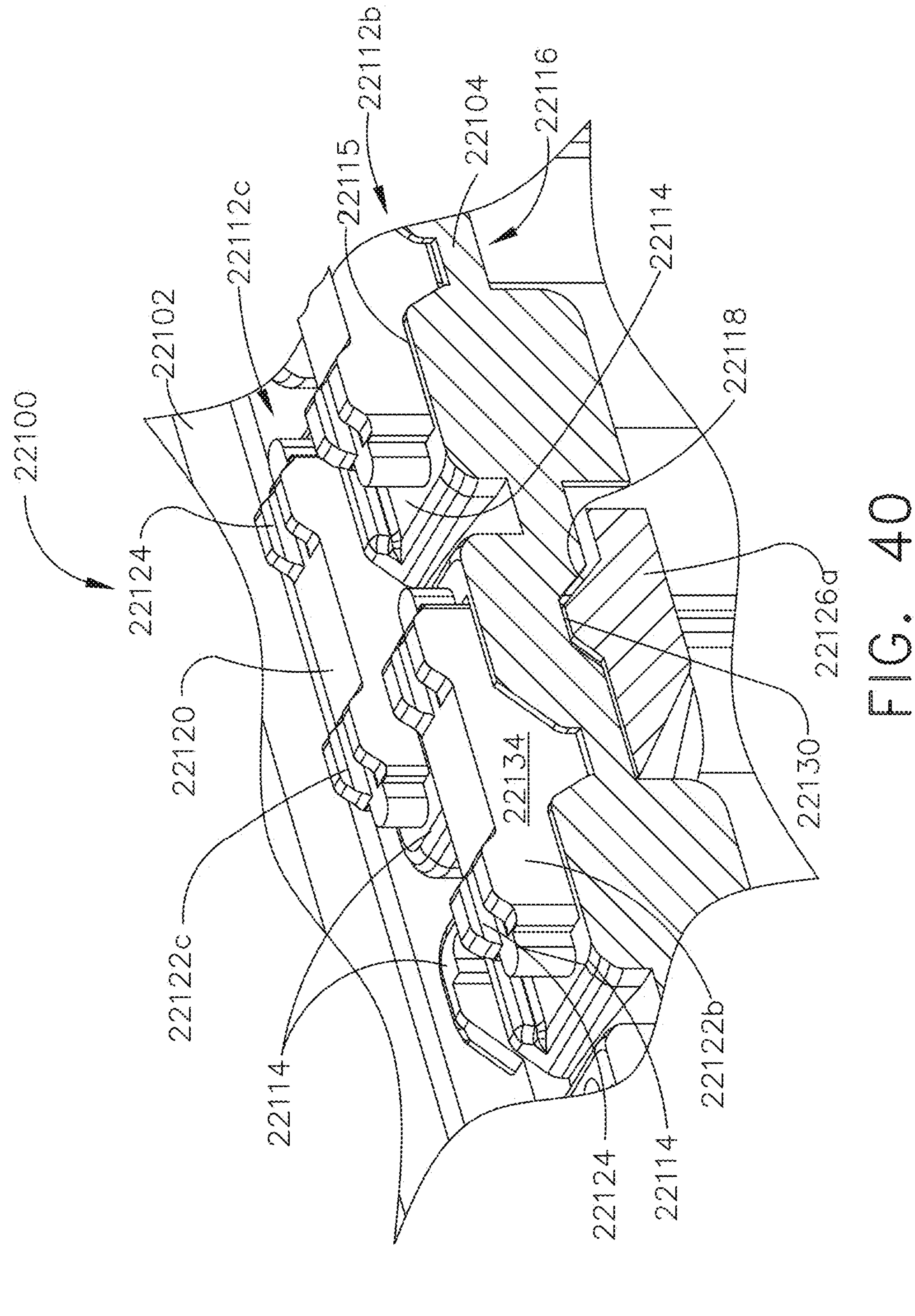
FIG. 40 is a perspective cross-section view of a portion of the staple cartridge of FIG. 38 taken along the plane shown in FIG. 38, depicting a driver in a fully fired position therein, according to various aspects of the present disclosure.

Referring now to FIGS. 38-40, a staple cartridge 22100 is shown. The staple cartridge 22100 is similar in many aspects to the staple cartridge 20100 (FIG. 24). For example, the staple cartridge 22100 includes a body 22102 extending along a longitudinal axis A. Staples are removably positioned in the body 22102. The staples can be ejected from the body 22102 and fired into tissue, for example, during a firing stroke. The staples are arranged in longitudinal rows on either side of the longitudinal axis A, which is aligned with a rotary drive shaft 22242 (FIG. 39) extending therethrough. The cartridge body 22102 also includes a deck 22104, which can be referred to as a tissue-supporting deck, for example. The deck 22104 is a laterally-curved tissue supporting deck and defines a curved tissue-facing surface from a first lateral side 22101 of the body 22102 to a second lateral side 22103 of the body 22102. A peak 22105 in the laterally-curved tissue supporting deck 22104 is defined at an intermediate portion of the body 22102. The peak 22105 can be positioned between the longitudinal rows of staples and overlie the longitudinal axis A, for example. In various instances, the rotary firing screw 22242 (FIG. 39) extends through a portion of the staple cartridge 22100.

The cartridge body 22102 also includes an array of pocket extenders or ridges 22114 extending from the tissue supporting deck 22104. The ridges 22114 extend around a perimeter or opening formed in the tissue supporting deck 22104 for a staple cavity. The ridges 22114 can be configured to grip and engage tissue positioned between the staple cartridge 22100 and an opposing anvil. In various instances, the ridges 22114 can limit and/or constrain tissue flow, for example. Additionally or alternatively, the ridges 22114 can be configured to guide the legs of the staples as they enter tissue and are directed into engagement with respective forming pockets on the staple-forming surface of the anvil. The ridges 22114 can extend around the proximal and distal ends of the staple cavities, for example. Proximally- and distally-positioned projections or pocket extensions can prevent outwardly-biased staple legs (of V-shaped staples, for example) from flaring outwardly and missing the target location in the forming pocket aligned therewith.

In certain aspects, adjacent ridges 22114 can be connected. For example, the ridges 22114 can be interconnected with respect to longitudinally-offset staple cavities and/or laterally-offset staple cavities.

In various instances, an array of laterally-offset ridges 22114 can define different heights. In various instances, the ridges 22114 can define different heights laterally along the width of the cartridge body 22102. Different heights can correspond to the lateral curve of the tissue supporting deck 22104 and/or different lengths for guiding the staples beyond the tissue-supporting deck 22104 and/or different tissue gaps when the end effector is clamped, for example. With respect to the cartridge body 22102, the ridges 22114 span three laterally-spaced rows of staple cavities **22112*a*, 22112*b*, 22112*c* and the ridges 22114 aligned with outer row 22112*c* are taller than the inner rows 22112*a*, 22112*b* and, thus, would guide the staple legs over a greater distance. However, the tissue gap is also larger over the outer rows 22112*c* than the inner rows 22112*a*, 22112*b* owing to the lateral curve of the tissue-supporting deck 22104** and the non-stepped/non-contoured tissue-clamping surface of the anvil.

The staples are positioned in cavities defined in the cartridge body 22102, similar to the cavities 20110 (FIG. 24). For example, the staples are arranged in longitudinal rows 22112 on either side of the longitudinal axis A. The cavity rows 22112 include an inner row **22112*a*, an intermediate row 22112*b*, and an outer row 22112*c* on each side of the longitudinal axis A. The intermediate row 22112*b* can be equilaterally-spaced between the inner row 22112*a* and the outer row 22112*c*. The rotary drive screw 22242 can be aligned with the longitudinal axis A, and can extend through the cartridge body 22102 adjacent to the inner cavity rows 22112*a*. The rotary drive screw 22242 can be between and parallel to the inner cavity rows 22112*a***, for example.

The inner rows **22112*a* hold inner staples, the intermediate rows 22112*b* hold intermediate staples, and the outer rows 22112*c*** hold outer staples. In various instances, the inner staples, the intermediate staples, and the outer staples can be identical. In other instances, the inner staples, the intermediate staples, and/or the outer staples can each be different with respect to staple type (e.g. wire or stamped), material, and/or size (e.g. different heights), for example.

In other instances, the staple cartridge 22100 may have a different arrangement of staples. For example, the staple cartridge 22100 may have less than three rows of staples on each side of the longitudinal axis A. In one aspect of the present disclosure, the staple cartridge 22100 may only have two rows of staples on each side of the longitudinal axis A. In still other instances, the staple cartridge 22100 can include four or more rows of staples on one or more sides of the longitudinal axis A. In various instances, the rows of staples may be asymmetrical relative to the longitudinal axis A. For example, the first side of the staple cartridge 22100 can have a different number of rows of staples than the second side of the staple cartridge 22100.

Figure 41:
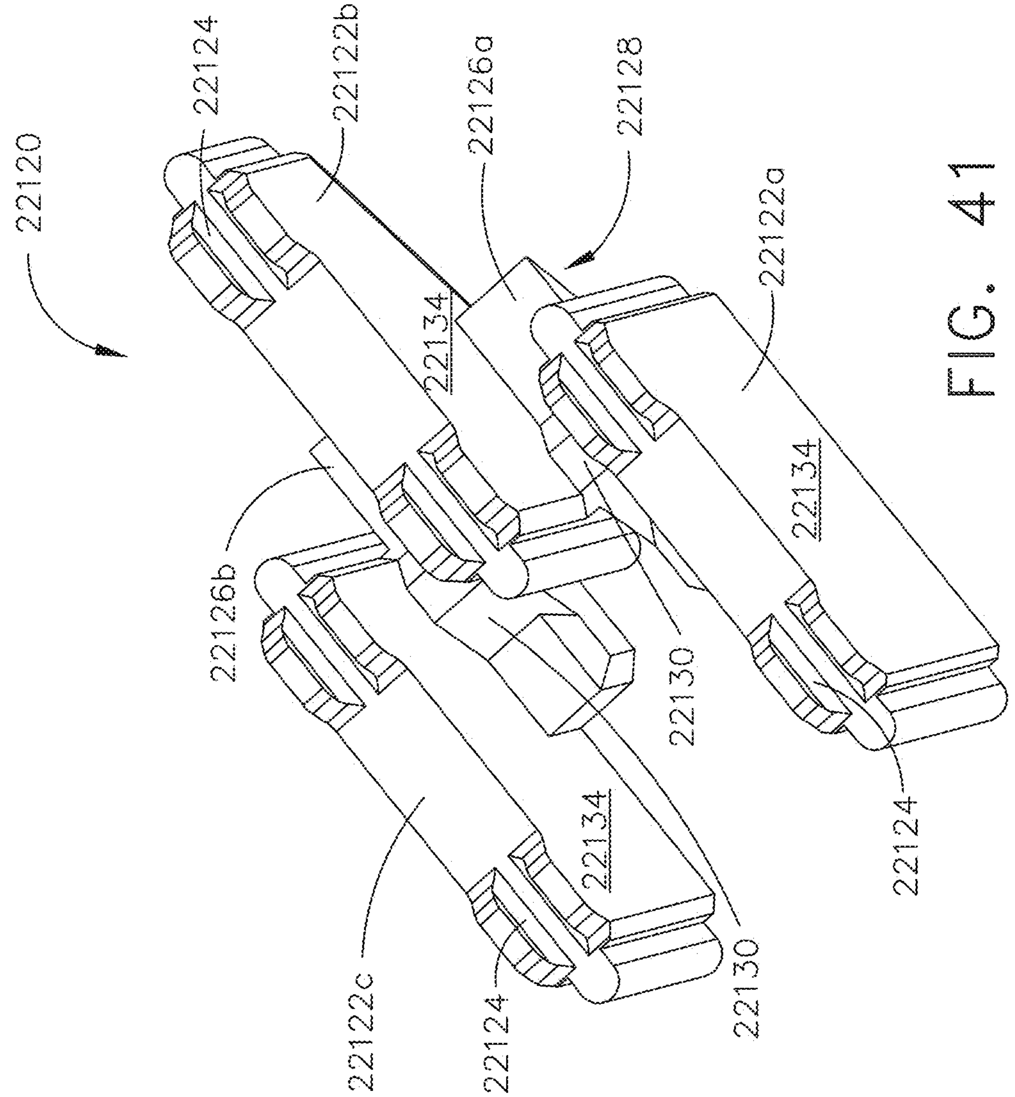
FIG. 41 is a perspective view of the driver of FIG. 40, according to various aspects of the present disclosure.
Figure 42:
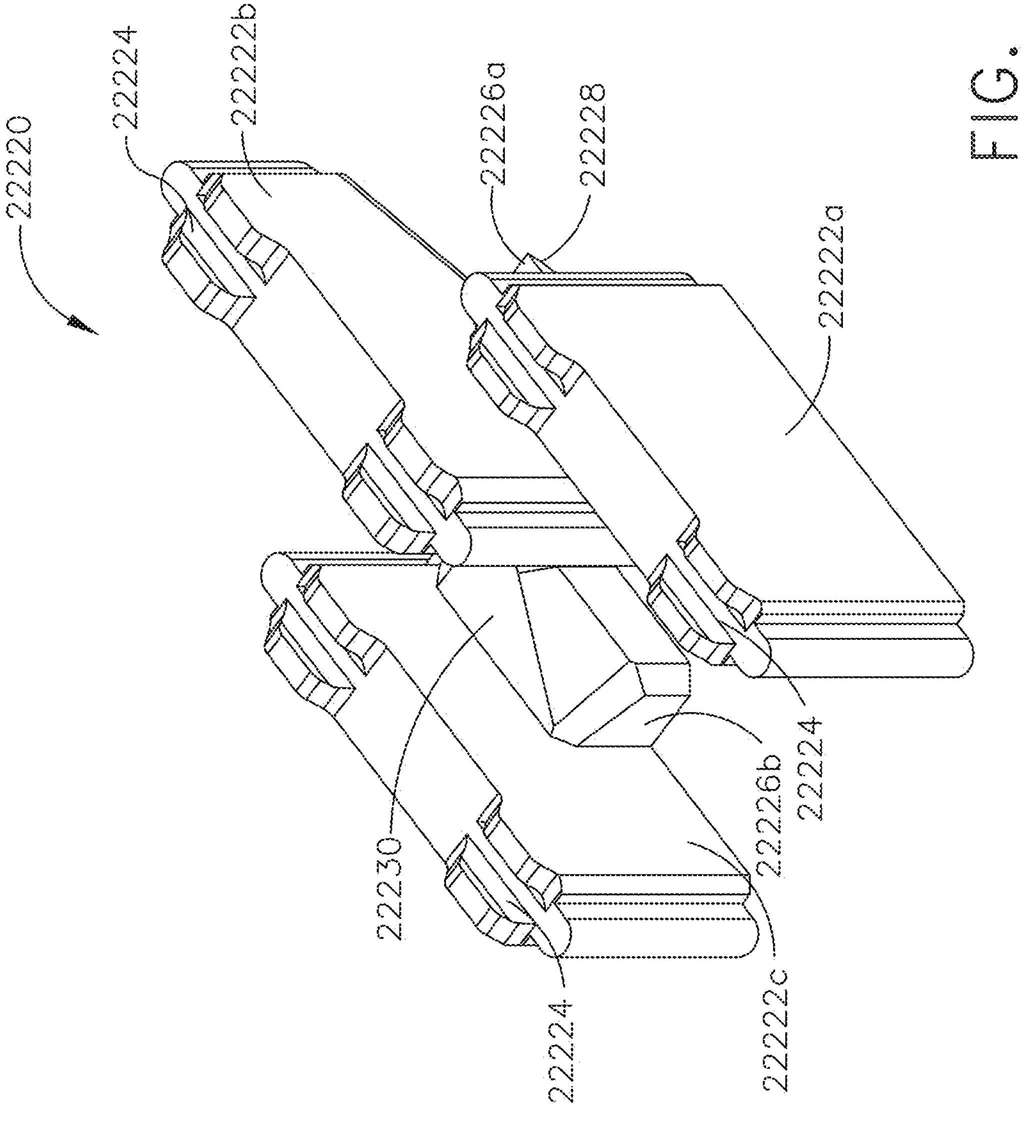
FIG. 42 is a perspective view of a driver, according to various aspects of the present disclosure.

The staple cavities in the cartridge body 22102 can each include a proximal end, a distal end, and lateral guide surfaces intermediate the proximal end and the distal end. The staple cavities are structured and dimensioned to guide drivers 22120 through the staple cavities toward the deck 22104. Referring primarily to FIG. 41, a driver 22120 is shown. Moreover, one driver 22120 is shown in the staple cartridge 22100 in FIGS. 41 and 42. Though one driver 22120 is depicted in these figures, the reader will appreciate that additional drivers like the driver 22120 would be incorporated into the staple cartridge 22100 to fire staples from additional staple cavities during a firing stroke.

The geometry of the staple cavities can complement the geometry of the drivers 22120. For example, lateral guide surfaces in each staple cavity are configured to guide side-walls 22134 of the driver 22120 as the driver 22120 moves through the staple cavity. Additionally or alternatively, the proximal end and/or the distal end of each staple cavity can include an upright groove configured to slidably receive an end and/or tongue thereof of the driver 22120. Alternative tongue and groove arrangements are also contemplated, which can be configured to guide the drivers 22120 through the staple cavities during firing of the staples from the staple cartridge 22100.

The drivers 22120 are configured to support and drive multiple staples from the cartridge body 22102 during a firing stroke. The drivers 22120 can movably support staples spanning two or more longitudinal rows 22112. For example, the drivers 22120 can movably support an inner staple, an intermediate staple, and an outer staple on the same side of the staple cartridge 22100.

The driver 22120 is a triple driver, which is configured to drive three staples simultaneously. The driver 22120 includes three support columns—an inner support column **22122*a* configured to support an inner staple in an inner row of staples, an intermediate support column 22122*b* laterally outboard of the inner support column 22122*a* configured to support an intermediate staple in an intermediate row of staples, and an outer support column 22122*c* laterally outboard of the intermediate support column 22122*b*** and configured to support an outer staple in an outer row of staples.

The driver 22120 also includes bridges 22126 extending between adjacent support columns 22122. For example, a first bridge **22126*a* extends between the inner support column 22122*a* and the intermediate support column 22122*b*, and a second bridge 22126*b* extends between the intermediate support column 22122*b* and the outer support column 22122*c*. The bridges 22126*a*, 22126*b* each include a ramped underside 22128 configured to be drivingly engaged by a sled during a firing stroke. For example, a sled 22150 (FIG. 39) can be configured to move along a firing path during a firing stroke. The sled 22150 can comprise a central portion aligned with the longitudinal axis A, a first rail configured to drivingly engage the ramped underside 22128 of the first bridge 22126*a*, and a second rail configured to drivingly engage the ramped underside 22128 of the second bridge 22126*b***. Sleds and firing motions thereof are further described herein.

Referring primarily to FIGS. 38 and 39, the tissue-supporting deck 22104 includes a tissue-facing side 22115 having the array of ridges 22114, which form a bumpy tissue-gripping surface. The tissue-supporting surface 22104 also includes an underside 22116 opposite the tissue-facing side 22115. The underside 22116 comprises a rutted surface having an array of ruts 22118 therein. The ruts 22118 can define a pattern of recesses and/or divots in the underside 22116. The tissue-supporting deck 22104 defines a deck height between the bumpy tissue-facing side 22115 and the rutted underside 22116. The deck height varies; however, a certain minimum height around the openings in the deck 22104 provides a minimum amount of guide length for the staples during the firing stroke. For example, if the deck were too thin around the staple cavities, the staples may not be adequately supported during deployment into the tissue and toward the forming pockets.

The drivers 22120 are configured to mate or nest with the rutted underside 22116 when the drivers 22120 are move to the fired positions. Referring again primarily to FIG. 41, the bridges **22126*a*, 22126*b* of the driver 22120 includes a projection 22130. The projections 22130 are surface contours and projections on an upper tissue-facing surface of the bridges 22126*a*, 22126*b* opposite the ramped underside 22128 of the bridges 22126*a*, 22126*b*. The projections 22130 are configured to be received in the ruts 22118 on the underside 22116 of the tissue-supporting deck 22104 when the drivers 22120 are moved to their fired positions. In the fired position, referring primarily to FIG. 40, the driver 22120 is overdriven relative to the deck 22104 such that a portion of the driver 22120 extends beyond the tissue-facing side 22115 and out of the cartridge body 22102**.

The top surface of the bridges **22126*a* and 22126*b* are symmetric relative to a longitudinal centerline of the respective bridge 22126*a*, 22126*b*. The centerline of each bridge 22126*a*, 22126*b* can be equidistant between the longitudinal axes defined by staple-supporting cradles 22124 of adjacent support columns 22122. The projections 22130 are symmetric relative to the longitudinal centerline of the respective bridge 22126*a*, 22126*b***.

In other instances, the drivers, the bridges thereof, and/or the top surfaces thereof, can be laterally asymmetric, as further described herein. Referring to a driver 22220 in FIG. 42, the driver 22200 is similar in many aspects to the driver 22120 (FIG. 41); however, the driver 22200 defines a lateral asymmetry with respect to the interconnecting bridges **22226*a*, 22226*b* and respective top surface 22230 thereon. The driver 22220 includes three support columns 22222*a*, 22222*b*, 22222*c* each having a staple-supporting cradle 22224. The bridges 22226*a*, 22226*b* connect laterally adjacent support columns 22222*a*, 22222*b*, 22222*c*. The bridges 22226*a*, 22226*b* includes a ramped underside 22228, which is driven by a sled during a firing stroke, as further described herein. The top surface 22230 of the bridges 22226*a*, 22226*b* includes a diagonal surface and is asymmetric relative to a centerline through the bridge 22226*a*, 22226*b* and aligned with a firing path of a sled rail during a firing stroke. The centerline of each bridge 22226*a*, 22226*b* is equidistant between the axes aligned with adjacent staple-supporting cradles 22224** and staple bases/crowns therein.

The top surface 22230 of each bridge **22226*a*, 22226*b* includes a laterally-sloped top surface, which is configured to complement a portion of the contoured underside of a tissue-supporting deck, such as the rutted underside 22116 (FIGS. 39 and 40). Such bridge configurations may provide improved column-to-column support, which can allow the overall bridges 22226*a*, 22226*b*** to be thinner while sufficiently supporting the staples across multiple rows.

Figure 43:
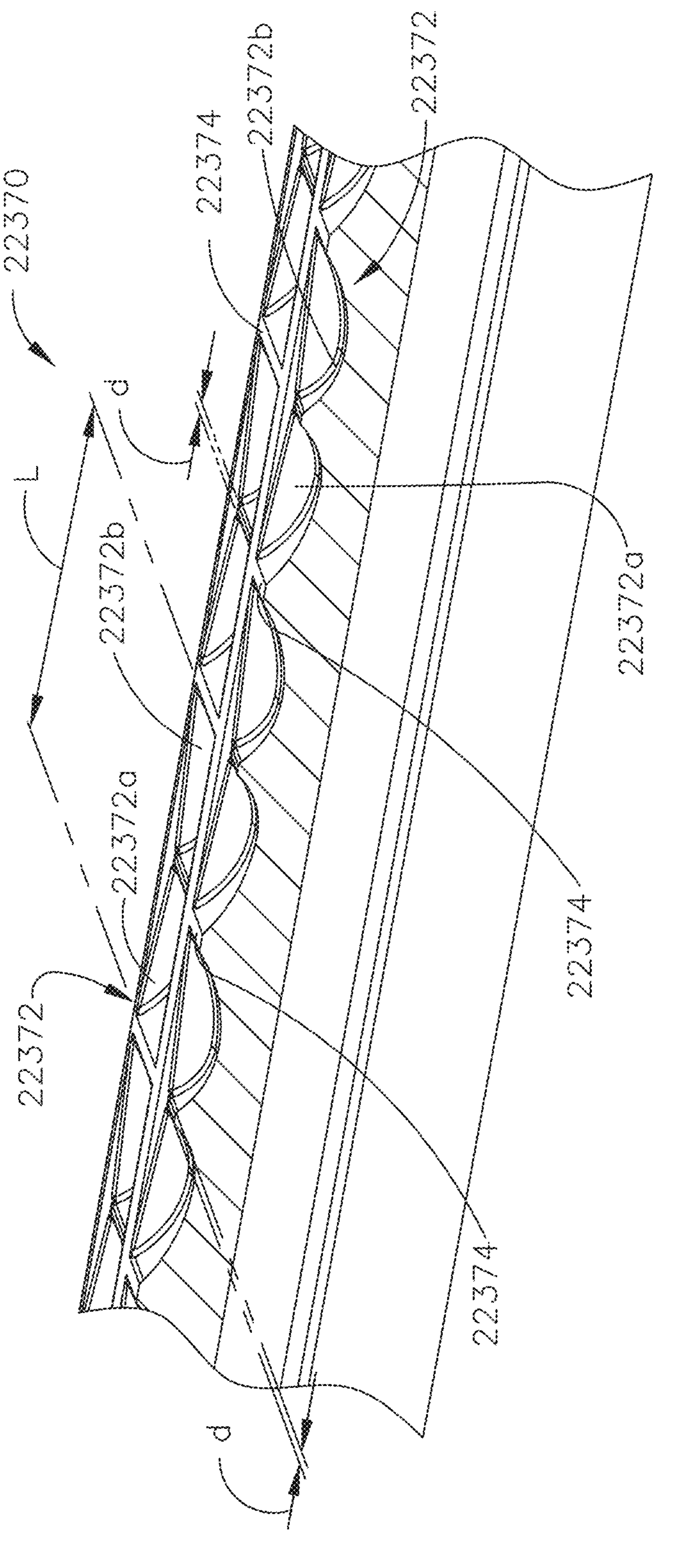
FIG. 43 is a perspective cross-section view of a portion of an anvil, according to various aspects of the present disclosure.

An anvil 22370 for a surgical end effector is shown in FIG. 43. The anvil 22370 includes a tissue compression surface 22374 and pairs of staple-forming pockets 22372 formed into the tissue compression surface 22374. Each pair of staple-forming pockets 22372 includes a proximal pocket **22372*a* and a distal pocket 22372*b*. The pockets can be aligned with the legs of a staple, e.g. the wire legs of a staple. During the firing stroke, the tips of the staple legs can be received within the staple-forming pockets 22372 and formed into B-form staples, for example. In certain aspects of the present disclosure, the length of the staple-forming pockets 22372 can be configured to match the wire diameter of the staple aligned therewith. For example, the proximal pocket 22372*a* and the distal pocket 22372*b* in a first pair of staple-forming pockets 22372 in the anvil 22370 can have a first pocket length while the proximal pocket 22372***a* and the distal pocket 22372*b* in a second pair of staple-forming pockets 22372 in the anvil 22370 can have a different pocket length. The first pocket length can correspond to a different staple wire diameter than the second pocket length. In various aspects, larger wire diameter staples can correspond to short pocket lengths.

The space d between a proximal pocket 22372*a* and a distal pocket 22372*b* in a pair of staple-forming pockets 22372 can be minimized in certain instances to maximize the longitudinal forming length of the staples. Generally, staples are over-bent during the forming process to compensate for staple spring-back. However, over-bending of staples can be reduced when the forming pockets are shorter and, thus, steeper in certain instances. Shorter and steeper staple pockets, which define a larger space or gap d between the proximal pocket 22372*a* and the distal pocket 22372*b* in a pair of staple-forming pockets 22372, can reduce spring-back. Shorter and steeper staple pockets can curve the staple legs more and deform the staples more plastically to reduce spring-back, for example. Moreover, shorter and steeper staple pockets can improve sequential staple leg bends in certain instances. Referring to the space d in FIG. 43, the proximal pocket 22372*a* and the distal pocket 22372*b* in a pair of staple-forming pockets 22372 can be shortened and the overall pair can maintain the same length L such that a larger space d is defined between the proximal pocket 22372*a* and the distal pocket 22372*b*.

For example, in an end effector, the staples and/or the drivers can vary from row-to-row. In certain instances, the staples can be shorter, comprise a different wire diameter, be lifted by a driver having a different height and/or a different amount of overdrive. In certain instances, shorter staple forming pockets, as described above, can be utilized with the one row of staples and not an adjacent row of staples in the same anvil. For example, shorter staples can utilize the shortened pockets to improve sequential staple leg bends, e.g. two sequential bends on each staple leg to assume a B-shape. In still other instances, staples along an inside row of staples, i.e. adjacent to a longitudinal knife path, can utilize the shortened pockets to bend the staples more plastically and reduce spring-back to form a tighter row. In these instances, the distance d in FIG. 43 can be different from row-to-row.

A staple cartridge, such as the staple cartridge 20100 (FIG. 24) and the staple cartridge 22100 (FIG. 39), for example, include components having minimum size limitations to ensure suitable strength, stiffness, support, and/or manufacturing requirements are met. These minimum size limitations can make it difficult to optimize and/or increase the tissue gap in view of the other constraints on the surgical end effector. As an example, the minimum height of a tissue-supporting deck is 0.01 inches in certain instances due to molding constraints. As another example, the minimum height of the bridge between support columns on a driver is 0.022 inches in certain instances due to driver strength constraints. As another example, the minimum height of the driver (e.g. support column thereof) is 0.066 inches in certain instances due to driver roll constraints. As another example, the minimum height of the staple legs is 0.166 inches in certain instances, 0.160 inches in other instances, 0.150 inches in other instances, 0.102 inches other instances, and 0.085 inches in other instances based on the type of staple cartridge and targeted tissue. As another example, the minimum thickness of the anvil is 0.134 inches and, in certain instances, 0.154 inches due to anvil stiffness and strength constraints. In view of such minimum size constraints, it can be advantageous in certain instances to reduce the minimum size limitations and/or double count certain size limitations or portions thereof in a stack-up of components.

For example, portion of the drivers can nest in recesses in the underside of the tissue-supporting deck in certain instances to reduce certain minimize size limitations. In various instances, to ensure the tissue-supporting deck maintains an appropriate height, the recesses can be aligned with localized regions along the tissue-supporting deck with an increased height, such as below pocket extenders/tissue-gripping ridges, for example. In other instances, one or more additional recesses in the underside of the tissue-supporting deck can be configured to receive a portion of the driver and/or bridge thereof. Exemplary staggering of interlocking features between the inner surfaces of the staple cartridge and the drivers is shown in FIG. 39, for example. Other driver features could similarly be received within corresponding recesses on the underside of the tissue-supporting deck.

To reduce vertical stack-up dimensions of multiple components, the tissue-supporting deck of a staple cartridge, such as the staple cartridge 20100 (FIG. 24) and the staple cartridge 22100 (FIG. 39), for example, can have predefined clearance holes therethrough, which can be separate and distinct from the staple cavities. The predefined holes along the length and/or width of the staple cartridge can receive features of the drivers (e.g. portions of the bridge) in the driver's fully fired, and in various instances overdriven, positions. Additionally or alternatively, the tissue-supporting deck can include frangible or "break locations", which are configured to be physically broken by the drivers upon moving to their fully fired positions.

Additionally, the staple cartridges such as the staple cartridge 20100 (FIG. 24) and the staple cartridge 22100 (FIG. 39), for example, can further include selectively compressible and expandable features to reduce vertical stack-up dimensions. The drivers and/or cartridge body can include such features.

For example, vertically-expandable drivers can be configured to reduce resting or unfired heights of the drivers within the staple cartridge. The drivers can be telescoping and can define a height that is approximately 50% of its final height when in the unfired position. In such instances, the staples can sit lower in the cartridge body prior to firing. In certain instances, a first part of the sled rail can activate the driver by overcoming a significant snap feature with the body of the driver and expanding it to its final height. Then, a second part of the sled rail can complete the firing of the driver to eject the staple(s) supported thereon out of the cartridge body. The first of the sled rail can be narrower than the second part of the sled rail.

Additionally or alternatively, the tissue-supporting deck can comprise a variable-height, injection molded deck, which can compress when a predefined tissue load is applied to increase the tissue gap. As the sled fires the drivers and staples, the sled and/or the drivers can locally push the deck back into the tissue to an increased height momentarily in order to temporarily decrease the tissue gap. The tissue-support deck can then relax or otherwise return to the compressed state corresponding to an increased tissue gap after the sled has passed.

For example, the cartridge body or tissue-supporting deck thereof can include selectively positioned wall segments, which can be thin and configured to buckle under the predefined tissue load while still maintaining appropriate alignment between the staples and the staple-forming pockets in the anvil. In certain instances, an electrically-actuated material (e.g. electroactive polymers) can be incorporated in the tissue-supporting deck. Components or features formed with such a material can become soft and/or more readily compressible when a current is applied thereto and rigid and/or less readily compressible when no current is applied. In certain instances, portions of the drivers can be received in the tissue-supporting deck when the material is energized and, thus, deformable to accommodate the additional structures therein.

In certain instances, 4D printed materials can facilitate selective collapse of the tissue-supporting deck of the staple cartridge, such as the staple cartridge 20100 (FIG. 24) and the staple cartridge 22100 (FIG. 39), for example. For example, the cartridge body can include a 4D printed material that is printed on a top portion or upper half thereof. The 4D printed material can be heat sensitive. In certain instances, the material can have a glass transition point between room temperature and the temperature of the human body. For example, the material can become soft and deflectable, thus, increasing the tissue gap, when the cartridge is clamped onto tissue. In such instances, the increased heat from the patient can increase the heat of the 4D printed material to effect the shape change. When the cartridge body subsequently cools (e.g. is removed from thermal transfer contact with tissue), the 4D printed material can return to its original shape and/or height. In the original and recovered state, the tissue-supporting deck can be taller than in the heated and collapsed state, for example. The increased height in the original and recovered state can ensure the staples stored in the staple cartridge remain protected and are not protruding from the cartridge body prior to being fired, for example.

Figure 44:
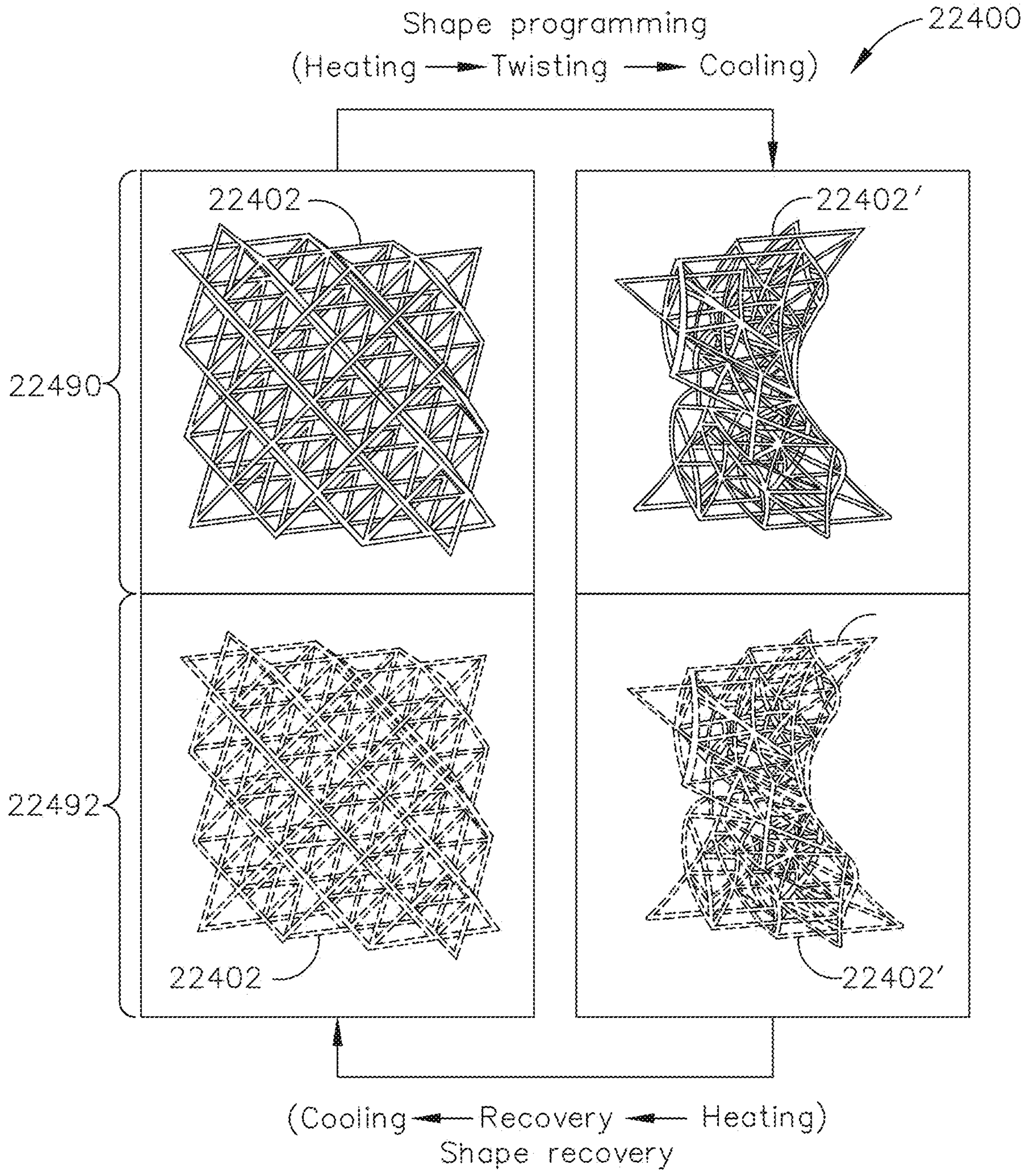
FIG. 44 is a schematic depicting a deformation process for a 4D printed matrix for a staple cartridge, according to various aspects of the present disclosure.

Referring now to FIG. 44, a deformation and recovery process 22400 for a 4D printed matrix on a cartridge body is depicted. During a shape programming stage 22490, the 4D printed matrix 22402 is heated, deformed from an original configuration to a deformed configuration 22402', and then cooled. During a shape recovery state 22492, the 4D printed matrix 22402' is heated and returns to its original configuration 22402, and then cooled. Shape programing and recovery of 4D printed materials is further described in the article "4D Printing Reconfigurable, Deployable and Mechanically Tunable Metamaterials" from Materials Horizon, Issue 6, 2019 by Chen Yang et al.

In certain instances, 4D printed matrixes can be used in combination with foldable or collapsible drivers, for example, which are further described herein. The 4D printed matrixes on the staple cartridge, for example, can be configured to selectively fold an interfering driver feature to consolidate and/or condense the footprint and stack-up within the staple cartridge at certain temperatures. The interfering features can then unfold when withdrawn from the interference condition, such as when the cartridge body resumes the original, undeformed state. In various aspects, the driver can be fully expanded when actively lifting and firing the staples. In certain instances, the driver can encounter an interfering surface near the fully fired position thereof, and an upper portion of the driver can be configured to fold into itself. The 4D matrix can form the interference surface in certain instances.

A user may want to install a staple cartridge into a channel of an end effector or disposable loading unit quickly and easily during a surgical procedure. A robust connection can also be desired. Certain robust connections can require a clinician to overcome significant resistance and/or frictional forces between interfering components. Additionally or alternatively, a robust connection may have minimal clearances and require precise alignment of the components by the clinician. Though a robust connection between the staple cartridge and the channel may be desired, it may be helpful to make the installation of the staple cartridge quicker, easier, and/or to require less force and/or effort on the part of the clinician.

In certain instances, a stapling assembly can include leveraging features which can facilitate installation of a staple cartridge into a channel. For example, the channel and the staple cartridge can include complementary geometric alignment features. Upon placing the alignment feature of the staple cartridge against the alignment feature of the channel, the alignment feature of the channel can provide a fulcrum or abutment surface about which the staple cartridge is leveraged to properly align the staple cartridge with the channel. When the staple cartridge is properly aligned owing to the abutting relationship between the alignment features, additional alignment features (e.g. a distal lug and notch) can facilitate further connection between the staple cartridge and the channel.

In certain instances, a spring can bias the staple cartridge distally along a longitudinal axis perpendicular to an insertion axis to fully and securely seat the staple cartridge in the channel. Additionally or alternatively, a distal firing force during a firing stroke can further shift the staple cartridge distally to interconnect ramped surfaces on the alignment features (e.g. distal edges of the distal lug and notch). Alternative spring-loaded and/or resilient features are contemplated to further secure the staple cartridge to the channel upon appropriate placement of the staple cartridge relative to the channel. In certain instances, a user-activated release can be configured to release one or more resilient attachment features between the staple cartridge and the channel. In other instances, the firing stroke can result in the release and/or breakage of one or more resilient attachment features.

In one example, a stapling assembly can include a staple cartridge including a cartridge body defining a longitudinal axis, wherein the cartridge body comprises a proximal cartridge alignment feature and a distal cartridge alignment feature. The stapling assembly can further include a channel dimensioned to receive the staple cartridge, wherein the channel comprises a sidewall comprising a proximal channel alignment feature and a distal channel alignment feature positioned to receive the distal cartridge alignment feature upon positioning the proximal cartridge alignment feature in abutting engagement with the proximal channel alignment feature and moving the staple cartridge along an insertion axis to a first position in the channel. The insertion axis can be perpendicular to the longitudinal axis. A spring can be configured to bias the staple cartridge distally within the channel along the longitudinal axis from the first position to a fully seated position. The proximal alignment features can include contoured abutment surfaces. The distal alignment features can includes a notch and a lug having complementary wedge-shaped distal ends.

In various instances, the improved cartridge retention and release features can increase engagement retention forces while allowing the user to release the staple cartridge from the channel with a substantially lower force. For example, a user can slide the staple cartridge proximally by overcoming a minimal spring force to quickly and easily remove the staple cartridge from the channel. In certain instances, the force required to remove a spent or fired staple cartridge can be less than the force required to remove a new, unfired staple cartridge. For example, a firing stroke, or even a partial firing stroke, can be configured to disengage and/or release certain resilient attachment features connecting the staple cartridge to the channel.

Figure 45:
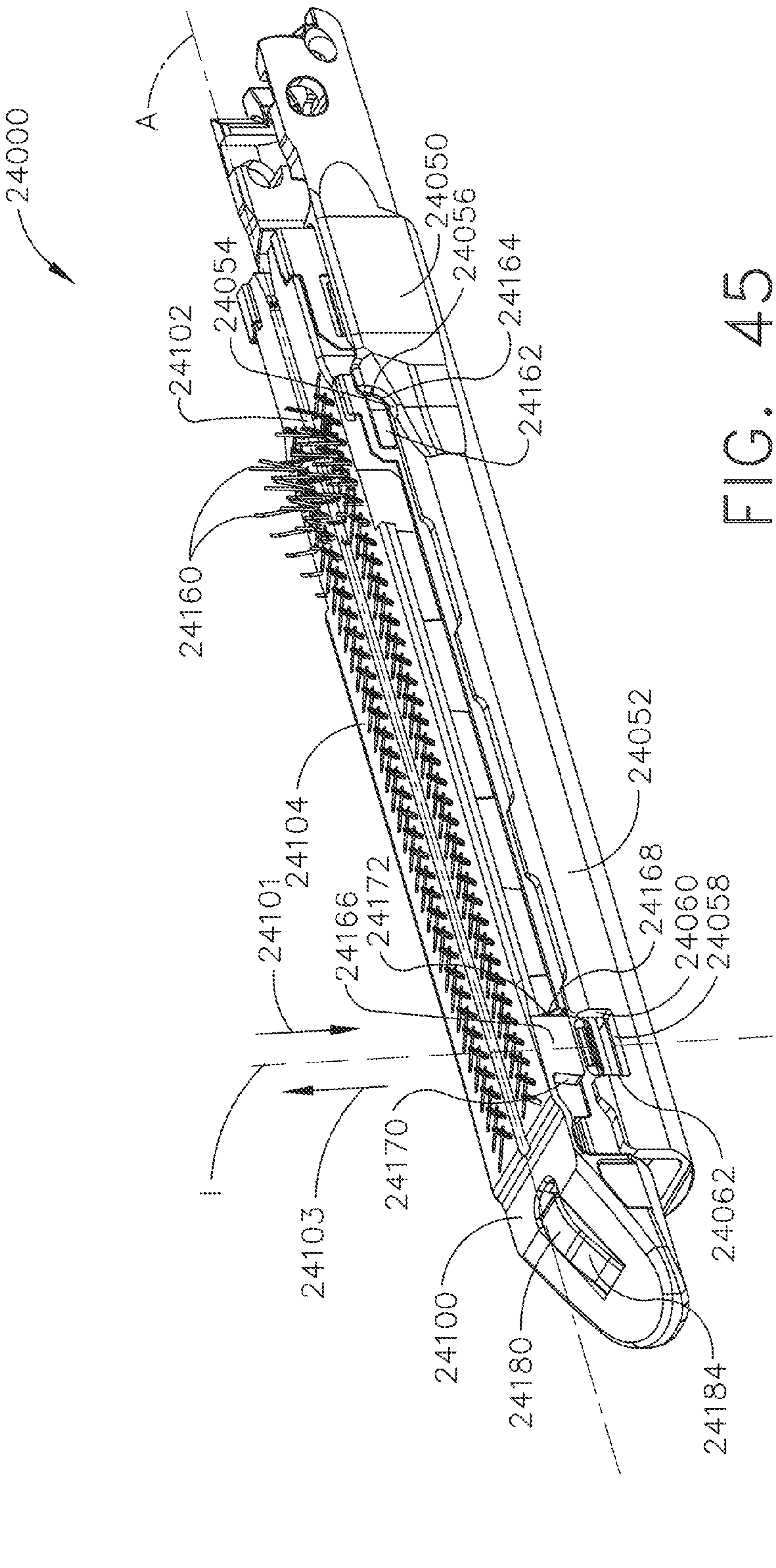
FIG. 45 is a perspective view of a staple cartridge and a channel, depicting alignment and leveraging features for installing the staple cartridge into the channel, further depicting the staple cartridge in an aligned and partially installed configuration relative to the channel, according to various aspects of the present disclosure.
Figure 46:
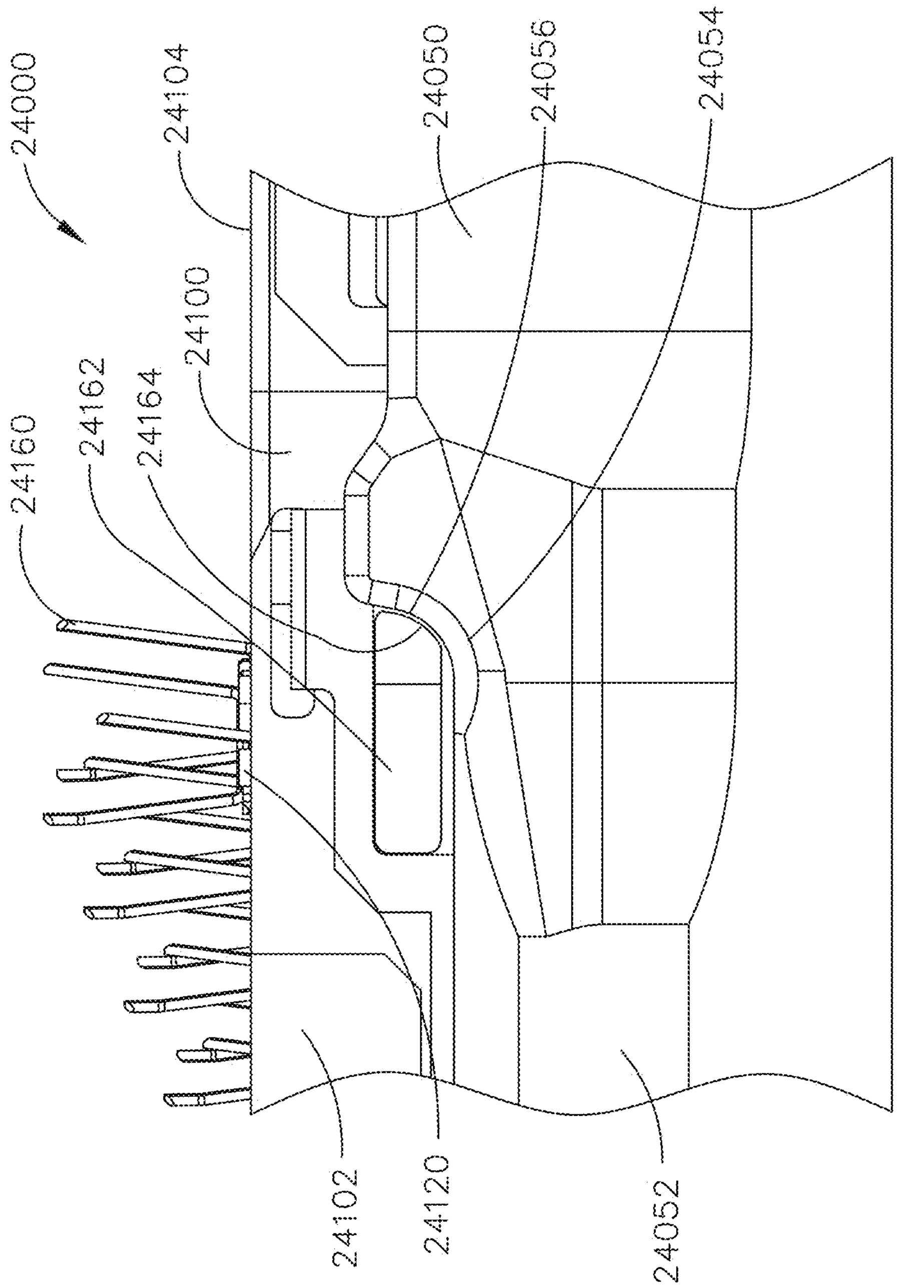
FIG. 46 is an elevation view of a proximal portion of the staple cartridge and the channel of FIG. 45 depicting the staple cartridge in the aligned and partially installed configuration, according to various aspects of the present disclosure.

Referring now to FIG. 45, a stapling assembly 24000 is shown. The stapling assembly 24000 includes a channel 24050 and a staple cartridge 24100 removably positioned in the channel 24050. The staple cartridge 24100 is a disposable, single-use component, which is configured to be removed from the channel 24050 after a firing stroke and surgical procedure therewith. The channel 24050 can be reusable and configured to receive replacement staple cartridge assemblies therein. In other instances, the staple cartridge 24100 can be removed from the channel 24050, loaded with additional staples, and reinstalled in the channel 24050. The channel 24050 can be a component of a disposable loading unit and/or a modular stapling assembly including an anvil and/or a shaft portion in certain instances.

The staple cartridge 24100 can be similar in certain aspects to the staple cartridge 20100 (FIG. 24). For example, the staple cartridge 24100 includes a cartridge body 24102 having a tissue-supporting deck 24104, staples 24160 removably positioned in the cartridge body 24102, and drivers 24120 movably supporting the staples 24160. The staples 24160 comprise a base from end-to-end and the base of the staples 24106 are obliquely-oriented relative to a longitudinal axis A along the length of the staple cartridge 24100. The staples 24160 can be configured to form a compliant staple line which allows a degree of twisting and/or stretching while minimizing damage to the tissue. In certain instances, the cartridge body 24102 can include staples in a plurality of longitudinal rows having longitudinally-aligned staples in longitudinal rows parallel to the longitudinal axis A, as further described herein.

The cartridge body 24102 includes at least one alignment nub 24162 having a proximal alignment surface 24164. In various instances, an alignment nub 24162 can protrude laterally from each side of the cartridge body 24102. The proximal alignment surface 24164 defines a curved proximal edge of the alignment nub 24162. In various instances, the alignment nubs 24162 on either side of the cartridge body 24102 can be symmetrical about the longitudinal axis A.

The cartridge body 24102 further includes an alignment lug 24166 having a proximal end 24168 and a distal end 24170. One alignment lug 24166 is positioned on each side of the cartridge body 24102. The proximal end 24168 defines an upright or vertical surface relative to the tissue-supporting deck 24104. The distal end 24170 of the alignment lug 24166 defines a wedge shape having a ramped distal surface. The ramped distal surface can form a narrower dimension along the deck 24104 and a wider dimension at the opposite end of the alignment lug 24166. In various instances, an alignment lug 24166 can be positioned on each side of the cartridge body 24102, and the alignment lugs 24166 can be symmetrical about the longitudinal axis A. The alignment lugs 24166 are closer to the distal end of the cartridge body 24102 than the alignment nubs 24162.

The channel 24050 includes lateral sidewalls 24052 forming a U-shaped channel. The staple cartridge 24100 can be releasably secured in the U-shaped channel between the sidewalls 24052. The sidewalls 24052 and/or other portions of the channel 24050 can include resilient snap-fit features for engaging the staple cartridge 24100. Each sidewall 24052 includes an alignment feature 24054 including a proximal alignment contour 24056. The proximal alignment contour 24056 comprises an edge, which is configured to catch the proximal alignment surface 24164 of the alignment nub 24162. The proximal alignment contour 24056 resists longitudinal displacement of the alignment nub 24162 in the proximal direction beyond the proximal alignment contour 24056. As further described herein, the alignment feature 24054 can act as a fulcrum or support about which the staple cartridge 24100 is leveraged during insertion and installation of the staple cartridge 24100 into the channel 24050.

The channel 24050 further includes an alignment notch 24058 having a proximal end 24060 and a distal end 24062. An alignment notch 24058 is positioned on each side of the channel 24050. The proximal end 24060 defines an upright or vertical surface in the sidewall 24052 and the distal end 24062 defines another upright surface in the sidewall 24052, which is not parallel with the vertical surface at the proximal end 24060. The upright surface defining the distal end 24062 of the alignment notch 24058 can define a sloped or ramped distal surface, which can form a wedge shape having a narrower dimension along an upper edge of the sidewall 24052 and a wider dimension at the opposite end of the notch 24058. In various instances, the alignment notches 24058 can be symmetrically positioned about the longitudinal axis A. The alignment notches 24058 are closer to the distal end of the cartridge body 24102 than the alignment nubs 24162. As further described herein, each alignment notch 24058 is positioned and dimensioned to receive one of the alignment lugs 24166 therein.

The alignment features between the channel 24050 and the staple cartridge 24100 are configured to interact to facilitate a quick and easy installation of the staple cartridge 24100 into the channel 24050. For example, to quickly align the alignment lugs 24166 with the alignment notches 24058, a clinician can draw the alignment nubs 24162 proximally into abutting engagement with the corresponding alignment features 24054 on the channel 24050. The proximal alignment contour 24056 on the proximal alignment feature 24054 acts as a longitudinal stop, which prevents further proximal displacement of the staple cartridge 24100 relative to the channel 24050. The contoured proximal edge 24164 of the alignment nubs 24162 can match or complement the contoured profile of the proximal alignment contour 24056. Upon mating of the complementary profiles, the alignment lugs 24166 are also each aligned with their corresponding alignment notch 24058.

A spring 24172 is positioned between an upright surface of the alignment lug 24166 and an upright surface of the alignment notch 24060. More specifically, the spring 24172 is positioned between the proximal end 24168 of the alignment lug 24166 and the proximal end 24060 of the alignment notch 24060. The spring 24172 is configured to bias the ramped distal end 24170 of the alignment lug 24166 distally into mating contact with the ramped distal end 24062 of the channel 24050 upon insertion of the staple cartridge 24100 into the channel 24050. The spring 24172 can be compressed between the upright proximal end 24060 of the alignment notch 24060 and the upright proximal end 24168 of the lug 24166 when the alignment nubs 24162 are in abutting engagement with the proximal alignment contours 24056 and the staple cartridge 24100 and alignment lugs 24166 thereof are moved in an installation direction 24101 parallel to an installation axis I into the channel 24050. The installation axis I is perpendicular to the longitudinal axis A.

In use, the cartridge body 24102 and the nubs 24162 thereof can be leveraged against the proximal alignment contour 24056 of the channel 24050 as the staple cartridge 24100 is moved along the installation axis I into the channel. The proximal leverage location of the alignment contour 24056 can improve the mechanical advantage of installing the staple cartridge 24100 and distal lugs 24166 thereof into the channel 24050. The nubs 24164 can slide downward into the channel 24050 as the staple cartridge 24100 moves in the installation direction 24101 into a first position, or an inserted position. After the staple cartridge 24100 has been moved to a first position, in which the staple cartridge 24100 is inserted, but not fully seated in the channel 24050, the spring 24172 is configured to shift the staple cartridge 24100 distally in a direction parallel to the longitudinal axis L into a second position, in which the staple cartridge 24100 is fully seated in the channel 24050.

Figure 47:
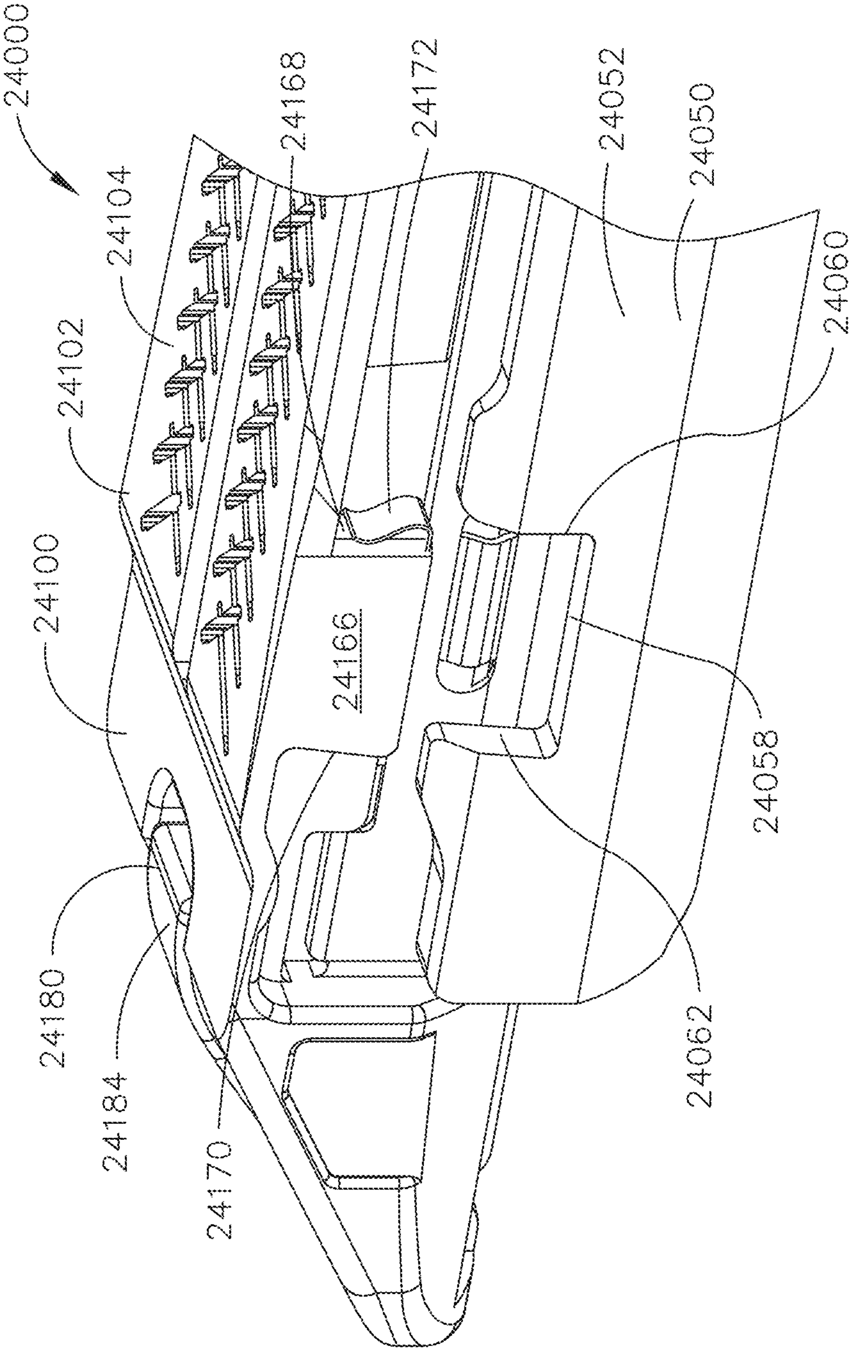
FIG. 47 is a perspective view of a distal portion of the staple cartridge and the channel of FIG. 45, depicting the staple cartridge in the aligned and partially installed configuration, according to various aspects of the present disclosure.

Referring primarily to FIG. 47, the spring 24172 is a flat spring. The spring 24172 is a cantilevered spring having a first end mounted to the alignment lug 24166, a second end opposite the first end, and a curved portion intermediate the first end and the second end. The curved portion can define an S-shaped curve, which is compressible with minimal force and/or effort by the clinician upon alignment of the proximal alignment contours 24056, 24164 and leveraging of the staple cartridge 24100 proximally against the alignment feature 24054. Upon release of the leveraging force and compressive force to the spring 24172, the spring 24172 is configured to rebound and bias the staple cartridge 24100 distally relative to the channel 24050 into a fully seated position (FIG. 48).

In the fully seated position (FIG. 48), the distal ramped ends 24062, 24170 of the alignment lug 24166 and the alignment notch 24058, respectively, are in mating engagement. The undercut geometry of the distal ends 24062, 24170 is configured to secure the staple cartridge 24100 in the channel 24050 until the spring 24172 is compressed by a user-applied force to draw the staple cartridge 24100 proximally along the longitudinal axis A and then upward in a direction 24103 parallel to the installation axis I and opposite to the installation direction 24101 to remove the staple cartridge 24100 from the channel 24050.

In certain instances, a firing element is configured to apply a distal force to the staple cartridge 24100 during a firing stroke to further secure the staple cartridge 24100 in the channel 24050. For example, the ramped distal ends 24062, 24170 can form an interlock between the staple cartridge 24100 and the channel 24050 when the staple cartridge 24100 is pushed distally. In certain instances, the distal firing force and undercut geometry of the ramped distal ends 24062, 24170 can secure the staple cartridge 24100 to the channel 24050 even without the distal biasing force of the spring 24172. For example, the stapling assembly 24000 may not include a spring configured to bias the staple cartridge 24100 relative to the channel 24050 in the direction of the firing stroke. The reader will appreciate that in stapling assemblies utilizing a distal-to-proximal firing stroke, for example, the undercut interlock between the staple cartridge 24100 and the channel 24050 can be at a proximal end 24168, 24060 of the alignment lug 24166 and alignment notch 24058, respectively.

Figure 48:
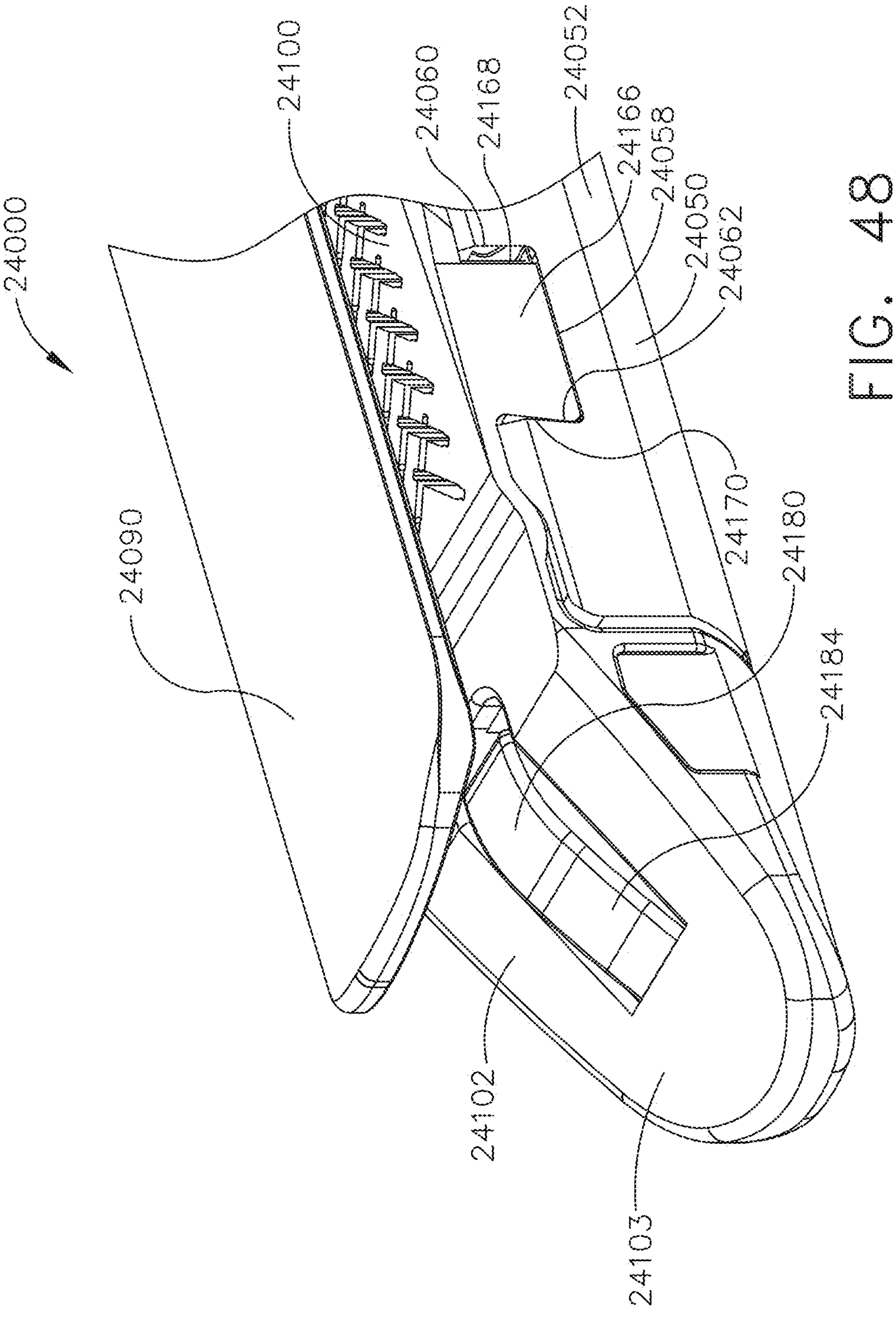
FIG. 48 is a perspective view of a distal portion of the staple cartridge and the channel of FIG. 45, depicting the staple cartridge installed and fully seated in the channel, further depicting an anvil in a clamped configuration relative to the staple cartridge, according to various aspects of the present disclosure.
Figure 49:
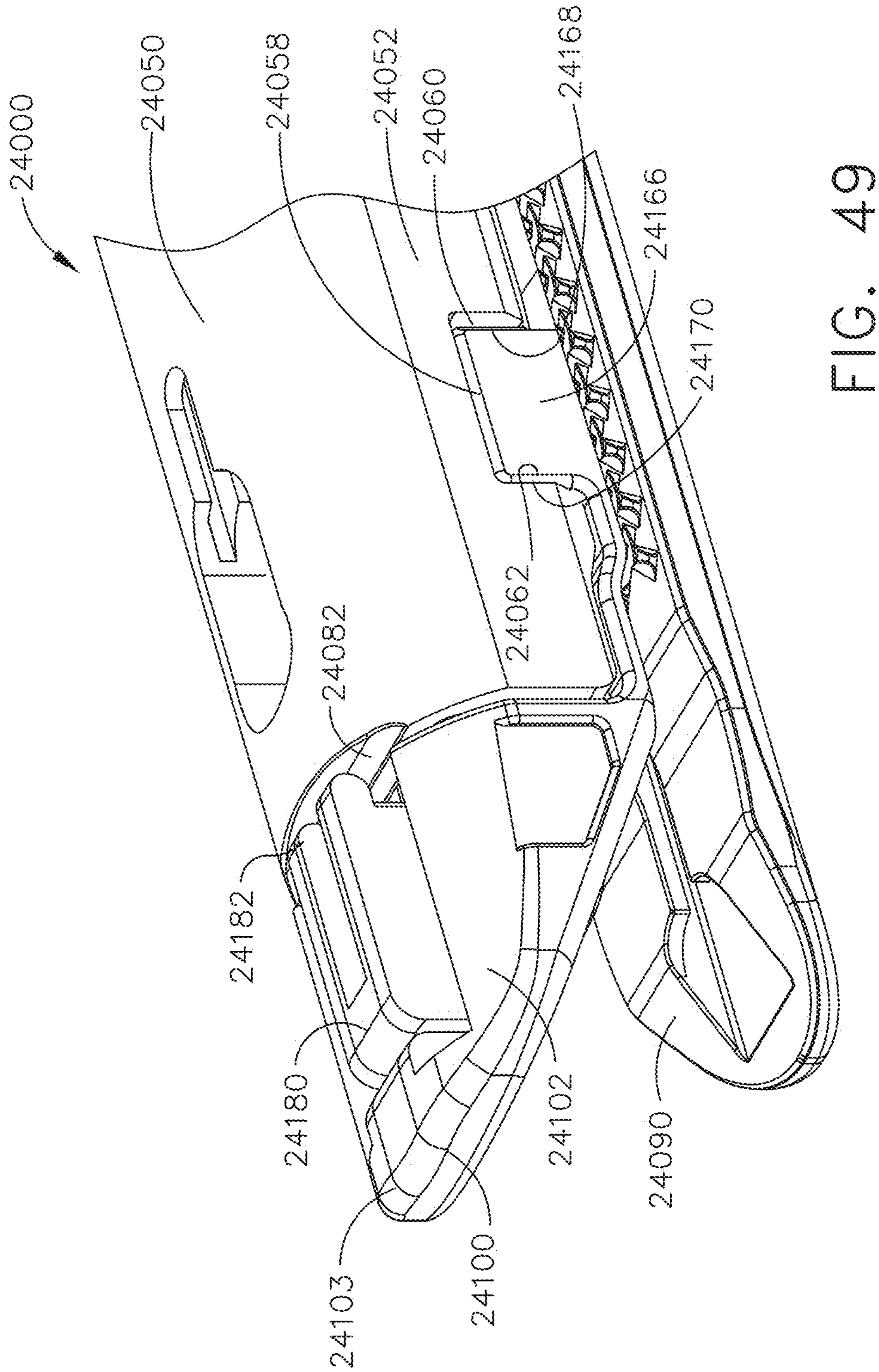
FIG. 49 is a perspective view of the distal portion of the staple cartridge, the channel, and the anvil of FIG. 48, depicting the staple cartridge installed and fully seated in the channel, and further depicting a latch on the underside of the staple cartridge in a latched position relative to the channel, according to various aspects of the present disclosure.

Referring primarily to FIGS. 47-48, the stapling assembly 24000 is shown with an anvil 24090 in the clamped configuration relative to the channel 24050 and the staple cartridge 24100 fully seated therein. The cartridge body 24102 includes a distal nose 24103 with a lock 24180. The lock 24180 includes a latching arm 24182 on an underside of the cartridge body 24102. The latching arm 24182 is configured to overlap a portion of the channel 24050 when the staple cartridge 24100 is fully seated in the channel 24050. For example, the channel 24050 includes a ledge or shelf 24082 on the underside thereof facing the latching arm 24182. The lock 24180 is movable between a first position (FIG. 49), in which the latching arm 24182 secures the distal nose 24103 of the cartridge body 24102 to the distal end of the channel 24050 by overhanging the shelf 24082, and a second position, in which the latching arm 24182 releases the shelf 24082 facilitating release of the staple cartridge 24100 from the channel 24050.

The lock 24180 also includes an anvil-facing release button 24184 opposite the latching arm 24182. The anvil-facing release button 24184 can be flush, or substantially flush, with the top surface of the distal nose 24103. The anvil-facing release button 24148 can be depressed by a clinician to drive the lock 24180 downward and/or distally to release the latch 24182 from engagement with the shelf 24082. In certain instances, the lock 24180 can be comprised of a resilient and/or deformable material, which can flex upon receiving a user input on the anvil-facing release button 24184 to move the latching arm 24182 to the second position. In other instances, the lock 24180 can pivot relative to the cartridge body 24102 to move the latching arm 24812 to the second position.

Figure 50:
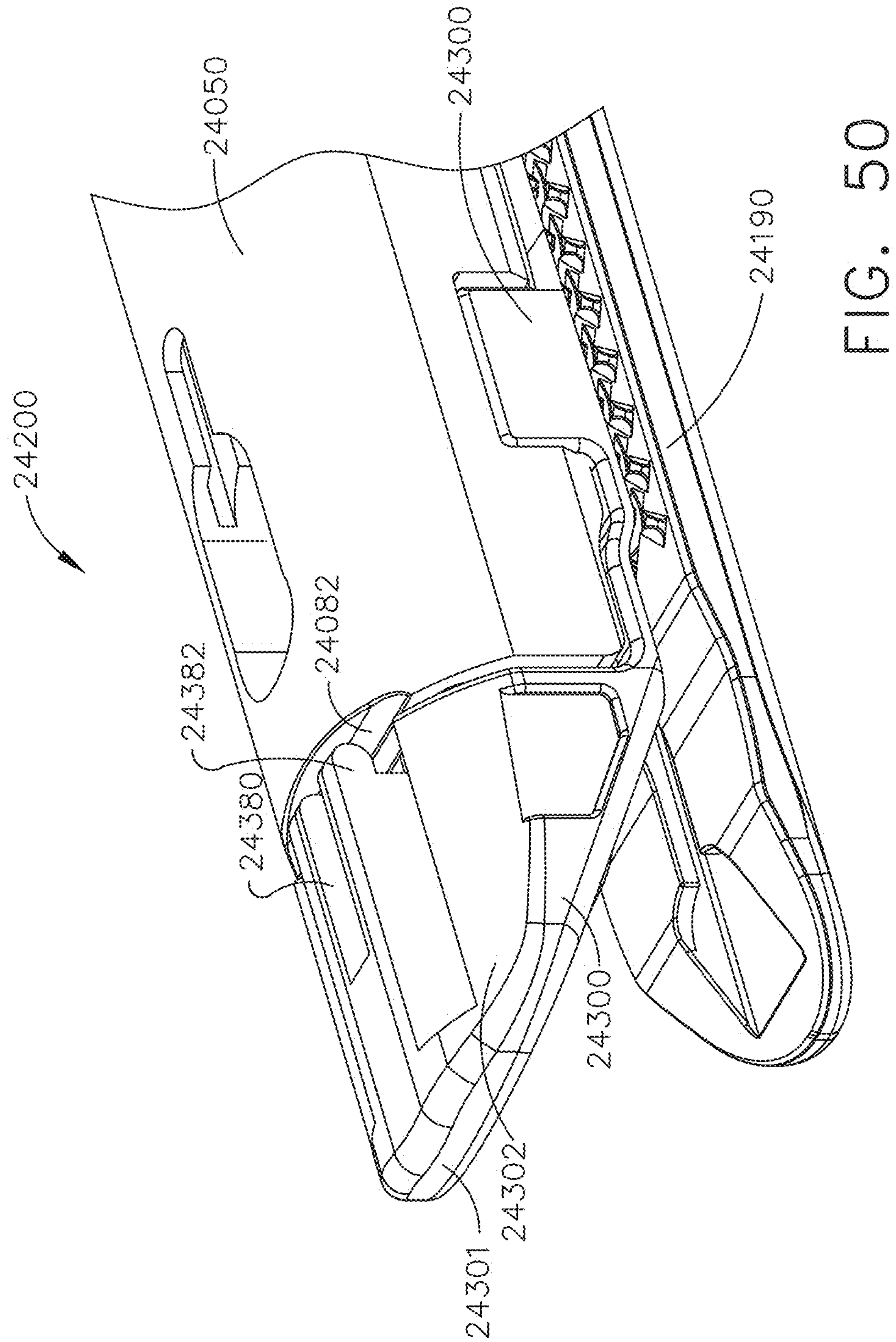
FIG. 50 is a perspective view of a distal portion of a staple cartridge, a channel, and an anvil, depicting the staple cartridge installed in the channel and the anvil in a clamped configuration relative to the staple cartridge, further depicting a flexible latch on the underside of the staple cartridge in a latched position relative to the channel, according to various aspects of the present disclosure.

In other instances, the distal nose of a cartridge body can be deflectable to releasably engage retention features along the distal edge of the elongate channel. For example, referring now to FIG. 50, a stapling assembly 24200 is shown with the anvil 24190 in the clamped configuration relative to the channel 24050 and a staple cartridge 24300 fully seated therein. The staple cartridge 24300 is identical to the staple cartridge 24100; however, the distal nose 24301 is comprised of a flexible material, or a flexible portion forming a lock 24380 having a latching arm, which is configured to flex in and out of engagement with the shelf 24082 on the underside of the channel 24050. In certain instances, the entire distal nose 24301 can be flexible to facilitate flexure of the latching arm 24382 out of engagement with the ledge 24082. In other instances, only the lock 24380 and/or latching arm 24382 thereof is flexible enough to disengage the ledge 24082.

In various instances, the cartridge body 24302 can be a composite cartridge body comprised of different materials in different regions such that the flexibility of the unitary composite cartridge body can vary from region to region. For example, the cartridge body 24302 can be 3D-printed and include flexible and/or resilient materials for the lock 24380 and/or latching arm 24382 and less flexible and/or less resilient materials for adjacent regions in the cartridge body. Additionally or alternatively, in certain instances, adjacent portions can be printed with materials having the same or similar relatively low durometers as the lock 24380 and/or latching arm 24382; however, embedded metallic within the cartridge body, such as a metal frame and/or longitudinal support, for example, can increase the overall strength and stiffness of the cartridge body.

Additional alignment and retention features between the staple cartridge and the channel are contemplated, which can improve retention and release of the staple cartridge relative to the channel. Various features can improve the ease of aligning the components and the force required to remove the staple cartridge from the channel while maintaining sufficient retention forces between the staple cartridge and the channel. These additional alignment and retention features can be combined with the proximal alignment features between the staple cartridge and the channel further described herein.

Figure 51:
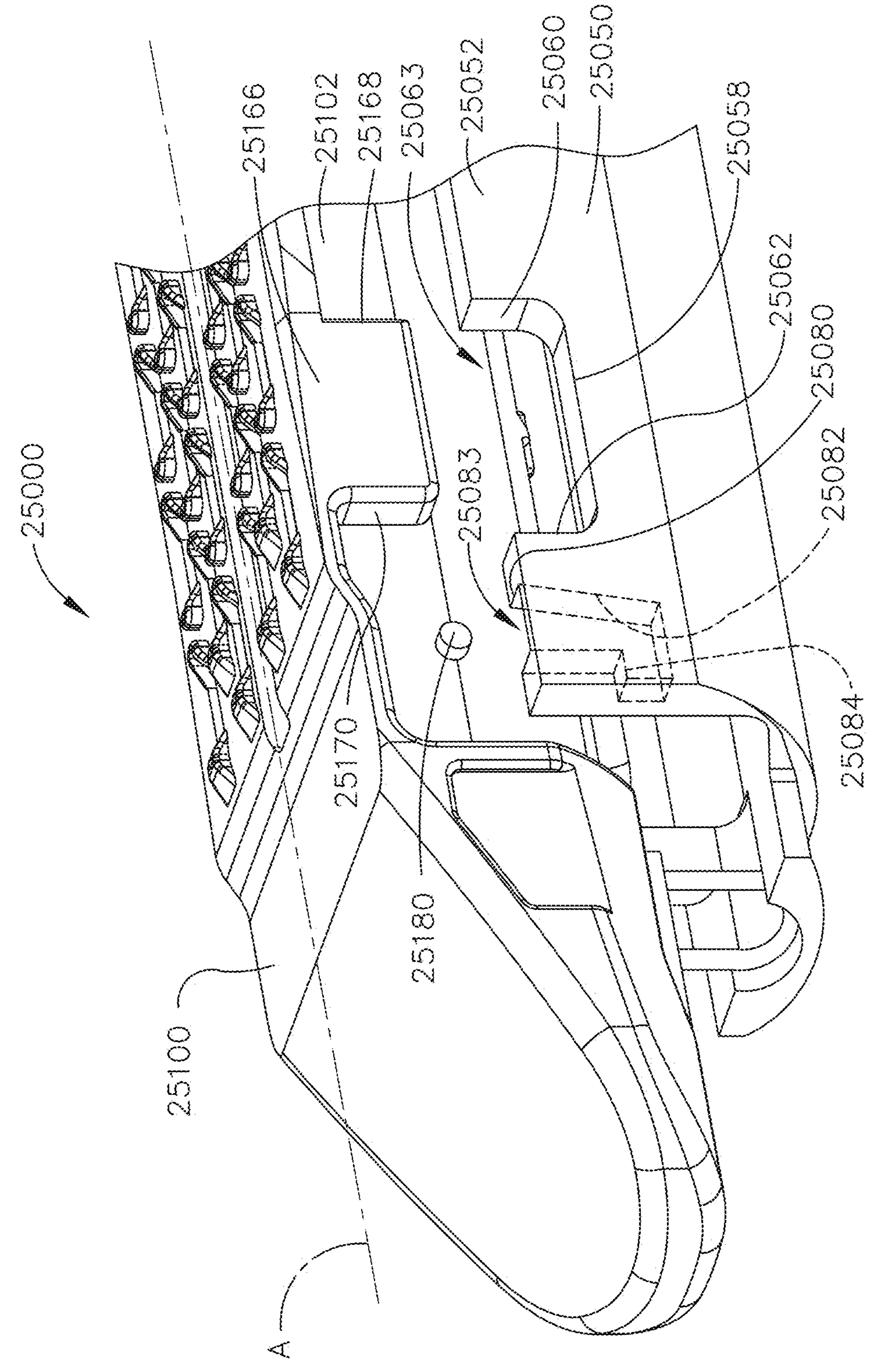
FIG. 51 is a perspective view of a channel and a staple cartridge, depicting alignment and leveraging features for installing the staple cartridge into the channel, further depicting the staple cartridge in an aligned and partially installed configuration relative to the channel, according to various aspects of the present disclosure.

A stapling assembly 25000 is shown in FIG. 51. The stapling assembly 25000 is similar in many aspects to the stapling assembly 24000 and includes a staple cartridge 25100 and a channel 25050; however, the stapling assembly includes alternative proximal alignment and retention features between the staple cartridge 25100 and the channel 25050. Additionally, the staple cartridge 25100 includes longitudinal rows of staple cavities in a cartridge body 25102 thereof and longitudinally-aligned staples positioned in the staple cavities. The staple cavities are oriented parallel to a longitudinal axis A extending along a longitudinal slot and centerline of the cartridge body 25102.

The cartridge body 25102 includes an alignment lug 25166, which comprises a proximal end 25168 and a distal end 25170. An alignment lug 25166 can be positioned on each side of the cartridge body 25102. The proximal end 25168 can define an upright or vertical surface, and the distal end 24170 can also comprise an upright or vertical surface. The upright surfaces defining the proximal and distal ends 25168, 25170, respectively, can be parallel or substantially parallel. In various instances, an alignment lug 25166 can be positioned on each side of the cartridge body 25102 and the alignment lugs 25166 can be symmetrical about a centerline through the cartridge body 25102.

The staple cartridge 25100 also includes a lateral pin 25180 protruding outwardly from the cartridge body 25102. Another symmetrically-positioned lateral pin 25180 can protrude laterally outward on the other side of the cartridge body 25102.

The channel 25050 includes lateral sidewalls 25052 forming a U-shaped channel. The staple cartridge 25100 can be releasably secured in the U-shaped channel between the sidewalls 25052. The channel 25050 further includes an alignment notch 25058, which comprises a proximal end 25060 and a distal end 25062. An alignment notch 25058 can be positioned on each side of the channel 24050 to receive a corresponding alignment lug 25166. The proximal end 24060 defines an upright or vertical surface in the sidewall 24052 and the distal end 24062 defines another upright surface in the sidewall 24052. The upright surfaces can be parallel or substantially parallel.

In other instances, the distal ends 25062, 25170 of the alignment notch 25058, 25166, respectively, can be undercut, as further described herein, to further secure the staple cartridge 25100 to the channel 25050 when the staple cartridge 25100 is fully seated in the channel 25050.

The channel 25050 further includes a slot 25084 defining an internal track for the lateral pin 25180. The slot 25080 includes a V-shaped or tapered entry portion 25082 extending parallel to an insertion direction of the staple cartridge 25100 and a terminal portion 25084 extending parallel to a longitudinal axis of the cartridge body. The V-shaped entry portion 25082 provides a wider entry region 25083 for the lateral pin 25180 into the slot 25084, which ensures the clinician does not need to align the staple cartridge 25100 to the channel 25050 with exacting accuracy. Moreover, the wider entry region 25083 to the slot 25084 can define a larger range of longitudinal positions for the staple cartridge 25100 relative to the channel 25050 than the allowable range of longitudinal positions to align the alignment lug 25166 with an entry region 25063 of the alignment notch 25058.

The alignment features between the channel 25050 and the staple cartridge 25100 are configured to interact to facilitate a quick and easy installation of the staple cartridge 25100 into the channel 25050. For example, to quickly align the alignment lugs 25166 with the alignment notches 25058, a clinician can position the staple cartridge 25100 anywhere in the larger range of longitudinal positions for positioning the lateral pin 25180 in the entry portion 25083 of the slot 25080. As the lateral pin(s) 25180 move along the narrowing track of the V-shaped portion 25082 of the slot 25080, the lug(s) 25166 can be funneled into alignment with the alignment notches 25058.

In various instances, the staple cartridge 25100 can drop into the channel 25050 with minimal interference or frictional resistance. For example, the staple cartridge 25100 may not be secured to the channel 25050 with robust friction-fit features between the staple cartridge 25100 and the channel 25050. Instead of such friction-fit features or in addition thereto, the geometry of the slot 25080 can secure the staple cartridge 25100 in the channel 25050. For example, frictional forces exerted on the staple cartridge 25100 during a proximal-to-distal firing stroke can move the lateral pin 25180 distally along the terminal portion 25084 of the slot 25080 and shift the staple cartridge 25100 distally in the channel 25050. In such instances, the firing forces can move the lug(s) 25166 into their distal-most positions flush with the distal ends 25062 of the alignment notches 25058.

In various instances, to remove a spent staple cartridge 25100 from the channel 25050, a clinician can draw the staple cartridge 25100 proximally to remove the lateral pin 25180 from the terminal portion 25084 of the slot 25080. When the staple cartridge 25100 is shifted proximally by a clinician, which requires minimal force and exertion, the clinician can quickly and easily lift the staple cartridge 25100 out of the channel 25050.

Figure 52:
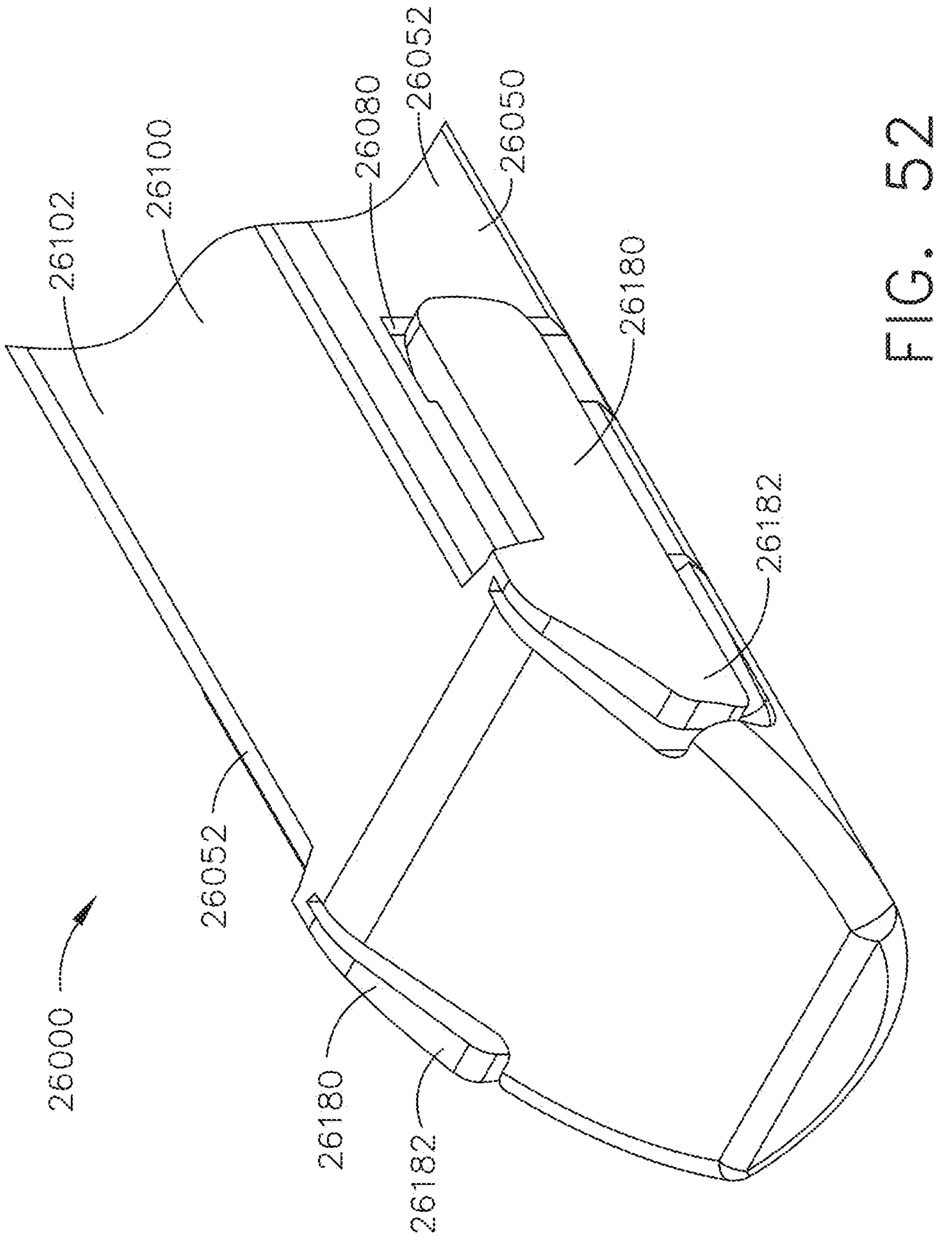
FIG. 52 is a perspective view of a portion of a staple cartridge and a channel, depicting lateral latching arms of the staple cartridge engaged with lateral passages in sidewalls of the channel, according to various aspects of the present disclosure.
Figure 53:
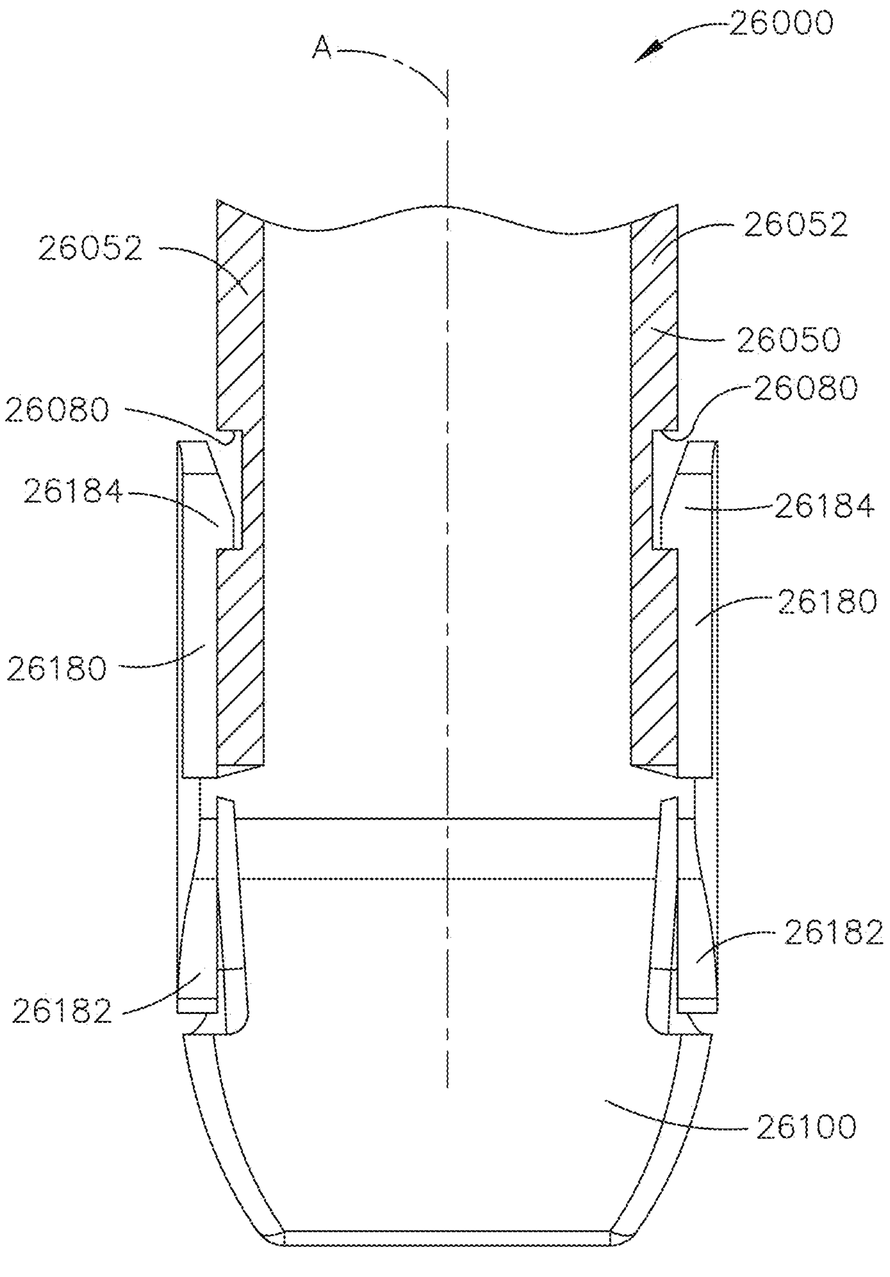
FIG. 53 is a plan partial cross-section view of the portion of the staple cartridge and the channel of FIG. 52, depicting the lateral latching arms of the staple cartridge engaged with lateral passages in sidewalls of the channel, according to various aspects of the present disclosure.
Figure 54:
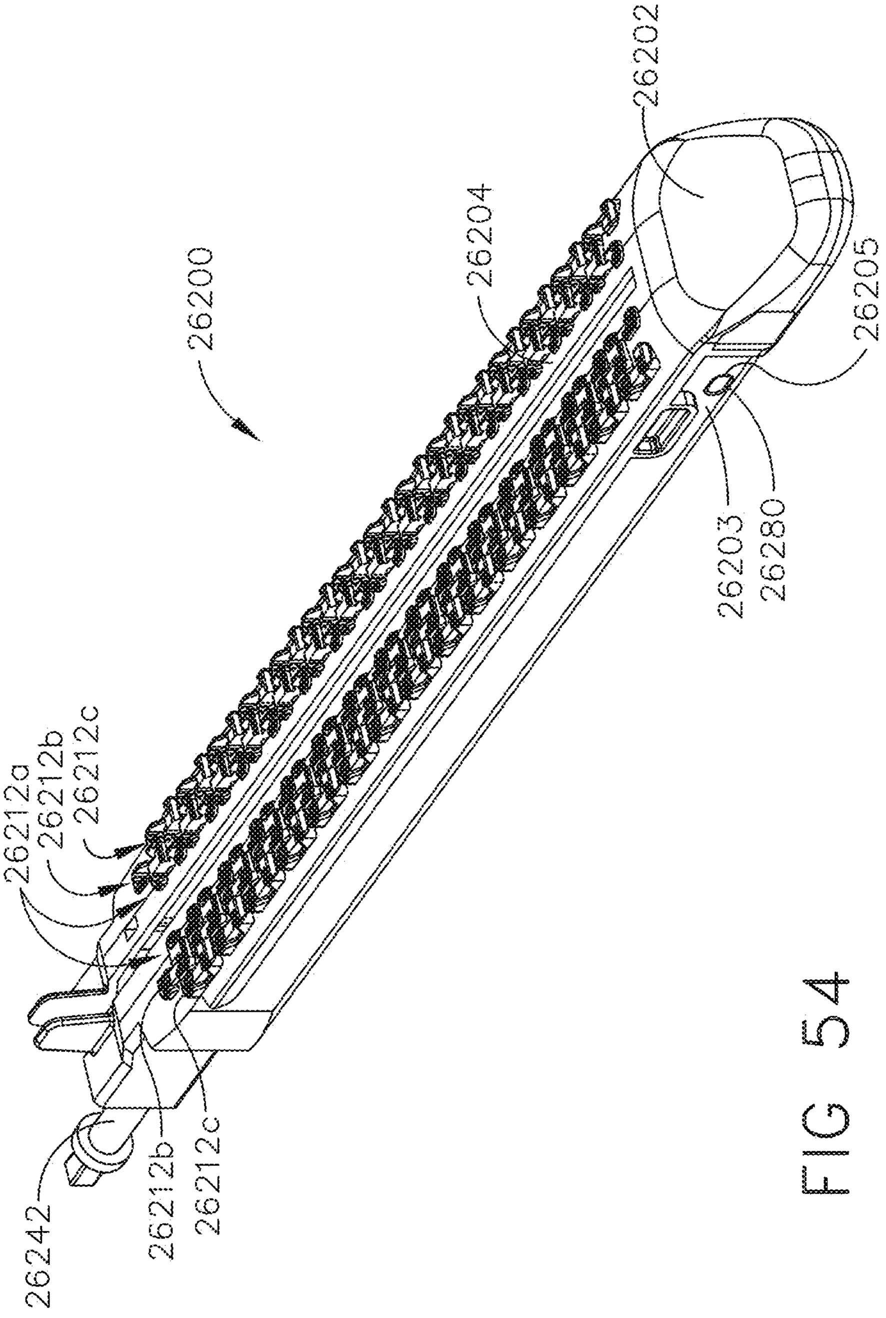
FIG. 54 is a perspective view of a staple cartridge and a rotary drive screw, according to various aspects of the present disclosure.
Figure 55:
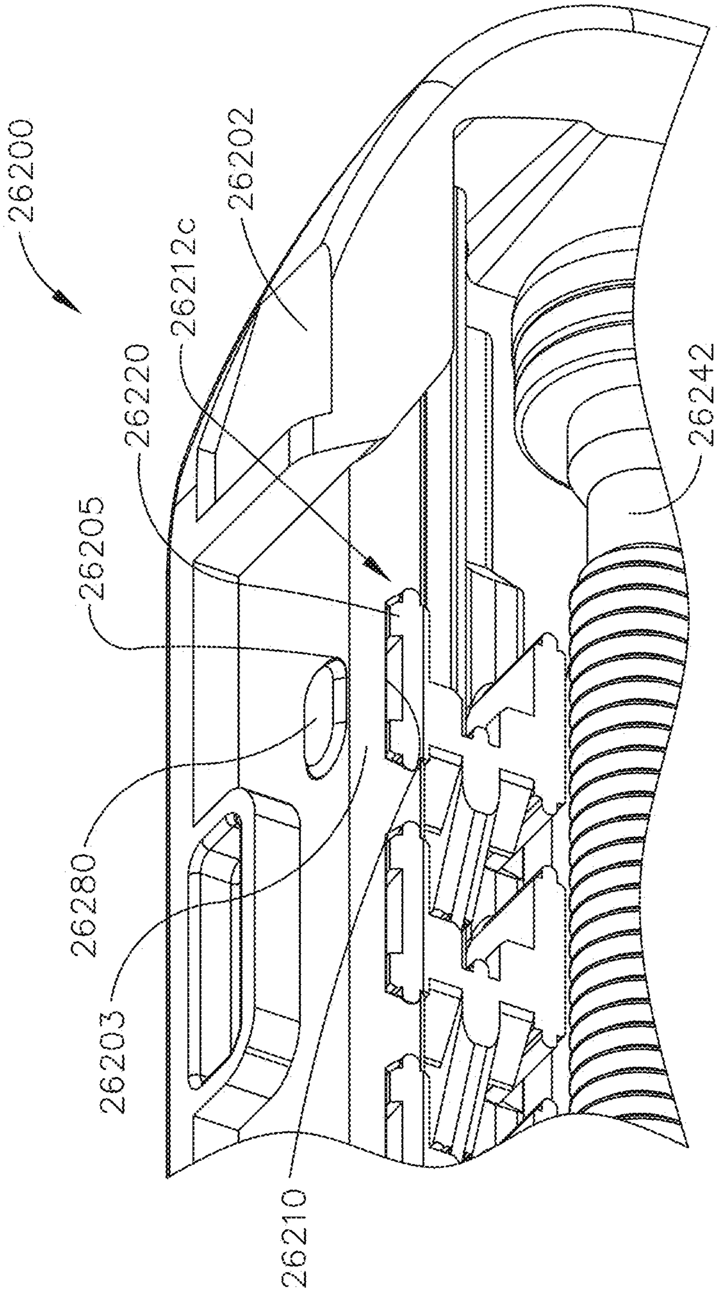
FIG. 55 is a perspective view of a distal portion of the staple cartridge and the rotary drive screw of FIG. 54, depicting a cartridge body and drivers with the drivers in their unfired positions in the cartridge body, according to various aspects of the present disclosure.
Figure 56:
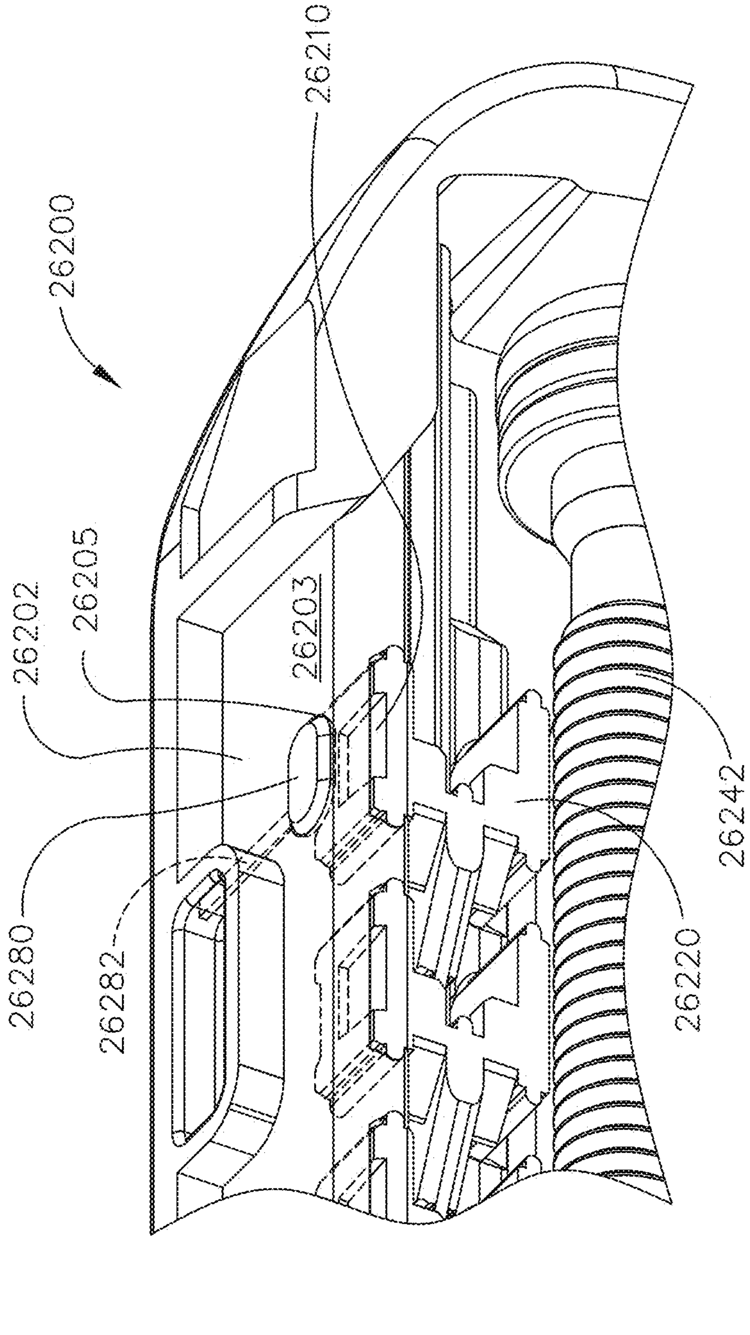
FIG. 56 is a perspective view of the distal portion of the staple cartridge and the rotary drive screw of FIG. 55 with the drivers in their unfired positions and depicting hidden internal features with dashed lines for illustrative purposes, according to various aspects of the present disclosure.
Figure 57:
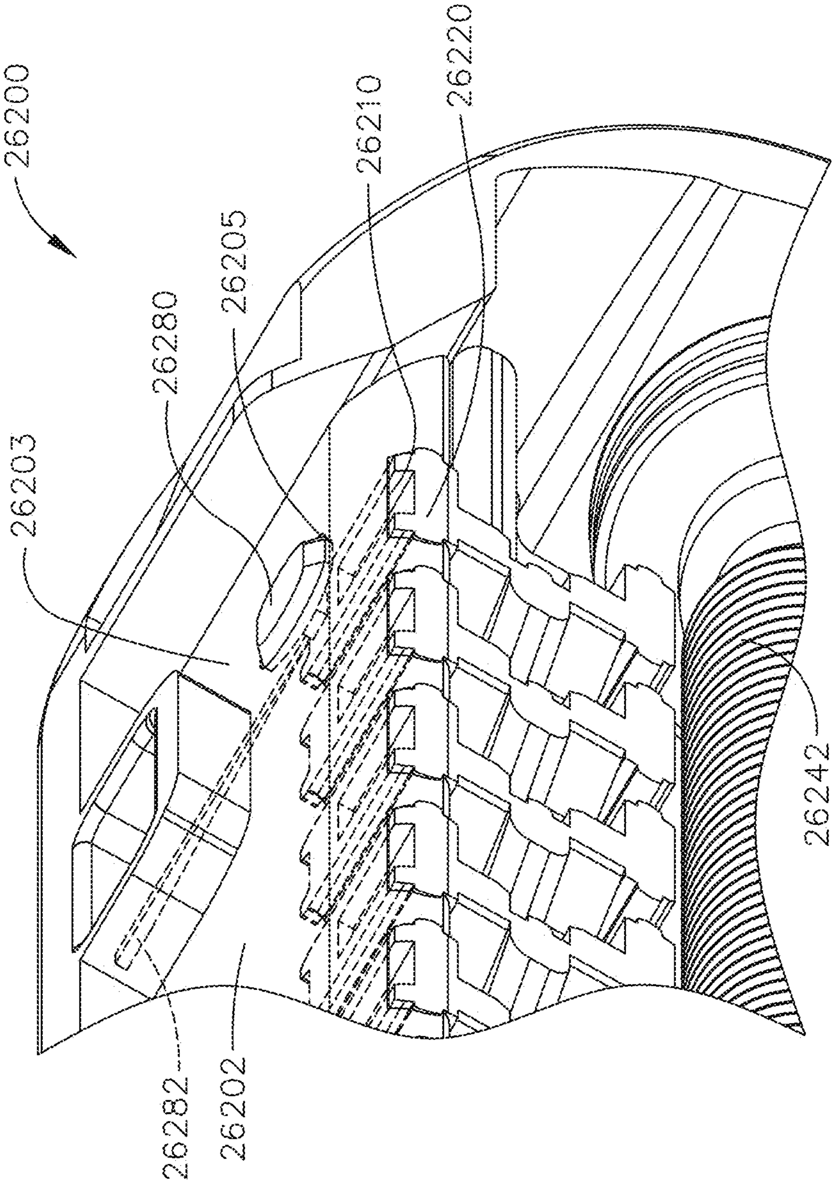
FIG. 57 is another perspective view of a distal portion of the staple cartridge and the rotary drive screw of FIG. 55 with the drivers in their unfired positions and depicting hidden internal features with dashed lines for illustrative purposes, according to various aspects of the present disclosure.

An alternative latching mechanism between a staple cartridge 26100 and a channel 26050 for a stapling assembly 26000 is shown in FIGS. 52 and 53. The staple cartridge 26100 is similar in many aspects to the various staple cartridges described herein and can include a cartridge body 26102 having staples and staple-supporting drivers movably positioned within the cartridge body 26102. The channel 26050 includes opposing sidewalls 26052 forming a U-shaped channel profile, which are configured to receive the staple cartridge 26100 therebetween or at least mostly therebetween. For example, the staple cartridge 26100 includes lateral latching arms 26180 that are configured to releasably engage lateral recesses 26080 along an outside surface of the sidewalls 26052.

The latching arms 26180 extend along lateral sides of the staple cartridge 26000 and can be integrally formed with (e.g. molded with) the cartridge body 26102. For example, the cartridge body 26102 and the latching arms 26180 can be a unitary, single-piece component. In various instances, the latching arms 26180 can be deflectable. The latching arms 26180 includes a user-actuation button 26182 and a catch 26184. The catch 26184 is longitudinally offset from the user-actuation button 26182. A lever arm extends between the user-actuation button 26182 and the catch 26184 such that an actuation of the button 26182 is configured to deflect the catch 26184. For example, an inwardly-exerted actuation to the button 26182, is configured to deflect the catch 26184 outward out of engagement with the lateral recess 26080. In certain instances, deflection of the catch 26184 upon a clinician's actuation to the button 26182 is configured to remove the catch 26184 from the recess 26080. In other instances, the catch 26184 can move to a less engaged and, thus, more easily overcome position relative to the recess 26080. A clinician can apply a pinching motion to the buttons 26182 to simultaneously actuate both buttons 26182 and deflect both catches 26184 out of engagement with the recesses 26080.

In various instances, to install the staple cartridge 26100 in the channel 26050, the staple cartridge 26100 can be moved vertically in an insertion direction until a portion of the cartridge body 26102 rests in the channel 26050. In this position, the latching arms 26180 can be aligned with longitudinal guides along the outer surface of the sidewalls 26052. As the cartridge body 26102 is slid proximally toward a fully seated position in the channel 26050, the latching arms 26180 move along the longitudinal guides and the catches 26184 snap into the recesses 26080 to secure the staple cartridge 26100 in the fully seated position. When the staple cartridge 26100 is fully seated in the channel 26050 and the catches 26184 are engaged or locked in the recesses 26080, the width of the stapling assembly can still be within the traditional sized trocar (e.g. a 12-mm profile). To release the staple cartridge 26100 from the channel 26050, a clinician pinches the buttons 26182 to bias the catches 26184 outward from the recesses 26080 such that the clinician can remove the staple cartridge 26100 by drawing it distally along the longitudinal axis A and/or vertically away from the channel 26050.

In certain instances, the cartridge body 26102 is plastic and the latching arms 26180 are also plastic. For example, the cartridge body 26102 and the latching arms 26180 can be a molded composite plastic component.

In other instances, the cartridge body can be a composite assembly of plastic and metal. For example, the latching arms can be metallic springs, which are formed with the cartridge body. The latching arms can be insert molded metallic arms. Metal latching arms can provide a greater spring constant and a snappier latching feature than plastic arms in certain instances.

In certain instances, a stapling assembly can include a frangible cartridge retention feature, which is configured to secure a staple cartridge in the channel until the frangible cartridge retention feature is intentionally broken by a user. For example, a clinician can intentionally break the cartridge retention feature and/or the feature can be broken during the firing stroke, such as at or near the completion of the firing stroke. Breaking of the frangible cartridge retention feature, can reduce the retention force between the staple cartridge and the channel such that a clinician can remove the staple cartridge with a lower amount of force. In various instances, when the frangible feature is broken, it can remain connected to the staple cartridge body. For example, referring again to the lock 24380 in FIG. 50, the lock can include a frangible portion, which is configured to crack, but not fall off, when the user applies an intentional action to the staple cartridge to remove it from the channel.

In certain instances, a staple cartridge can include a detent that is engaged with the channel and is released from the channel upon completion of the firing stroke. Referring now to FIGS. 54-59, a staple cartridge 26200 is shown, which is similar in many aspects to the staple cartridge 20100 (FIG. 24). For example, the staple cartridge 26200 includes a cartridge body 26202 including a tissue-supporting deck 26204 having staple cavities defined therein; the staple cavities are arranged in three longitudinal rows 26212*a*, 26212*b*, 26212*c* on each side of a rotary drive screw 26242, which is similar to the firing screw 261 (see FIGS. 4 and 5) in many aspects. Staples in the staple cartridge 26200 are supported by drivers 26220, which are similar in many aspects to the triple driver 20120 (FIG. 26). For example, the driver 26220 include three parallel staple-supporting cradles configured to support staples such that the driver 26220 is configured to fire staples from the inner row 26212*a*, the intermediate row 26212*b*, and the outer row 26212*c* simultaneously.

Figure 58:
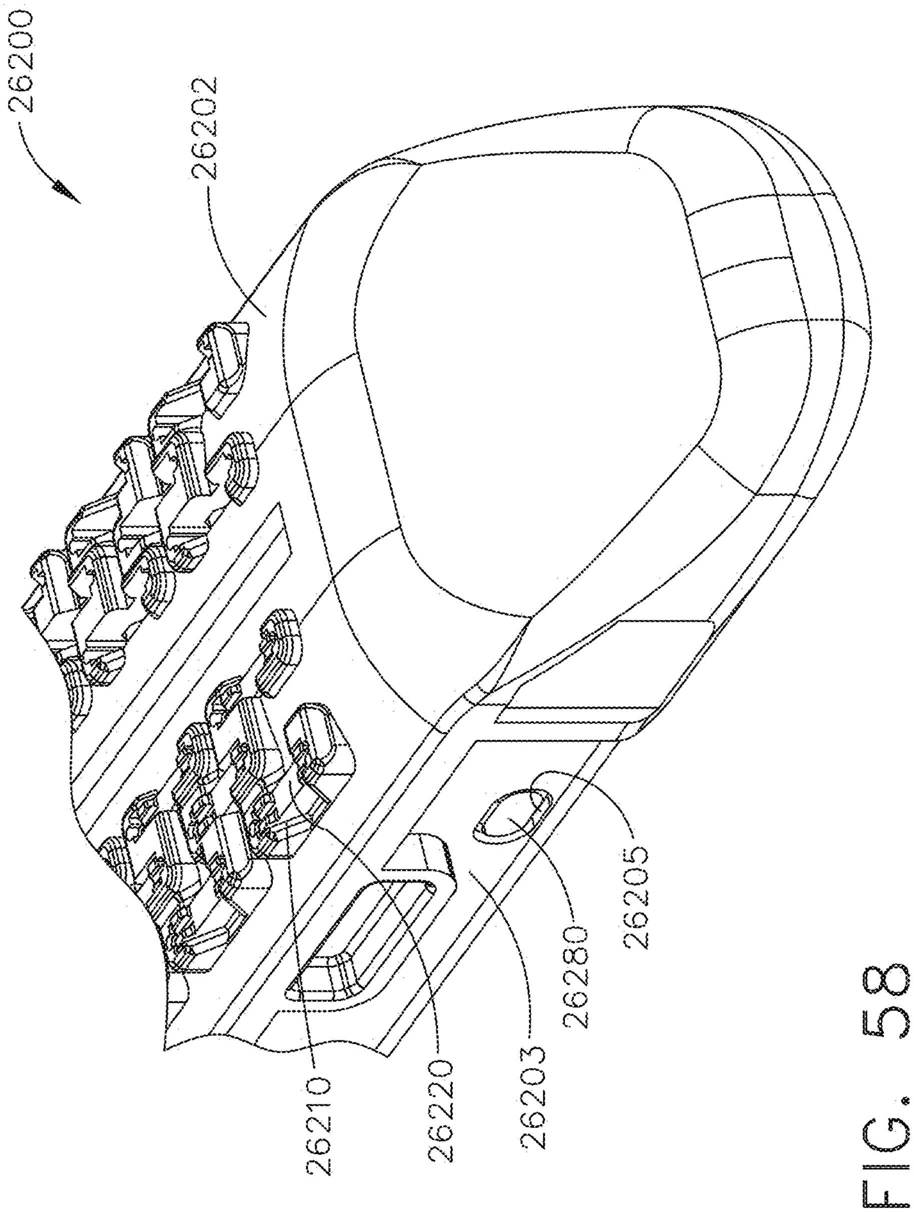
FIG. 58 is a perspective view of a distal portion of the staple cartridge of FIG. 54 with the drivers moved to their fired positions in the cartridge body, according to various aspects of the present disclosure.
Figure 59:
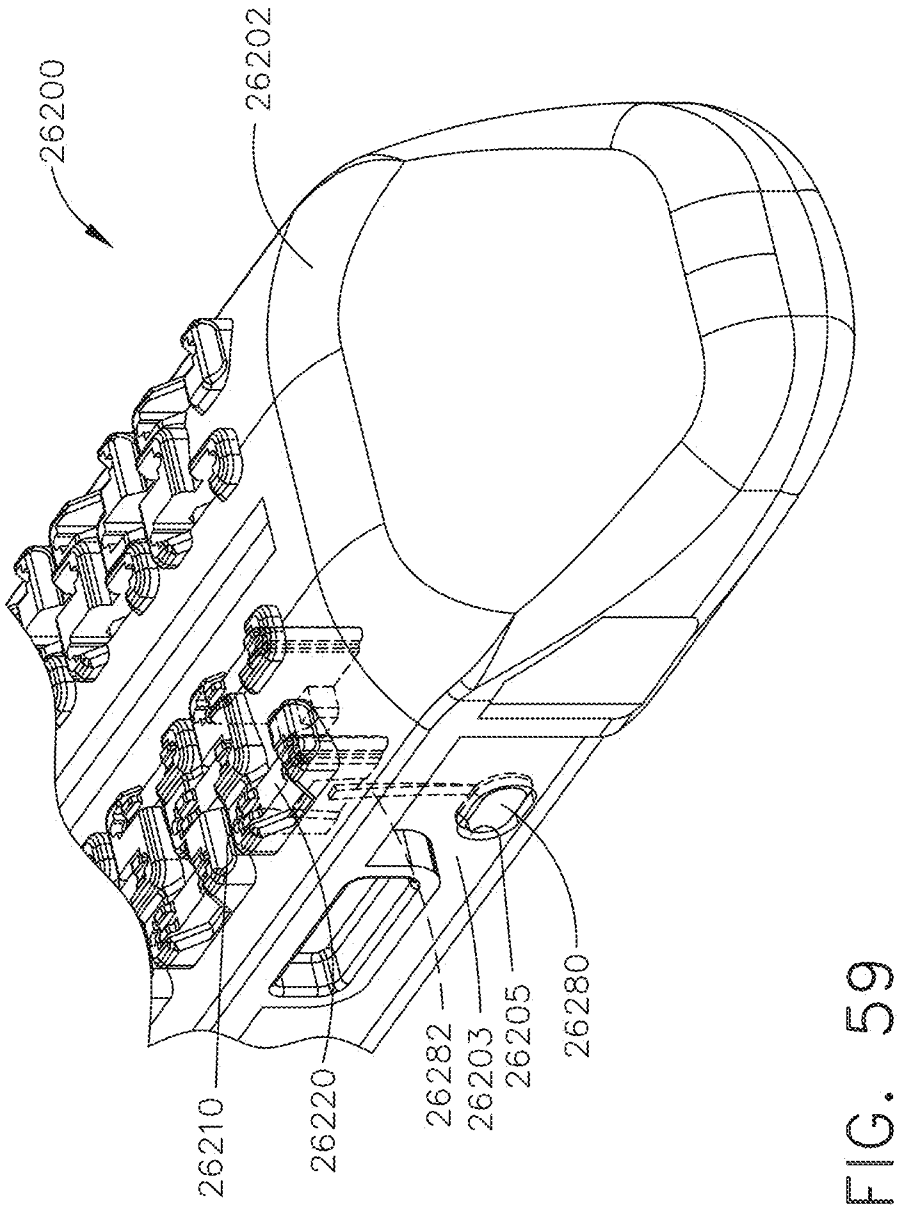
FIG. 59 is a perspective view of the distal portion of the staple cartridge of FIG. 58 with the drivers in their fired positions and depicting hidden internal features with dashed lines for illustrative purposes, according to various aspects of the present disclosure.

The staple cartridge 26200 includes a detent 26280 that releasably engages the channel. The detent 26280 is movable between a locked configuration (FIGS. 54-57) and an unlocked configuration (FIGS. 58 and 59). In certain instances, an interior-facing side of a channel sidewall, which is positioned adjacent to the cartridge body 26202, can include a recess dimensioned and structured to receive the detent 26280 in the locked configuration. For example, the channel 20852 (FIG. 99) includes distal recesses 20853. The recess is configured to hold the detent 26280 and, thus, the staple cartridge 26200 relative to the channel until the detent 26280 is moved to the unlocked configuration. In other instances, the outward bias of the detent 26280 against the channel sidewall is configured to frictionally engage the channel without placement of the detent 26280 in a recess. Opposing detents 26280 on opposite sides of the staple cartridge 26000 are configured to frictionally-engage the channel to hold the staple cartridge 26000 therein.

The detent 26280 is housed in the distal-most staple cavity 26210 in the outer row 26212*c*. A through-hole 26205 is defined in an outer wall 26203 of the cartridge body 26202 into the distal staple cavity 26210 in the outer row 26212*c*. The detent 26280 is aligned with the through-hole 26205 and protrudes from the cartridge body 26202 at the through-hole 26205 when the detent 26280 is in the locked configuration (FIGS. 54-57). A bar 26282 extends from the detent 26280 and is operably engaged with the driver 26220 in the distal-most staple cavity 26210.

When the distal-most driver 26220 is in the unfired position (FIGS. 54-57), the distal-most driver 26200 can bias the detent 26280 into the locked position. Referring now to FIGS. 58 and 59, at the completion of the firing stroke when the distal-most driver 26200 is lifted by the sled through the staple cavity and toward the tissue-supporting deck 26204, the distal-most driver 26220 can move away from the detent 26280 and engage the bar 26282. As the distal-most driver 26220 moves along the bar 26282, the driver 26220 is configured to bias the bar laterally outward, which pivots the detent 26280 inward into and/or through the through-hole 26205 and out of engagement with the channel. In such instances, the distal-most driver 26220 releases the snap feature, i.e. the detent 26280, when the firing stroke is completed.

In certain instances, multiple driver-releasable detents can be positioned along the length of the cartridge body 26202. In certain instances, longitudinally-staggered and/or longitudinally-symmetrically detents can be positioned along both sides of the cartridge body 26202. In addition to the drive-releasable detent 26280, the sled can be configured to release snap-fit or detent features in certain aspects of the present disclosure. Moreover, in certain instances, the driver(s) can be configured to snap or break the detent 26280 and/or the bar 26282 thereof during the firing stroke to release the attachment features.

In various instances, the staple cartridge assemblies herein can include driver retention features configured to prevent the release of the drivers from the cartridge bodies. For example, certain staple cartridges include a metal pan, which is heat-staked or thermoformed to the cartridge body after the drivers are installed in the fastener cavities. The metal pan(s) can wrap around an underside of the cartridge body and hold the drivers therein. In certain instances, the drivers can be retained without a separate metal pan to create additional space in the small form factor of the cartridge assembly. For example, as further described herein, heat stakes between the cartridge body and the drivers can retain the drivers. Additionally or alternatively, the cartridge body can be over-molded with a metal pans. For example, driver retention features can include thermoformed interference features between the drivers and the cartridge body and/or insert molded components within the cartridge body.

Figure 60:
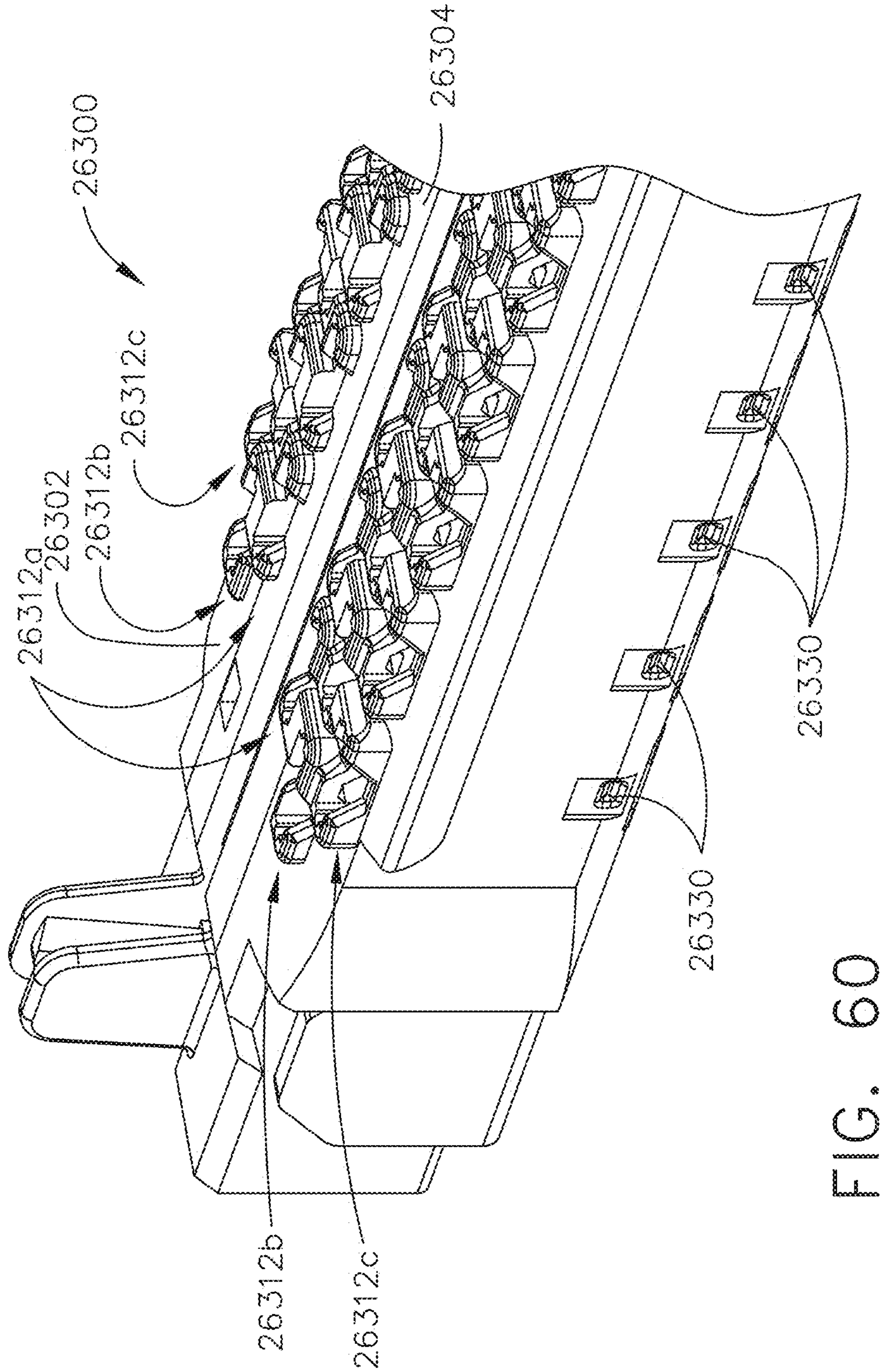
FIG. 60 is a perspective view of a proximal portion of a staple cartridge having a row of indentations, according to various aspects of the present disclosure.
Figure 61:
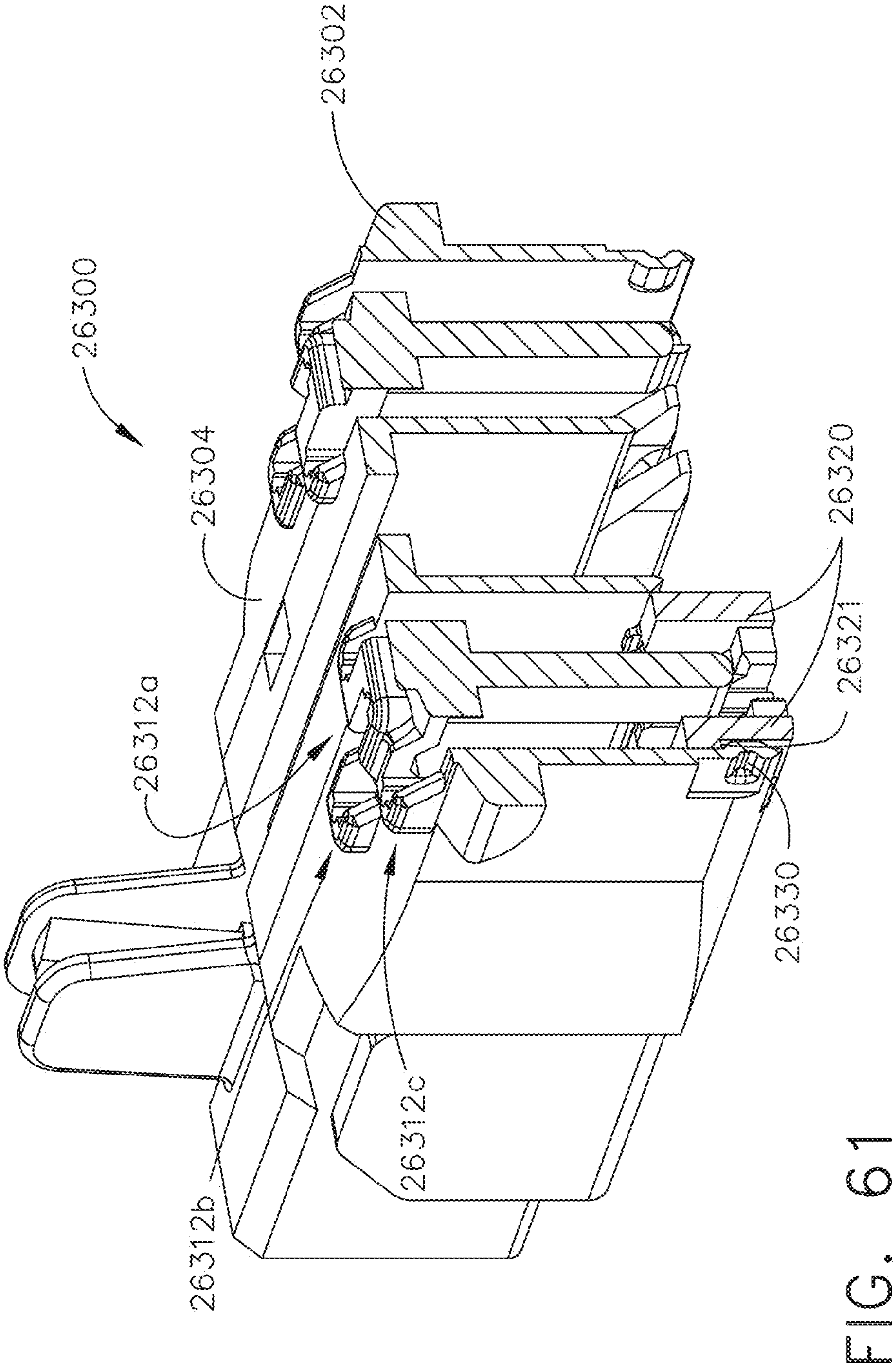
FIG. 61 is a perspective cross-section view of the staple cartridge of FIG. 60, depicting an indentation in the cartridge body engaged with a lip on a sidewall of a driver, according to various aspects of the present disclosure.

A staple cartridge 26300 is shown in FIGS. 60 and 61. The staple cartridge 26300 is similar in many aspects to the staple cartridge 20100 (FIG. 24). For example, the staple cartridge 26300 includes a cartridge body 26302 including a tissue-supporting deck 26304 having staple cavities defined therein; the staple cavities are arranged in three longitudinal rows 26312*a*, 26312*b*, 26312*c* on each side of the cartridge body 26302. Staples in the staple cartridge 26300 are supported by drivers 26320 (FIG. 61), which are similar in many aspects to the triple driver 20120 (FIG. 26). For example, the driver 26320 includes three parallel staple-supporting cradles configured to support staples such that the driver 26320 is configured to fire staples from the inner row 26312*a*, the intermediate row 26312*b*, and the outer row 26312*c*.

The cartridge body 26302 includes a row of indentations 26330, or dimples, along a lower portion of the cartridge body 26302. The row of indentations 26330 can be positioned to engage and retain the drivers 26320 when the drivers 26320 are in their unfired positions. In FIG. 60, each indentation 26330 is configured to engage a driver 26320. For example, each driver 26320 can be held is position by an indentation 26330 adjacent to the outer surface of the adjacent staple-supporting column thereof. The indentations 26330 in the cartridge body 26302 can prevent the drivers from falling out of the cartridge body 26302 when the drivers 26320 are in their unfired and down-most positions.

The indentations 26330 in the cartridge body 26302 are configured to engage a recess 26321 in the outer surface of the driver 26320. The recess 26321 can include an upper lip or boundary, which prevents vertical displacement of the driver 26320 relative to the cartridge body 26302. In various instances, the indentations 26330 and the corresponding recesses 26320 can be thermoformed, melted, or otherwise coupled with a heat staking process. Heat staking is further described herein.

Because the drivers 26320 are triple drivers, a heat stake connection between the outer wall of the driver 26320 and the cartridge body 26302 can hold the entire driver 26320, including the intermediate support column and the inner support column, in position in the cartridge body 26302. The interference connection between the indentations 26330 and the recesses 26321 can be overcome by the sled during a firing stroke to sequentially release and lift the drivers 26320 as the sled moves along the row of indentations 26330. In certain instances, a series of heat-stakes along an inside surface in the cartridge body 26302 can engage each driver 26320 during a firing motion. In such instances, the driver 26320 can catch multiple vertical catches or dimples during the firing motion.

Figure 62:
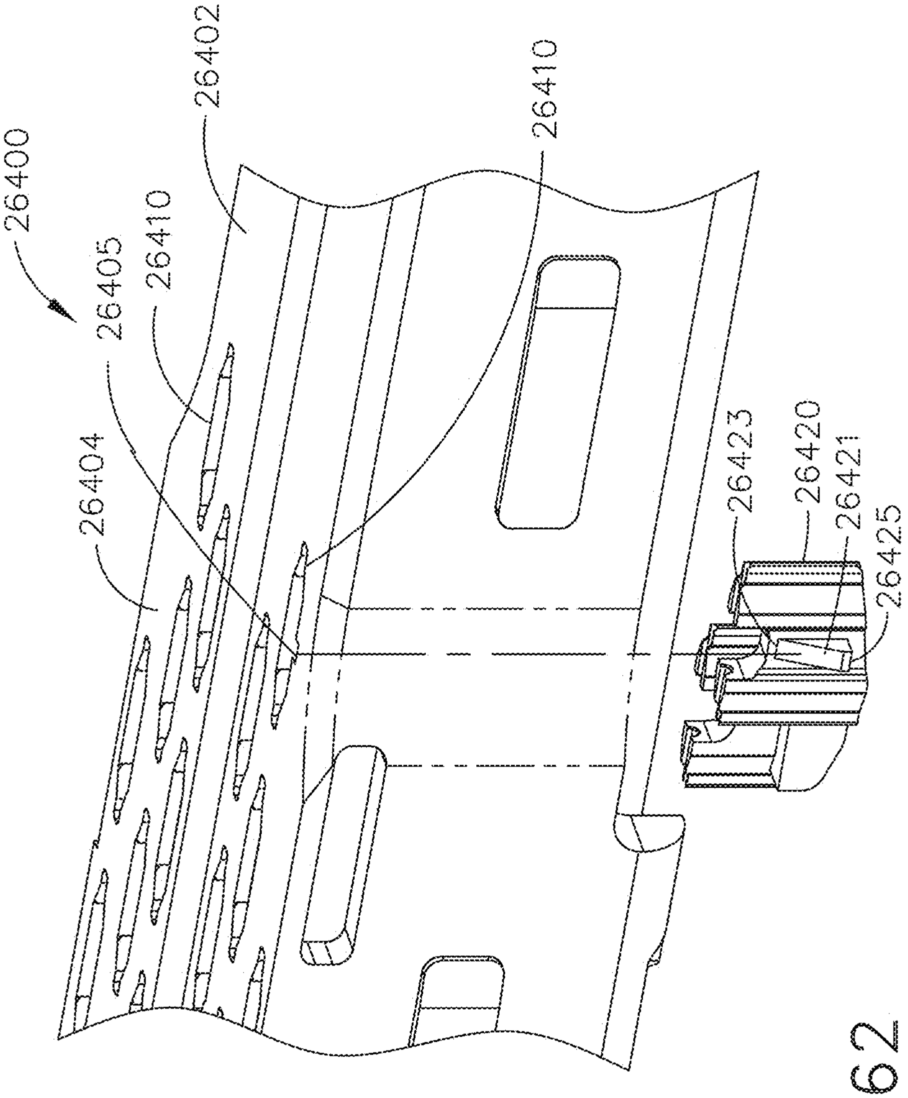
FIG. 62 is a perspective exploded view of a portion of a cartridge body and a driver having interference features for engaging the cartridge body, according to various aspects of the present disclosure.

In certain instances, the drivers and the cartridge body can include interference features molded into the drivers and/or the cartridge body. Referring to FIG. 62, a staple cartridge 26400 is similar in many aspects to the staple cartridge 20100 (FIG. 24). For example, the staple cartridge 26400 includes a cartridge body 26402 including a tissue-supporting deck 26404 having staple cavities 26410 defined therein; the staple cavities 26410 are arranged in three longitudinal rows on each side of the cartridge body 26402. Staples in the staple cartridge 26400 are supported by drivers 26420 (FIG. 62), which are similar in many aspects to the triple driver 20120 (FIG. 26); however, the driver 26420 is a double driver. The retention features described herein with respect to the driver 26420 can be incorporated into a single driver and/or a triple driver in other instances.

The drivers 26420 include an integrally-formed wedge 26421, which is narrower along a top edge 26423 of the wedge 26421 and thicker along a bottom edge 26425 of the wedge 26421. The wedge 26421 is positioned on a sidewall of a staple support column and is configured to abut a sidewall of the staple cavity 26410. For example, the staple cavity 26410 includes a vertical groove 26405, which is aligned with the wedge 26421. The wedge 26421 is configured to move along the vertical groove 26405 as the driver 26420 is lifted upward by a sled during a firing stroke. To accommodate the wedge 26421, the cartridge walls are configured to flex outward when the driver 26420 is inserted into the cartridge body 26402. In use, the firing force by the sled is sufficient to overcome the interference fit and lift the driver 26420. Stated differently, in the depicted embodiment, the wedge 26421 is configured to travel through the vertical groove 26405; however, the depth of the groove 26405 is not sufficient to allow free and clear passage of the wedge 26421 therethrough. The narrow top edge 26423 can fit in the groove without interference; however, between the narrow top edge 26423 and the thicker bottom edge 26425, the wedge 26421 can interfere with the cartridge body 26402 despite the vertical groove 26405. The interference connection between the wedge 26421 and the vertical groove 26405 is configured to hold the driver 26420 in position within the staple cavity 26410 during the firing motion and resist downward motion; the interference can be overcome by the sled during a firing stroke to sequentially release and lift the drivers 26420 as the wedge 26421 traverses the cartridge body 26402 along the row of indentations 26330. The cartridge body 26402 can continue to flex as the driver 26420 and wedge 26421 thereof move through the cavity 26410.

Figure 63:
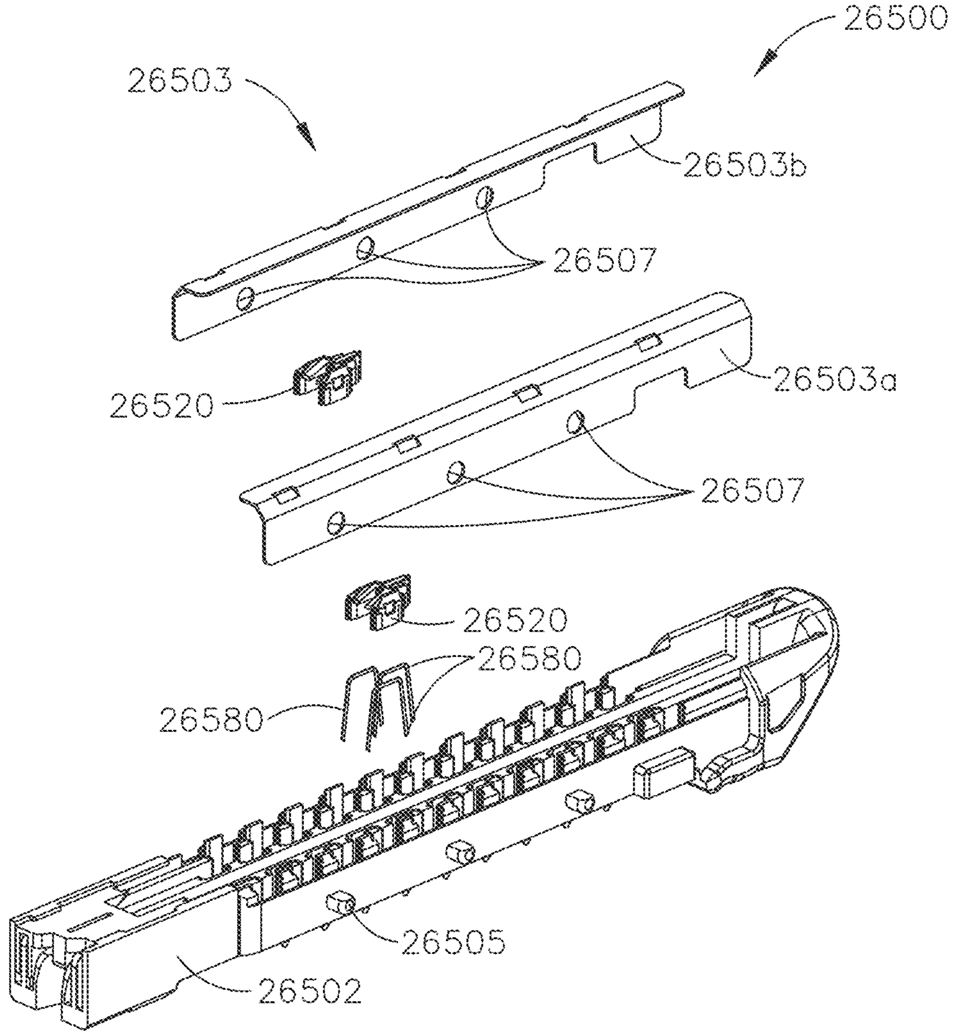
FIG. 63 is a perspective exploded view of a staple cartridge, according to various aspects of the present disclosure.

Referring now to FIG. 63, a staple cartridge 26500 is shown. The staple cartridge 26500 includes a cartridge body 26502 having staple cavities defined therein; the staple cavities are arranged in three longitudinal rows on each side of the cartridge body 26502. Staples 26580 in the staple cartridge 26500 are supported by drivers 26520, which are similar in many aspects to the triple driver 20120 (FIG. 26). The staple cartridge 26500 is similar in many aspects to the staple cartridge 20100 (FIG. 24); however, the staple cartridge 26500 also includes an insert molded metal frame 26503 within the cartridge body 26502. The insert molded metal frame 26503 is a two-part assembly including a first pan 26503*a* and a second pan 26503*b*, which extends along the sides of the cartridge body 26502. The pans 26503*a*, 26503*b* can be insert molded with the cartridge body 26502, snap-fit to the cartridge body 26502 with a friction fit between bosses 26505 along the length of the cartridge body 26502 and openings 26507 in the pans 26503*a*, 26503*b*, and/or can be heat staked to the cartridge body 26502 by deforming bosses 26505 along the length of the cartridge body 26502 within the openings 26507 in the pans 26503*a*, 26503*b*.

In one aspect, flat, non-bent pans can be insert molded with the cartridge body 26502 (e.g. the pans 26503*a*, 26503*b* can initially define a linear profile instead of an L-shaped profile). The cartridge body 26502 can be formed with an over-molded metal sheet along the lateral side(s) thereof, for example. Then, the exposed length of the over-molded metal sheets can be bent around a portion of the underside of the cartridge body 26502 to at least partially overlap some of the staple cavities to retain the drivers 26520 in the cartridge body 26502 from the underside thereof. In certain instances, the drivers can be triple drivers spanning outer staple cavities, intermediate staple cavities, and inner staple cavities. The bent portion of the metal sheet can overlap, or substantially overlap, the lower portion of the outer staple cavities to maintain the drivers in the cartridge body.

Alternatively, an L-shaped pan like the pans 26503*a*, 26503*b* can be snap-fit to the lateral sides of the cartridge body 26502 to retain the drivers in the cartridge body 26502 from the underside thereof without insert molding the pans 26503*a*, 26503*b* to the cartridge body 26502.

Figure 64:
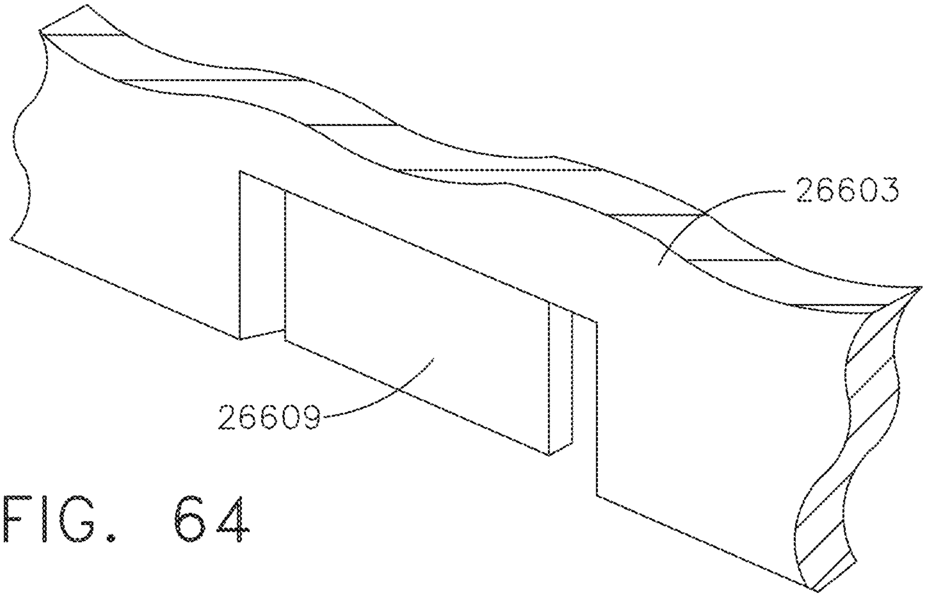
FIG. 64 is perspective view of a portion of a cartridge frame and arm thereof in an unformed configuration, according to various aspects of the present disclosure.
Figure 65:
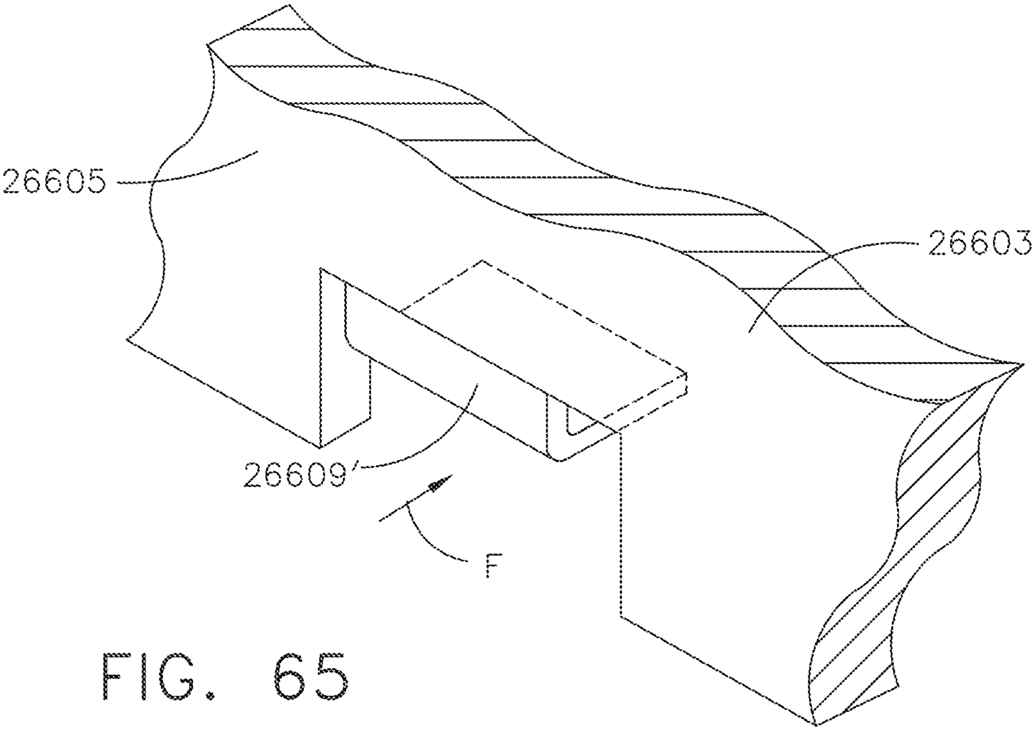
FIG. 65 is a perspective view of the portion of the cartridge frame and the arm of FIG. 64, depicting the arm in a formed configuration, according to various aspects of the present disclosure.

In one aspect, the pans 26503*a*, 26503*b* can be insert molded with the cartridge body 26502 and can include exposed bendable metallic flanges or arms, that are bent around the cartridge body 26502 after the drivers 26520 have been installed in the staple cavities. For example, referring now to FIGS. 64 and 65, a portion of a metal frame or pan 26603 for a cartridge body, such as the cartridge body 26502 (FIG. 63) or the cartridge body 20102 (FIG. 24) is shown. The pan 26603 can be insert molded with the cartridge body. For example, the pan 26603 includes a frame portion 26605 over which the cartridge body has been molded. The pan 26603 also includes an arm 26609. The arm 26609 can be deformed from an initial configuration (FIG. 64) to a bent arm 26609' configuration (FIG. 65) with a deformation force in the direction F (FIG. 65), to wrap the arm 26609 around a lower portion of the staple cavities and retain the drivers therein.

In various aspects of the present disclosure, the various techniques for forming a piece of metal over the outer staple cavities to retain the drivers therein can be applied to the inner staple cavities in certain instances. For example, in various aspects of the present disclosure, the staple cartridge can include a support brace, such as the support brace 650 fitted within the staple cartridge 640 (see FIGS. 19 and 20). As further described herein, the staple cartridge 640 and the support brace 650 can be assembled together prior to installing the staple cartridge 640 into the channel 630. In certain instances, such a support brace 650 or other insert molded longitudinal frame member within the cartridge body can include a metal sheet, pan, or arm, which can be bent around an underside of the cartridge body to retain the drivers in the inner rows of staple cavities.

As described herein, driver retention and/or interlocking features with the cartridge body can be heat staked to retain the drivers in the cartridge body. In at least one aspect of the present disclosure, each driver can include a corresponding heat stake feature with the cartridge body. It can be important to ensure the heat stake depth is sufficient to keep the drivers from disengaging but does not cause interference with the drivers in their unfired or down positions. The heat stake and orbital forming techniques can be controlled to ensure sufficient engagement.

Figure 67:
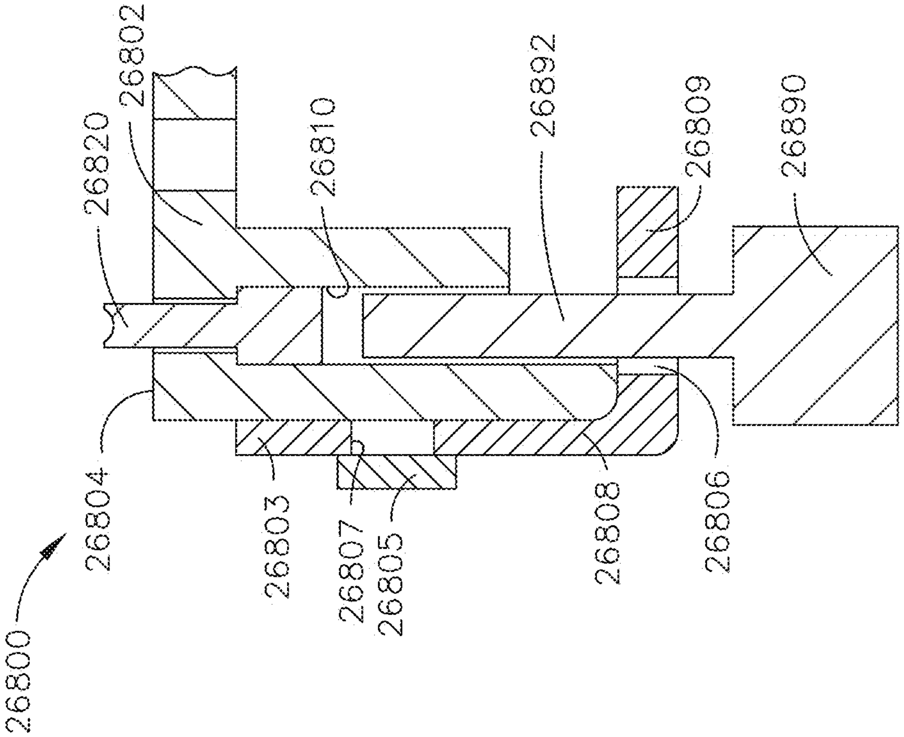
FIG. 67 is an elevation cross-section view of a cartridge body and a cartridge frame during a heat staking process, according to various aspects of the present disclosure.
Figure 66:
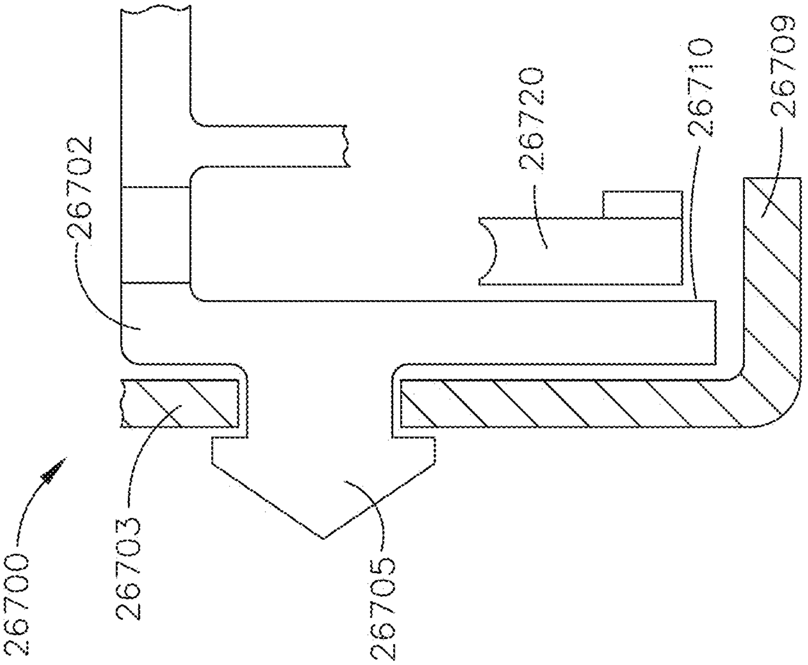
FIG. 66 is an elevation cross-section view of a cartridge body and a cartridge frame depicting a heat staked retention feature therebetween, according to various aspects of the present disclosure.
Figure 68:
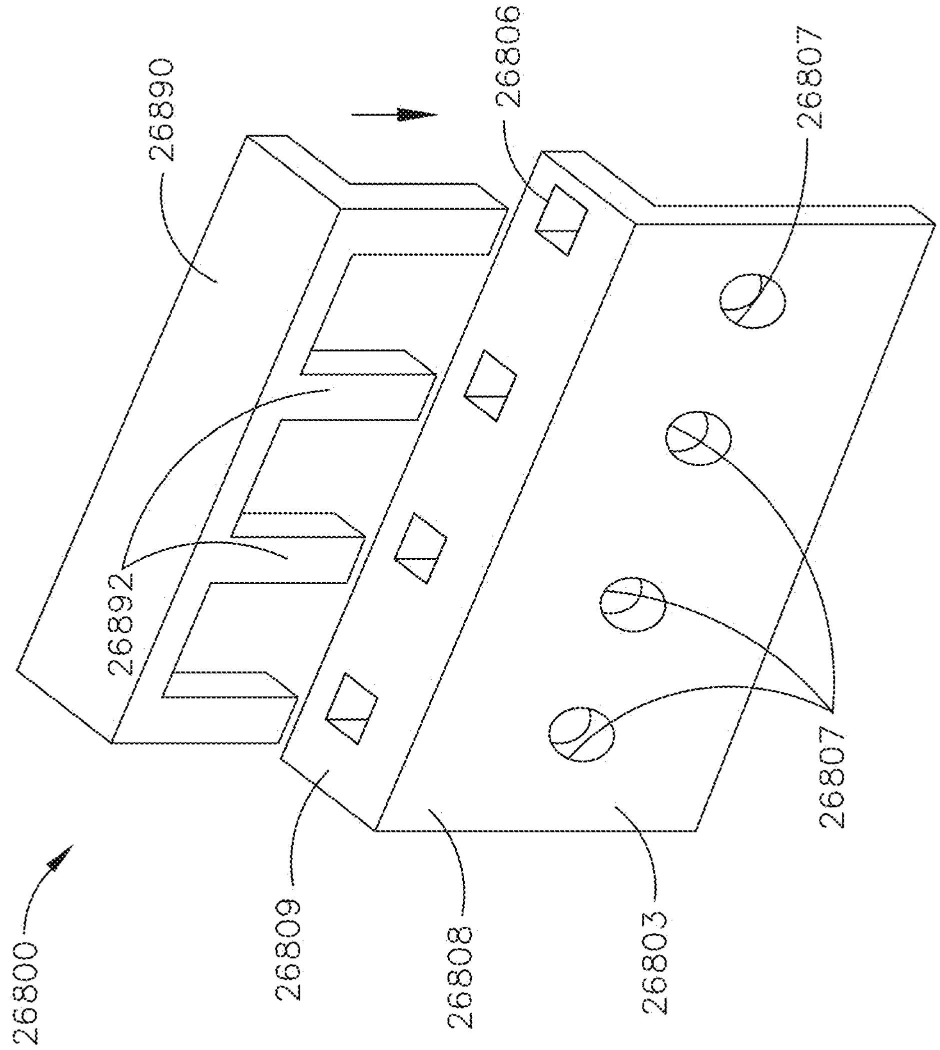
FIG. 68 is a perspective view of a cartridge frame and an insert support for use during the heat staking process of FIG. 67, according to various aspects of the present disclosure.

Referring now to FIG. 67, portions of a staple cartridge 26700 are shown, including a cartridge body 26702 having a driver 26720 therein. The staple cartridge 26700 is similar in many aspects to the staple cartridge 20100 (FIG. 24) but also includes a longitudinal support frame 26703 and heat staked retention features 26705 between the cartridge body 26702 and the longitudinal support frame 26703. In various instances, the heat staking can be done against a solid sheet of metal to secure the cartridge body 26702 to the longitudinal support frame 26703. Then, the drivers 26720 can be installed in the staple cavities. For example, the driver 26720 and a staple can be installed in a staple cavity 26710. After the drivers 26720 have been installed, the longitudinal support frame 26703 can be bent over the underside of the cartridge body 26702 to retain the drivers 26720 therein. For example, a portion 26709 of the longitudinal support frame 26703 can overlay openings in the underside of the staple cartridge body 26702 associated with the outer staple-supporting column on the driver 26720 and outer staple cavity 26710.

An insert support can be utilized in certain heat staking operations, which can reduce the amount of pressure and improve consistency. For example, a removable insert support or backer can be positioned behind each heat stake. Moreover, the insert supports can push the drivers into an upward position while staking to protect the drivers from deformation or other effects of the heat staking operation.

Referring to FIG. 67, a heat staking operation for a staple cartridge 26800 is shown in which a cartridge body 26802 is being secured to a longitudinal support frame 26803 with a heat stake 26805. The staple cartridge 26800 is similar in many aspects to the staple cartridge 20100 (FIG. 24) but also includes the longitudinal support frame 26803 and the heat stake 26805. The longitudinal support frame 26803 includes an upright sheet 26808 and an orthogonal flange 26809 extending therefrom to form an L-shaped profile. The upright sheet 26808 includes openings 26807 therethrough, which are aligned with the heat stakes 26805. The orthogonal flange 26809 also includes openings 26806 therethrough, which are configured to receive fingers 26892 of an insert support 26890 therein.

During a heat staking operation, the L-shaped support frame 26803 is positioned alongside a length of the cartridge body 26802 and the insert support 26890 is positioned relative to the support frame 26803 and the cartridge body 26802 such that the fingers 26892 extend through the openings 26806 in the orthogonal flange 26809 and into staple cavities 26810. The fingers 26892 are configured to push drivers 26820 upwards toward a tissue-supporting deck 26804 of the cartridge body 26802. After the heat stakes 26805 have been formed between the cartridge body 26802 and the L-shaped support frame 26803, the insert support 26890 can be removed from the staple cartridge 26800 allowing the drivers 26820 to move downward and assume their unfired positions in the staple cavities 26810. The orthogonal flange 26809 is configured to overlay a portion of the underside of the cartridge body 26802 and may overlap multiple staple-supporting columns (e.g. an outer column and an intermediate column) and/or a bridge between two adjacent staple-supporting columns to hold the drivers 26820, which span multiple rows of staple cavities 26810, in the cartridge body 26802.

As further described herein, certain end effector components may be constructed using 3D printing technology to improve component capabilities. In certain instances, 3D printing can allow the printed component to exhibit metamaterial properties, for example. A metamaterial is a synthetic composite material with a structure such that it exhibits properties not usually found in natural materials. 3D printing is one technique used to create a metamaterial by forming components with two or more materials and/or structures therein. In other instances, insert molding and over-molding can generate composite components that may have metamaterial properties in certain instances.

Composite end effector components may exhibit greater structural strength and stiffness while allowing precision in the forming of small detailed features and can provide improved frictional properties in certain instances. For example, a metal-plastic composite cartridge body can exhibit certain metamaterial properties in that it may be stronger and stiffer than a similar injection-molded, entirely plastic, or composite, cartridge body, for example, while still allowing precision with respect to small detailed features. In certain instances, a metal-plastic composite cartridge body can demonstrate improved frictional properties with respect to the drivers movably positioned within each staple cavity. Certain composite metal-plastic components can be formed with insert molding or over-molding. In other instances, 3D printing can allow for the creation of complex geometries and/or material combinations that may otherwise be too costly and time consuming to manufacture with conventional molding techniques or, in certain instances, may even be impossible to manufacture absent 3D printing technology.

Figure 69:
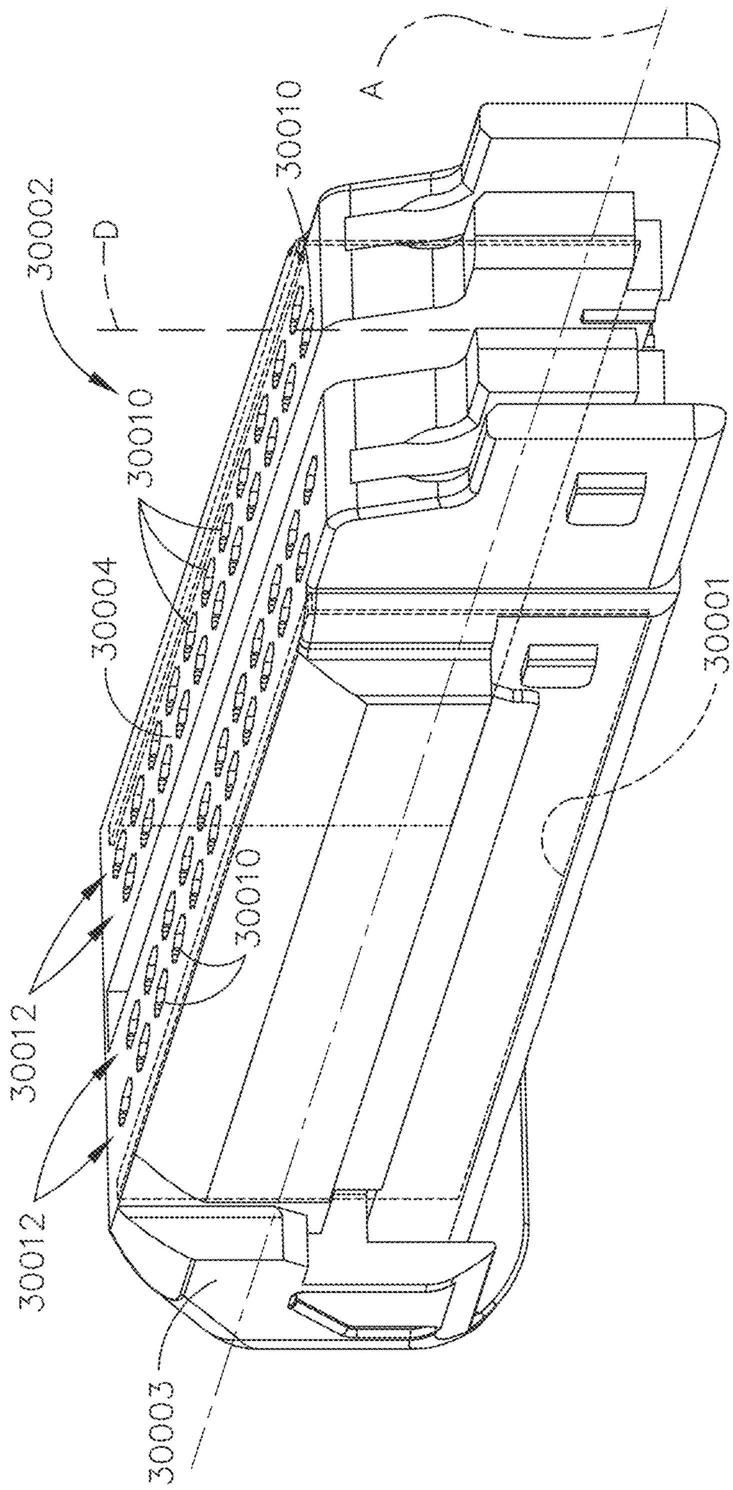
FIG. 69 is a perspective view of a composite cartridge body including a metal pan and plastic composite material, depicting the hidden metal pan with dashed lines for illustrative purposes, according to various aspects of the present disclosure.
Figure 70:
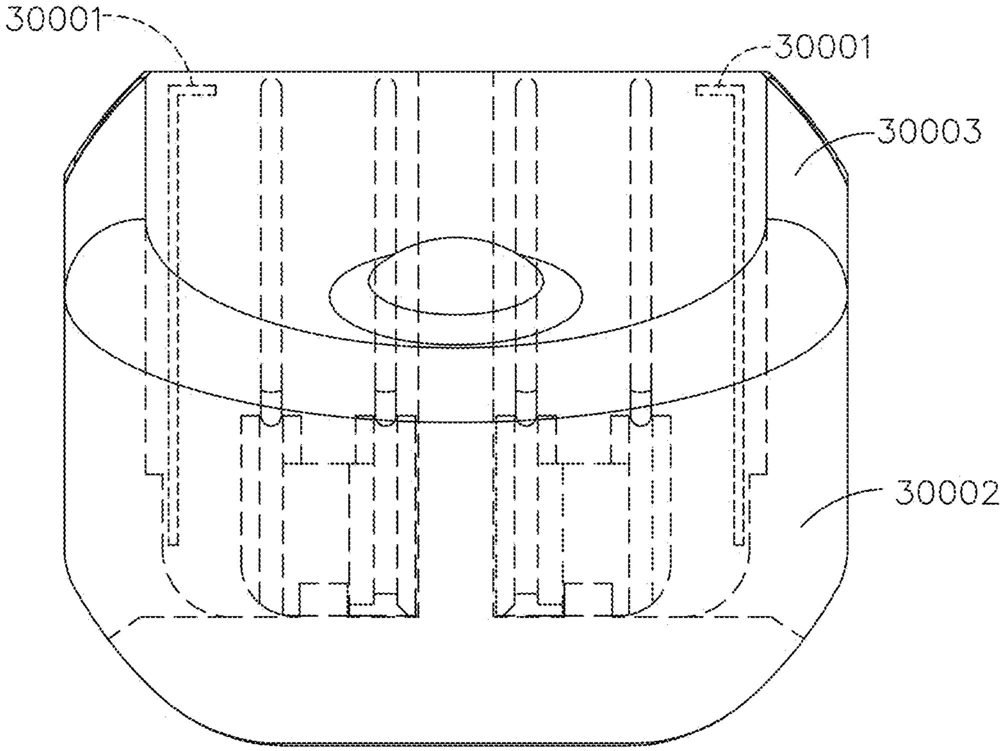
FIG. 70 is an elevation view of the composite cartridge body of FIG. 69 depicting the hidden metal pan with dashed lines for illustrative purposes, according to various aspects of the present disclosure.

Referring to FIG. 69, for example, a composite metal-plastic cartridge body 30002 is shown. The composite metal-plastic cartridge body 30002 can provide metamaterial properties in certain instances. Additionally or alternatively, the composite metal-plastic body can allow improved integration of electronic components, such as electronic sensors and flexible circuits.

In one aspect, the cartridge body 30002 is formed with a stamped metal frame 30001 or two or more pans that are stamped and otherwise formed into a skeleton shape for the cartridge body 30002. A plastic material 30003 is then molded over the metal frame 30001. In such instances, the metal frame 30001 can be insert molded to the plastic material 30003. The metal-plastic composite cartridge body 30002 can exhibit increased strength and collapse stiffness in comparison to entirely plastic cartridge bodies, i.e. injection molded cartridge body without a metal frame therein. Plastic material 30003 over a metal or composite frame can provide a structural functioning frame with intricate driver guidance features molded into the plastic material 30003.

The metal frame 30001 can comprise a thin metallic framework and the plastic material can be injection molded with structural members, in certain instances. In one aspect, the metal frame can constitute an integrated pan or pans, as further described herein, which can save space in the cartridge body and/or increase the tissue gap. Additionally, metal can be utilized for certain components related to lockouts, cartridge identification, and resetting. The metal can be less prone to breaking or cracking in certain instances and can withstand significant forces, which may be helpful for lockout components and/or mechanical keys (e.g. an extending tab or post) to prevent insertion of the staple cartridge into an incompatible channel and/or device Certain metallic components can be resilient during a firing stroke reset, i.e. when retracting the sled during manufacturing to test cartridge and ensure all components have been installed. Moreover, a composite metal-plastic cartridge body can facilitate smart cartridge technology, integrated wiring, and/or flexible circuits.

In certain instances, the metal frame 30001 could have flanges that interconnect or span multiple walls and/or columns in the cartridge body. For example, certain walls in the cartridge body can be thinner than other walls and the flanges can connect a thinner wall with a thicker wall to better distribute a torque load, rather than twisting the support. In certain instances, the main standing support walls in the cartridge body can be connected to an adjacent thicker support walls by the metal frame. For example, a thinner interior cartridge wall can be coupled to a thicker exterior cartridge wall to improve force distributions during clamping and/or firing.

In other instances, a composite plastic-metal cartridge body can be 3D-printed. The orientation of the 3D build forming the composite plastic-metal cartridge body can be optimized to ensure smooth driver motions during the firing stroke. For example, referring again to FIG. 69, the cartridge body 30002 includes staple cavities 30010 arranged in a plurality of longitudinal rows 30012. The staple cavities 30010 are defined though a tissue-supporting deck 30004 and into the cartridge body 30002. Drivers, such as the drivers 20120 (FIG. 26), further described herein, can support staples in the cartridge body 30002.

The composite plastic-metal cartridge body 30002 can be printed layer-upon-layer along the longitudinal axis A of the cartridge body 30002. Stated differently, the orientation of the 3D build can be orthogonal to the longitudinal axis A and/or orthogonal to the tissue-supporting deck 30004. When the directional 3D printing of the cartridge body 30002 is perpendicular to the longitudinal axis A (e.g. proximal-to-distal), the build layers can be aligned with the direction of driver motion during the firing stroke. Referring again to FIG. 69, each staple cavity 30010 extends along an axis D, which is perpendicular to the longitudinal axis A. As a sled moves through the cartridge body 30002 along the longitudinal axis A, each drivers is lifted upwards along its respective D axis toward the tissue-supporting deck 30004. The build direction is parallel to the staple cavities' D axes along which the drivers move during a firing stroke. Aligning the 3D build layers with the direction of driver motion can prevent driver binding and hang-ups as the drivers are lifted by the sled during the firing stroke, in certain instances.

The 3D build for a composite plastic-metal cartridge body is proximal-to-distal in certain instances. In other instances, the 3D build can be distal-to-proximal, for example. Support structures for certain 3D builds can be minimized when building the narrower body portion on top of a wider distal nose of the cartridge body, in certain instances.

In various instances, a 3D-printed composite cartridge body can include different infill percentages and/or different materials to obtain metamaterial properties related to improving the strength of the cartridge body while minimizing frictional forces during the firing stroke. Moreover, the support walls of such a cartridge body can define open spaces, voids, and/or cells therebetween. In various instances, the spaces between the support walls, such as the thin walls between the staple cavities, for example, can be configured to allow for improved bending resistance during a clamping load. For example, the spaces between the support walls of the cartridge body can include 3D-printed internal fillets, chamfers, and/or struts, which are configured to improve the open cell strength of the support walls.

Certain cartridge bodies described herein may include a smaller cross-sectional geometry, less material, and/or thinner support walls owing to the footprint of a central firing screw (e.g. the firing screw 261 in FIGS. 4 and 5) therethrough, which takes up real estate in the compact form factor of the cartridge body. High loads on the cartridge body during the firing stroke can exert deformation forces on the cartridge body, which may result in deformation of the cartridge body or portions thereof. For example, the thin walls separating the staple cavities can tend to bend or buckle in certain instances, which can direct the drivers and staples supported thereon out of alignment with the forming pockets in the anvil. In any event, connecting the lateral sides of the cartridge body with a bridge can strengthen the cartridge body and help to maintain alignment between the staples in the staple cavities and their associated forming pockets in the anvil even when subject to high loads.

Figure 71:
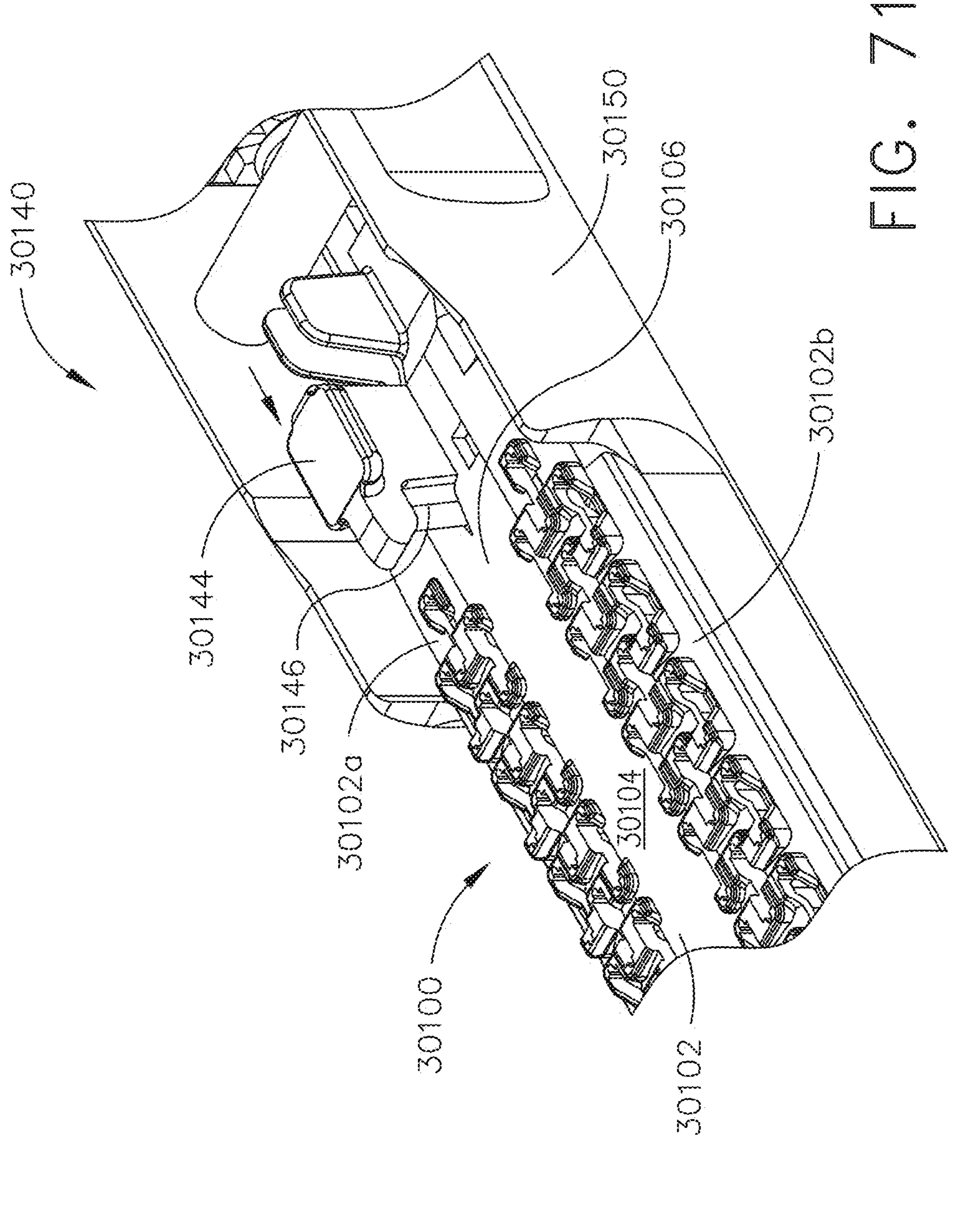
FIG. 71 is a perspective view of a portion of a surgical end effector including a staple cartridge positioned therein, according to various aspects of the present disclosure.
Figure 72:
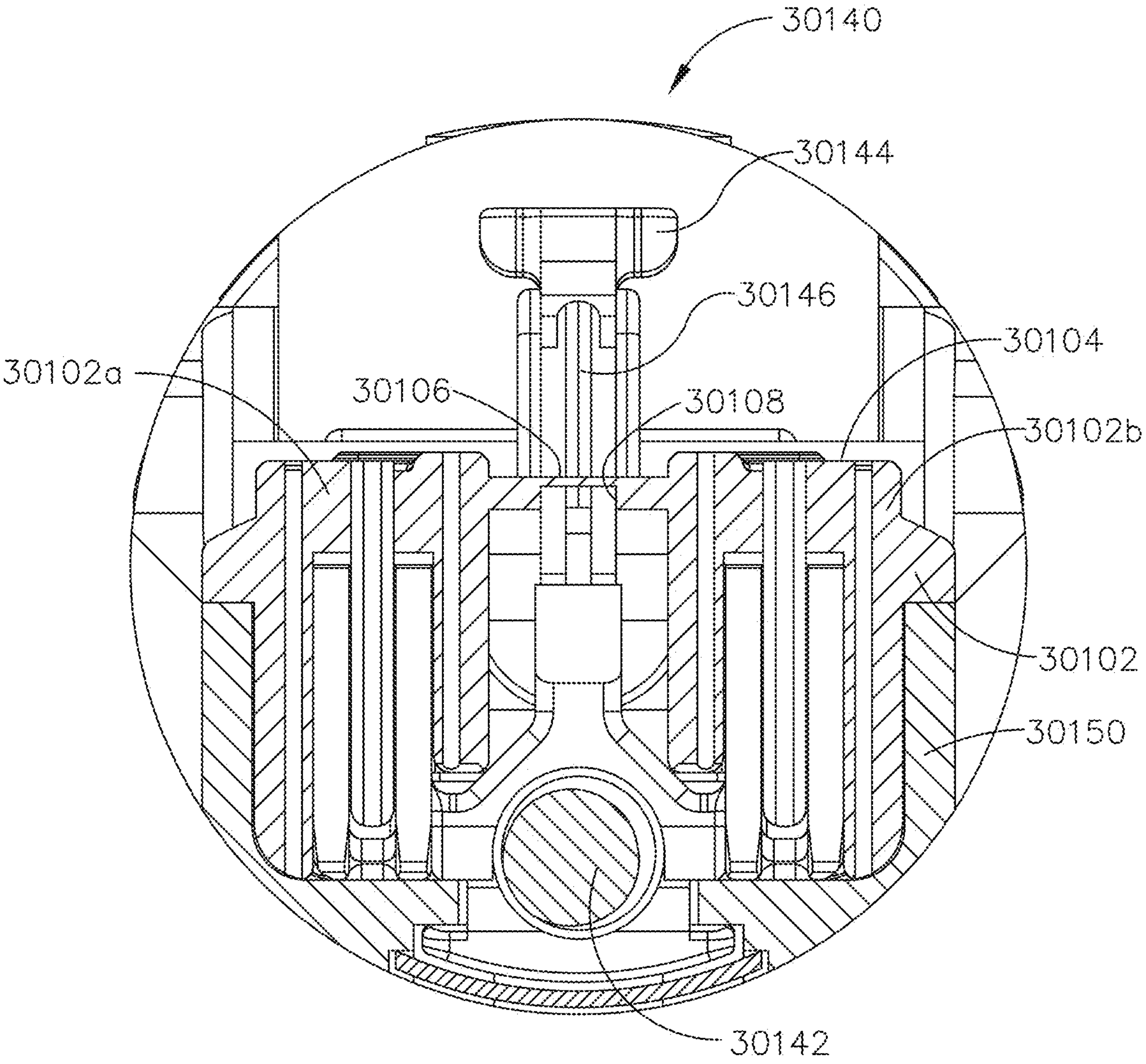
FIG. 72 is an elevation cross-section view of the portion of the surgical end effector and staple cartridge of FIG. 71, according to various aspects of the present disclosure.

Referring now to FIGS. 71 and 72, portions of a surgical end effector 30140 are shown. The surgical end effector 30140 is similar in many aspects to the surgical end effector 20240 (FIG. 29). For example, the end effector 30140 includes a staple cartridge 30100, which is similar in many aspects to the staple cartridge 20100 (FIG. 24) and includes a cartridge body 30102 and three rows of staple cavities on each side of a rotary drive screw 30142 (FIG. 72), which is similar in many aspects to the drive screw 261 (see FIGS. 4 and 5) and the rotary drive screw 20242 (FIG. 29), for example. The staple cartridge 30100 is installed in a channel 30150. A firing member 30144 having an upright cutting edge 30146 is configured to move along the rotary drive screw 30142 through the staple cartridge 30100 during a firing stroke to advance the sled and lift the drivers and staples thereon into forming contact with forming pockets in the anvil.

The cartridge body 30102 is similar in many aspects to the cartridge body 20102 (FIG. 24), for example; however, the cartridge body 30102 further includes a bridge 30106 extending between two lateral sides 30102*a*, 30102*b* of the cartridge body 30102. The bridge 30106 covers a longitudinal knife-receiving slot 30108 defined in the cartridge body 30102, along which a portion of the firing member 30144 moves during a firing stroke. The bridge 30106 forms a contiguous tissue-supporting deck 30104 between the two lateral sides 30102*a*, 30102*b* of the cartridge body 30102. In various instances, the bridge 30106 can improve the strength of the cartridge body 30102, for example, and may help to maintain alignment of the staples with the forming pockets on the anvil especially when firing under high loads, for example. In such instances, the bridge 30106 can mitigate lateral staple misalignment resulting from high clamping loads, for example.

The bridge 30106 is a frangible portion, which is configured to be cut or transected by the upright cutting edge 30146 of the firing member 30144 during a firing stroke. In various instances, the geometry of the bridge 30106 is configured to mitigate the risk of splintering. For example, the geometry can allow for a predictable geometry and orientation of destruction of the bridge 30106. In instances in which the cartridge body 30102 is 3D-printed, for example, the cartridge body 30102 can include a different material, different infill percentage, and/or different infill geometry along the bridge 30106 or portions of the bridge 30106 compared to adjacent portions of the cartridge body 30102, which can further facilitate transection of the bridge 30106 during the firing stroke without damaging the firing member 30144 and/or splintering the cartridge body 30102 from the firing load.

In certain instances, as further described herein, the staple cartridge 30100 can include a single-use knife, for example, which can transect the bridge 30106 during the firing stroke. Where a single-use knife is utilized, the knife does not risk becoming dull for a subsequent firing stroke upon transecting the frangible portion of the bridge 30106. The bridge 30106 can comprise a plastic molded and/or 3D-printed component, for example, which can be easily transected by the upright cutting edge 30146 without significant resistance thereof. In other instances, a reusable knife can be used to cut the bridge 30106.

Figure 73:
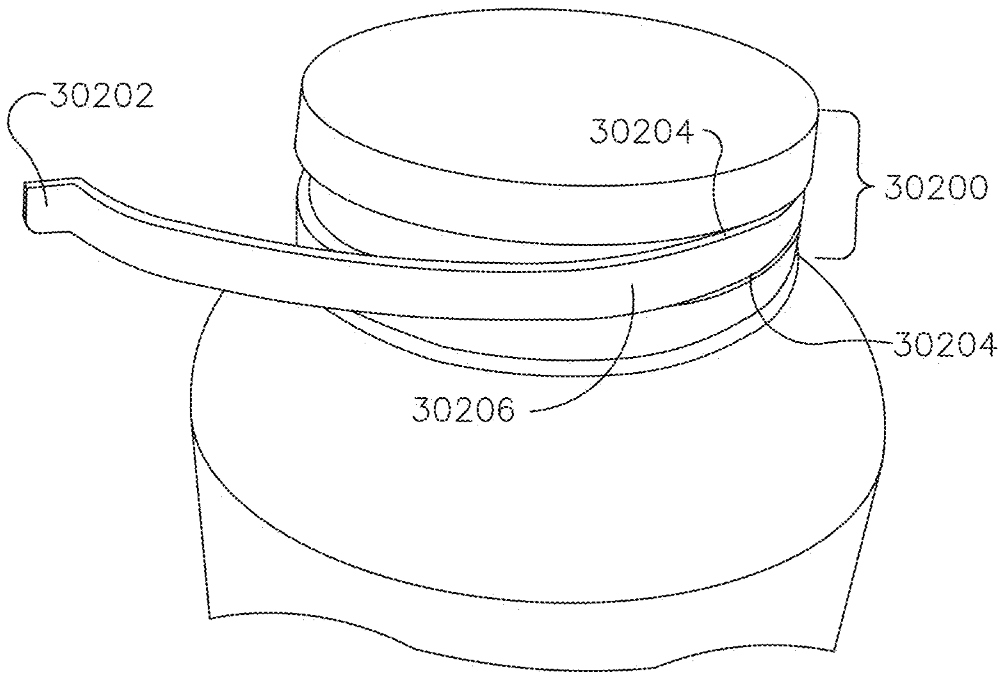
FIG. 73 is a perspective view of a tamper-evident tear-away lid, according to various aspects of the present disclosure.
Figure 74:
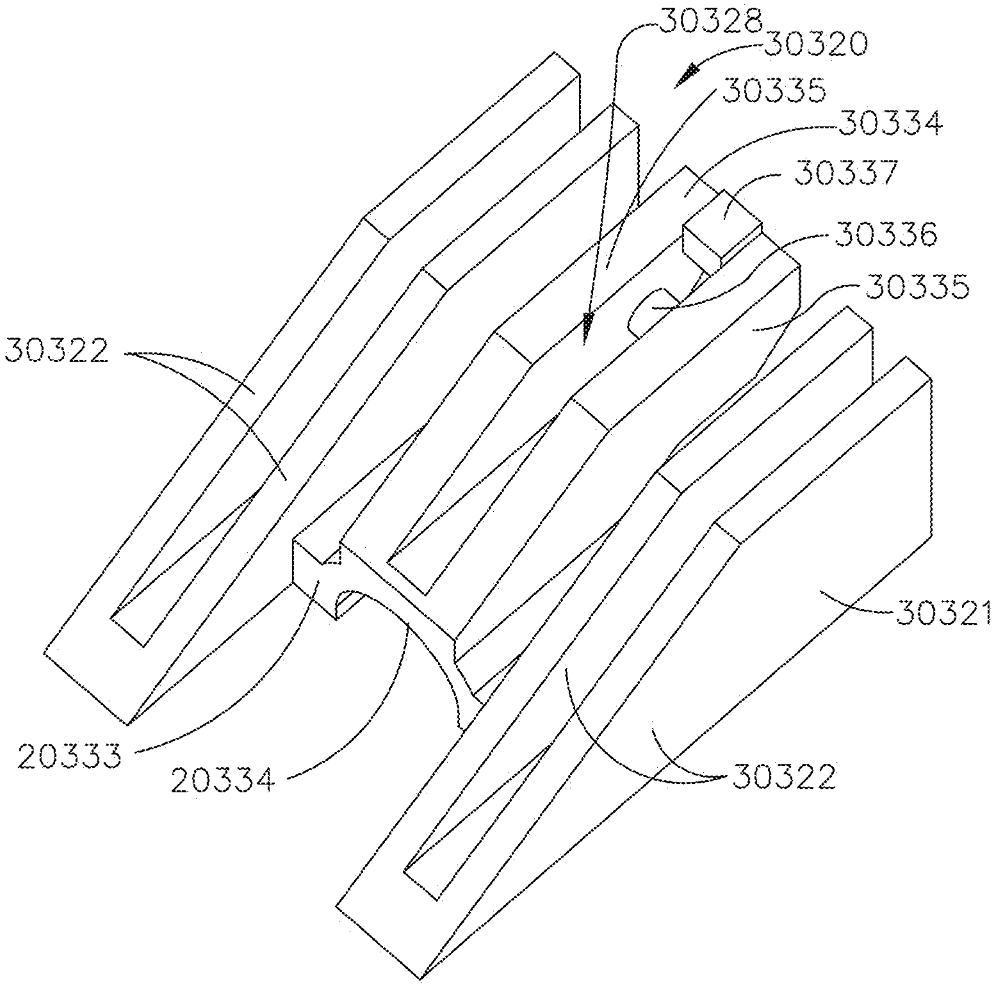
FIG. 74 is a perspective view of a body of a sled assembly, according to various aspects of the present disclosure.
Figure 75:
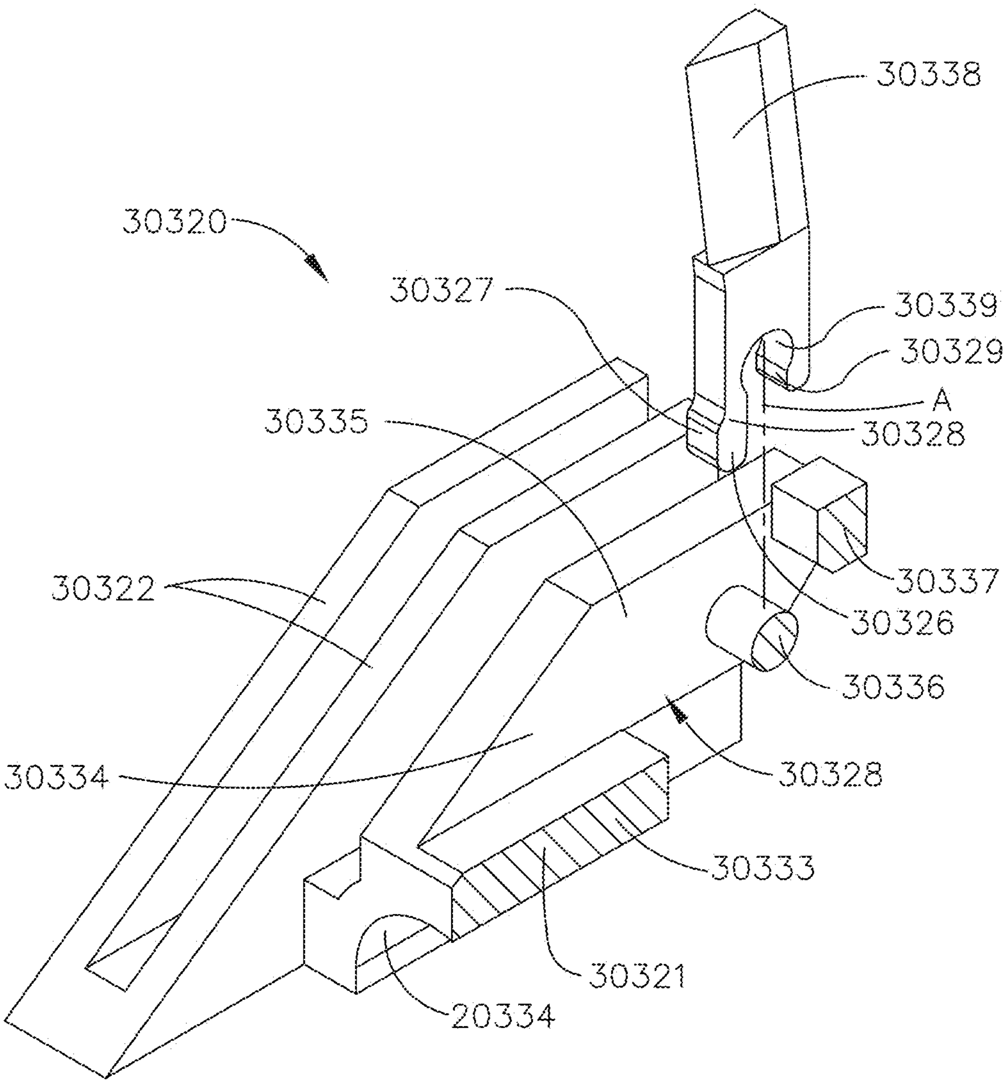
FIG. 75 is a perspective, exploded cross-section view of the sled assembly of FIG. 74 including the body and a knife, according to various aspects of the present disclosure.
Figure 76:
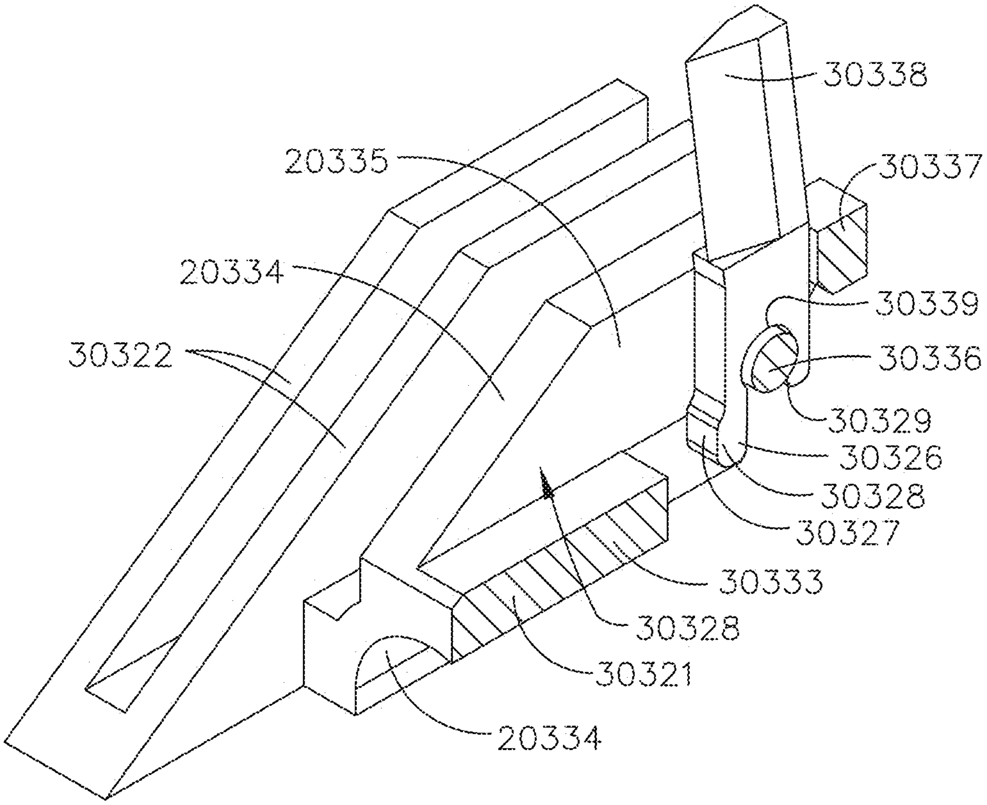
FIG. 76 is a perspective cross-section view of the sled assembly of FIG. 74, according to various aspects of the present disclosure.

In certain instances, the bridge 30106 can include rows of perforations and/or break/tear lines along which the bridge 30106 is configured to separate from the cartridge body 30202. Referring to FIG. 73, for example, a tamper-evident lid 30200 includes a frangible portion 30206 having a tear tab 30202 and defined by break lines 30204 between the frangible portion and the rest of the lid 30200. The frangible portion 30206 can be removed or separated from the tamper-evident lid 30200 along the break lines 30204. Similarly, the bridge 30106 can be removed from the cartridge body 30102 along break lines, which facilitate separation of the bridge 30106 from the cartridge body 30102. In certain instances, the bridge 30106 can be interrupted with pockets along the sidewall of the knife-receiving slot 30108. Deflected and/or separated portions of the bridge 30106 can be configured to move into the pockets during the firing stroke, rather than being pushed out of the cartridge body 30102 and into tissue clamped therebetween.

In certain instances, as further described herein, a replaceable staple cartridge can include a single-use knife, which may provide a fresh cutting edge for each firing stroke. However, to cut tissue clamped between the jaws of an end effector, the knife should extend beyond the tissue-supporting deck of a staple cartridge, in various instances. Such a protruding knife and cutting edge risks unintentional and/or inadvertent contacts outside of the firing stroke, which may damage tissue and/or dull the cutting edge. For example, the cutting edge may inadvertently contact and/or cut the tissue of a patient and/or clinician before the firing stroke, such as when the staple cartridge is being loaded into the end effector. In other instances, upon completion of the firing stroke, the cutting edge may remain in a distal protruding position and may inadvertently contact and/or cutting the tissue of a patient and/or clinician when the end effector unclamps the tissue and is being withdrawn from the surgical site. Additional unintentional tissue contact scenarios are contemplated.

In various instances, a tissue-transecting knife can be mounted to a sled in the staple cartridge. As the sled moves through the firing stroke, the knife can also move through the cartridge body. Moreover, the sled can interact with the firing member (e.g. the I-beam or E-beam) in the end effector. For example, the sled and knife thereon can be releasably coupled to the firing member, such that the sled and knife are advanced distally during a firing stroke. In certain instances, the sled and the knife can be retracted proximally along with the firing member upon completion or termination of the firing stroke. In such instances, the knife can be reset and/or returned to a proximal position in the cartridge body before the firing member permits the opening of the jaws. In such instances, the protruding knife and cutting edge thereof can returned to a predictable and/or at least partially-shielded position at the proximal end of the cartridge body. In other instances, a sled can include multiple separable components (e.g. a two-part sled), and a portion of the sled can be retracted proximally, while another portion of the sled remains in a distal position. In certain aspects, the retractable portion of the sled can include the knife. In still other instances, the non-retractable portion of the sled can include the knife, which can be directed downward into the cartridge body as the retractable portion of the sled moves past it. In certain instances, a portion of the sled can interact with a lockout feature to prevent a firing stroke when the cartridge is missing and/or spent.

In one aspect of the present disclosure, a firing member can include a distally-extending hook and the sled can include a proximal cavity dimensioned to receive the distally-extending hook. Moreover, the knife can be pivotably coupled to the sled and positioned to selectively engage and retain the distally-extending hook in the sled. For example, the distally-extending hook can hook around a portion of the knife. In various instances, interconnection of the distally-extending hook and the knife is configured to hold the knife in a protruding position relative to the cartridge body.

In such instances, the knife can be moved to the protruding position, in which the cutting edge is positioned to transect tissue clamped between the jaws, when the firing member is advanced into engagement with the sled. Prior to the firing stroke, the knife can be pivoted into a shielded position, in which at least a portion of the cutting edge is shielded by the sled and/or cartridge body. Moreover, upon completion of the firing stroke, the firing member can return with the sled to a proximal position in the cartridge body and return to its shielded position. In various instances, the foregoing arrangement may avoid certain inadvertent tissue contacts outside of the firing stroke.

Referring now to FIGS. 74-77, a sled assembly 30320 for an end effector 30340 (FIG. 77) is shown. The end effector 30340 is similar in many aspects to the end effector 200 (see FIGS. 4 and 5) and is configured to cut and staple the tissue of a patient. The end effector 30340 can include a cartridge jaw and an anvil jaw, for example, and the cartridge jaw can be configured to receive a staple cartridge 30300 having a tissue-supporting deck 30304, which is similar in many aspects to the staple cartridge 220 (see FIGS. 4 and 5), for example. The end effector 30340 also includes a rotary drive screw and a firing member 30342, which are similar to the firing screw 261 (see FIGS. 4 and 5) and the firing member 270 (see FIGS. 4 and 5), respectively. The cartridge jaw is configured to receive the staple cartridge 30300, including staples that can be ejected when the firing member 30342 is advanced within the staple cartridge 30300. For example, the firing member 30342 is driven through the end effector 30340 upon a rotation of the firing screw during a firing stroke to advance the sled assembly 30320.

The firing member 30342 includes a body portion 30343, upper cam members 30344 extending laterally from both sides of the body portion 30343, and lower cam members 30345 extending laterally from both sides of the body portion 30343. The upper cam members 30344 are configured to cammingly engage an upper jaw, or anvil, of the end effector 30340 during a firing stroke, and the lower cam members 30345 are configured to cammingly engage a lower jaw, or elongate channel of the end effector 30340 during the firing stroke.

Further to the above, a longitudinal opening extends through the body portion 30343. The longitudinal opening is configured to receive the rotary drive screw described above. The body portion 30343 further includes a cutout region 30349 configured to receive a firing drive nut 30350. The firing drive nut 30350 is configured to threadably engage the rotary drive screw to convert rotary motion of the rotary drive screw into translation of the firing member 30342. The firing drive nut 30350 also includes laterally-extending members 30351 that extend from both sides of the firing drive nut 30350. The laterally-extending members 30351 are aligned with the lower cam members 30345. As such, the cam members 30345, 30351 cooperate to cammingly engage the lower jaw of the end effector 30340 during the firing stroke.

The body portion 30343 of the firing member 30342 also includes a distal nose portion 30346, that extends distally and forms a distal sled-abutment surface 30352. A distal extension 30347 extends from the distal sled-abutment surface 30352 in a substantially distal direction and is configured to selectively interlock with the sled assembly 30320. More specifically, the distal extension 30347 includes a transverse portion or catch 30348 extending in a direction transverse to the distal direction. The distal extension 30347 and the catch 30347 form a hooked geometry, which selectively engages a portion of the sled assembly 30320, as further described herein.

The sled assembly 30320 includes a sled body 30321 and a knife 30338 having rails 30322 positioned to engage drivers, such as the drivers 20120 (FIG. 26), for example. The rails 30322 are configured to lift the drivers toward the tissue-supporting deck 30304 of the staple cartridge 30300. A central portion 30333 of the sled body 30321 moves along a central longitudinal path in the staple cartridge 30300 during a firing stroke. In various aspects, the central portion 30333 includes an upright hub 30334 having sidewalls 30335, which are dimensioned and structured to move along a longitudinal slot in the staple cartridge 30300. The central portion 30333 also includes an arced underside profile 30334 dimensioned and positioned to accommodate the rotary drive screw without interference.

The upright hub 30334 includes a recess or space 30328 between the sidewalls 30335 and a shaft or pin 30336 extending between the sidewalls 30335. A stop 30337 also extends between the sidewalls 30334, and is further described herein. The knife 30338 of the sled assembly 30320 is pivotably mounted to the pin 30336 at a hub 30339. In various aspects, the hub 30339 can define a hub diameter that permits rotation of the knife 30338 about the pin 30336. Moreover, the knife 30338 includes a mounting slot 30329 having a narrower width than the hub diameter and into which the pin 30336 passes to secure the hub 30339 to the pin 30336. In various instances, the knife 30338 can be snap-fit or press-fit onto the pin 30336, for example. Referring to an exploded view of the sled assembly 30320 in FIG. 75, the knife 30338 can be moved along the assembly axis A to rotatably mount the knife 30338 to the sled body 30321.

In various instances, the knife 30338 can pivot into a downward or recessed position relative to the sled body 30321. For example, the knife 30338 and cutting edge thereof can face generally downward, for example, and/or be shielded by the sidewalls 30335 when the knife 30338 is in the recessed position. In certain instances, a biasing element is configured to bias the knife 30338 toward the recessed position.

Figure 77:
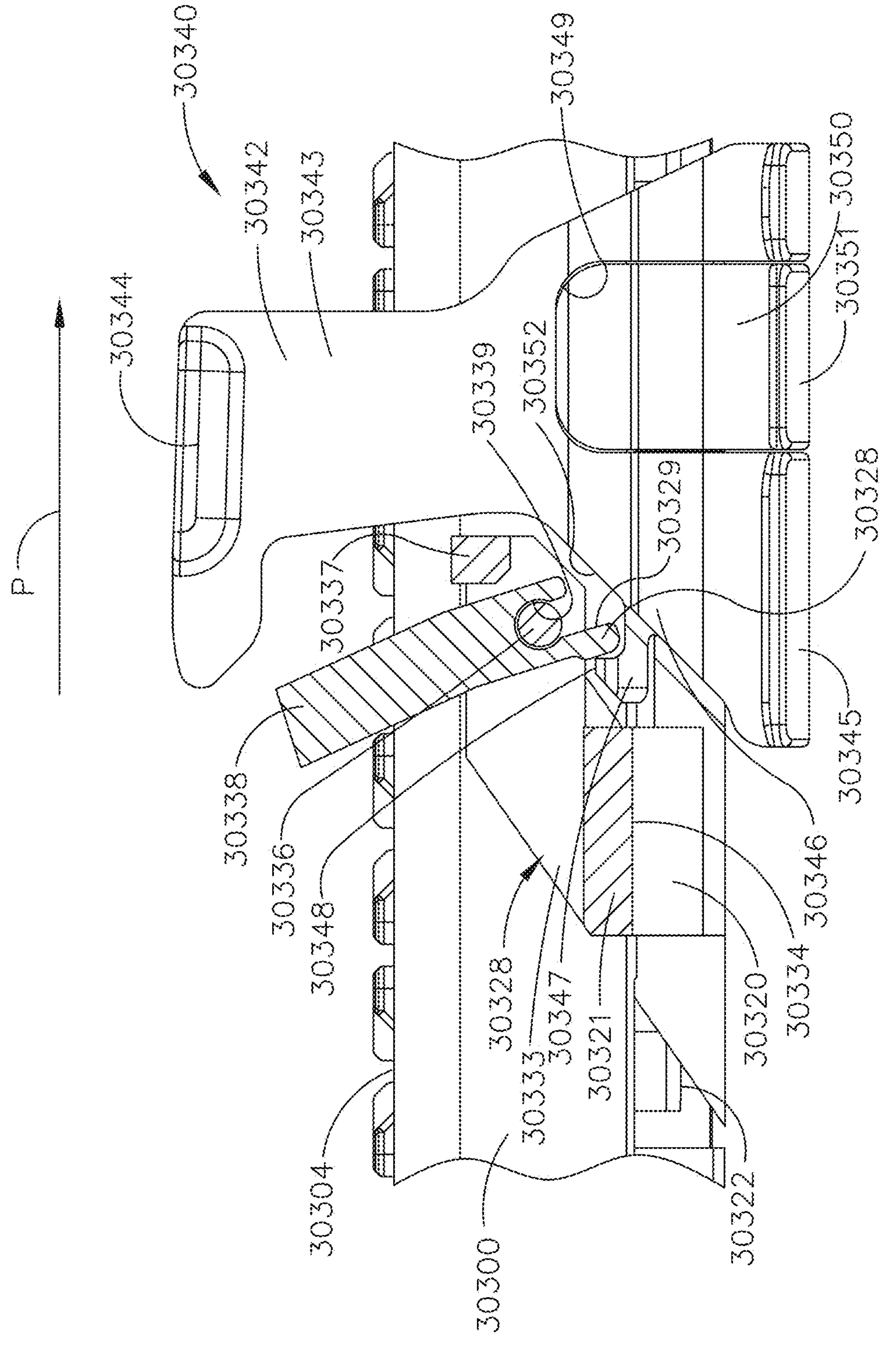
FIG. 77 is an elevation partial cross-section view of an end effector with portions removed for illustrative purposes, depicting a firing member, a cartridge body, and the sled assembly of FIG. 74, according to various aspects of the present disclosure.
Figure 78:
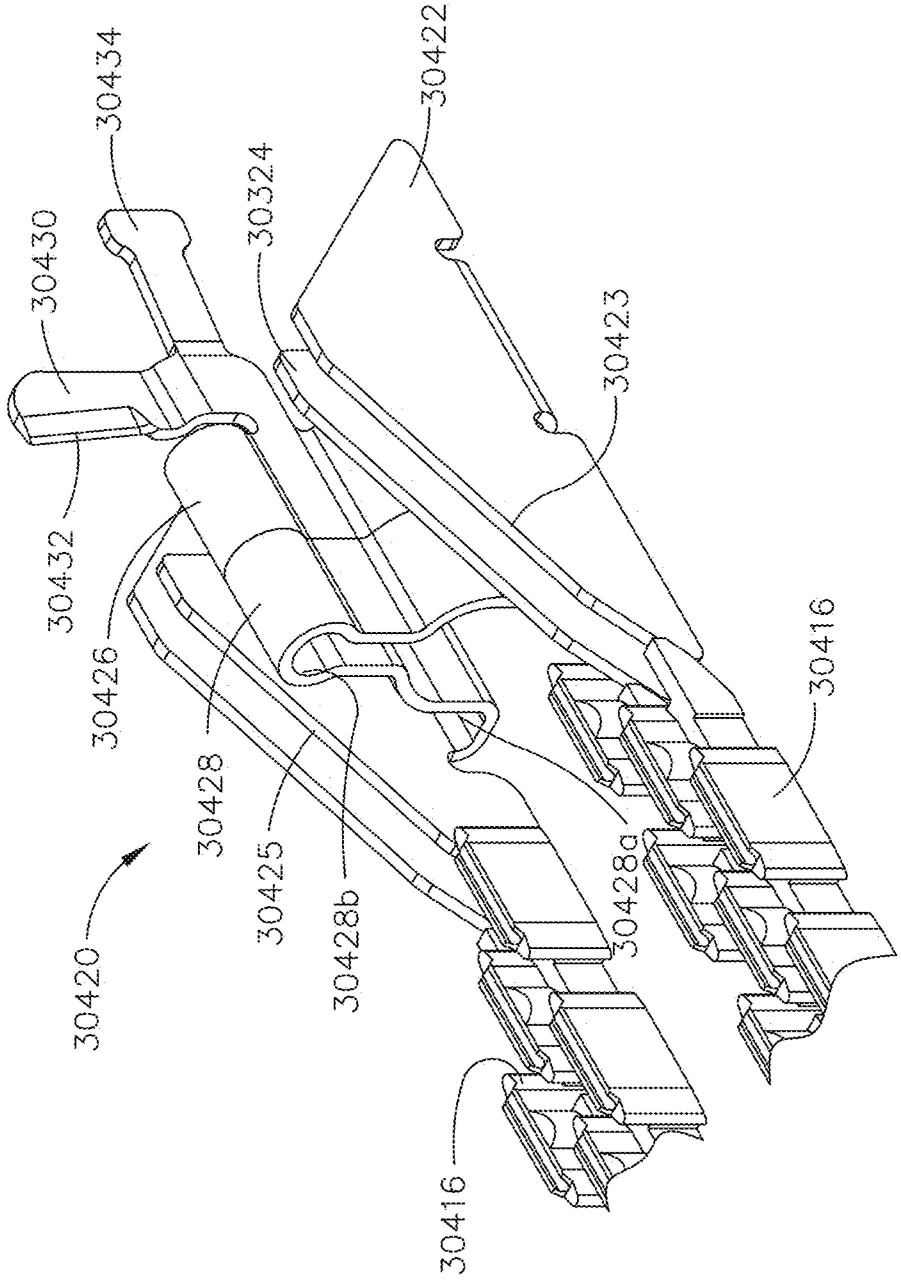
FIG. 78 is a perspective view of a sled assembly aligned with rows of drivers, according to various aspects of the present disclosure.

Referring primarily now to FIG. 77, during a firing stroke, the firing member 30340 is advanced distally into the staple cartridge 30300, which drives the distal extension 30347 and catch 30348 into the space 30328 between the sidewalls 30335 of the upright hub 30334. Upon insertion into the space 30348, the catch 30348 can hook around an end portion 30328 of the knife 30338. The end portion 30328 of the knife 30338 defines a planar abutment surface 30327 and bulbous end 30327 about with the catch 30348 extends to securely hold the catch 30348 against the planar abutment surface 30327. In such instances, the catch 30348 is held in the space 30328 at a location distal to the end portion 30328 of the knife 30338. Moreover, the knife 30338 is rotated into a protruding position, in which the cutting edge protrudes out of the cartridge body 30302 and into a tissue gap defined between the tissue-supporting surface 30304 and the anvil. In various instances, the distal extension 30347 and/or the end portion 30328 are configured to flex under a defined load during a distal firing motion to resiliently couple the distal extension 30347 in the space 30328 of the sled assembly 30320.

Thereafter, the firing member 30340 can advance the sled assembly 30320 distally. As the sled assembly 30320 moves distally, the knife 30338 is pushed in a clockwise direction from the orientation shown in FIG. 77. Resistance to the firing motion (e.g. tissue) can be configured to rotate the knife 30338 in the clockwise direction. The knife 30338 can be rotated in a clockwise direction from the orientation in FIG. 77 into abutting engagement with the stop 30337, which is configured to prevent further clockwise rotation of the knife 30038. In such instances, the knife 30338 is maintained in an upright or protruding position relative to the tissue-supporting deck 30304 during a distal motion of the firing stroke. For example, the abutment surface 30327 can be flush, or substantially flush, against an inside surface of the catch 30348.

A proximal retraction motion of the firing member 30320 is shown in FIG. 77 in which the firing member 30320 is withdrawn in the proximal direction P. Retraction of the firing member 30320 in the proximal direction B is configured to draw the distal extension 30347 and the catch 30348 proximally, which exerts a force on the end portion 30328 also in the proximal direction. In turn, this force on the end portion 30328 is configured to rotate the knife 30338 in the counterclockwise direction while retracting the sled assembly 30320 along with the firing member 30320. In various instances, a slight clockwise rotation of the knife 30338 is configured to pivot a cutting edge of the knife 30338 downward into an orientation less likely to contact and/or cut tissue, for example.

In various instances, the interconnection between the firing member 30340 and the sled assembly 30320 is configured to ensure that the sled assembly 30320 and the knife 30338 thereof are reset in a proximal position in the staple cartridge 30300 before the jaws are released from engagement by the cam members 30344, 30345, 30351 of the firing member 30340 and permitted to open. When firing member 30340 is further retracted and withdrawn from the staple cartridge 30300, the distal extension 30347, catch 30348, and/or the end portion 30328 can be configured to deflect to release the distal extension 30347 from the sled body 30321 and pivot the knife 30338 further counterclockwise from the orientation in FIG. 77 to a shielded orientation.

In certain aspects of the present disclosure, a sled can be stamped from a sheet of metal. In certain instances, the sled can be a two-part sled formed from two stamped sheets. The stamped sleds can having substantially W-shaped profiles in certain instances. The knife can be integral with one of the stamped sheets, for example. In certain instances, the two-part sled can include a first stamped component, which is retractable with the firing member, and a second stamped component, which is not retracted with the firing member. In a proximal, unfired position, the second stamped component is configured to interact with and overcome a missing and spent cartridge lockout. In a distal, fired position from which the second stamped component is not retracted by the firing member, the missing and spent cartridge lockout is configured to engage the firing member and prevent a firing stroke.

The two-part sled and lockout arrangement can prevent a firing stroke when the staple cartridge is missing from the end effector and/or when a spent or empty staple cartridge is installed in the end effector. Moreover, the sled being formed from two stamped metal sheets can provide a lower cost sled, in certain instances, with an integrated knife and cutting edge(s), coupling feature(s) for the firing member, and lockout engagement feature(s). Such a stamped metal sled can prevent bending or mushrooming of the sled rails under high staple-forming loads and may prevent breaking or cracking of the sled in certain instances. Moreover, the stamped metal sled can define thin rails allowing for more plastic (or other material(s)) in the cartridge body, which can improve the strength of the cartridge body including the strength of the support walls between the staple cavities. In certain instances, the thin profile of a stamped metal sled can allow the drivers to be positioned closer together and can better accommodate a rotary drive screw in certain instances.

Referring now to FIGS. 74-89, a sled assembly 30420 for an end effector 30440 (see FIG. 82) is shown. The end effector 30440 is similar in many aspects to the end effector 200 (see FIGS. 4 and 5) and is configured to cut and staple the tissue of a patient. The end effector 30440 includes a cartridge jaw 30450 and an anvil jaw 30454, for example, and the cartridge jaw 30450 is configured to receive a staple cartridge 30400 having a cartridge body 30402 and a tissue-supporting deck 30404, which is similar in many aspects to the staple cartridge 220 (see FIGS. 4 and 5), for example. The end effector 30440 also includes a firing drive system 30339 that includes a rotary drive screw 30442 and a firing member 30441, which are similar to the firing screw 261 (see FIGS. 4 and 5) and the firing member 270 (see FIGS. 4 and 5), respectively. The cartridge jaw 30450 defines a channel having opposing sidewalls 30452, which are configured to receive the staple cartridge 30400, including staples that can be ejected when the firing member 30441 is advanced through the staple cartridge 30400. For example, the firing member 30341 is driven through the end effector 30340 upon a rotation of the rotary drive screw 30442 during a firing stroke to advance the sled assembly 30420.

Figure 81:
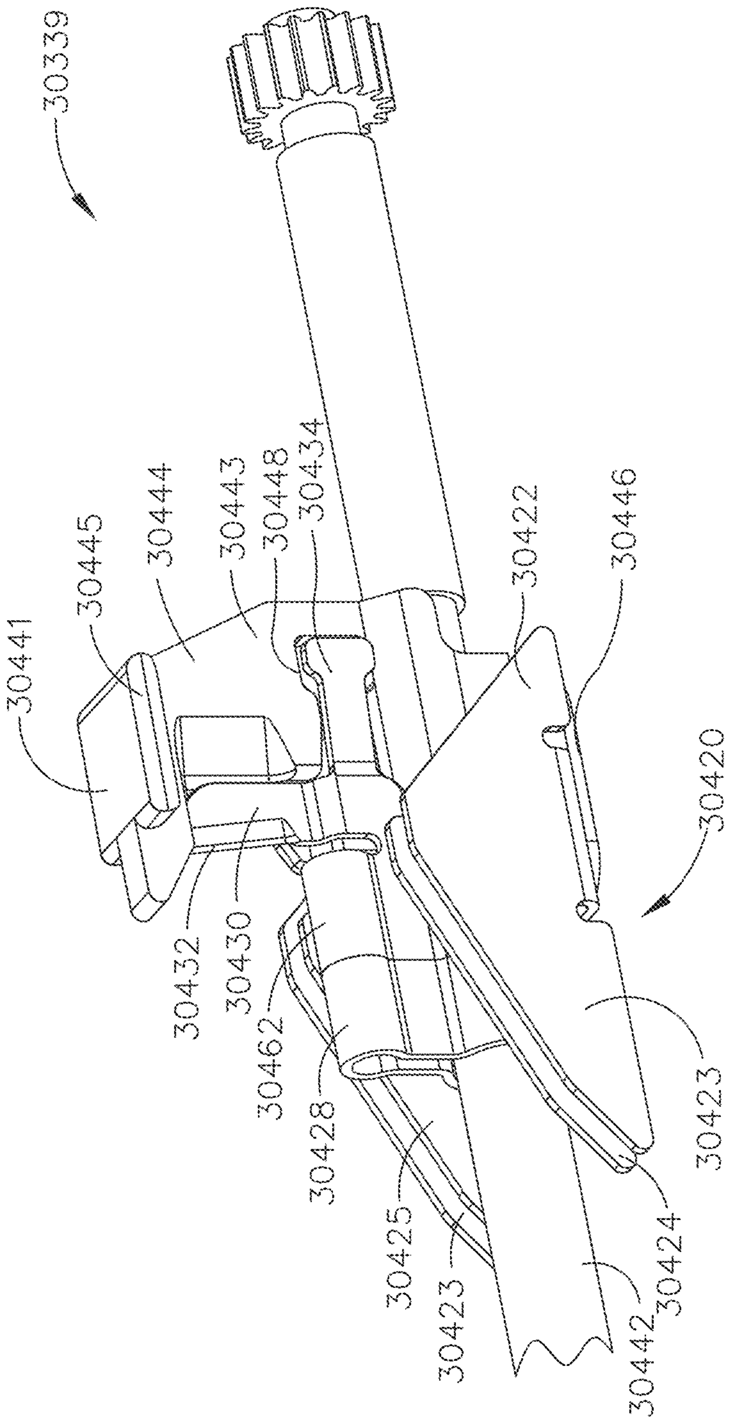
FIG. 81 is a perspective view of the sled assembly of FIG. 78 engaged with a firing system including a rotary drive screw and a firing member threadably coupled to the rotary drive screw, according to various aspects of the present disclosure.

Referring primarily to FIG. 81, the firing member 30441 includes a body portion 30443, upper cam members 30444 extending laterally from both sides of the body portion 30443, and lower cam members 30445 extending laterally from both sides of the body portion 30443. The upper cam members 30444 are configured to cammingly engage the anvil jaw 30454 of the end effector 30440 during a firing stroke, and the lower cam members 30445 are configured to cammingly engage the cartridge jaw 30450 of the end effector 30400 during the firing stroke.

Further to the above, a longitudinal opening extends through the body portion 30343. The longitudinal opening is configured to receive the rotary drive screw 30442 described above. In certain instances, the rotary drive screw 30442 can be threadably coupled to the body portion 30343 and, in other instances, can be threadably coupled to a firing drive nut housed therein, as further described herein.

Referring primarily to FIGS. 78-81, the sled assembly 30420 includes two discrete sleds-a proximal sled 30422 and a distal sled 30424. Each sled 30422, 30424 is a separate and discrete stamped component. For example, each sled 30422, 30424 can be formed with a separate stamping. The sleds 30422, 30424 are formed from a stamped sheet of material, such as a metal sheet. In at least one aspect, the sleds 30422, 30424 are formed from steel sheets; however, other materials are also contemplated. The proximal sled 30422 and the distal sled 30422 cooperate to engage drivers 30416 housed in the cartridge body 30402. The drivers 30416 can be triple drivers in various instances, and can be similar in many aspects to the drivers 20120 (FIG. 26), for example.

The proximal sled 30422 and the distal sled 30424 can be connected with a push-connection. Stated differently, while the proximal sled 30422 is applying a pushing force to the distal sled 30424, the sleds 30422, 30424 can remain connected. Absent the pushing force, the sleds 30422, 30424 are separable components which can be selectively moved and relocated in certain instances.

Each sled 30422, 30424 includes a pair of stamped wedges, which form the rails. The proximal sled 30422 includes outer rails 30423 for the sled assembly 30420, and the distal sled 30424 includes inner rails 30425 for the sled assembly 30420. An outer rail 30423 and an inner rail 30425 can be configured to move along each side of the staple cartridge during a firing stroke and can be aligned with a row of drivers 30416. Between the rails 30423, 30425, the proximal and distal sleds 30422, 30424 includes a central upright portion 30426, 30428, respectively, defining a lower arced profile 30426*a*, 30428*a* to accommodate the rotary drive screw 30442 (FIG. 81) therethrough. The central upright portions 30426, 30428 also include a key 30426*b*, 30428*b*, respectively, which are configured to align and guide the sleds 30422, 30424 through the cartridge body 30402. The keys 30426*b*, 30428 are arcuate loops although other geometries are also contemplated. Orthogonal flanges connect the central upright portions 30426, 30428 to their respective rails 30423, 30425, for example. The orthogonal flanges have the same thickness as the associated rails 30423, 30425 owing to their stamped formation.

Figure 88:
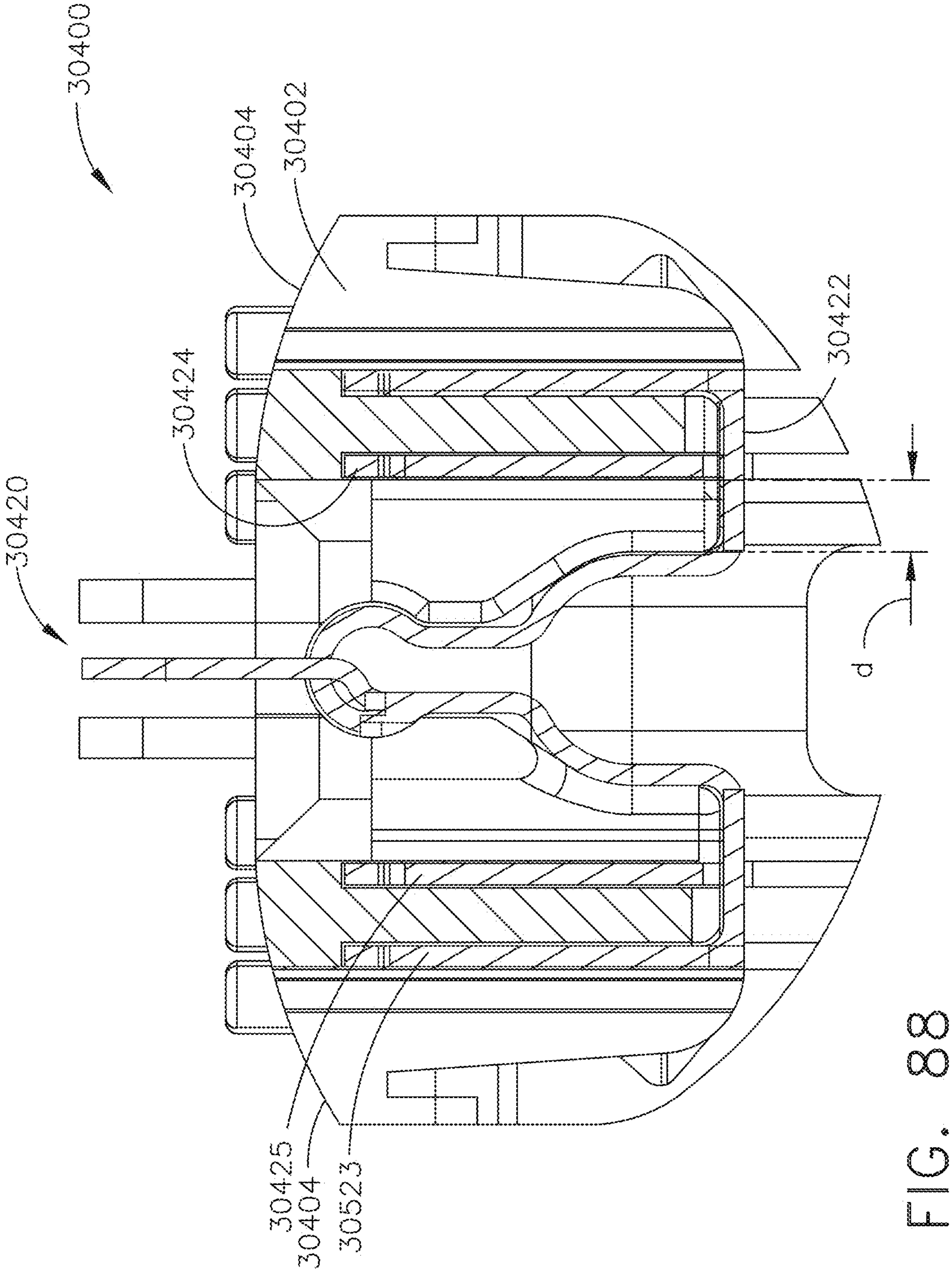
FIG. 88 is an elevation cross-section view of the staple cartridge of FIG. 85, according to various aspects of the present disclosure.
Figure 89:
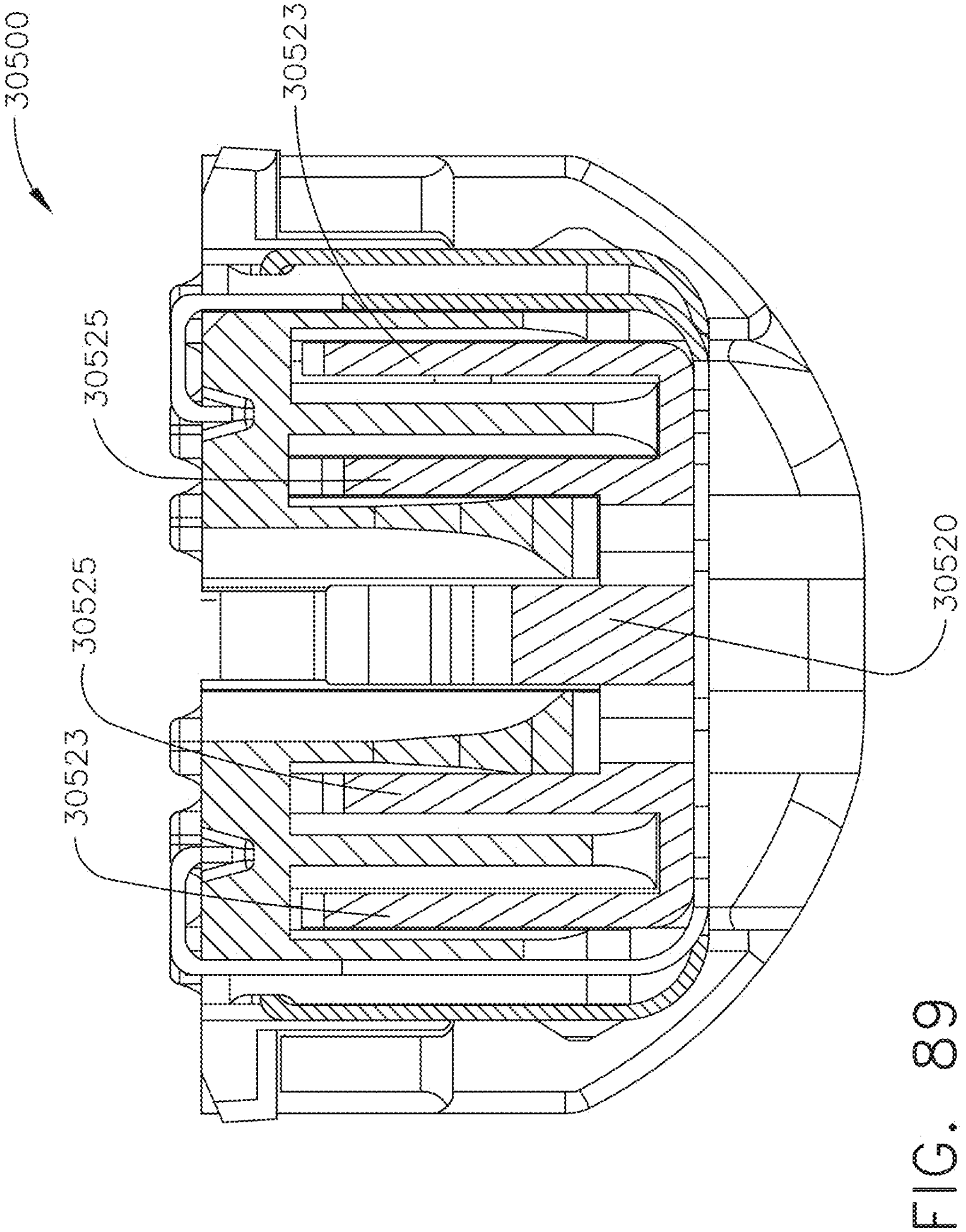
FIG. 89 is an elevation cross-section view of a staple cartridge, according to various aspects of the present disclosure.

The sled assembly 30420 is shown in a staple cartridge in FIG. 88. The thickness of the metal sheet can correlate to the thickness of the rails 30423, 30425. In such instances, the inner rails 30423 necessarily have the same thickness, and the outer rails 30423 necessarily have the same thickness. In at least one aspect, the inner rails 30423 and the outer rails 30423 can have the same thickness though stamped separately. In any event, being formed from thin metal sheets, the sled assembly 30420 can have a reduced thickness while still withstanding high loads without bending and/or breaking. For example, the rails 30423, 30425 can be narrower than the cartridge walls between staple cavities in adjacent longitudinal rows. Comparatively, referring to a staple cartridge 30500 in FIG. 89 having the same overall width and staple line geometry, inner and outer rails 30523, 30525 of a sled 30530 (e.g. a molded plastic sled) in a cartridge body 30502 can be wider than the rails 30423, 30425. In such instances, the cartridge body 30502 may have less space and, thus, less material and associated strength to support the inner row of drivers, for example.

Figure 79:
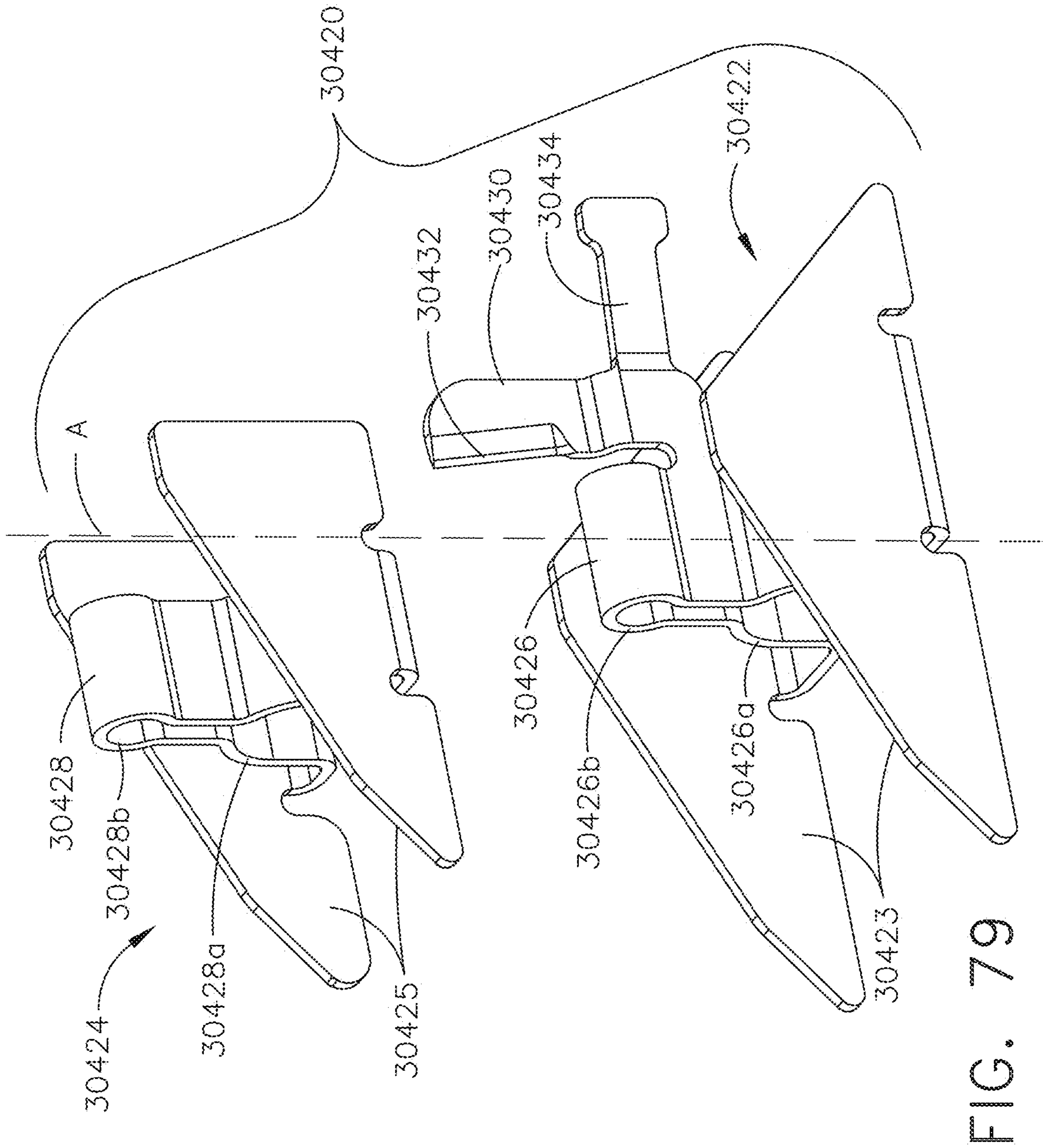
FIG. 79 is a perspective exploded view of the sled assembly of FIG. 78, according to various aspects of the present disclosure.
Figure 80:
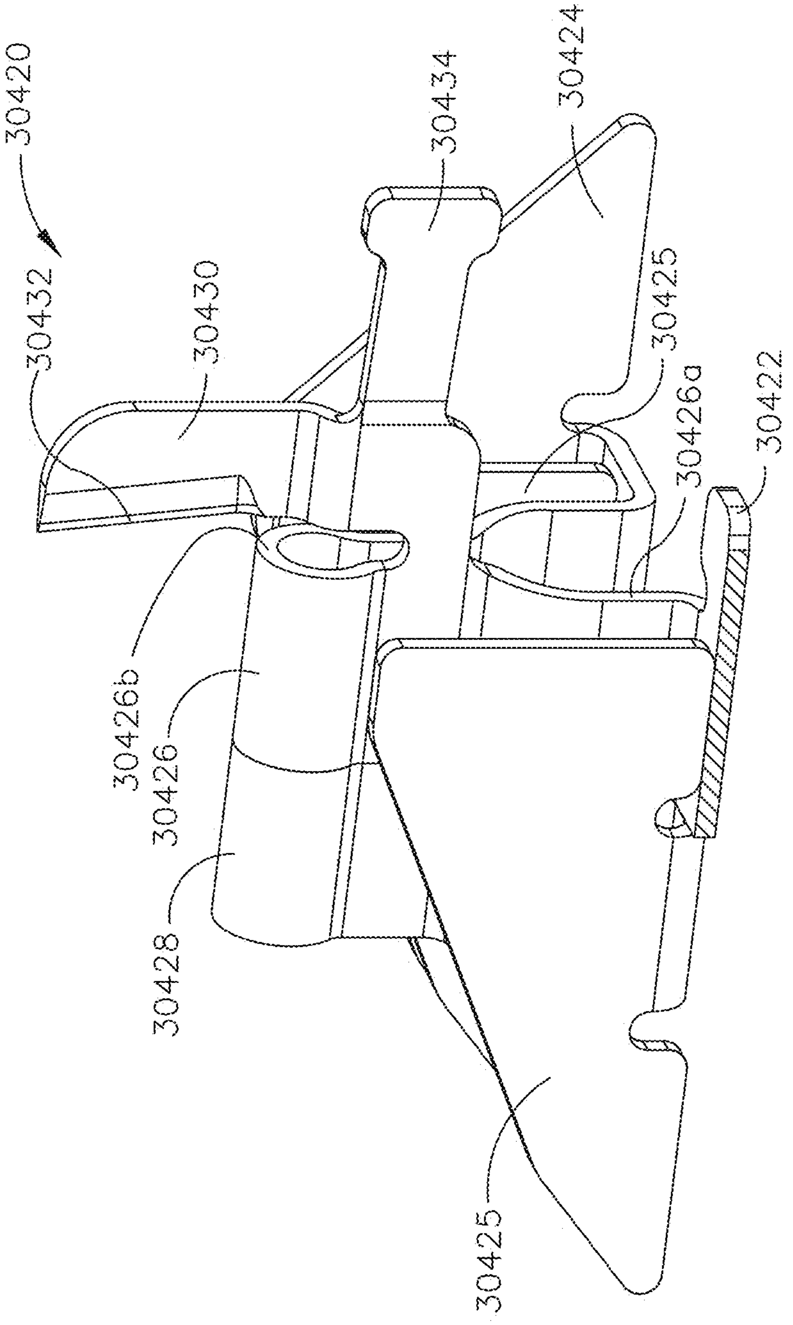
FIG. 80 is a perspective partial cross-section view of the sled assembly of FIG. 78, according to various aspects of the present disclosure.

The proximal sled 30422 and the distal sled 30424 can be aligned and assembled along an assembly axis A (FIG. 79). When assembled, the central upright portions 30426, 30428 can be longitudinally staggered and a proximal portion of the inner rails 30425 can rest on the orthogonal flanges of the proximal sled 30422 (see FIG. 80). Moreover, the orthogonal flanges of both sleds 30422, 30424 are configured to slide or otherwise move along a lower support surface, such as an inner surface of the cartridge jaw 30450 (see FIG. 82).

Figure 82:
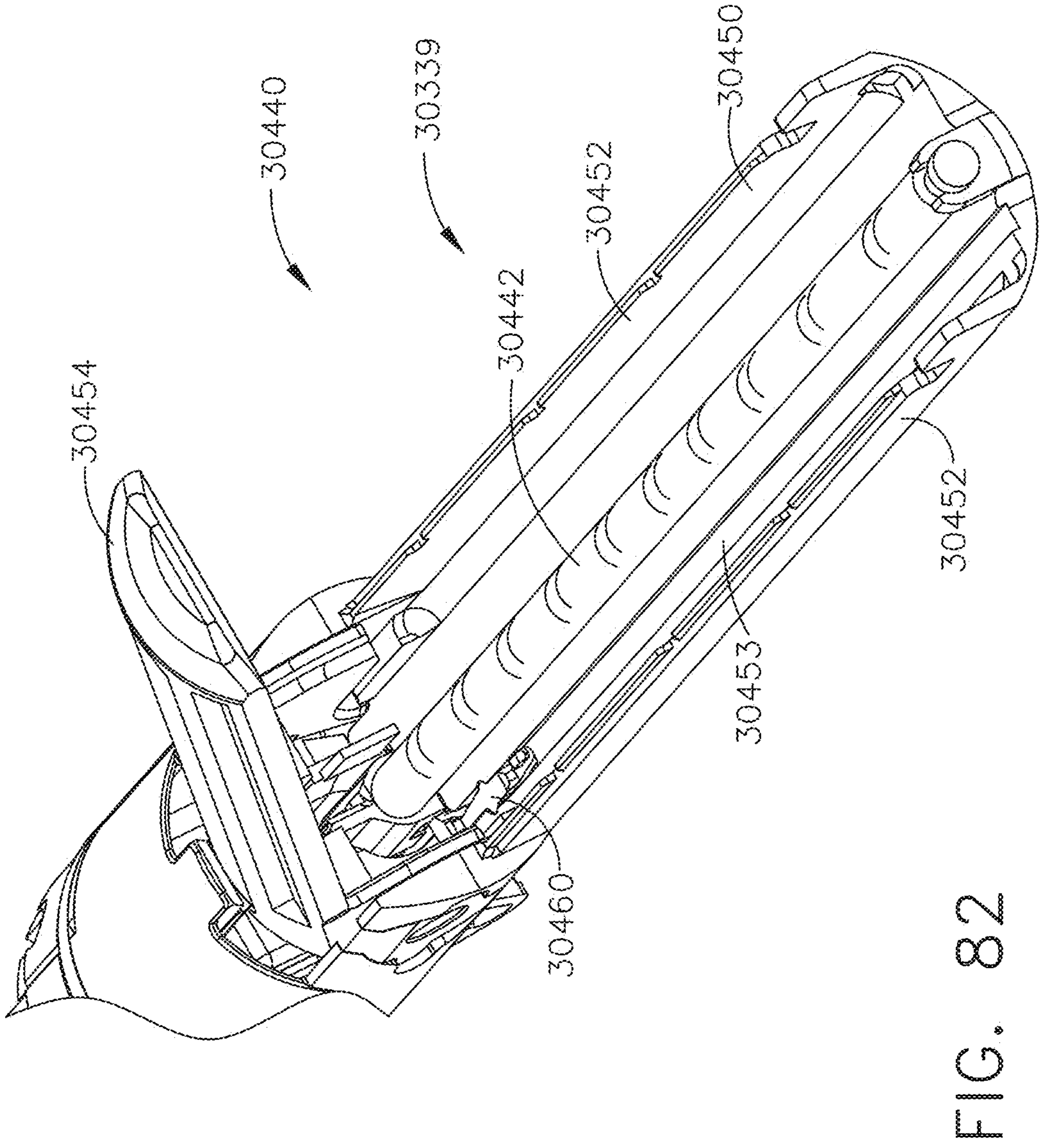
FIG. 82 is a perspective view of an end effector including a lockout in a locked configuration, according to various aspects of the present disclosure.

Referring still to FIGS. 78-81, the proximal sled 30422 also includes an integral knife 30430 having a distal-facing cutting edge 30432. The knife 30430 can be cut into the sheet of material, for example, when the proximal sled 30422 is stamped. The proximal sled 30422 also includes a proximal tail or extension 30434, which is configured to releasably couple with the firing member 30441 (FIG. 81), when the staple cartridge 30400 and the driver assembly 30420 thereof are installed in the cartridge jaw 30450 (FIG. 82). The proximal extension 30434 is T-shaped and includes a lateral bias, which is configured to facilitate coupling with a T-shaped recess 30448 (FIG. 81) in the firing member 30441. For example, referring to FIG. 87, the proximal extension 30434 can initially reside in a notch in the cartridge body 30402, which can hold the proximal sled 30422 in position relative to the cartridge body 30402. Then, when the firing member 30442 moves distally, the proximal extension 30434 bends into the T-shaped recess 30448 to lock the proximal sled 30422 to the firing member 30442. Alternative complementary profiles are also contemplated for coupling the proximal extension 30434 and the firing member 30441.

Figure 87:
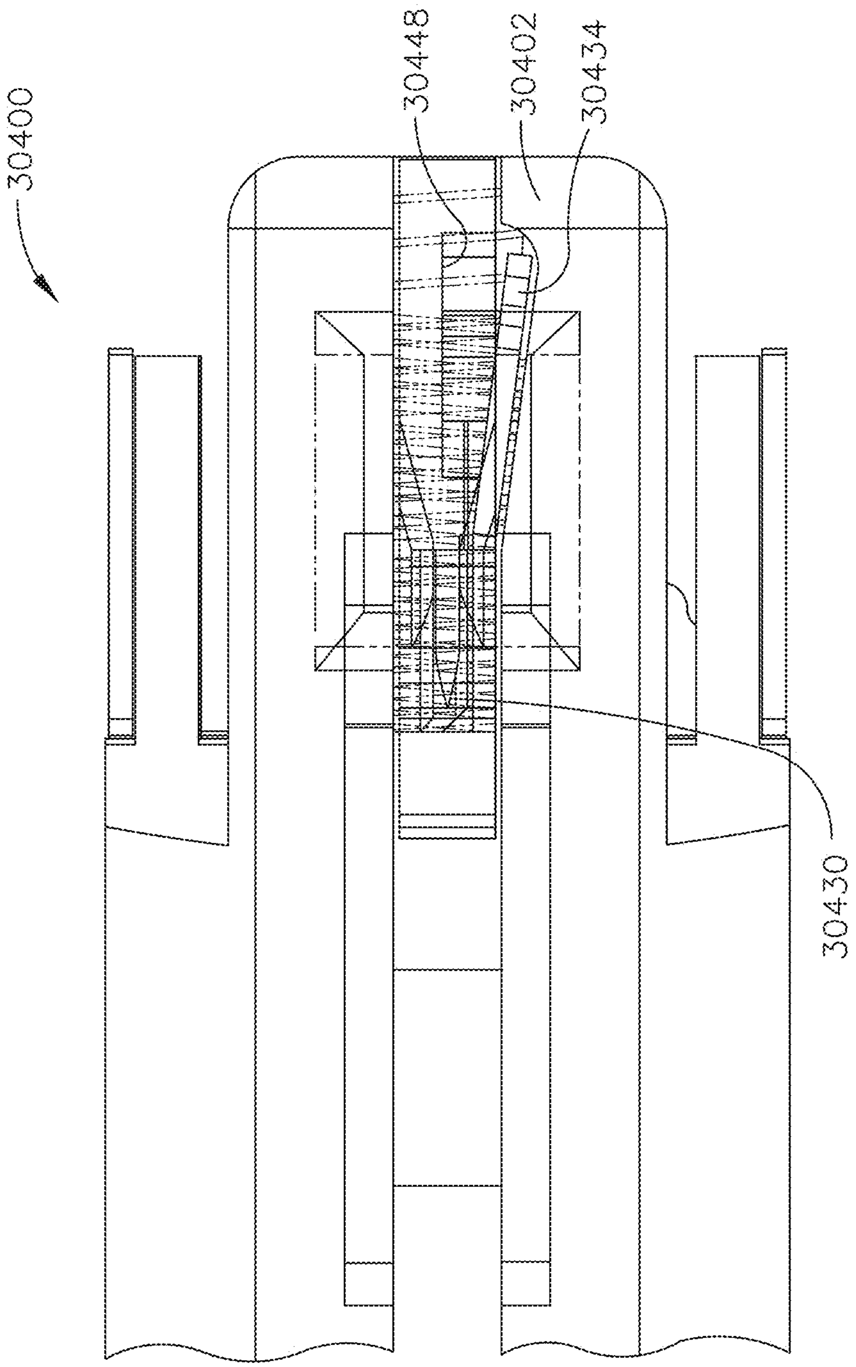
FIG. 87 is a plan view of a portion of the underside of the staple cartridge and the sled assembly of FIG. 85, depicting a portion of the firing assembly with phantom lines for illustrative purposes, according to various aspects of the present disclosure.

In various instances, when the staple cartridge 30400 is installed in the cartridge jaw 30450, the firing member 30441 can be aligned with the driver assembly 30420, and can be configured to move into driving engagement with the driver assembly 30420, as shown in FIG. 81, when the firing member 30441 moves an initial distance distally during a firing stroke. Referring to FIG. 87, deflection of the proximal extension 30434 into the recess 30448 is permitted when the firing member 30441 starts to move proximally, for example.

The proximal extension 30434 can be biased into holding engagement with the recess 30448 in the body 30443 of the firing member 30441 and can remain in engagement with the recess 30448 during proximal and distal displacement(s) of the firing member 30441 until the firing member 30441 is finally withdrawn proximally out of the staple cartridge 30400, or nearly out of the staple cartridge 30400, at the completion of the firing stroke. When the firing member 30441 is releasably attached to the proximal sled 30422, the upright body portion 30443 of the firing member 30441 is aligned with the knife 30430. As shown in FIG. 81, the body portion 30443 can support the knife 30430 as the knife 30430 is advanced through tissue. In various instances, the additional support from the body portion is configured to prevent deflection of the knife 30430 away from the firing path and longitudinal axis of the end effector 30440.

The distal sled 30424 is pushed distally by the proximal sled 30422 during the firing stroke. The distal sled 30424 further includes a foot 30429 (FIG. 86), which extends downward from the rails 30245 and/or orthogonal flange. The foot 30429 can be configured to move through a slot in the cartridge jaw 30450 during the firing stroke as the firing member 30441 pushes the proximal sled 30422, which pushes the distal sled 30424 distally during the firing stroke. In various instances, the foot 30429 is configured to engage a lockout in the end effector 30440 when the distal sled 30424 is parked in a proximal, unfired position. The distal sled 30424 and lockout features thereof are further described herein.

Figure 83:
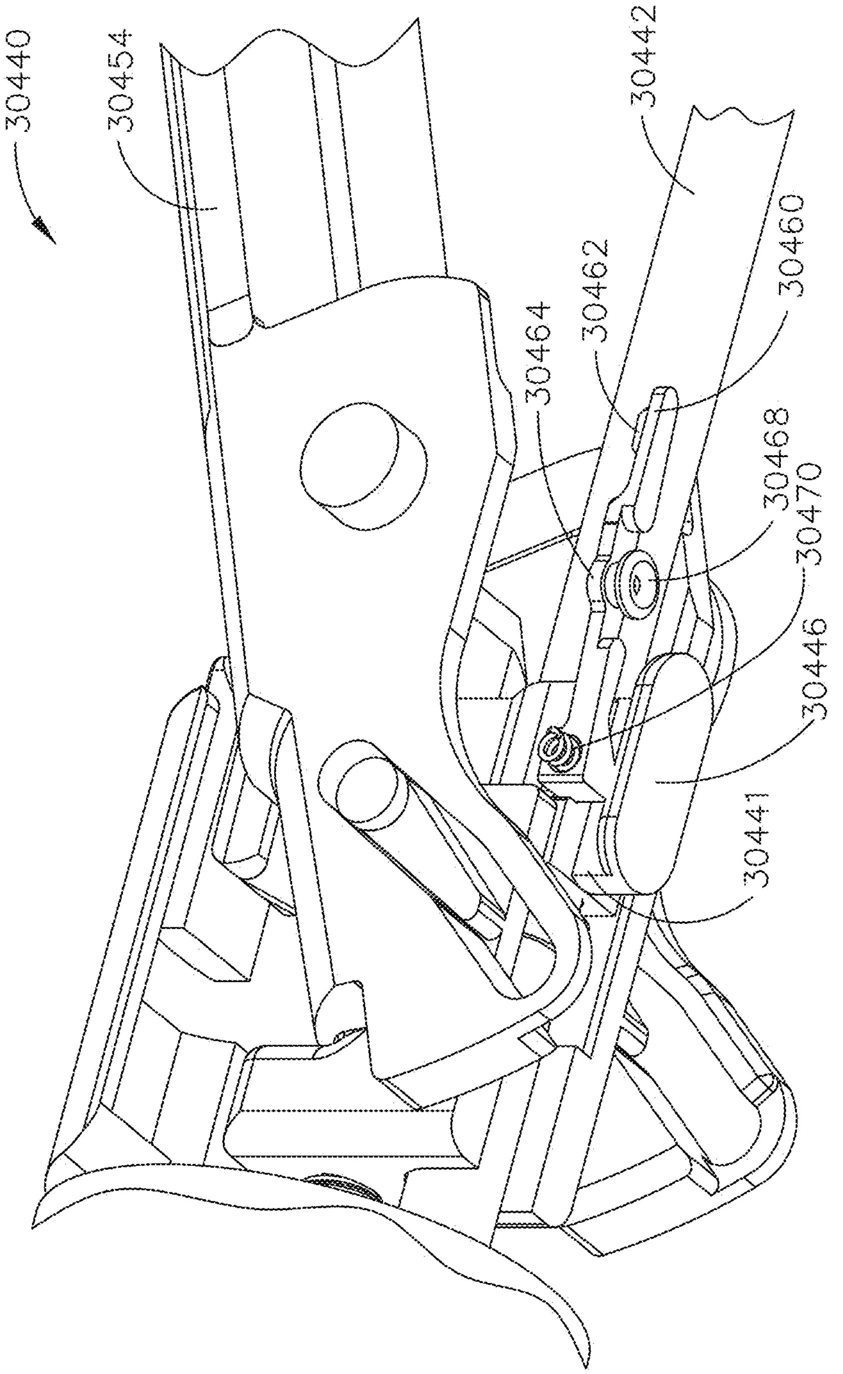
FIG. 83 is a perspective view of a portion of the end effector of FIG. 82 with parts removed for illustrative purposes, depicting the lockout in the locked configuration, according to various aspects of the present disclosure.
Figure 84:
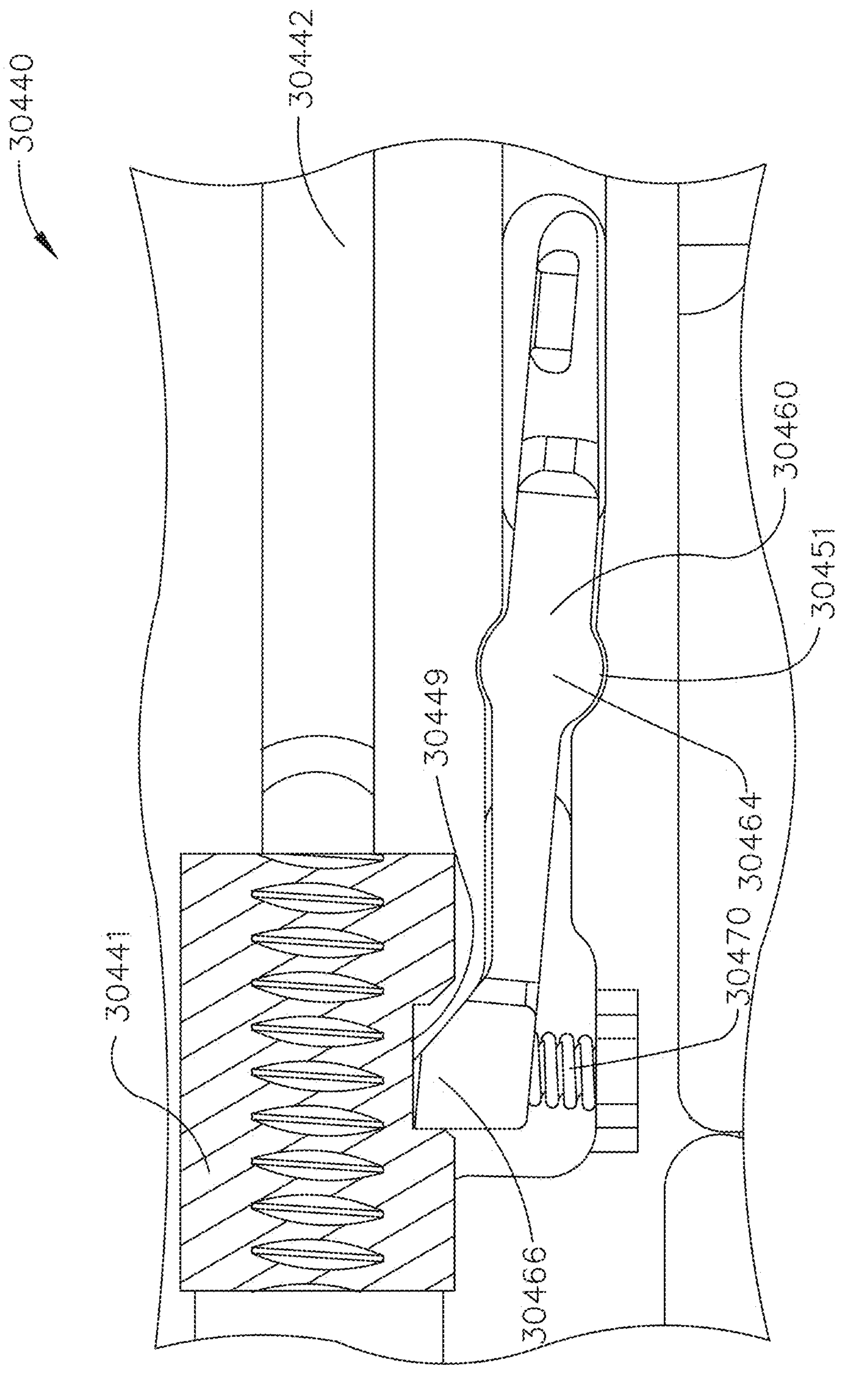
FIG. 84 is an elevation cross-section view of a portion of the end effector of FIG. 82, depicting the lockout in the locked configuration, according to various aspects of the present disclosure.
Figure 85:
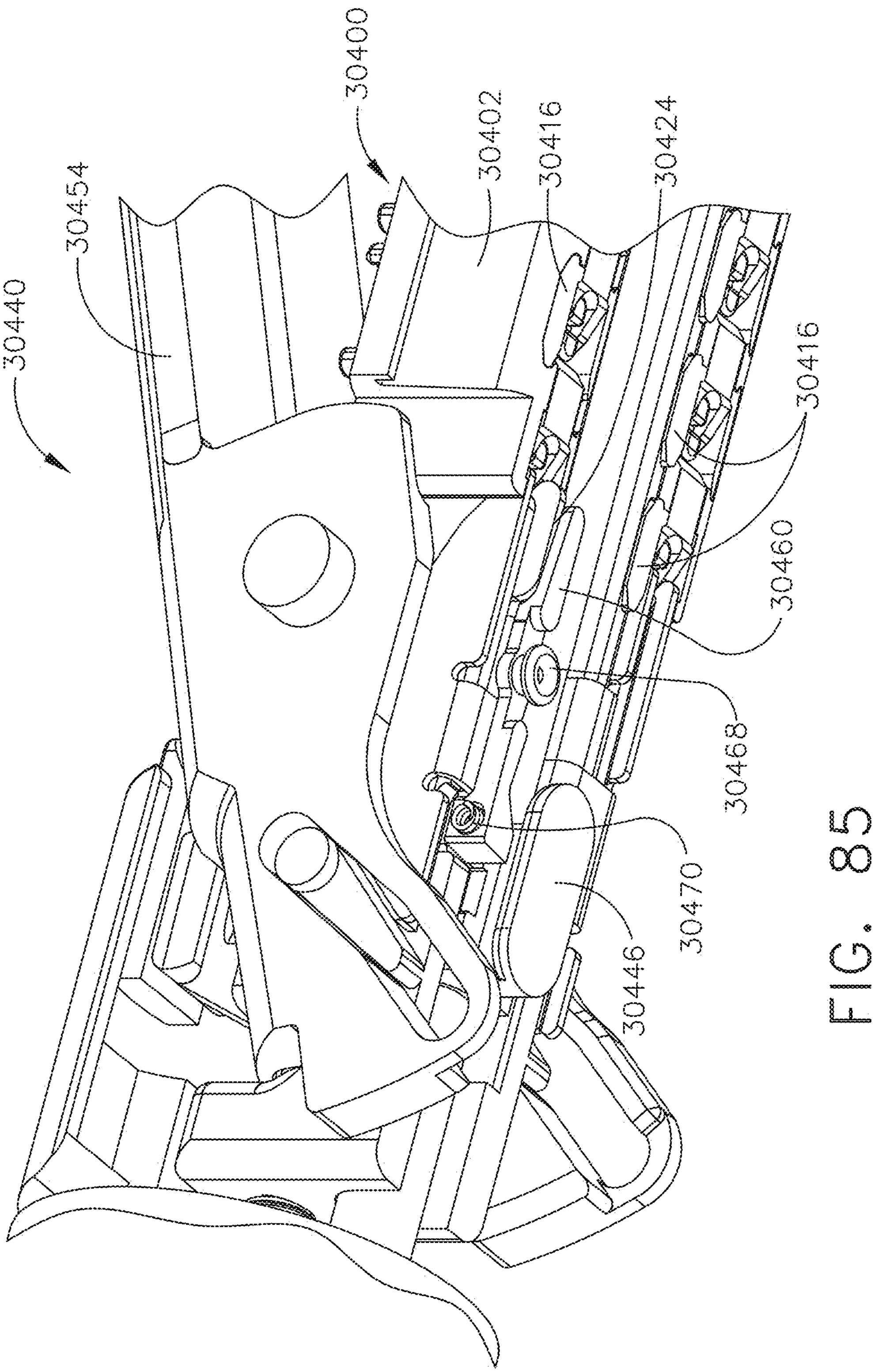
FIG. 85 is a perspective view of a portion of the end effector of FIG. 82 with parts removed for illustrative purposes, depicting a staple cartridge including the sled assembly of FIG. 78 installed in the end effector, further depicting the lockout in the unlocked configuration, according to various aspects of the present disclosure.
Figure 86:
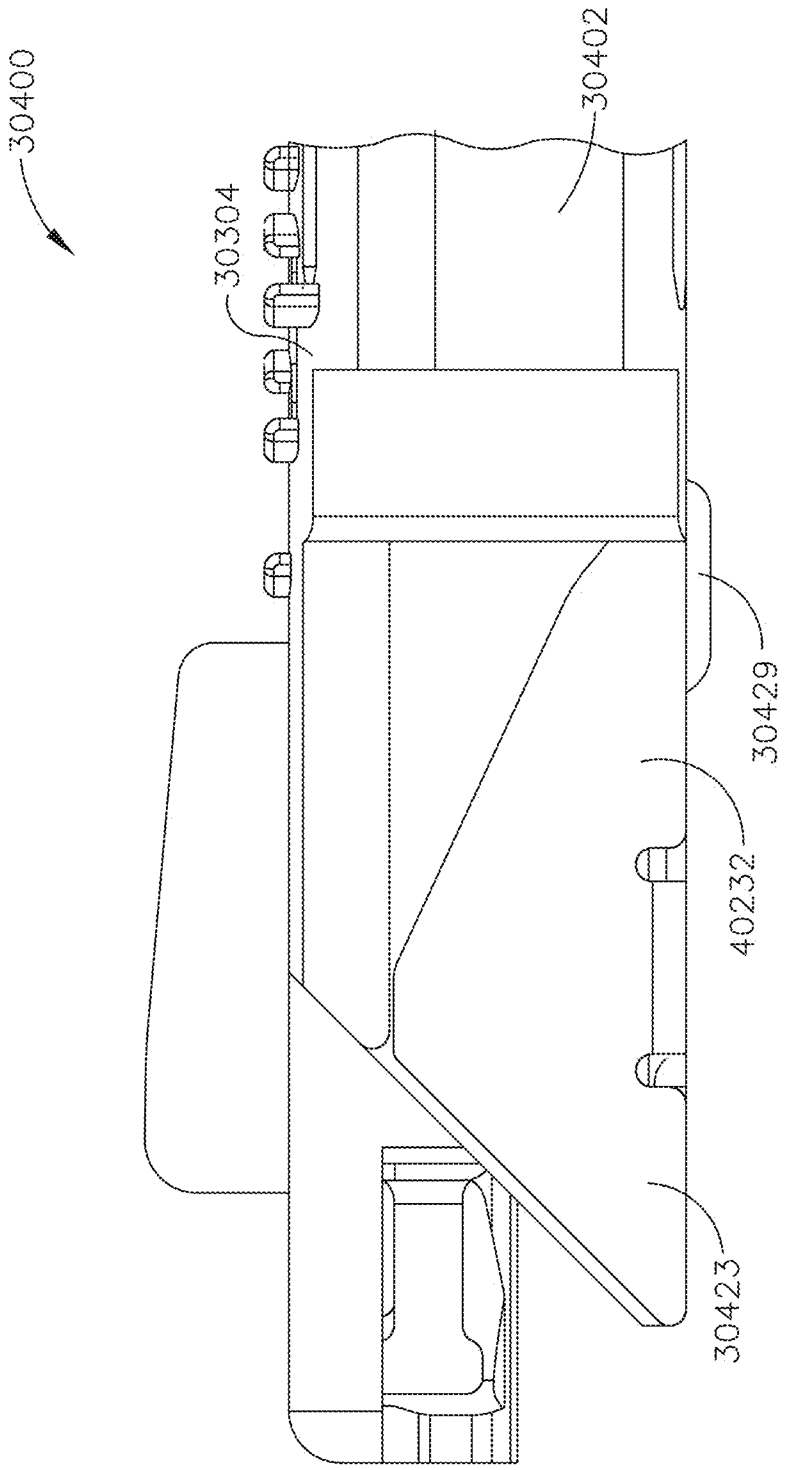
FIG. 86 is an elevation view of a portion of the staple cartridge and the sled assembly of FIG. 85, depicting the sled assembly in an unfired position, according to various aspects of the present disclosure.

Referring primarily to FIGS. 82-84, the end effector 30440 includes a lockout arm 30460, which is selectively engaged by the distal sled 30424. The lockout arm 30460 is movable between a locked position (FIGS. 82-84), in which a firing stroke is prevented, and an unlocked position (FIG. 85), in which a firing stroke is permitted. The lockout arm 30460 is flexibly positioned in a longitudinal recess 30453 in the channel portion of the cartridge jaw 30450 and is configured to pivot about a central pivot portion 40646 in certain instances.

The lockout arm 30460 includes a proximal end 30466 that is biased into a lockout notch 30449 in the firing member 30341. For example, a spring 30470 positioned in the cartridge jaw 30450 is configured to push the proximal end 30466 into the lockout notch 30449 of the firing member 30341 when the firing member 30341 is in a proximal, pre-firing stroke position. When the proximal end 30466 of the lockout arm 30460 is received in the lockout notch 30449, the lockout arm 30460 is configured to resist translation of the firing member 30441 and, thus, prevent the firing stroke The sled assembly 30420 is configured to overcome the lockout arm 30460 by removing the proximal end 30466 thereof from the lockout notch 30449. More specifically, when the distal sled 30424 is positioned in a proximal, unfired position in the staple cartridge 30400, the foot 30429 of the distal sled 30424 is positioned to engage a distal end 30462 of the lockout arm 30460 (see FIG. 85). The pivot portion 30464 of the lockout arm 30400, which is between the proximal end 30466 and the distal end 30462, is held in an arcuate support 30451 in the cartridge jaw 30450. The pivot portion 30464, and thus the entire lockout arm 20468, is configured to pivot about the arcuate support 30451 in certain instances.

For example, the lockout arm 30460 pivots from the locked position to the unlocked position when the staple cartridge 30400 is installed in the end effector 30440 and the distal sled 30424 is in the proximal unfired position, which indicates that the staple cartridge is not spent or empty. The lockout arm 30460 pivots from the unlocked position to the locked position when the firing member 30441 pushes the proximal sled 30422 distally, which pushes the distal sled 30422 distally. When the foot 30429 on the bottom of the distal sled 30422 moves out of engagement with the distal end 30462 of the lockout arm 30460, the lockout arm 30460 pivots due to the biasing force of the spring 30470. When the firing member later returns to a proximal position after a firing stroke and attempts to move the lockout notch 30449 past the lockout arm 30460, the spring 30470 pushes the proximal end 30466 of the lockout arm 30460 into the lockout notch 30449 to prevent the firing stroke. The foot 30429 moves along the longitudinal recess 30453 in the channel 30450 during the firing stroke.

As described herein, the two-part sled assembly 30420 is configured to selectively overcome the lockout arm 30460 to permit a firing stroke. Moreover, the sled assembly 30420 includes an integral knife 30430, which is a single-use knife 30420 have a suitably sharp cutting edge 30432 for transecting tissue clamped by the end effector 30440. The single-use knife 30420 is retracted proximally upon completion of the firing stroke and along with the firing member 30441. Moreover, because the firing beam 30441 includes opposing cams 30445, 30446, the firing member 30441 can ensure that the jaws 30450, 30542 remain closed until the knife 30420 is returned to a proximal position in the staple cartridge 30400.

As described herein, certain surgical devices can include a reusable knife, which is incorporated into the surgical device, such as a distal-facing knife edge on a firing member, for example. Upon completion of a firing stroke, the reusable knife can be retracted out of the staple cartridge and subsequently re-fired with another staple cartridge. In such applications, the surgical device, including the reusable knife thereof, can be cleaned and sterilized between surgical procedures.

In other instances, a single-use knife can be utilized with a surgical device. For example, a staple cartridge can include a single-use knife which is only used with that particular staple cartridge. When the staple cartridge is removed from the surgical device, the single-use knife is removed, as well. When a replacement staple cartridge is installed in the surgical device, a new single-use knife is provided therewith. In certain instances, the single-use knife can remain in the staple cartridge for the duration of the firing stroke and even after the firing stroke when the staple cartridge is removed from the surgical device. In certain instances, the cutting edge of the single-use knife can be at least partially shielded by a feature of the staple cartridge after the firing stroke and/or when the staple cartridge is removed from the surgical device. In certain instances, the knife or a portion thereof can be folded or otherwise deformed and/or pushed from a protruding orientation downward into the staple cartridge.

For example, a staple cartridge can include a two-part sled assembly including a proximal sled and a distal sled. The proximal sled can connect to a firing member upon insertion of the two-part sled assembly into a surgical device. The distal sled can include an upright cutting edge. During a firing stroke, the firing member is configured to push the proximal sled distally, which, in turn, pushes the distal sled distally to transect tissue. Upon completion of the firing stroke, the proximal sled can be retracted proximally by the firing member and can separate from the distal sled. As the proximal sled is retracted proximally, a central ledge of the proximal sled is configured to move over the upright cutting edge to fold the cutting edge downward into the cartridge body. In various instances, the proximal sled can also include support features for supporting the upright cutting edge during the firing stroke.

In certain instances, the two-part sled assembly can be manufactured from stamped metal sheets, which can be a low cost alternative to other manufacturing techniques. A stamped metal sled assembly can have thinner rails yet be stronger than a plastic sled for the same size staple cartridge, in certain instances. Moreover, a stamped metal sled assembly can form staples with less spring back and/or allow the staples to be positioned closer together in a staple line, in certain instances. In certain instance, the knife can be configured to dive and/or be deformed into the cartridge body anywhere along the length of the firing stroke and only the proximal stamped sled component can return with the firing member. The folding and/or deformation of the knife during the proximal retraction of the firing member and proximal stamped sled component can ensure the knife is not reused during a subsequent surgical operation. The proximal stamped sled component and the firing member can be positioned to support the distal stamped sled component and the knife thereof during the distal firing stroke in certain instances.

Referring now to FIGS. 90-98, a two-part sled assembly 30620 is shown. The sled assembly 30620 includes two discrete sleds—a proximal sled 30622 and a distal sled 30624. Each sled 30622, 30624 is a separate and discrete stamped component. For example, each sled 30622, 30624 can be formed with a separate stamping. The sleds 30622, 30624 are formed from a stamped sheet of material, such as a metal sheet. In at least one aspect, the sleds 30622, 30624 are formed from steel sheets; however, other materials are also contemplated. The proximal sled 30622 and the distal sled 30622 cooperate to engage drivers 30616 (FIG. 92) housed in a cartridge body 30602. The drivers 30616 can be triple drivers in various instances, and can be similar in many aspects to the drivers 20120 (FIG. 26), for example.

The proximal sled 30622 and the distal sled 30624 can be connected with a push-connection. Stated differently, while the proximal sled 30622 is applying a pushing force to the distal sled 30624, the sleds 30622, 30624 can remain connected. Absent the pushing force, the sleds 30622, 30624 are separable components that can be selectively moved and relocated in certain instances.

Each sled 30622, 30624 includes a pair of stamped wedges, which form the rails. The proximal sled 30622 includes outer rails 30623 for the sled assembly 30620, and the distal sled 30624 includes inner rails 30625 for the sled assembly 30620. An outer rail 30623 and an inner rail 30625 can be configured to move along each side of the staple cartridge during a firing stroke and can be aligned with a row of drivers 30616. The proximal sled 30622 includes a central upright portion 30626 and orthogonal flanges 30621 connecting the central upright portion 30426 to each outer rail 30623. The orthogonal flanges 30621 are configured to ride along a lower support surface during a firing stroke (e.g. along an inside surface of a cartridge jaw) and have the same thickness as the outer rails 30423 owing to the stamped formation of the proximal sled 30622. The central upright portion 20426 is dimensioned to fit around a portion of the distal sled 20624 and defines a ledge 30627.

The distal sled 30624 includes a central upright portion 30628 and orthogonal flanges 30619 connecting the central upright portion 30626 to each inner rail 30625. The orthogonal flanges 30619 are configured to ride along a lower support surface during a firing stroke (e.g. along an inside surface of a cartridge jaw) and have the same thickness as the inner rails 30625 owing to the stamped formation of the distal sled 30624. The central upright portion 30628 defines a lower arced profile 30626*a* dimensioned to accommodate a rotary drive screw 30642 (FIG. 92) therethrough. The rotary drive screw 30642 is similar to the firing screw 261 (see FIGS. 4 and 5) in many aspects. The central upright portion 30628 further includes an extending knife 30629 having a distally-facing cutting edge 30630. The central upright portion 30626 of the proximal sled 30622 is configured to fit around the central upright portion 30628 of the distal sled 30622 except the extending knife 30629 which extends beyond the ledge 30627 and upper edge of the central upright portion 30626. The distal sled 30624 also includes an anti-retraction arm 30632, which can be biased laterally into engagement with the cartridge body 30602 to prevent proximal retraction of the distal sled 30624 after the firing stroke. In certain instances, an anti-retraction arm 30632 can be positioned on each lateral side of the distal sled 30624.

Figure 92:
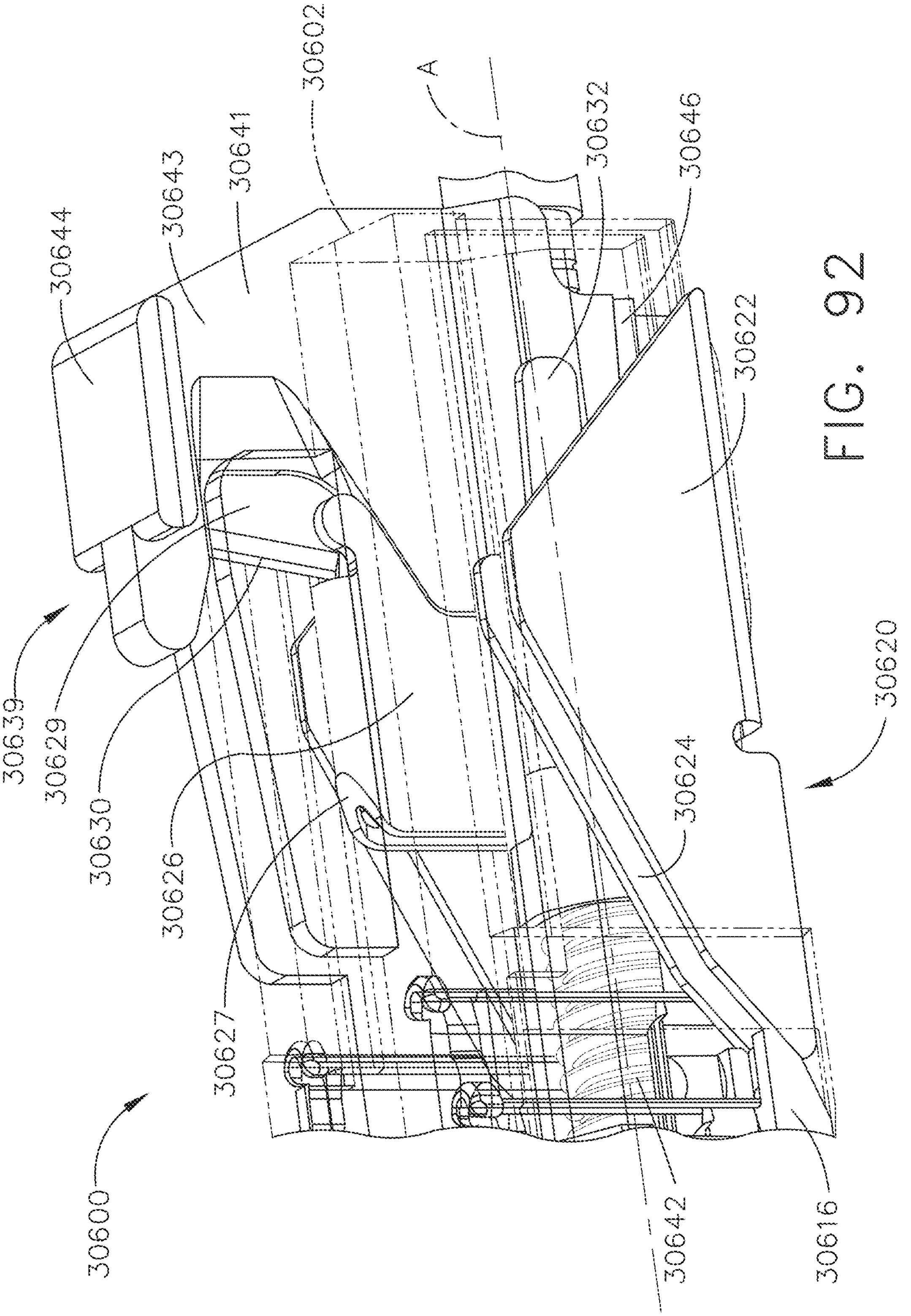
FIG. 92 is a perspective view of the firing member and the sled assembly of FIG. 90 relative to a cartridge body which is shown in phantom lines for illustrative purposes, depicting the firing assembly in a first advanced configuration in which the firing member is moved into driving engagement with the sled assembly, which is moved into driving engagement with drivers in the cartridge body, according to various aspects of the present disclosure.
Figure 93:
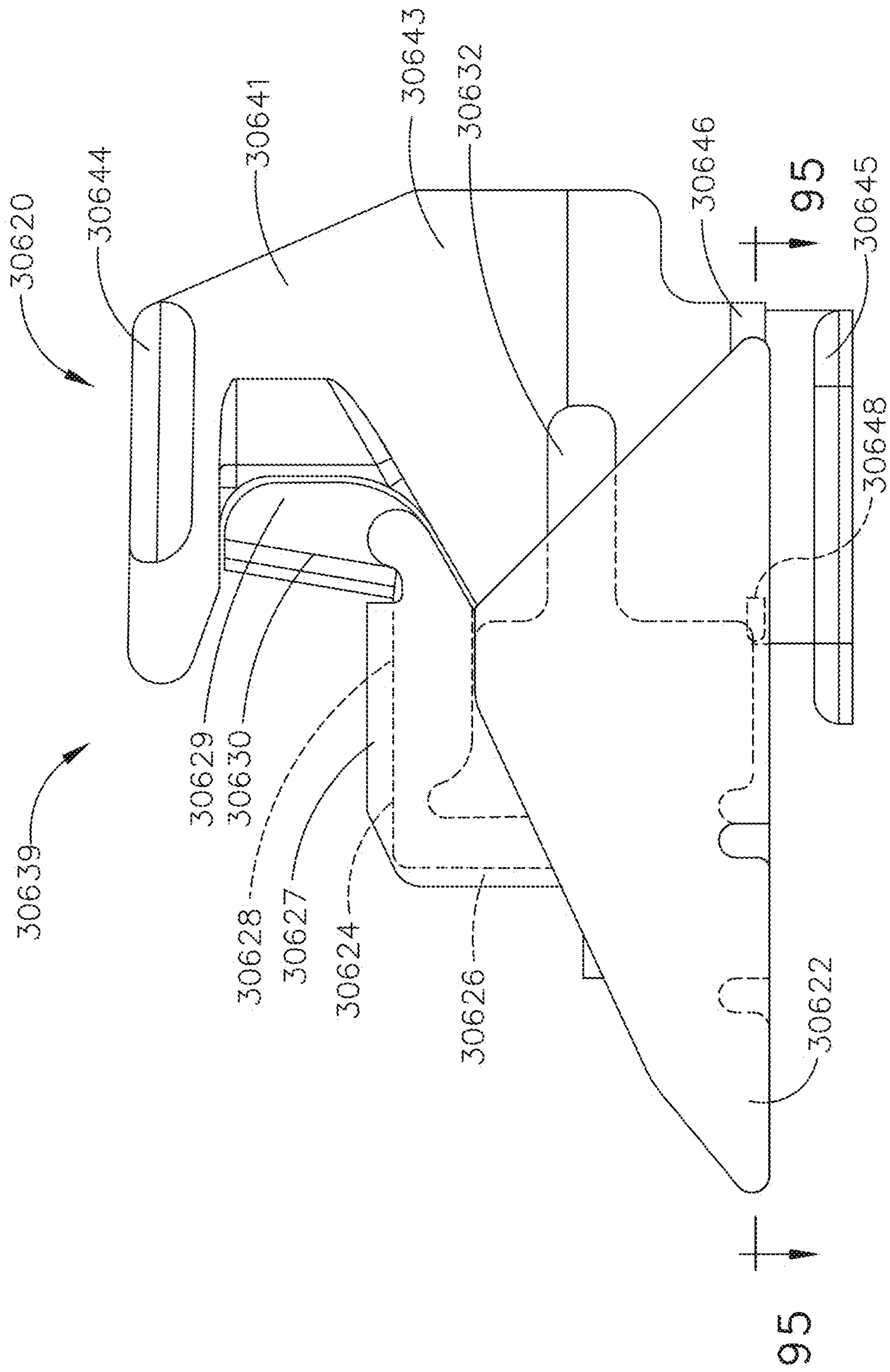
FIG. 93 is an elevation view of the firing member and the sled assembly of FIG. 90 with certain hidden features shown with dashed lines for illustrative purposes, depicting the firing member in the first advanced configuration, according to various aspects of the present disclosure.

Referring primarily to FIG. 92, the sled assembly 30620 is a component of a staple cartridge 30600, which also includes the cartridge body 30602, drivers 30616, and staples removably positioned in the cartridge body 30602. In various instances, the staple cartridge 30600, including the sled assembly 30620 thereof, can be releasably installed in a surgical device or an end effector thereof having a cartridge jaw, an anvil jaw, and a firing member, as further described herein. Upon completion of the stapling motion, the staple cartridge 30600, including the sled 30620 thereof, can be removed from the end effector. When installing the staple cartridge 30600 in the surgical end effector, the sled assembly 30620 can be aligned with the firing member in the surgical end effector and the distal sled 30622 can be releasably coupled to the firing member when the staple cartridge 30600 is installed in the surgical end effector.

Figure 90:
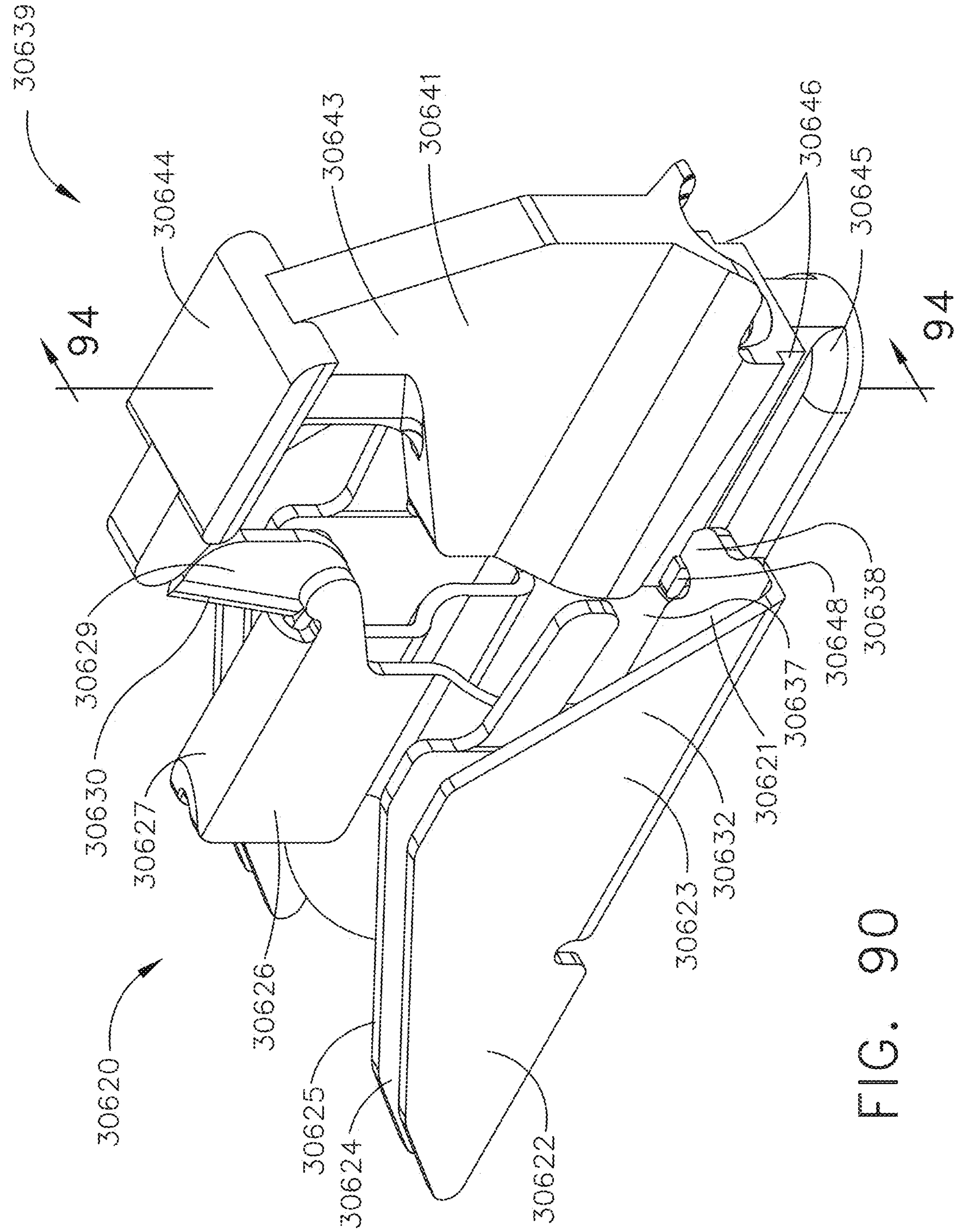
FIG. 90 is a perspective view of a firing member and a sled assembly, depicting the firing member in an unfired configuration, according to various aspects of the present disclosure.
Figure 91:
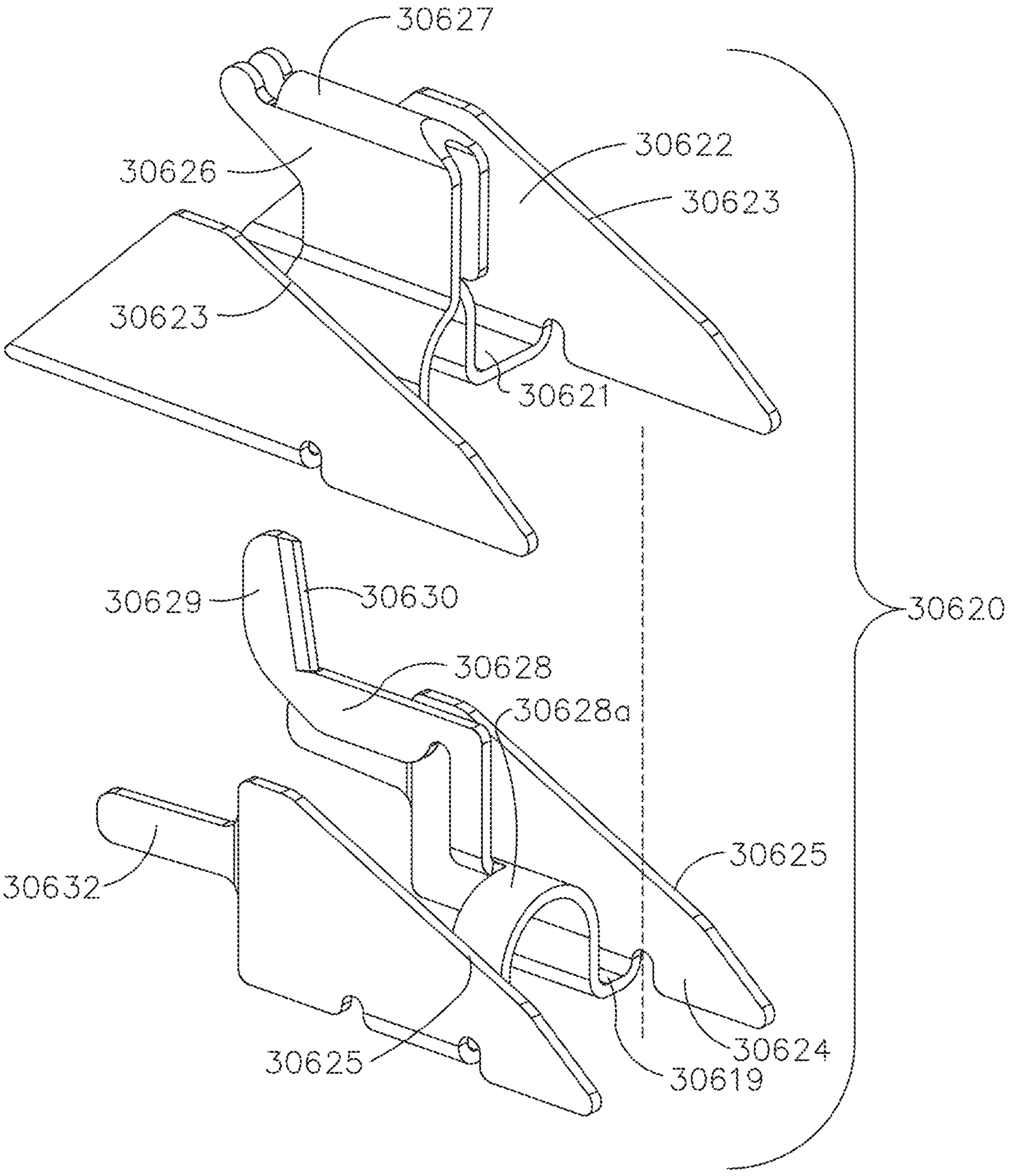
FIG. 91 is an exploded view of the sled assembly of FIG. 90, according to various aspects of the present disclosure.

Referring now to FIG. 90, a firing member 30641 for use with the sled assembly 30620 is shown. When assembled together, the firing member 30641 and the sled assembly 30620 form a firing assembly 30639, which is configured to be advanced along the rotary drive screw 30642 during a firing stroke. The firing member 30641 includes an upright body portion 30643, upper cam members 30644 extending laterally from both sides of the body portion 30643, and lower cam members 30645 extending laterally from both sides of the body portion 30643. The upper cam members 30644 are configured to cammingly engage an upper jaw, or anvil, of the end effector during a firing stroke, and the lower cam members 30645 are configured to cammingly engage a lower jaw, or elongate channel of the end effector during the firing stroke. The cam members 30644, 30645 are configured to clamp the jaws of the end effector 30640 and define a tissue gap during a firing stroke, as further described herein with respect to various firing member (e.g. I-beams and E-beams).

Figure 95:
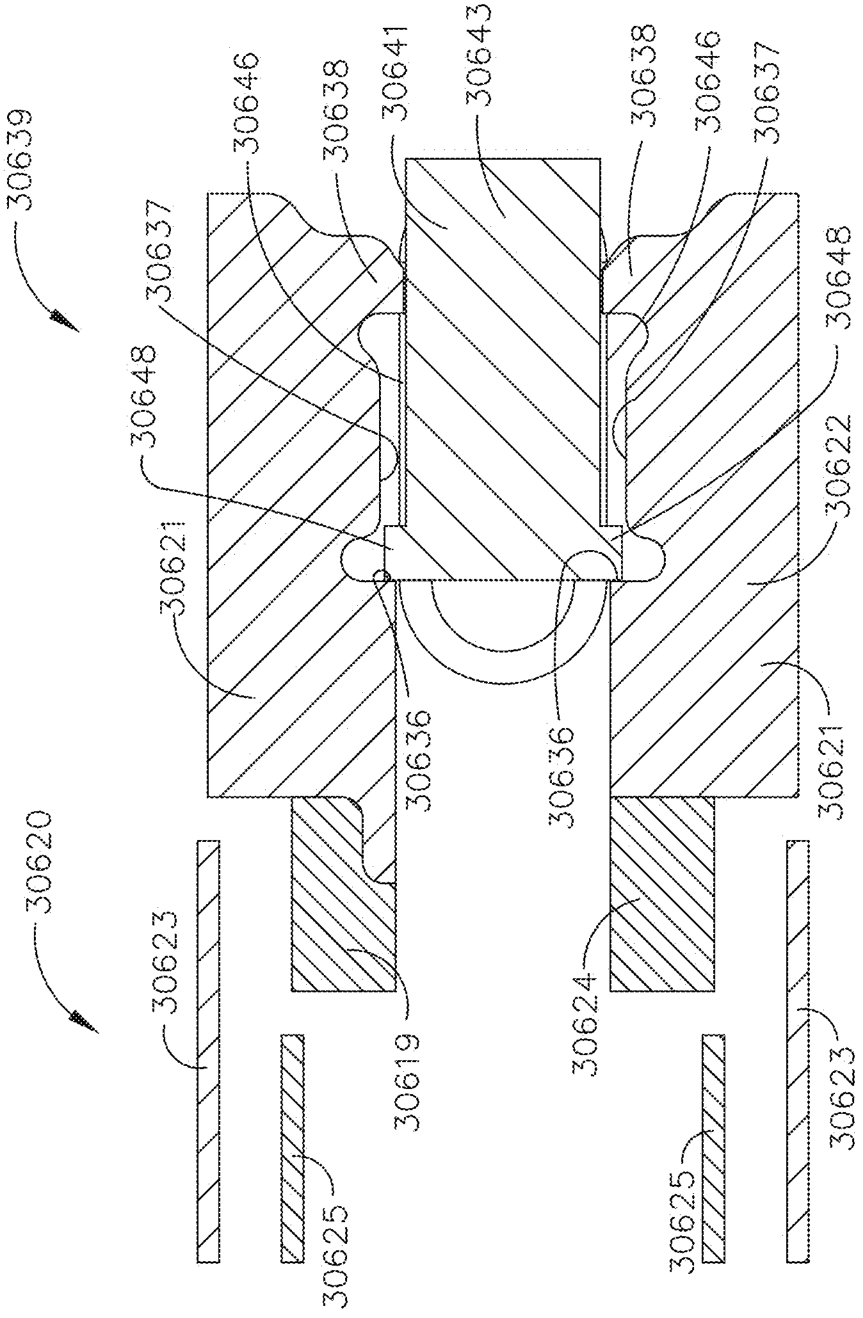
FIG. 95 is an elevation cross-section view of the firing member and the sled assembly of FIG. 90 taken along the plane indicated in FIG. 93, depicting the firing member in the first advanced configuration, according to various aspects of the present disclosure.

As shown in FIG. 90, when the staple cartridge 30600 including the sled assembly 30620 is installed in a surgical end effector, the sled assembly 30620 is brought into releasable engagement with the firing member 30641. More specifically, the proximal sled 30622 includes proximal fingers 30638, which extend laterally inward into longitudinal tracks 30637 along each inside edge of the orthogonal portions 30621. Moreover, the firing member 30641 includes ridges 30648 positioned within respective slots 30646 into the body portion 30645. Owing to the angle of insertion of the staple cartridge 30600 relative to the firing member 30641, the proximal fingers 30641 are lifted over the ridges 30648 and positioned in the slots 30646 in the firing members 30641 to releasably retain the proximal sled 30622 to the firing member 30641. Referring primarily to FIG. 95, the engagement features between the proximal sled 30622 and the firing member 30641 are symmetrical about a longitudinal axis A through the staple cartridge 30600 and aligned with the firing drive screw 30641 (FIG. 92). In other instances, the engagement features may only be positioned on one side of the firing assembly 30639.

When the staple cartridge 30600 is properly seated in the surgical end effector and the proximal sled 30622 is releasably held to the firing member 30641, a firing stroke can be initiated. At the outset of the firing stroke, the firing member 30641 is advanced distally and the firing assembly 30639 assumes the first advanced configuration of FIGS. 92-95. In this initial portion of the firing stroke, the firing member 30641 moves distally relative to the proximal sled 30622. For example, the proximal fingers 30638 move through the slots 30646 in the firing member 30641 as the ridges 30648 move along the tracks 60637. The firing member 30641 is advanced distally until the ridges 30648 on the firing member 30641 abut the ends of the tracks 30637, as shown in FIG. 95. Stated differently, the proximal sled 30622 includes hard stops 30636 in the orthogonal portions 30621 at the distal ends of the tracks 30637 (FIG. 95). The ridges 30648 cannot move distally past the hard stops 30636. In short, the firing member 30641 moves relative to the proximal sled 30622 until the ridges 30648 abut the hard stops 30636 at which point the firing assembly 30639 is in the first advanced configuration.

In the first advanced configuration, the firing member 30641 is positioned to push the proximal sled 30622 and the proximal sled 30622 is positioned to push the distal sled 30624. In effect, the firing member 30341 is in pushing engagement with the sled assembly 30620 and can push the collective sled assembly 30620 distally to fire the staples and cut tissue. In the first advanced configuration, the upright body portion 30643 of the firing member 30641 is pushed distally into abutting engagement with the knife 30629. In this configuration, the firing member 30641 is configured to support the knife 30629 during the firing stroke.

Upon completion of the firing stroke or a portion thereof, the firing member 30641 can be retracted proximally. Proximal retraction of the firing member 30641 is configured to unclamp the jaws in various instances, as further described herein. The proximal retraction motion is shown in FIGS. 96A-96D. In a first retracted configuration (FIG. 96A), the firing member 30641 has been retracted proximally and moved relative to the sled assembly 60620 including relative to the proximal sled 60622. For example, the firing member 30641 is permitted to move proximally relative to the proximal sled 60622 until the ridges 30648 abut the proximal ends of the tracks 30637. The proximal ends of the tracks 30637 are defined by the proximal fingers 30638 extending laterally inward into the slot 30645 in the firing member 30641. In the first retracted configuration, the ridges 30648 abut the distal ends of the proximal fingers 30638.

Figure 96A:
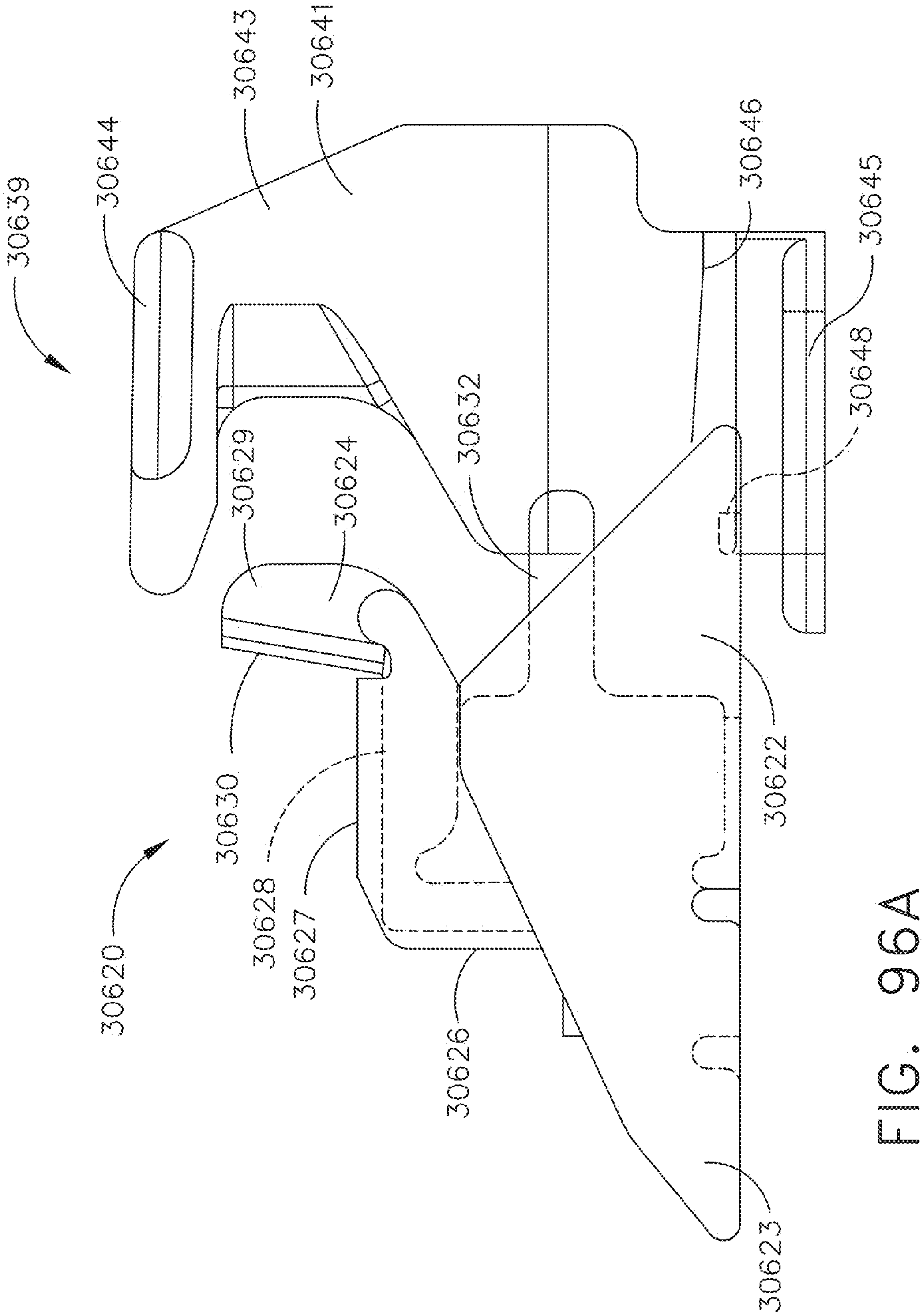
FIG. 96A is an elevation view of the firing member and the sled assembly of FIG. 90 with certain hidden features shown with dashed lines for illustrative purposes, depicting the firing member in a first retracted configuration, according to various aspects of the present disclosure.
Figure 96B:
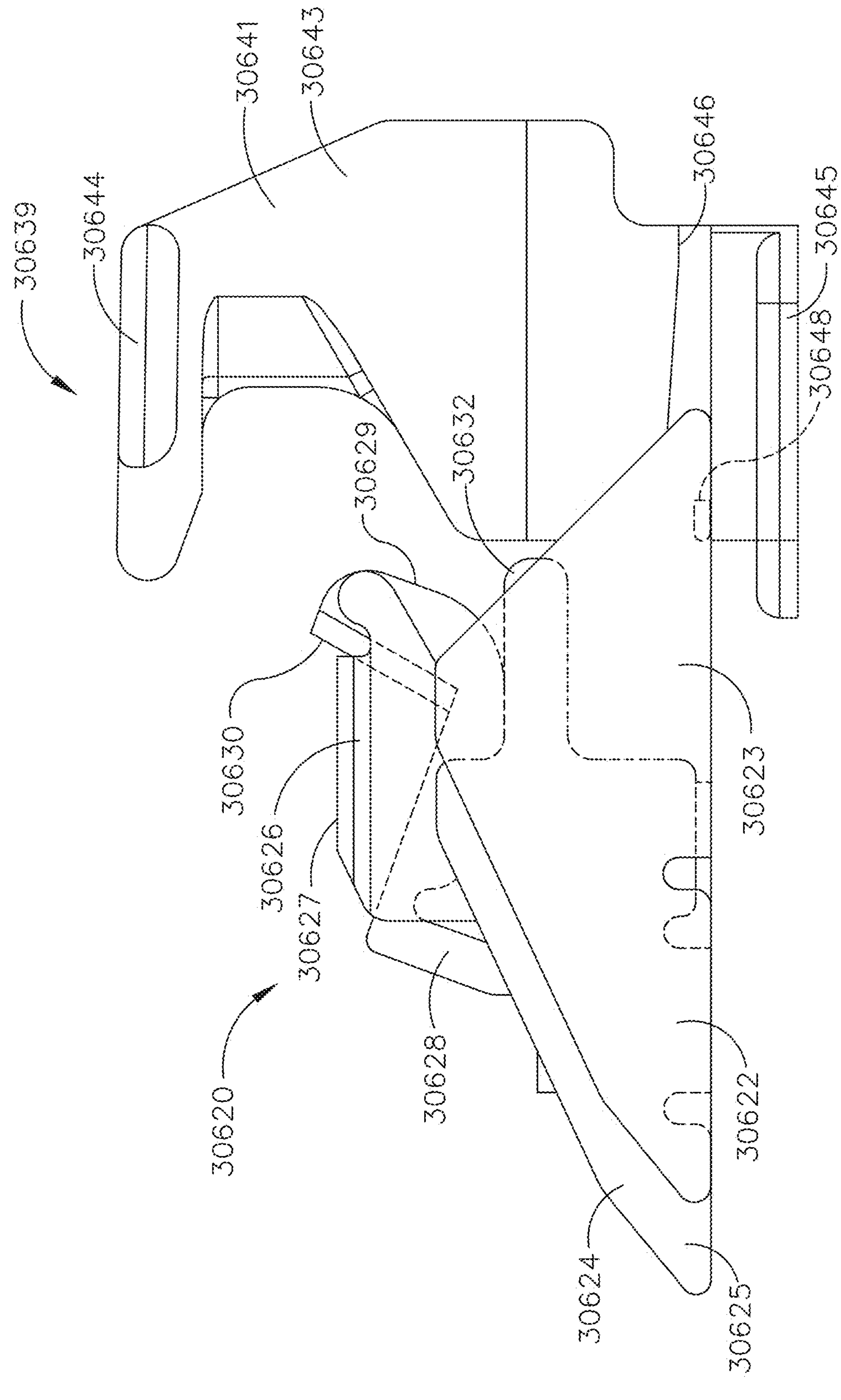
FIG. 96B is an elevation view of the firing member and the sled assembly of FIG. 90 with certain hidden features shown with dashed lines for illustrative purposes, depicting the firing member in a second retracted configuration, according to various aspects of the present disclosure.
Figure 96C:
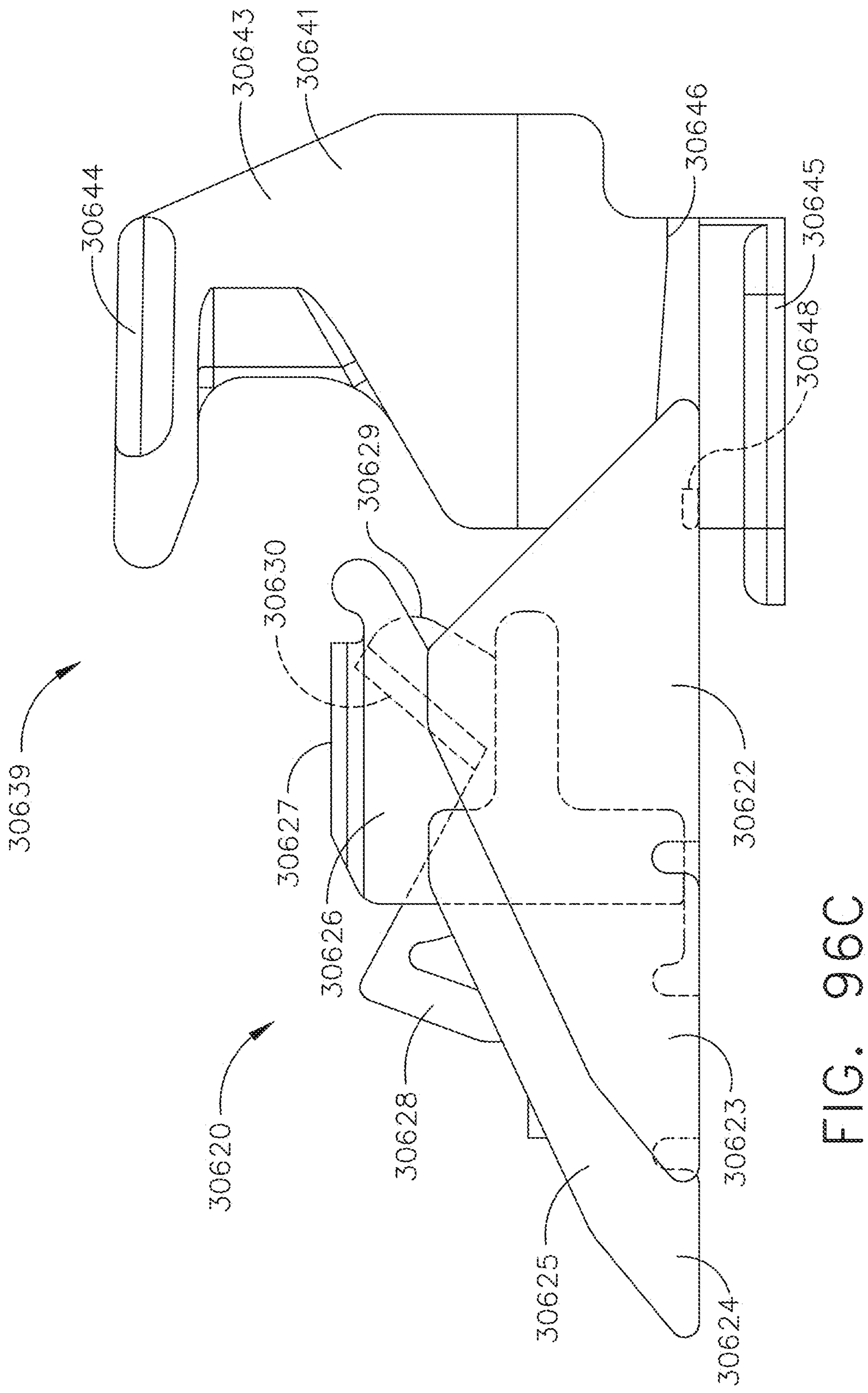
FIG. 96C is an elevation view of the firing member and the sled assembly of FIG. 90 with certain hidden features shown with dashed lines for illustrative purposes, depicting the firing member in a third retracted configuration, according to various aspects of the present disclosure.
Figure 96D:
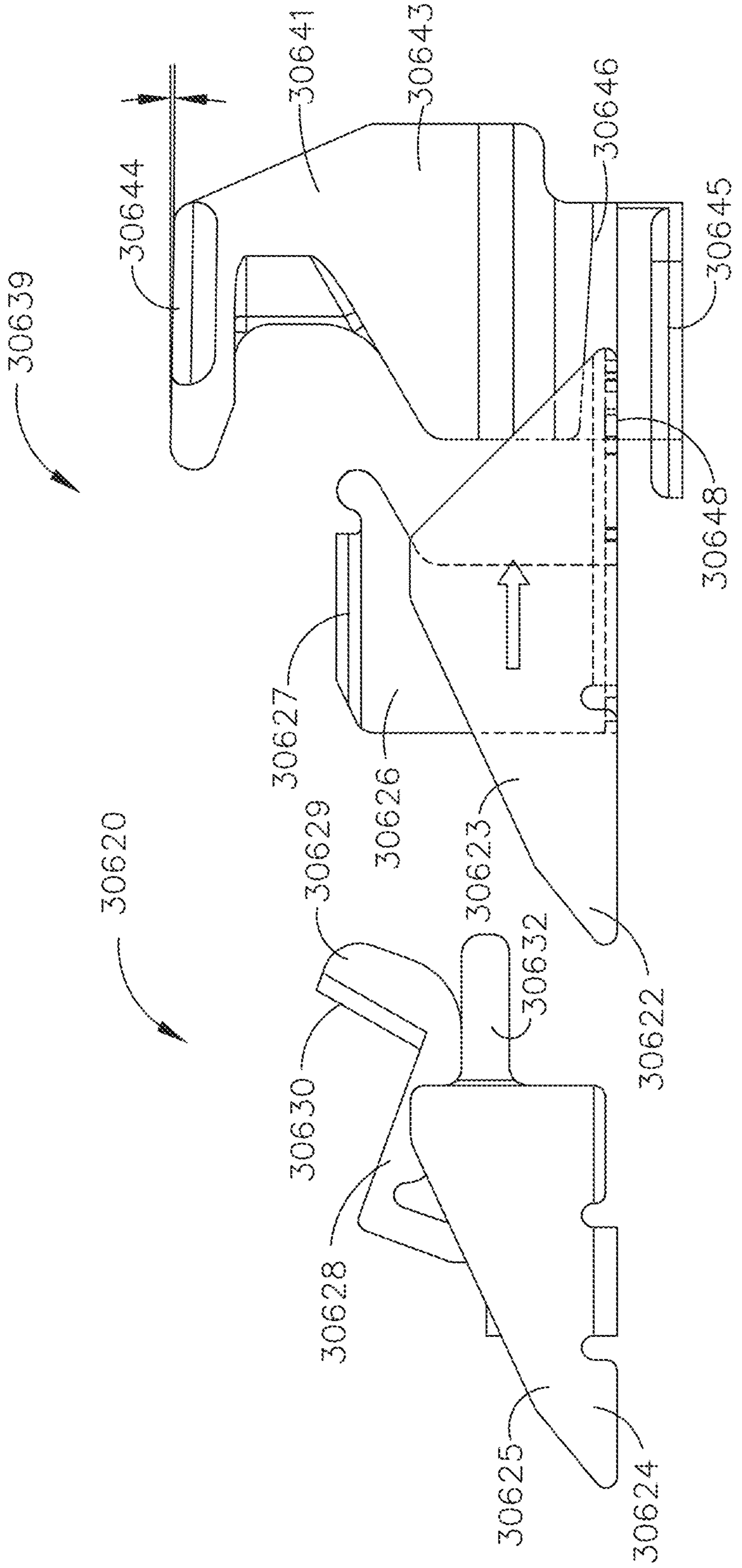
FIG. 96D is an elevation view of the firing member and the sled assembly of FIG. 90 with certain hidden features shown with dashed lines for illustrative purposes, depicting the firing member in a fourth retracted configuration, according to various aspects of the present disclosure.

From the first retracted configuration, the firing member 30641 is configured to retract the proximal sled 30622 along with the firing member 30641. The anti-retraction arms 30632 on the distal sled 30624 are configured to hold the distal sled 30624 in place in the cartridge body 30602 as the proximal sled 30622 is retracted. In the second retracted configuration (FIG. 96B), the ledge 30627 on the central upright portion 30626 of the proximal sled 30622 is pulled over the upward-protruding knife 30629 to deform or fold the knife 30629 downward under the ledge 30627. The central upright portion 30628 of the distal sled 30624, which supports the knife 30629, comprises a slender beam having at least one corner or bend, which can be deflected by the ledge 30627 moving over the knife 30629. The bends can include a hollowed inside corner to facilitate bending when the downward force of the ledge 30627 is applied thereto. The central upright portion 30628 and the knife 30629 thereof continue to be pushed downward when the firing assembly moves from the second retracted configuration to the third retracted configuration (FIG. 96C). From the third retracted configuration to the fourth retracted configuration (FIG. 96C), the firing member 30641 continues to draw the proximal sled 30622 away from the distal sled 30624 and knife 30639 thereof, which has been folded and/or deformed by the ledge 30627 during the proximal retraction motion of the proximal sled 30622.

Figure 97:
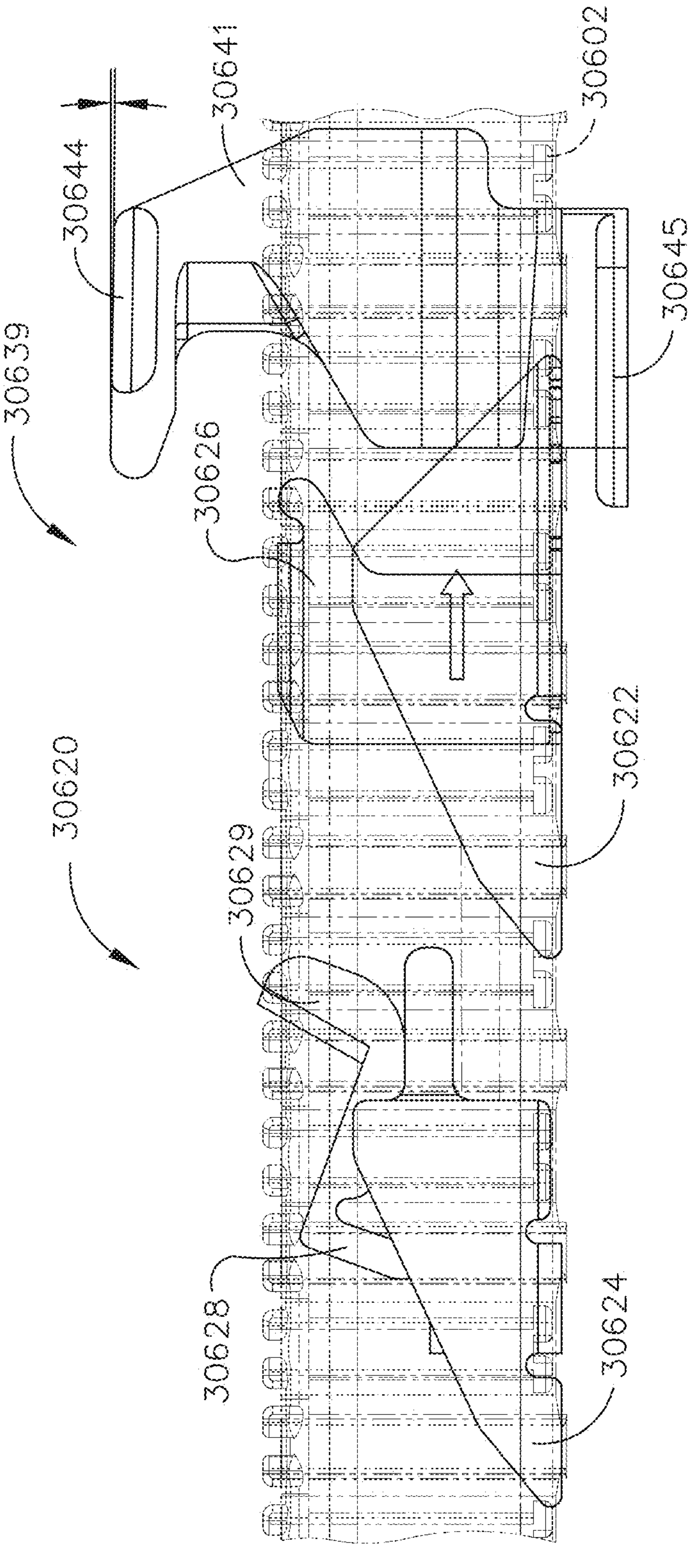
FIG. 97 is an elevation view of the firing member and the sled assembly of FIG. 90 relative to the cartridge body of FIG. 92, depicting the firing member in the fourth retracted configuration of FIG. 96D, wherein the cartridge body is shown in phantom lines for illustrative purposes, according to various aspects of the present disclosure.
Figure 98:
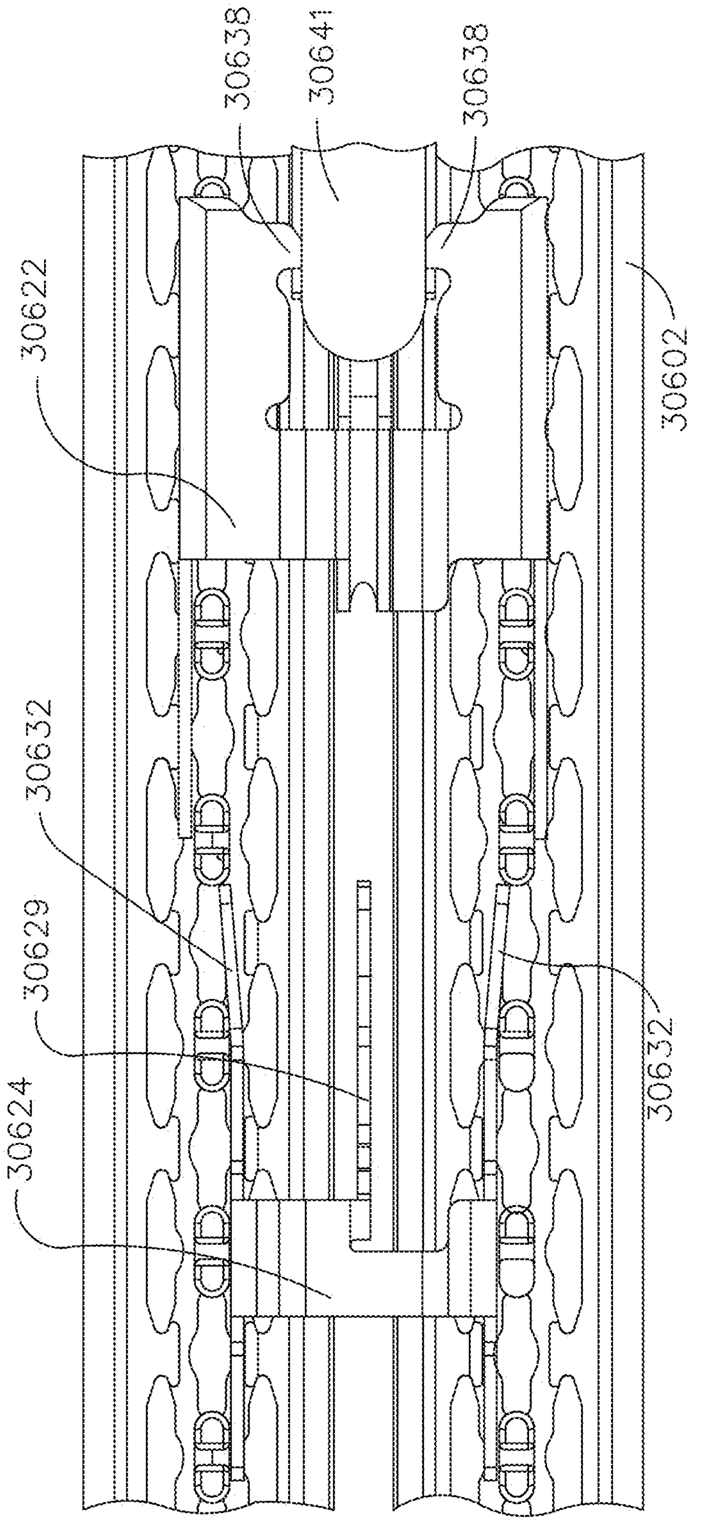
FIG. 98 is a plan view of the firing member and the sled assembly of FIG. 90 and the cartridge body of FIG. 92, depicting the firing assembly in the fourth retracted configuration of FIG. 96D, according to various aspects of the present disclosure.

Referring primarily to FIGS. 97 and 98, the distal sled 30624 is retained in a distal portion of the cartridge body 30602 and the proximal sled 30622 and the firing member 30641 are retracted proximally. In various instances, after the cams 30644, 30645 of the firing member 30641 are retracted out of engagement with the camming surfaces in the anvil jaw and the cartridge jaw, the jaws can be opened and the spent/fired staple cartridge 30600 can be removed from the end effector. For example, owing to the removal angle of the staple cartridge 30600, the proximal fingers 30638 can be lifted over the ridges 30648 to disengage the proximal sled 30622 from the firing member 30641. In such instances, the staple cartridge 30600 including the bent/deformed knife 30629 shielded within the cartridge body 30602 can be removed and replaced with a new staple cartridge.

Certain staple cartridges described herein can include a central longitudinal support frame and/or a rotary drive screw extending along a substantial length of the staple cartridge. In various instances, the structures along the center of the staple cartridge can occupy a significant portion of the staple cartridge footprint and, notably, take up a significant width, which can impact the arrangement of staple cavities, staple drivers, and staples therein. Certain modifications to a staple line can impact hemostasis. Adjustments to the staple line configuration such as number of staples and spacing therebetween within a longitudinal row, lateral spacing between longitudinal rows, and variations in number of staples, spacing therebetween, and placement of proximal-most staples (i.e. offset) can be adjusted from row-to-row. Various staple line configurations are described herein, which are configured to optimize hemostasis and balance firing forces within the small footprint of the various staple cartridge assemblies described herein.

The sled is subjected to significant forces during a firing stroke. For example, as the sled engages the drivers and lifts the drivers and staples thereon through the tissue and into forming contact with the anvil, significant transverse loads can be applied to the sled rails. To smooth the force-to-fire during a firing stroke, the staple patterns on opposing sides of the cartridge can be longitudinally offset.

Figure 118:
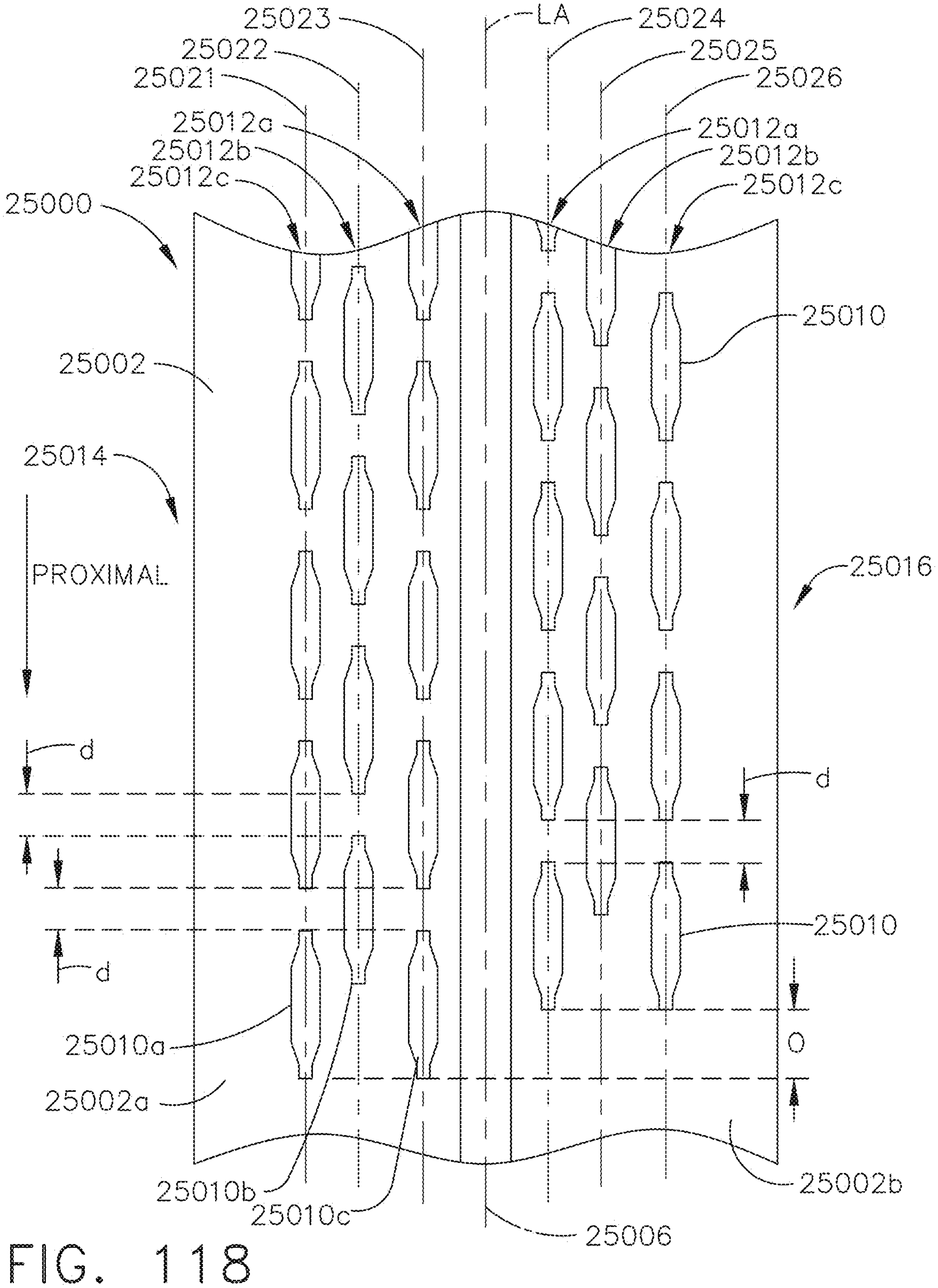

Referring now to FIG. 118, a staple cartridge 25000 has a cartridge body 25002 and staple cavities 25010 defined in the cartridge body 25002. The staple cavities 25010 are dimensioned and structured to hold drivers and staples therein, as further described herein. A longitudinal slot 25006 divides the cartridge body 25002 into a first side 25002*a* and a second side 25002*b*. The staple cavities 25010 are arranged in two patterns: a first pattern 25014 on the first side 25002*a* of the longitudinal slot 25006, and a second pattern 25016 on the second side 25002*b* of the longitudinal slot 25006. Each pattern 25014, 25016 includes an inner row 25012*a*, an intermediate row 25012*b*, and an outer row 25012*c*. However, the first pattern 25014 is different than the second pattern 25016.

More specifically, the first pattern 25014 is longitudinally offset from the second pattern 25016 by a distance, or longitudinal offset, O. Consequently, the first pattern 25014 and the second pattern 25016 are not symmetric relative to the longitudinal axis A. The first pattern 25014 includes proximal-most staples cavities, and the second pattern 25016 includes proximal-most staple cavities. The longitudinal offset O between the proximal ends of the proximal-most staple cavities on either side of the longitudinal axis L is the longitudinal offset O.

As further described herein, triple drivers include three staple-supporting columns connected by bridges. The triple drivers define a longitudinal length from the proximal end of the proximal-most support column to the distal end of the distal-most support column. The longitudinal length is length along the longitudinal axis A, e.g. the proximal-to-distal length of a driver configured to fire staples from a first cavity 25010*a*, a second cavity 25010*b*, and a third cavity 25010*c*. The proximal-to-distal length of a triple driver can be 0.1936 inches in certain instances. Other lengths are also contemplated.

Figure 94:
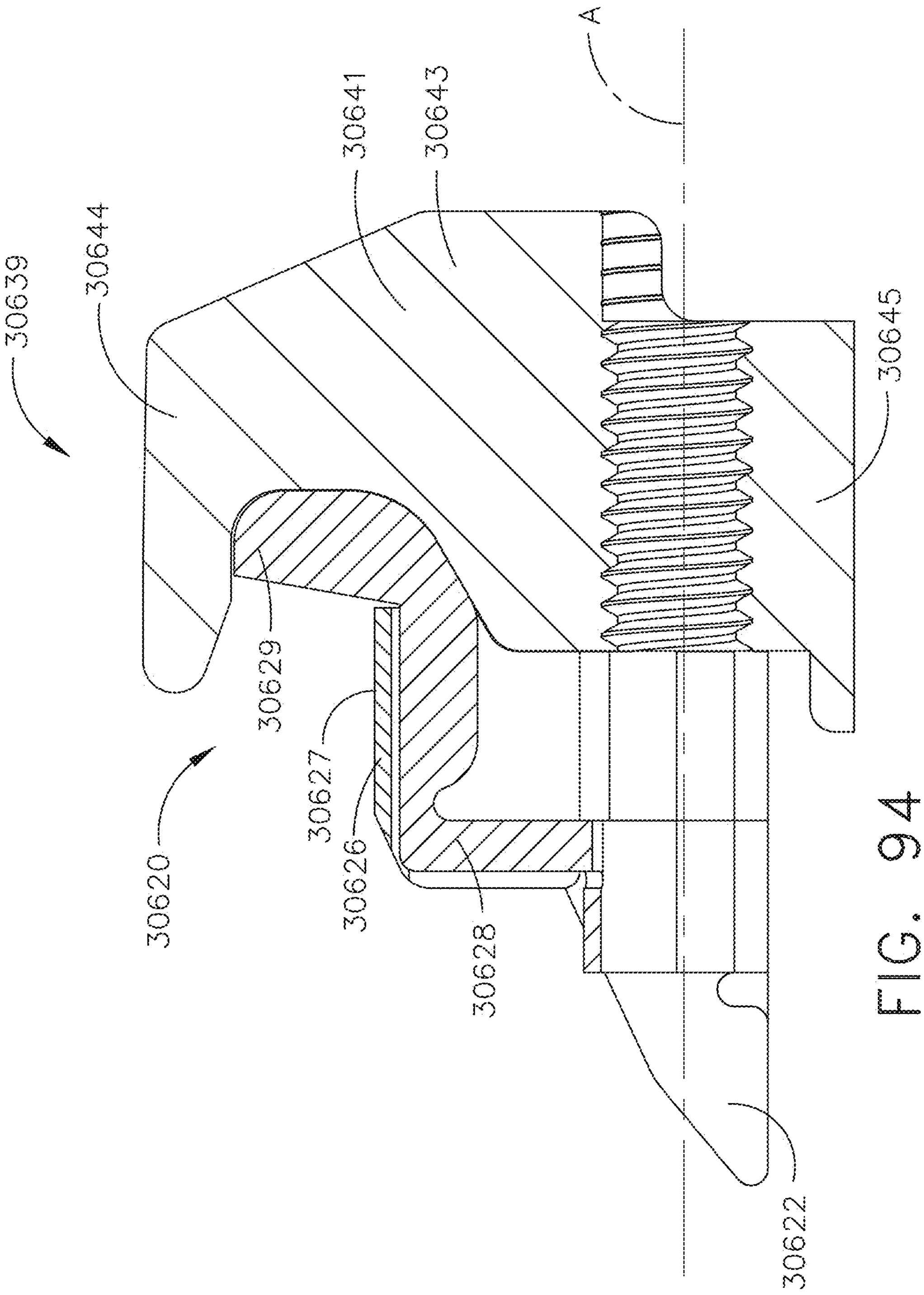
FIG. 94 is an elevation cross-section view of the firing member and the sled assembly of FIG. 90 taken along the plane indicated in FIG. 90, depicting the firing member in the first advanced configuration, according to various aspects of the present disclosure.
Figure 119:
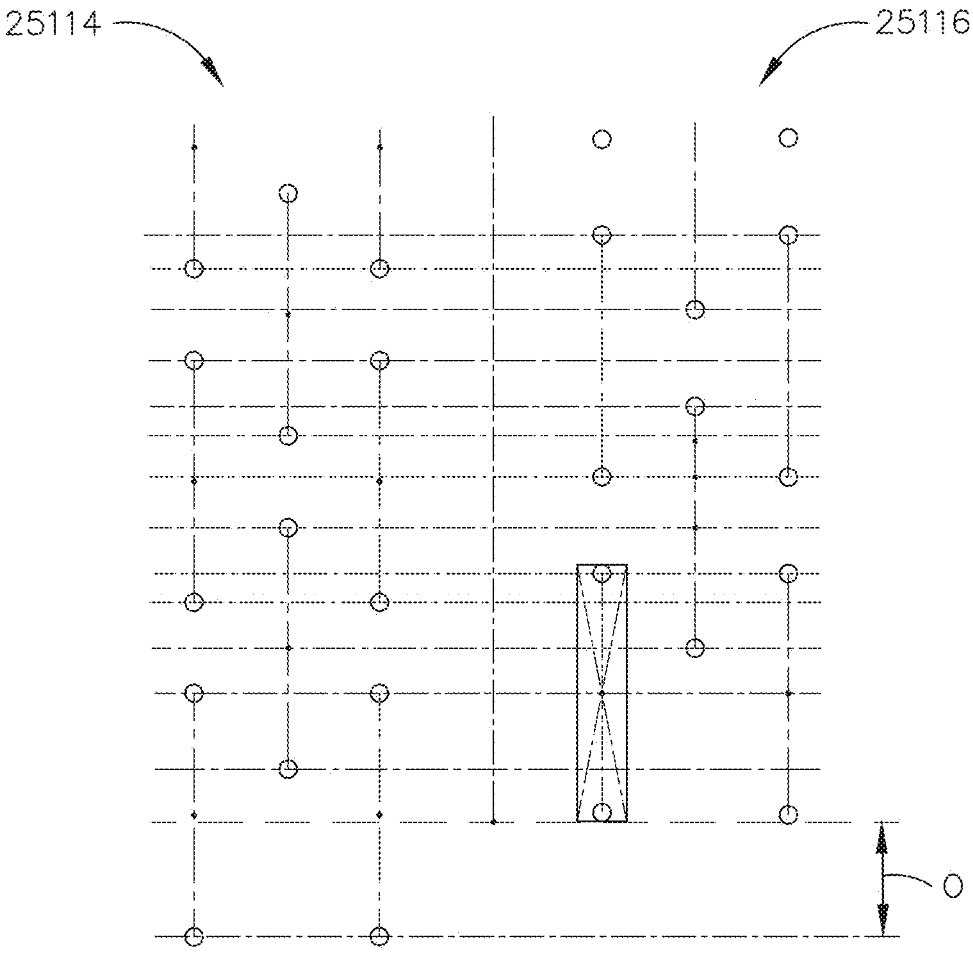
Figure 120:
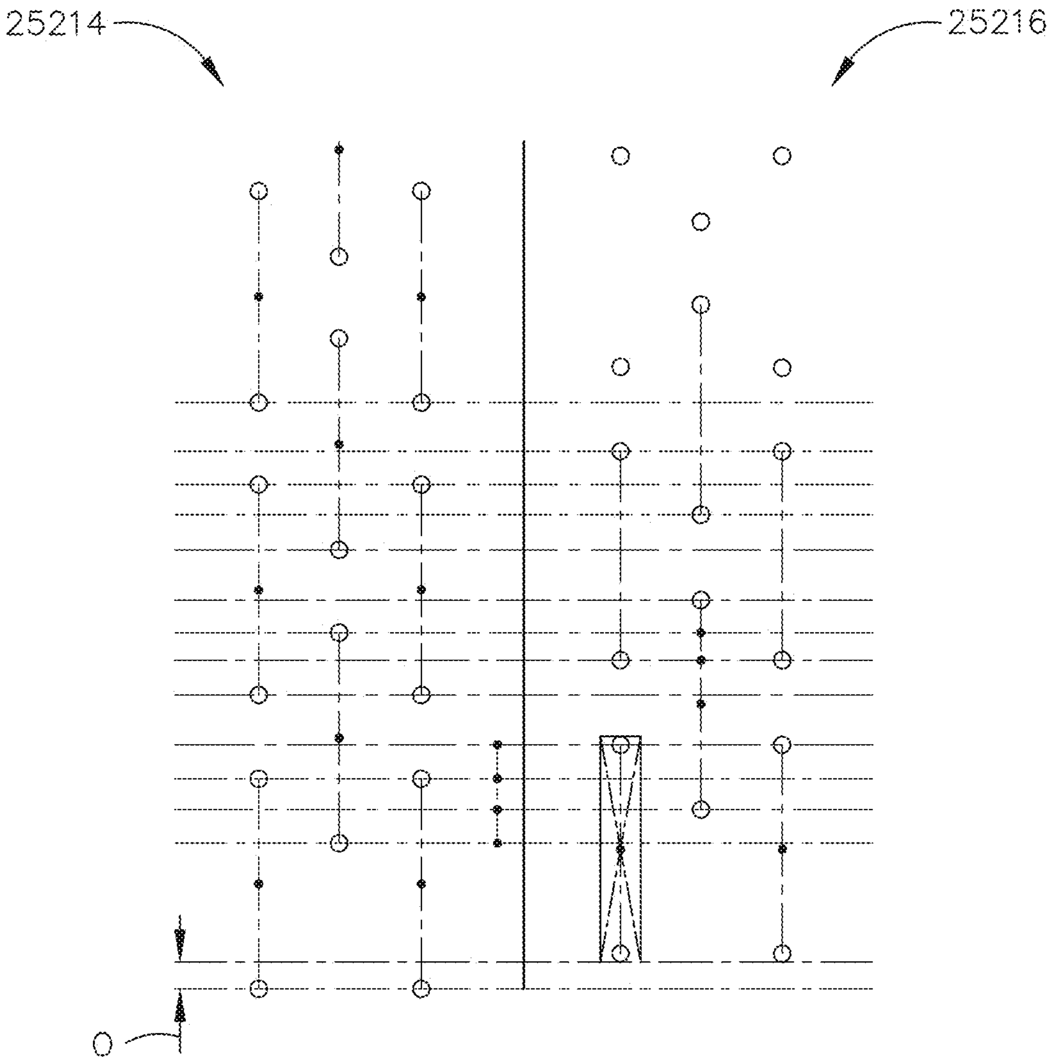

The longitudinal offset is configured to smooth the force-to-fire of the sled during the firing stroke in various instances. In various instances the longitudinal offset O is approximately 25% of the longitudinal length of the triple drivers housed in the staple cavity. In other instances, the longitudinal offset O can be less than 25% or more than 25% of the longitudinal length of the triple driver. For example, a longitudinal offset O of 5% to 35% of the longitudinal length of the triple driver is contemplated. Referring to FIG. 119, a longitudinal offset of 29.5% between a first pattern 25114 and a second pattern 25116, which corresponds to approximately 0.0573 inches for a 0.1936 inch proximal-to-distal length triple driver, is utilized. In other instances, referring to FIG. 120, a longitudinal offset of 9.2% between a first pattern 25215 and a second pattern 25216, which corresponds to approximately 0.0178 inches for a 0.1936 inch proximal-to-distal length triple driver, is utilized. FIGS. 94-96 only depict a portion of each pattern 25014, 25016, 25114, 25115, 25214, 25216, and the same pattern continues until the distal end of the staple cavities in certain instances.

In certain instances, the triple drivers can be triangular, and the drivers on one side of the cartridge body are not aligned with the drivers on the opposite side of the cartridge body. An asymmetric arrangement of triple drivers in a cartridge body can allow the sled to be asymmetric about a longitudinal centerline. In such instances, one side of the cartridge body can have additional space at the proximal end where that side of the driver is longitudinally offset in a distal direction. The additional space can accommodate lockout components and/or rotary driver supports. Exemplary lockouts and rotary driver supports are further described herein. In certain instances, lockout components and rotary drive supports can be at least partially side-by-side in the proximal end of the cartridge body.

In other instances, the sled rails can be longitudinally offset to balance the force-to-fire. For example, the sled rail(s) on a first side of the sled can be longitudinally offset from the sled rail(s) on the opposite side of the sled by 25% of the longitudinal length of the triple drivers housed in the cartridge body 25002.

Referring again to FIG. 94, in certain instances, the longitudinal rows 25012*a*, 25012*b*, 25012*c* on each side 25002*a*, 25002*b* can be laterally spaced differently. For example, the inner row 25012*a* and the intermediate row 25012*b* on the second cartridge side 25002*b* are closer together than the inner row 25012*a* and the intermediate row 25012*b* on the first cartridge side 25002*a*. The distance between axis 25024 and axis 25025 is less than the distance between axis 25022 and axis 25023, for example. Moreover, the outer row 25012*c* and the intermediate row 25012*b* on the second cartridge side 25002*b* are farther apart than the outer row 25012*c* and the intermediate row 25012*b* on the first cartridge side 25002*a*. The distance between axis 25026 and axis 25025 is greater than the distance between axis 25021 and axis 25022, for example. Moreover, on both sides of the cartridge body 25002, the lateral spacing between the inner row 25012*a* and the intermediate row 25012*b* is different than the lateral spacing between the intermediate row 25012*c* and the outer row 25012*c*.

In other instances, none of the rows of staple patterns on one side of a cartridge body, e.g. one side of the longitudinal knife slot, can be a repeated pattern. A non-repeating and unique pattern in each row can permit customizations row-to-row to ensure a maximum number of staple cavities fit in the cartridge body, especially in a proximal region near the tissue stops. Moreover, in certain instances, the staple pattern can utilize the same drivers, e.g. the same triple driver, along the entire length of the staple line. In such instances, only a single type of driver is utilized in the staple cartridge, which can improve manufacturing processes. In certain instances, proximal-most and/or distal-most fastener cavities in the inner row and the outer row can be offset, for example.

Figure 121:
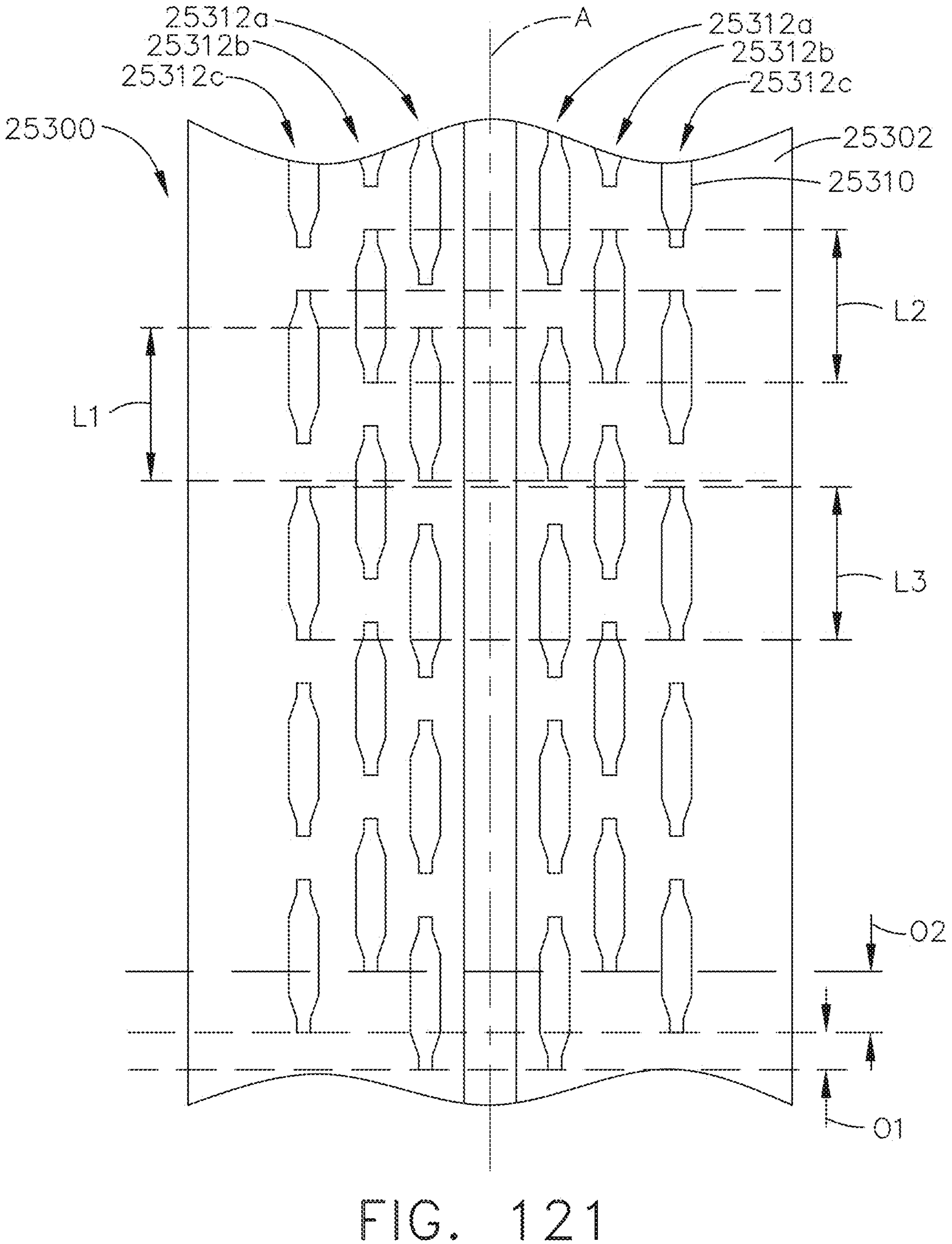

Referring now to FIG. 121, a staple cartridge 25300 has a cartridge body 25302 and staple cavities 25310 defined in the cartridge body 25302. The staple cavities 25310 are dimensioned and structured to hold drivers and staples therein, as further described herein. A longitudinal slot divides the cartridge body 25302 into a first side and a second side. The staple cavities 25010 are arranged in two patterns: a first pattern on the first side of the longitudinal slot, and a second pattern on the second side of the longitudinal slot. Each pattern 25315 includes an inner row 25312*a*, an intermediate row 25312*b*, and an outer row 25312*c*. The first pattern is the same as the second pattern (e.g. a symmetrical, mirror image about the longitudinal axis L). FIG. 121 only depicts a portion of each pattern 25314, 25316, and the same pattern continues until the distal end of the staple cavities in certain instances.

In the first and second patterns, the proximal-most staple cavity is longitudinally offset from the second proximal-most staple cavity by a first distance, or longitudinal offset, O1. Additionally, in the first and second patterns, the second proximal-most staple cavity is longitudinally offset from the third proximal-most staple cavity by a second distance, or longitudinal offset, O2. The first longitudinal offset O1 is less than 50% of the staple crown lengths L1, L2, and L3, of staples in the inner row 25312*a*, intermediate row 25312*b*, and the outer row 25312*c*, respectively. The second longitudinal offset O2 is selected based on the longitudinal offset O1 to stagger the staples fired from the intermediate row 25312*c* relative to the staples fired from the inner rows 25312*a* and the outer rows 25312*c*. Stated differently, the second longitudinal offset O2 is selected to provide at least a small degree of longitudinal overlap row-to-row. The second longitudinal offset O2 is greater than the first longitudinal offset O1.

Referring still to the patterns, the rows 25312*a*, 25312*b*, 25312*c* on each side are different from the other rows on that side. More specifically, the number of cavities and spacing between the cavities in the same; however, the starting location of the rows 25312*a*, 25312*b*, 25312*c* differs.

Moreover, each row 25312*a*, 25312*b*, 25312*c* extends along an axis that is parallel to the longitudinal axis L. The lateral spacing of the rows 25312*a*, 25312*b*, 25312*c*, i.e. the spacing of the axes along which the rows extend, can be different. For example, on both sides 25302*a*, 25302*b*, the lateral spacing between the inner row 25312*a* and the intermediate row 25312*b* is less than the lateral spacing between the intermediate row 25312*b* and the outer row 25312*c*.

In certain instances, rows on the same side can be configured to receive different staples and/or can be aligned with forming pockets configured to form the staples to different sizes and/or geometries. For example, on the same side but in different rows, certain staples can be larger than the staples in other rows and/or can be configured to be formed to a taller formed height than the staples in other rows. Additionally, or alternatively, staples from the same side can be formed into a 2D, planar configuration while staples on that same side are configured to be formed into a 3D, non-planar staple.

As further described herein, triple drivers include three staple-supporting columns connected by bridges. In various instances, the staple patterns 25314 and 25316 can be fired exclusively with triple drivers. Stated differently, a single type of driver can fire all of the staples from the patterns 25314, 25316.

Other staple patterns having non-identical rows are also contemplated. For example, in certain instances, the inner row and the outer row can be symmetrical about the intermediate row until the proximal-most cavity and/or cavities which are positioned closer together to accommodate the tissue stops. In such instances, the inner row and the outer row would have some longitudinally aligned staples row-to-row and other non-longitudinally aligned staples row-to-row. In other instances, one of the rows could have fewer staples than the other rows. For example, the outer row could have few staples, which are spaced longitudinally farther apart.

Figure 122:
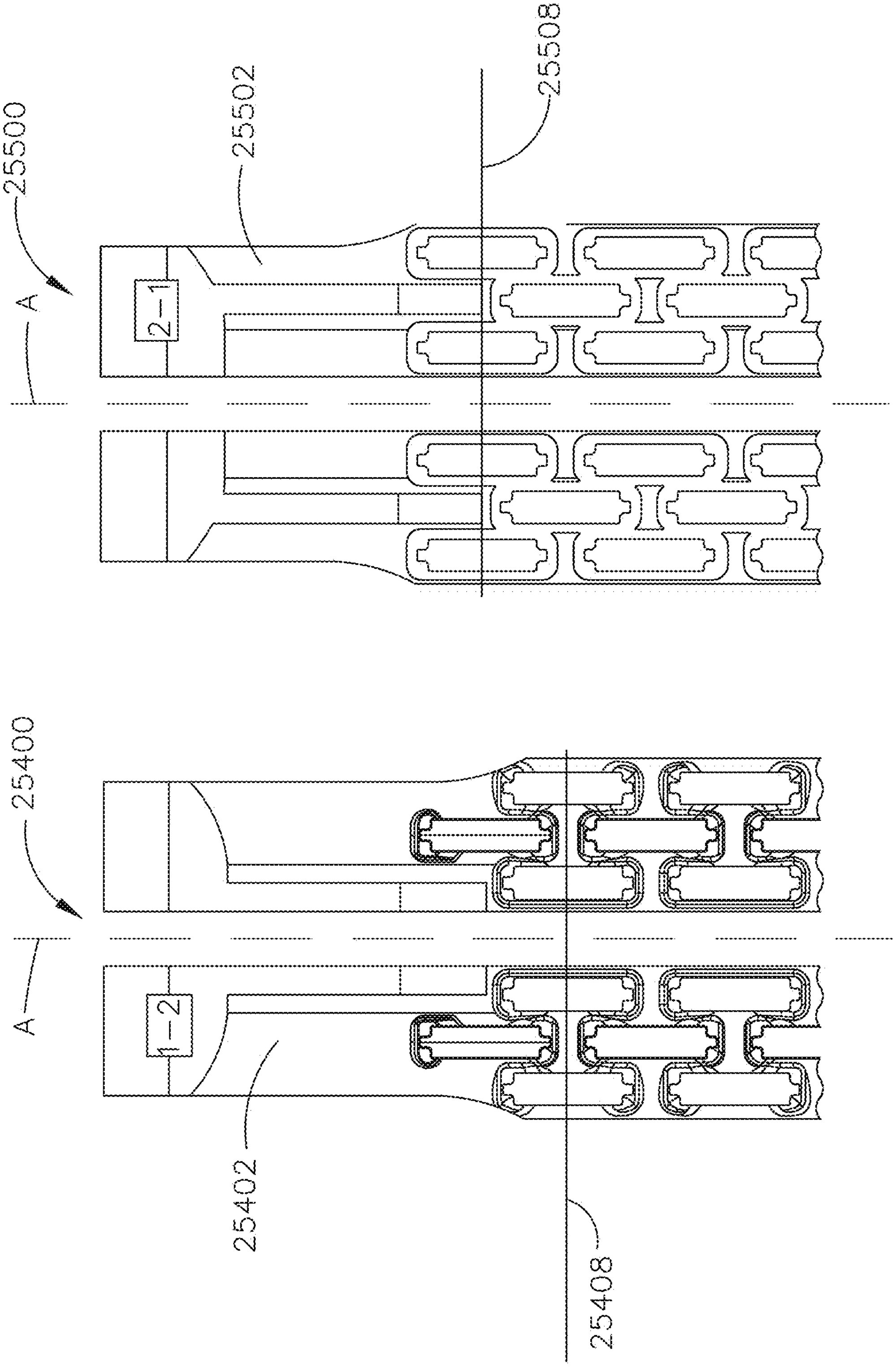

Referring now to FIG. 122, two staple cartridges 25400 and 25500 are shown side-by-side for comparative purposes. The staple cartridges 25400, 25500 includes cartridge bodies 25402, 25502, respectively, and three rows of staple cavities 25410, 25510, respectively, on each side of a longitudinal A. The staple cartridges 25400, 25500 are similar in many aspects to the various staple cartridges described herein.

Each staple cartridge 25400, 25500 also includes a datum 25408, 25508, respectively, corresponding to the distal end of a tissue stop. When the clinician initially locates the target tissue between the anvil and the staple cartridge, it is important that the target tissue be located so that the knife does not cut into the target tissue unless it is first stapled. Tissue stops can be provided on the proximal end of the anvil body to prevent the target tissue from moving proximally past the proximal most staple pockets in the staple cartridge.

In certain instance, a cartridge body can include at least one totaled or combined staple length on each side of the longitudinal axis A proximal to the tissue stop. A combined staple length is sum of the length of one or more staples or portions thereof positioned proximal to the tissue stop. The sum of those individual lengths is equivalent to the combined staple length. For example, referring to the staple cartridge 25400, one full staple and two half staples are proximal to the tissue stop for a combined staple length of two staples. However, because at least one combined staple length is desired proximal to the tissue stop datum 25408, there is little room to shift the tissue stop datum 25408 proximally.

Conversely, referring to the staple cartridge 25500, the tissue stop is in a relatively more proximal position relative to the proximal end of the staple cartridge 25500 and the proximal-most fastener cavities. Moreover, the combined staple length on each side of the cartridge body still meets the goal of at least one combined staple length proximal to the tissue stop datum 25508. Having two staple cavities longitudinally aligned, or closely aligned, at the proximal end of a pattern of staple cavities can allow the tissue stop to move proximally while still maintaining a suitable combined staple length proximal to the tissue stop.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, published as U.S. Patent Application Publication No. 2014/0263552, now abandoned;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006, now abandoned; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical stapler sled assembly, comprising:
(a) a first sled body having a pair of first rails; and
(b) a second sled body arranged in an overlapping relationship with the first sled body and having a pair of second rails,
wherein the surgical stapler sled assembly is longitudinally translatable within a surgical stapler end effector so that each first rail and each second rail cammingly engages a respective plurality of staple drivers to eject staples from the surgical stapler end effector.

2. The surgical stapler sled assembly of claim 1, wherein at least one of the first rails or the second rails comprises a metal.

3. The surgical stapler sled assembly of claim 1, wherein a bottom surface of one of the first or second sled bodies overlies a top surface of the other of the first or second sled bodies.

4. The surgical stapler sled assembly of claim 1, wherein the first rails are disposed laterally inwardly of the second rails.

5. The surgical stapler sled assembly of claim 4, wherein a bottom surface of the first sled body overlies a top surface of the second sled body.

6. The surgical stapler sled assembly of claim 4, wherein the second sled body comprises an upright protrusion disposed between the first rails and between the second rails.

7. The surgical stapler sled assembly of claim 1, wherein the first sled body includes a first central body portion that interconnects the first rails, and the second sled body includes a second central body portion that interconnects the second rails, wherein the first and second central body portions are arranged in the overlapping relationship.

8. The surgical stapler sled assembly of claim 7, wherein a distal-most end of the first sled body is longitudinally offset from a distal-most end of the second sled body.

9. The surgical stapler sled assembly of claim 8, wherein the distal-most end of the first sled body is proximal to the distal-most end of the second sled body.

10. The surgical stapler sled assembly of claim 9, wherein the first central body portion overlies the second central body portion.

11. A surgical stapler sled assembly, comprising:
(a) an inner sled body having a pair of inner rails; and
(b) an outer sled body coupled with the inner sled body and having:
(i) a pair of outer rails, and
(ii) an upright protrusion disposed laterally between the outer rails,
wherein the inner and outer sled bodies are arranged in an overlapping relationship such that the inner rails are disposed laterally inwardly of the outer rails,
wherein the surgical stapler sled assembly is longitudinally translatable within a surgical stapler end effector so that each inner rail and each outer rail cammingly engages a respective plurality of staple drivers to eject staples from the surgical stapler end effector.

12. The surgical stapler sled assembly of claim 11, wherein at least one of the inner rails or the outer rails comprises a metal.

13. The surgical stapler sled assembly of claim 12, wherein the inner sled body comprises a metal.

14. The surgical stapler sled assembly of claim 11, wherein a bottom surface of the inner sled body overlies a top surface of the outer sled body.

15. The surgical stapler sled assembly of claim 11, wherein the inner sled body includes a first central body portion that interconnects the inner rails, and the second sled body includes a second central body portion that interconnects the outer rails, wherein the first and second central body portions are arranged in the overlapping relationship.

16. The surgical stapler sled assembly of claim 15, wherein a distal-most end of the inner sled body is proximal to a distal-most end of the outer sled body.

17. A method of making a surgical stapler sled assembly, comprising:

forming a first sled body with a pair of first rails;

forming a second sled body with a pair of second rails; and joining the first and second sled bodies such that the first rails are disposed laterally inwardly of the second rails, wherein the surgical stapler sled assembly is longitudinally translatable within a surgical stapler end effector so that each first rail and each second rail cammingly engages a respective plurality of staple drivers to eject staples from the surgical stapler end effector.

18. The method of claim 17, wherein forming the first sled body includes stamping a sheet of metal.

19. The method of claim 17, wherein forming the second sled body includes forming an upright protrusion laterally between the second rails, wherein joining the first and second sled bodies includes positioning the first rails laterally between the second rails and on either lateral side of the upright protrusion.

20. The method of claim 19, wherein joining the first and second sled bodies includes overlapping the first and second sled bodies.

* * * * *